United States Patent
Evans et al.

(10) Patent No.: US 10,920,199 B2
(45) Date of Patent: Feb. 16, 2021

(54) REPROGRAMMING PROGENITOR COMPOSITIONS AND METHODS OF USE THEREFORE

(71) Applicant: SALK INSTITUTE FOR BIOLOGICAL STUDIES, La Jolla, CA (US)

(72) Inventors: Ronald Evans, La Jolla, CA (US); Michael Downes, La Jolla, CA (US); Yasuyuki Kida, La Jolla, CA (US); Teruhisa Kawamura, La Jolla, CA (US); Zong Wei, La Jolla, CA (US); Ruth T. Yu, La Jolla, CA (US); Annette R. Atkins, La Jolla, CA (US)

(73) Assignee: SALK INSTITUTE FOR BIOLOGICAL STUDIES, La Jolla, CA (US)

(*) Notice: Subject to any disclaimer, the term of this patent is extended or adjusted under 35 U.S.C. 154(b) by 0 days.

(21) Appl. No.: 15/552,476

(22) PCT Filed: Feb. 26, 2016

(86) PCT No.: PCT/US2016/019911
§ 371 (c)(1),
(2) Date: Aug. 21, 2017

(87) PCT Pub. No.: WO2016/138464
PCT Pub. Date: Sep. 1, 2016

(65) Prior Publication Data
US 2018/0044642 A1 Feb. 15, 2018

Related U.S. Application Data

(60) Provisional application No. 62/126,417, filed on Feb. 27, 2015.

(51) Int. Cl.
*C12N 5/074* (2010.01)

(52) U.S. Cl.
CPC ........ *C12N 5/0696* (2013.01); *C12N 2501/39* (2013.01); *C12N 2506/02* (2013.01); *C12N 2506/1307* (2013.01)

(58) Field of Classification Search
CPC .............. C12N 5/0696; C12N 2501/39; C12N 2506/1307; C12N 2506/02
See application file for complete search history.

(56) References Cited

U.S. PATENT DOCUMENTS

| | | | | |
|---|---|---|---|---|
| 2009/0281191 | A1* | 11/2009 | Rangwala | A61K 31/00 514/615 |
| 2011/0165570 | A1* | 7/2011 | Feng | C12N 5/0696 435/6.11 |
| 2012/0302491 | A1* | 11/2012 | Narkar | A61P 25/00 514/1.1 |

FOREIGN PATENT DOCUMENTS

| | | |
|---|---|---|
| EP | 2940127 A1 | 11/2015 |
| JP | 2009533017 A | 9/2009 |
| JP | 2011522520 A | 8/2011 |
| WO | 2009136867 A1 | 11/2009 |
| WO | 2013159103 A1 | 10/2013 |
| WO | 2013/159103 A1 | 12/2013 |
| WO | 2014/104364 A1 | 7/2014 |

OTHER PUBLICATIONS

Taha et al. "Upregulation of pluripotency markers in adipose tissue-derived stem cells by miR-302 and leukemia inhibitory factor." Biomed Res Int. 2014;2014:941486. (Year: 2014).*
Prosksch et al. "Does the Human Skeletal Muscle Harbor the Murine Equivalents of Cardiac Precursor Cells?" Mol Ther. Apr. 2009; 17(4): 733-741. (Year: 2009).*
Rosello et al. "Mammalian genes induce partially reprogrammed pluripotent stem cells in non-mammalian vertebrate and invertebrate species." eLife. 2013; 2: e00036. (Year: 2013).*
Kim et al. "Technical note: Induction of pluripotent stem cell-like cells from chicken feather follicle cells.." J Anim Sci. Aug. 2017;95(8):3479-3486 (Year: 2017).*
Ishibashi et al. "ESAM is a novel human hematopoietic stem cell marker associated with a subset of human leukennias." Exp Hematol. Apr. 2016;44(4):269-81.e1. (Year: 2016).*
Hsiao et al. "Endogenous cardiac stem cell therapy for ischemic heart failure." J Clin Exp Cardiol. 2013;S11:007. (Year: 2013).*
Zhang et al. "Cardiac progenitor/stem cells on myocardial infarction or ischemic heart disease: what we have known from current research." Heart Fail Rev. Mar. 2014;19(2):247-58 (Year: 2014).*
Holmes et al. "Concise review: stem cell antigen-1: expression, function, and enigma." Stem Cells. Jun. 2007;25(6):1339-47. (Year: 2007).*
Tayeb et al. "Generation of human induced pluripotent stem cells by simple transient transfection of plasmid DNA encoding reprogramming factors." BMC Dev Biol 10, 81 (2010) (Year: 2010).*
Examiner Proposed Claim Amendments (Year: 2020).*
K. C. Lee et al., 2013, "Decoding the Pluripotency Network: The Emergence of New Transcription Factors." Biomedicines, 1(1):49-78.

(Continued)

*Primary Examiner* — Titilayo Moloye
(74) *Attorney, Agent, or Firm* — Melissa Hunter-Ensor; Leslie Serunian; Greenberg Traurig, LLP

(57) ABSTRACT

The invention generally features compositions comprising induced pluripotent stem cell progenitors (also termed reprogramming progenitor cells) and methods of isolating such cells. The invention also provides compositions comprising induced pluripotent stem cells (iPSCs) derived from such progenitor cells. Induced pluripotent stem cell progenitors generate iPSCs at high efficiency. In particular embodiments the invention is predicated upon increased expression of an estrogen related receptor and changes in the oxidative and glycolytic pathways.

14 Claims, 22 Drawing Sheets
Specification includes a Sequence Listing.

(56) References Cited

OTHER PUBLICATIONS

A. Nemajerova et al., 2012, "Two-factor reprogramming of somatic cells to pluripotent stem cells reveals partial functional redundancy of Sox2 and Klf4," Cell Death and Differentiation, 19:1268-1276.
English translation of Examination Report, dated Dec. 22, 2017, in corresponding Korean Application No. 10-2017-7026760, 4 pages.
English Translation of Notice of Reasons for Rejection (Office Action) in corresponding Japanese Patent Application No. 2017-545226, dated Feb. 21, 2018, (11 pages).
Examination Report for corresponding Australian Application No. 2016225076, dated Oct. 30, 2017, 4 pages.
Extended European Search Report, dated Oct. 18, 2018, received in corresponding European Patent Application No. 16756502.7, (12 pages).
English translation of final Office Action, dated Oct. 10, 2018, in corresponding Korean Patent Application No. 10-2017-7026760 (7 pages).
Buganim, Y. et al., "The Developmental Potential of iPSCs is Greatly Influenced by Reprogramming Factor Selection," Cell Stem Cell, vol. 15, No. 3, Sep. 1, 2014, pp. 295-309.
Takahashi, K. et al., "Induction of Pluripotent Stem Cells from Adult Human Fibroblasts by Defined Factors," Cell, vol. 131, No. 5, Nov. 30, 2007, pp. 861-872.
Kida, Y. et al., "ERRs Mediate a Metabolic Switch Required for Somatic Cell Reprogramming to Pluripotency," Cell Stem Cell, vol. 16, No. 5, May 7, 2015, pp. 547-555.
Partial Supplementary European Search Report for corresponding European application 16756502.7, dated Jul. 27, 2018 (12 pages).
English translation of Preliminary Rejection received in corresponding Korean application No. 10-2017-7026760, dated Feb. 12, 2019 (2 pages).
Zhang, Y. et al., "Efficient Reprogramming of Naïve-Like Induced Pluripotent Stem Cells from Porcine Adipose-Derived Stem Cells with a Feeder-Independent and Serum-Free System," PLOS One, vol. 9 (2014), 13 pages.
Kida, YS et al., "ERRs Mediate a Metabolic Switch Required for somatic Cell Reprogramming to Pluripotency," Cell Stem Cell, May 7, 2015, vol. 16, pp. 1-17.
Kawaguchi, T. et al., "Generaltion of Naïve Bovine Induced Pluripotent Stem Cells Using PiggyBac Transposition of Doxycylcine-Inducible Transcription Factors," PLOS ONE, Aug. 19, 2015, vol. 10, pp. 1-18.
Examination Report, dated May 6, 2020, issued in corresponding Australian Patent Application No. 2018271254 (4 pages).
Examination Report, dated Apr. 29, 2020, issued in corresponding European Patent Application No. 16756502.7 (4 pages).
Office Action, dated Jun. 1, 2020, issued in corresponding Japanese Patent Application No. 2019040124 (3 pages).
English translation of the Office Action issued in corresponding Japanese Patent Application No. 2019040124, dated Jun. 1, 2020 (4 pages).
Zhang, Y. et al., "Efficient Reprogramming of Naïve-Like Induced Pluripotent Stem Cells from Porcine Adipose-Derived Stem Cells with a Feeder-Independent and Serum-Free System," PLOS One, vol. 9 (2014).
Kida, YS et al., "ERRs Mediate a Metabolic Switch Required for Somatic Cell Reprogramming to Pluripotency," Cell Stem Cell, May 7, 2015, vol. 16, pp. 1-9.
Kawaguchi, T. et al., "Generation of Naïve Bovine Induced Pluripotent Stem Cells Using PiggyBac Transposition of Doxycylcine-Inducible Transcription Factors," PLOS One, Aug. 19, 2015, vol. 10.
Huang, P-I et al., "Enhanced Differentiation of Three-Gene-Reprogrammed Induced Pluripotent Stem Cells into Adipocytes via Adenoviral-Mediated PGC-1alpha Overexpression," Int. J. Mol. Sci., (2011), vol. 12, pp. 7554-7568.
International Search Report and Written Opinion for corresponding PCT/US2016/019911, dated Jun. 21, 2016 (16 pages).

* cited by examiner

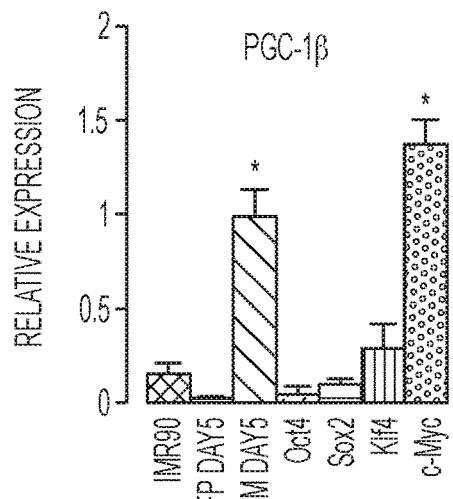
FIG. 1M
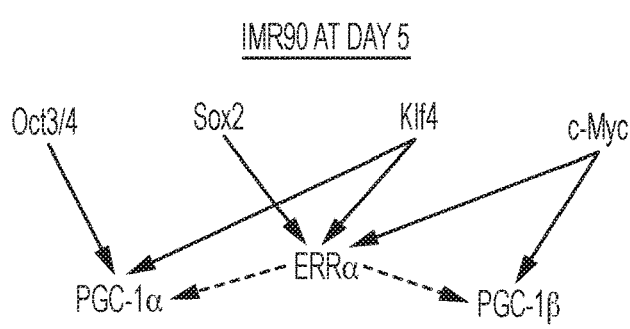
FIG. 1N
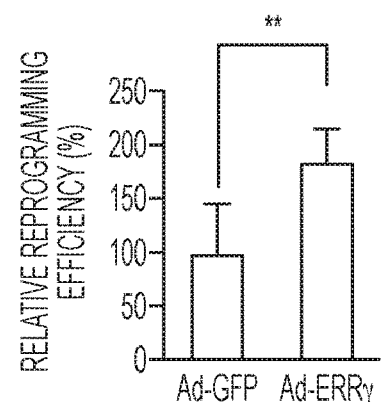
FIG. 1O
| HUMAN ERRa ENHANCER | GFP | T2A | LUCIFERASE | EF1a | Neo$^r$ |
FIG. 1P
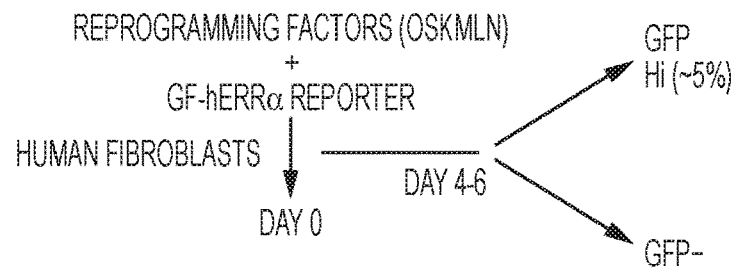
FIG. 1Q

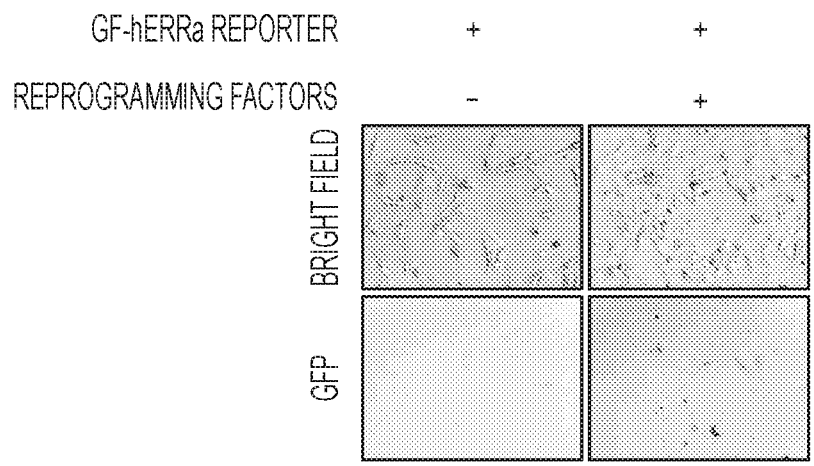
FIG. 1R
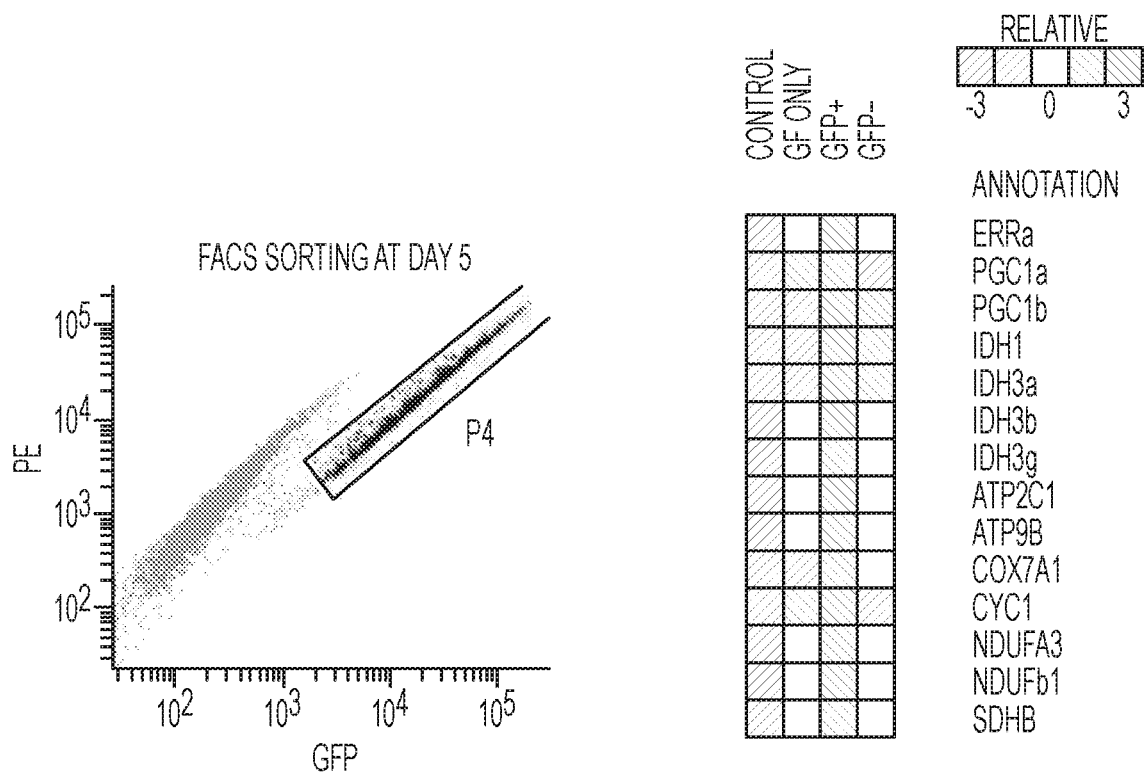
FIG. 1S
FIG. 1T

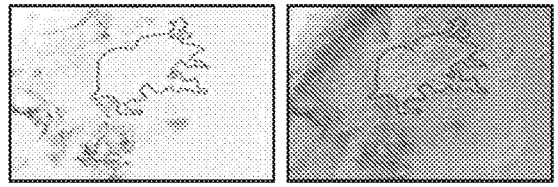
FIG. 5A
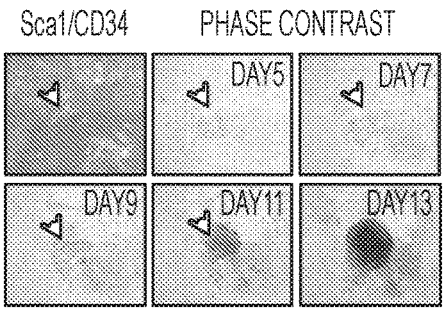
FIG. 5B
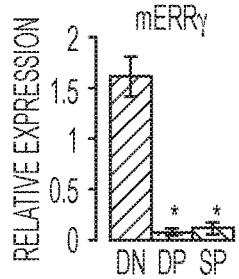
FIG. 5C
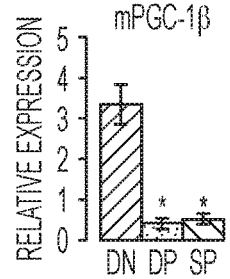
FIG. 5D
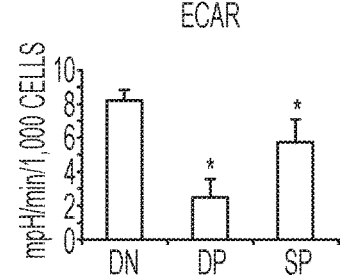
FIG. 5E
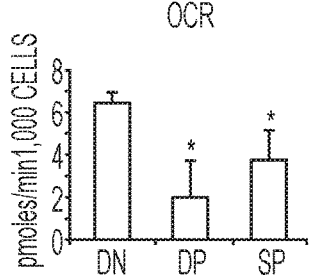
FIG. 5F
| MEF WITH OSKM | DOUBLE NEGATIVE (DN; Sca1⁻/CD34⁻) | DOUBLE POSITIVE (DP; Sca1⁺/CD34⁺) | SINGLE POSITIVE (SP; Sca1⁺/CD34⁻) | TOTAL |
|---|---|---|---|---|
| % CELL POPULATION AT DAY 5 | 5% | 35% | 60% | 100% |
| iPS COLONY NUMBER (RATIO=FRACTION/TOTAL) | 177.6 (63.6 ± 13.6%) | 20.9* (11.4 ± 8.0%) *p<0.05 vs DN (n=7) | 50.3** (25.1 ± 10.5%) **p<0.01 vs DN (n=7) | 248.7 (100%) |
| iPSC EFFICIENCY (FOLD=DN/DP) | 35.5% (~50 FOLD) | 0.60% | 0.84% | 2.49% |
FIG. 5G

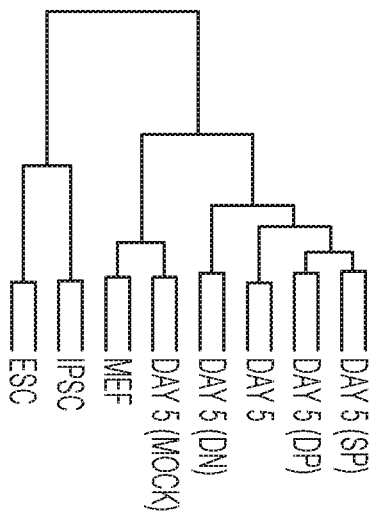
FIG. 7A
FIG. 7B
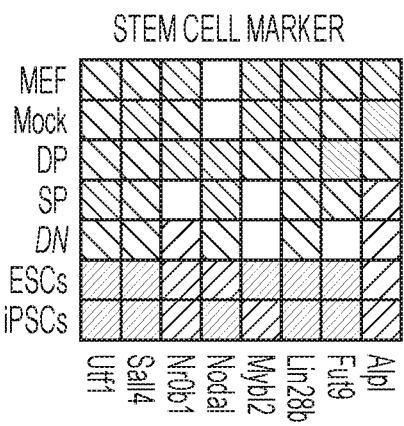
FIG. 7C
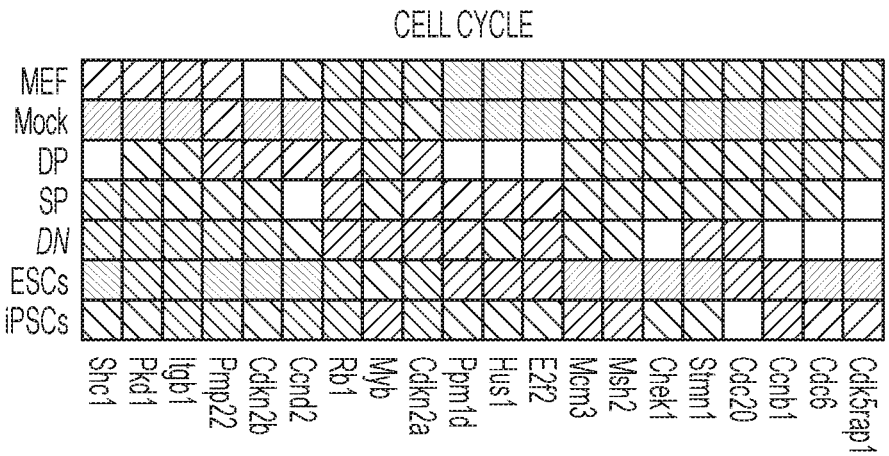
FIG. 7D

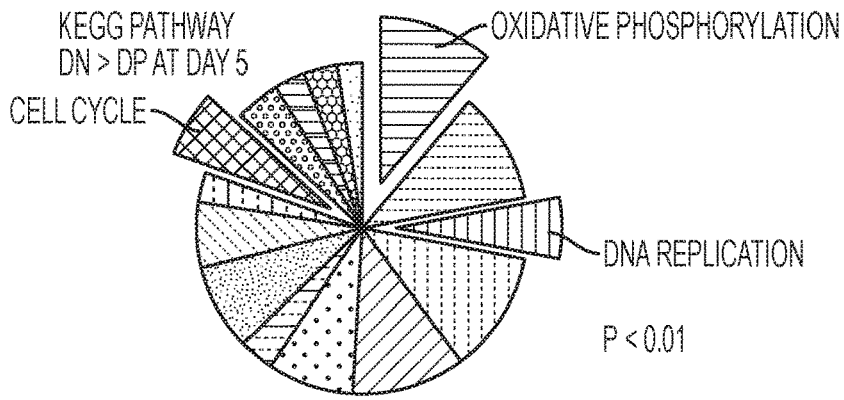
FIG. 8A
| GO TERM | p VALUE |
|---|---|
| mmu00190: OXIDATIVE PHOSPHORYLATION | 1.70E-09 |
| mmu00230: PURINE METABOLISM | 1.75E-04 |
| mmu00240: PYRIMIDINE METABOLISM | 1.81E-04 |
| mmu00670: ONE CARBON POOL BY FOLATE | 7.12E-04 |
| mmu04110: CELL CYCLE | 1.17E-03 |
| mmu00260: GLYCINE, SERINE AND THREONINE METABOLISM | 3.75E-03 |
| mmu00290: VALINE, LEUCINE AND ISOLEUCINE BIOSYNTHESIS | 1.37E-03 |
| mmu04115: p53 SIGNALING PATHWAY | 4.75E-03 |
| mmu00270: CYSTEINE AND METHIONINE METABOLISM | 7.25E-03 |
FIG. 8B
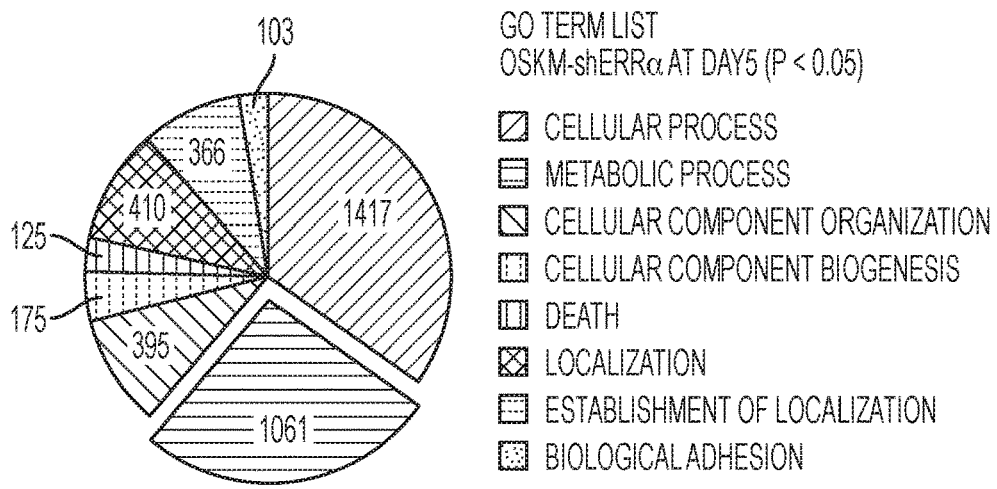
FIG. 8C

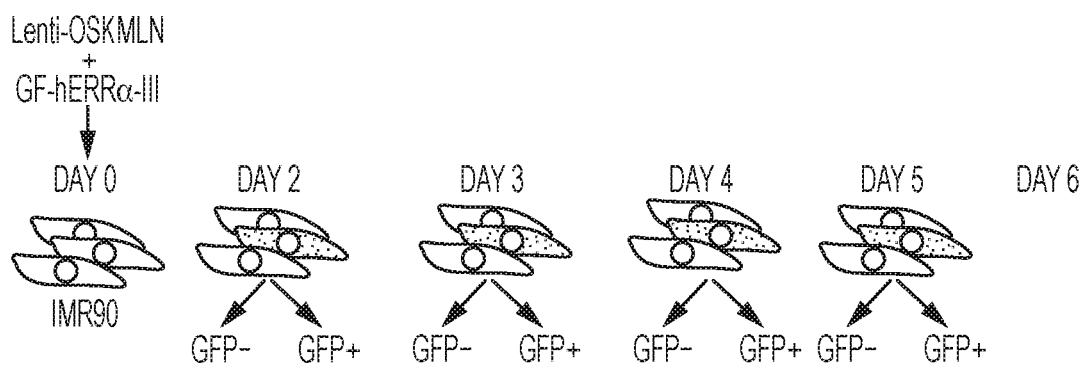

FIG. 10A

| NAME | NO. OF GENES | p-val |
|---|---|---|
| OXIDATIVE PHOSPHORYLATION | 116 | 0.00 |
| AMINOACYL TRNA BIOSYNTHESIS | 41 | 0.00 |
| PROTEASOME | 44 | 0.00 |
| NITROGEN METABOLISM | 23 | 0.00 |
| CITRATE CYCLE TCA CYCLE | 30 | 0.01 |
| PARKINSONS DISEASE | 112 | 0.00 |
| ALANINE ASPARTATE AND GLUTAMATE METABOLISM | 32 | 0.04 |
| NON HOMOLOGOUS END JOINING | 13 | 0.04 |
| GLYOXYLATE AND DICARBOXYLATE METABOLISM | 16 | 0.07 |
| CYSTEINE AND METHIONINE METABOLISM | 34 | 0.04 |
| VALINE LEUCINE AND ISOLEUCINE BIOSYNTHESIS | 11 | 0.09 |
| SYSTEMIC LUPUS ERYTHEMATOSUS | 132 | 0.02 |

FIG. 10B

REPROGRAMMING PROGENITOR COMPOSITIONS AND METHODS OF USE THEREFORE

CROSS REFERENCE TO RELATED APPLICATIONS

This application is the U.S. national phase application, pursuant to 35 U.S.C. § 371, of PCT international application Ser. No.: PCT/US2016/019911, filed Feb. 26, 2016, designating the United States and published in English, which claims the benefit of and priority to U.S. Provisional Application Ser. No. 62/126,417, filed Feb. 27, 2015, the contents of which are incorporated herein by reference.

SEQUENCE LISTING

The instant application contains a Sequence Listing which has been submitted electronically in ASCII format and is hereby incorporated by reference in its entirety. The ASCII copy, created on Nov. 3, 2020, is named 167776_010407US_SL.txt and is 210,140 bytes in size.

STATEMENT OF RIGHTS TO INVENTIONS MADE UNDER FEDERALLY SPONSORED RESEARCH

This invention was made with US government support under HD105278, DK057978, DK062434, and DK063491 awarded by the National Institutes of Health. The US government has certain rights in the invention.

BACKGROUND OF THE INVENTION

A need exists for cell-based compositions to repair or replace damaged or diseased tissues or organs. In the United States alone, thousands of patients die every year waiting for donor organs to become available because the need for transplantable organs far exceeds the supply. In addition, many serious medical conditions, such as neurodegenerative disorders, heart disease, and diabetes, could be helped by cell-based therapies. One limitation to the development of cell-based therapies is the lack of a reliable source of pluripotent stem cells.

SUMMARY OF THE INVENTION

As described below, the invention generally features compositions comprising induced pluripotent stem cell progenitors (also termed reprogramming progenitor cells) and methods of isolating such cells. The invention also provides compositions comprising induced pluripotent stem cells (iPSCs) derived from such progenitor cells. Induced pluripotent stem cell progenitors generate iPSCs at high efficiency.

In one aspect, the invention provides a method for selecting a mammalian induced pluripotent stem cell progenitor, the method involving isolating an induced pluripotent stem cell progenitor expressing one or more of Oct4, Sox2, Klf4 and cMyc, and having increased expression of an estrogen related receptor relative to a reference cell, thereby selecting an induced pluripotent stem cell progenitor.

In another aspect, the invention provides a method for selecting a mammalian induced pluripotent stem cell progenitor, the method involving isolating an induced pluripotent stem cell progenitor expressing one or more of Oct4, Sox2, Klf4 and cMyc, having reduced expression of Sca1 and CD34, and having increased expression of an estrogen related receptor relative to a reference cell, thereby selecting an induced pluripotent stem cell progenitor.

In yet another aspect, the invention provides a method of isolating a cell population enriched for induced pluripotent stem cell progenitors, the method involving isolating one or more induced pluripotent stem cell progenitors expressing Oct4, Sox2, Klf4 and cMyc, and having increased expression of an estrogen related receptor relative to a reference cell, and culturing the one or more mammalian induced pluripotent stem cell progenitors to obtain a cell population enriched for induced pluripotent stem cell progenitors.

In still another aspect, the invention provides a method of obtaining a murine induced pluripotent stem cell progenitor, the method involving expressing Oct4, Sox2, Klf4 and cMyc in a murine cell in culture, isolating from the culture a cell having reduced expression of Sca1 and CD34 and having increased expression of ERRγ relative to a reference cell, and culturing the cell to obtain an induced pluripotent stem cell progenitor. In one embodiment, the murine cell is a mouse embryonic fibroblast. In another embodiment, the cell further expresses an increased level of PGC-1β and/or IDH3 relative to a reference cell.

In another aspect, the invention provides a method of obtaining a human induced pluripotent stem cell progenitor, the method involving expressing Oct4, Sox2, Klf4 and cMyc in a human cell in culture, isolating from the culture a cell having increased expression of ERRα and/or PGC-1α and/or PGC-1β and/or IDH3 relative to a reference cell, thereby obtaining a human induced pluripotent stem cell progenitor.

In yet another aspect, the invention provides an induced pluripotent stem cell progenitor obtained according to the above aspects or any other aspect of the invention delineated herein or various embodiments of the above aspects or any other aspect of the invention delineated herein.

In still another aspect, the invention provides a method for generating a induced pluripotent stem cell progenitor or induced pluripotent stem cell, the method involving expressing recombinant estrogen related receptor (ERR) alpha or gamma in a cell expressing Oct4, Sox2, Klf4 and cMyc and culturing the cell, thereby generating a induced pluripotent stem cell progenitor or induced pluripotent stem cell. In one embodiment, the cell also expresses PGC-1α, PGC-1β, and/or IDH3. In another embodiment, the cell is Sca1⁻ CD34⁻. In yet another embodiment, the cell or cells include retroviral vectors encoding Oct4, Sox2, Klf4 and cMyc.

In another aspect, the invention provides a cellular composition containing an effective amount of an induced pluripotent stem cell or cellular descendant thereof in a pharmaceutically acceptable excipient. In one embodiment, the induced pluripotent stem cell is capable of giving rise to a pancreatic cell, neuronal cell, or cardiac cell.

In yet another aspect, the invention provides a kit containing an induced pluripotent stem cell or progenitor thereof obtained according to the above aspects or any other aspect of the invention delineated herein or various embodiments of the above aspects or any other aspect of the invention delineated herein.

In still another aspect, the invention provides an expression vector containing a promoter sequence of an oxidative or glycolytic pathway gene operably linked to a polynucleotide encoding a detectable polypeptide. In one embodiment, the promoter is sufficient to direct or enhance transcription of an ERR polynucleotide. In another embodiment, the vector is a lentiviral vector. In yet another embodiment, the promoter comprises an ERR alpha enhancer sequence. In still another embodiment, the promoter comprises at least about nucleotide positions 64072402-64073375 of chromosome 11.

In another aspect, the invention provides a mammalian cell containing the expression vector containing a promoter sequence of an oxidative or glycolytic pathway gene operably linked to a polynucleotide encoding a detectable polypeptide. In one embodiment, the cell further contains a polynucleotide sequence encoding one or more of Oct4, Sox2, Klf4 and cMyc.

In yet another aspect, the invention provides a method of selecting a cell having increased oxidative and/or glycolytic pathway activity, the method involving detecting an increase in the level or activity of a protein or polynucleotide listed in FIG. 7. In one embodiment, the cell contains an expression vector containing a polynucleotide sequence that is 5' of the open reading frame encoding said protein and that directs expression of said open reading frame. In another embodiment, the cell contains an expression vector containing a polynucleotide encoding a protein listed in FIG. 7 fused to a detectable polypeptide. In yet another embodiment, the detectable polypeptide is selected from the group consisting of GFP, RFP, YFP, and luciferase.

In still another aspect, the invention provides a method of selecting a cell having increased oxidative and/or glycolytic pathway activity, the method involving detecting an increase in levels of a reactive oxygen species.

In various embodiments of the above aspects or any other aspect of the invention delineated herein, the estrogen related receptor is ERRα, ERRβ or ERRγ. In various embodiments of the above aspects or any other aspect of the invention delineated herein, the cell further expresses an increased level of PGC-1α, PGC-1β, and/or IDH3 relative to a reference cell. In various embodiments of the above aspects or any other aspect of the invention delineated herein, the induced pluripotent stems cell progenitor is a human or murine cell. In various embodiments of the above aspects or any other aspect of the invention delineated herein, the induced pluripotent stem cell progenitor is obtained by expressing Oct4, Sox2, Klf4 and/or cMyc in a cell that is a fibroblast, embryonic fibroblast, human lung fibroblast, adipose stem cell, or IMR90 cell.

In various embodiments of the above aspects or any other aspect of the invention delineated herein, the induced pluripotent stem cell progenitor expresses Oct4, Sox2, Klf4 and cMyc. In various embodiments of the above aspects or any other aspect of the invention delineated herein, the reference cell expresses Sca1 and/or CD34 or a human ortholog or functional equivalent thereof. In various embodiments of the above aspects or any other aspect or the invention delineated herein, the reference cell fails to express detectable levels of one or more of Oct4, Sox2, Klf4 and cMyc. In various embodiments of the above aspects or any other aspect of the invention delineated herein, the cell or cells express undetectable levels of Sca1 and CD34 proteins or human orthologs thereof, or polynucleotides encoding said proteins. In various embodiments of the above aspects or any other aspect of the invention delineated herein, the cell or cells display an increased metabolic rate defined by increased extracellular acidification rate and/or oxygen consumption rate relative to a reference cell. In various embodiments of the above aspects or any other aspect of the invention delineated herein, ERRγ and/or PGC-1β expression is at least about 2, 5 or 10 fold higher than the level in a reference cell. In various embodiments of the above aspects or any other aspect of the invention delineated herein, polynucleotide expression level is determined by qPCR analysis. In various embodiments of the above aspects or any other aspect of the invention delineated herein, the cell or cells contains one or more retroviral vectors encoding Oct4, Sox2, Klf4 and cMyc. In various embodiments of the above aspects or any other aspect of the invention delineated herein, the induced pluripotent stem cells are hyper-energetic cells.

In various embodiments of the above aspects or any other aspect of the invention delineated herein, the cell or cells has increased in one or more of nicotinamide adenine dinucleotide (NADH), α-ketoglutarate, cellular ATP, NADH/NAD+ ratio, ATP synthase in mitochondria (ATP5G1), succinate dehydrogenase (SDHB), isocitrate dehydrogenase (IDH3) and NADH dehydrogenase (NDUFA2), superoxide dismutase 2 (SOD2), NADPH oxidase 4 (NOX4) and catalase (CAT) were increased about five days following expression of Oct4, Sox2, Klf4 and cMyc. In various embodiments of the above aspects or any other aspect of the invention delineated herein, the cell or cells has increased gene expression profile or activity in one or more pathways listed in FIG. 10B. In various embodiments of the above aspects or any other aspect of the invention delineated herein, the cell or cells has a decreased methylation level of an amino acid of a histone in a promoter or an enhancer region associated with genes that function in fibroblast identity relative to a reference cell. In various embodiments of the above aspects or any other aspect of the invention delineated herein, the cell or cells has an increased methylation level of an amino acid of a histone in a promoter or an enhancer region associated with genes that function in reprogramming relative to a reference cell. In various embodiments of the above aspects or any other aspect of the invention delineated herein, the reference cell does not express detectable ERRα. In various embodiments of the above aspects or any other aspect of the invention delineated herein, the histone is H3 histone, and the amino acid is a lysine located at fourth (4th) amino acid position from a N-terminal of the histone.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "induced pluripotent stem cell progenitor" also termed a "reprogramming progenitor" is meant a cell that gives rise to an induced pluripotent stem cell.

By "Sca1 polypeptide" is meant a protein or fragment thereof having at least 85% amino acid sequence identity to the sequence provided at NCBI Ref: NP_001258375.1 and having SCA1 antigenicity. An exemplary murine amino acid sequence is provided below:

MDTSHTTKSCLLILLVALLCAERAQGLECYQCYGVPFETSCPSITCPYPD
GVCVTQEAAVIVDSQTRKVKNNLCLPICPPNIESMEILGTKVNVKTSCCQ
EDLCNVAVPNGGSTWTMAGVLLFSLSSVLLQTLL

By "Sca1 polynucleotide" is meant any nucleic acid molecule encoding a Sca1 polypeptide or fragment thereof. An exemplary murine Sca1 nucleic acid sequence is provided at NCBI Ref NM_001271446.1, and reproduced below:

```
  1 cttaaccaat aaacatgatg gcctggaaaa ggttaagtac tgaaacccct ccctcttcag
 61 gatgccagct gggaggagct gaaggaaatt aaagtacttc agtccacatc tgacagaact
121 tgccactgtg cctgcaacct tgtctgagag gaagtaagga ctggtgtgag gagggagctc
181 ccttctctga ggatggacac ttctcacact acaaagtcct gtttgctgat tcttcttgtg
241 gccctactgt gtgcagaaag agctcaggga ctggagtgtt accagtgcta tggagtccca
301 tttgagactt cttgcccatc aattacctgc ccctaccctg atggagtctg tgttactcag
361 gaggcagcag ttattgtgga ttctcaaaca aggaaagtaa agaacaatct ttgcttaccc
421 atctgccctc ctaatattga agtatggag atcctgggta ctaaggtcaa cgtgaagact
481 tcctgttgcc aggaagacct ctgcaatgta gcagttccca atggaggcag cacctggacc
541 atggcagggg tgcttctgtt cagcctgagc tcagtcctcc tgcagacctt gctctgatgg
601 tcctcccaat gacctccacc cttgtccttt tatcctcatg tgcaacaatt cttcctggag
661 ccctctagtg atgaattatg agttataaga gctccaaggt gggagtagtg tgtgaaatac
721 catgttttgc ctttatagcc cctgctgggt aggtaggtgc tctaatcctc tctagggctt
781 tcaagtctgt acttcctaga atgtcatttt gttgtggatt gctgctcatg accctggagg
841 cacacagcca gcacagtgaa gaggcagaat tccaaggtat tatgctatca ccatccacac
901 ataagtatct gggtcctgc aatgttccca catgtatcct gaatgtcccc ctgttgagtc
961 caataaaccc tttgttctcc ca
```

By "CD34 polypeptide" is meant a protein or fragment thereof having at least 85% homology to the sequence provided at NCBI Ref: NP_001020280.1 (human) or NCBI Ref: NP_001104529.1 (murine).

An exemplary human amino acid sequence is provided below:

```
  1 mlvrrgarag prmprgwtal cllsllpsgf msldnngtat pelptqgtfs nvstnvsyqe
 61 tttpstlgst slhpvsqhgn eattnitett vkftstsvit svygntnssv qsqtsvistv
121 fttpanvstp ettlkpslsp gnvsdlstts tslatsptkp ytssspilsd ikaeikcsgi
181 revkltqgic leqnktssca efkkdrgegl arvlcgeeqa dadagaqvcs lllaqsevrp
241 qclllvlanr teissklqlm kkhqsdlkkl gildfteqdv ashqsysqkt lialvtsgal
301 lavlgitgyf lmnrrswspt gerlgedpyy tengggqgys sgpgtspeaq gkasvnrgaq
361 engtgqatsr nghsarqhvv adtel
```

An exemplary murine amino acid sequence is provided below:

MQVHRDTRAGLLLPWRWVALCLMSLLHLNNLTSATTETSTQGISPSVPTN
ESVEENITSSIPGSTSHYLIYQDSSKTTPAISETMVNFTVTSGIPSGSGT
PHTFSQPQTSPTGILPTTSDSISTSEMTWKSSLPSINVSDYSPNNSSFEM
TSPTEPYAYTSSSAPSAIKGEIKCSGIREVRLAQGICLELSEASSCEEFK

-continued
KEKGEDLIQILCEKEEAEADAGASVCSLLLAQSEVRPECLLMVLANSTEL
PSKLQLMEKHQSDLRKLGIQSFNKQDIGSHQSYSRKTLIALVTSGVLLAI
LGTTGYFLMNRRSWSPTGERLELEP By "CD34 polynucleotide" is meant any nucleic acid sequence encoding an CD34 polypeptide or fragment thereof.

An exemplary human CD34 nucleic acid sequence is provided at NCBI Ref NM_001025109.1:

```
   1 ccttttttgg cctcgacggc ggcaacccag cctccctcct aacgccctcc gcctttggga
  61 ccaaccaggg gagctcaagt tagtagcagc caaggagagg cgctgccttg ccaagactaa
 121 aaagggaggg gagaagagag gaaaaaagca agaatccccc accctctcc cgggcggagg
 181 gggcgggaag agcgcgtcct ggccaagccg agtagtgtct tccactcggt gcgtctctct
 241 aggagccgcg cgggaaggat gctggtccgc aggggcgcgc gcgcagggcc caggatgccg
 301 cggggctgga ccgcgctttg cttgctgagt ttgctgcctt ctgggttcat gagtcttgac
 361 aacaacggta ctgctacccc agagttacct acccagggaa cattttcaaa tgtttctaca
 421 aatgtatcct accaagaaac tacaacacct agtaccttg gaagtaccag cctgcaccct
 481 gtgtctcaac atggcaatga ggccacaaca acatcacag aaacgacagt caaattcaca
 541 tctacctctg tgataacctc agtttatgga aacacaaact cttctgtcca gtcacagacc
 601 tctgtaatca gcacagtgtt caccacccca gccaacgttt caactccaga gacaaccttg
 661 aagcctagcc tgtcacctgg aaatgtttca gacctttcaa ccactagcac tagccttgca
 721 acatctccca ctaaacccta tacatcatct tctcctatcc taagtgacat caaggcagaa
 781 atcaaatgtt caggcatcag agaagtgaaa ttgactcagg gcatctgcct ggagcaaaat
 841 aagacctcca gctgtgcgga gtttaagaag gacaggggga agggcctggc ccgagtgctg
 901 tgtgggagg agcaggctga tgctgatgct ggggcccagg tatgctccct gctccttgcc
 961 cagtctgagg tgaggcctca gtgtctactg ctggtcttgg ccaacagaac agaaatttcc
1021 agcaaactcc aacttatgaa aaagcaccaa tctgacctga aaaagctggg gatcctagat
1081 ttcactgagc aagatgttgc aagccaccag agctattccc aaaagaccct gattgcactg
1141 gtcacctcgg gagccctgct ggctgtcttg ggcatcactg gctatttcct gatgaatcgc
1201 cgcagctgga gcccccacagg agaaaggctg gcgaagacc ttattacac ggaaaacggt
1261 ggaggccagg gctatagctc aggacctggg acctcccctg aggctcaggg aaaggccagt
1321 gtgaaccgag gggctcagga aaacgggacc ggccaggcca cctccagaaa cggccattca
1381 gcaagacaac acgtggtggc tgataccgaa ttgtgactcg gctaggtggg gcaaggctgg
1441 gcagtgtccg agagagcacc cctctctgca tctgaccacg tgctaccccc atgctggagg
1501 tgacatctct tacgcccaac ccttccccac tgcacacacc tcagaggctg ttcttgggc
1561 cctacacctt gaggaggggc aggtaaactc ctgtcccttta cattcggc tccctggagc
1621 cagactctgg tcttctttgg gtaaacgtgt gacggggaa agccaaggtc tggagaagct
1681 cccaggaaca atcgatggcc ttgcagcact cacacaggac cccccttcccc tacccctcc
1741 tctctgccgc aatacaggaa ccccagggg aaagatgagc ttttctaggc tacaattttc
1801 tcccaggaag ctttgatttt taccgtttct tccctgtatt ttctttctct actttgagga
1861 aaccaaagta accttttgca cctgctctct tgtaatgata tagccagaaa aacgtgttgc
1921 cttgaaccac ttccctcatc tctcctccaa gacactgtgg acttggtcac cagctcctcc
1981 cttgttctct aagttccact gagctccatg tgccccctct accatttgca gagtcctgca
2041 cagttttctg gctggagcct agaacaggcc tcccaagttt taggacaaac agctcagttc
2101 tagtctctct ggggccacac agaaactctt tttgggctcc ttttctccc tctggatcaa
2161 agtaggcagg accatgggac caggtcttgg agctgagcct ctcacctgta ctcttccgaa
```

-continued

```
2221 aaatcctctt cctctgaggc tggatcctag cctatcctc tgatctccat ggcttcctcc 2281 tccctcctgc cgactcctgg gttgagctgt tgcctcagtc ccccaacaga tgcttttctg 2341 tctctgcctc cctcaccctg agccccttcc ttgctctgca cccccatatg gtcatagccc 2401 agatcagctc ctaacccctta tcaccagctg cctcttctgt gggtgaccca ggtccttgtt 2461 tgctgttgat ttctttccag aggggttgag cagggatcct ggtttcaatg acggttggaa 2521 atagaaattt ccagagaaga gagtattggg tagatatttt ttctgaatac aaagtgatgt 2581 gtttaaatac tgcaattaaa gtgatactga aacacaaaaa a
```

An exemplary murine CD34 nucleic acid sequence is provided at NCBI Ref: NM_001111059.1:

```
   1 ggggataagc cagcatcccc cacccactcc ggacagggag caggggagga gagccaatat 61 cccccacccc tgcgcagggc ggaggagcgc gtcccgcgcc gggccgcctc ctgcaccgag 121 cgcatctccg gagcggtaca ggagaatgca ggtccacagg gacacgcgcg cggggctcct 181 gctgccatgg cgctgggtag ctctctgcct gatgagtctg ctgcatctaa ataacttgac 241 ttctgctacc acggagactt ctacacaagg aatatcccca tcagttccta ccaatgagtc 301 tgttgaggaa aatatcacat ctagcatccc tggaagtacc agccactact tgatctatca 361 ggacagcagt aagaccacac cagccatctc agagactatg gtcaacttta cagttacctc 421 tgggatccct tcaggctctg gaactccaca cacttttttca caaccacaga cttccccaac 481 tggcatactg cctactactt cagacagtat ttccacttca gagatgacct ggaagtccag 541 cctgccatct ataaatgttt ctgattattc gcctaataat agcagctttg agatgacatc 601 acccaccgag ccatatgctt acacatcatc ttctgctccg agtgccatta agggagaaat 661 caaatgctct ggaatccgag aagtgaggtt ggcccagggt atctgcctgg aactaagtga 721 agcatctagt tgtgaggagt ttaagaagga aaagggagaa gatctaattc aaatactgtg 781 tgaaaaggag gaggctgagg ctgatgctgg tgctagtgtc tgctccctgc ttctagccca 841 gtctgaggtt aggcctgagt gtttgctgat ggtcttggcc aatagcacag aacttcccag 901 caaactccag cttatggaaa agcaccaatc tgacttgaga aagctgggga tccaaagctt 961 caataaacaa gatatcggga gccaccagag ctattcccga aagactctta ttgcattggt 1021 cacctctgga gttctgctgg ccatcttggg caccactggt tatttcctga tgaaccgtcg 1081 cagttggagc cctacaggag aaaggctgga gctggaacct tgatggctgt tgggaagaaa 1141 agaggctgca catgtagctg tacctgctct gcccccccc cactcctact tcctttgtgc 1201 tctcctcaca gtacctcaca accctgctta ccagataatg ctactttatt tctatactgt 1261 ccagggtgaa gacccttatt acacggagaa tggtggaggc cagggctata gctcaggacc 1321 tggggcctcc cctgagactc agggaaaggc caatgtgacc cgaggggctc aggagaacgg 1381 gaccggccag gccacttcca gaaacggcca ttcagcaaga caacatgtgg tggctgacac 1441 agaactgtga tttggttggg tggcaactg ggtggtatgc aggaaagtgg catctcttgt 1501 ctctgacttc atgctgcctt cagctcatgt ccggccttct cctattacat acacttctga 1561 aactgttcct gggactcttc accttgggga aggcagataa actgccttct gcacattcaa 1621 cttcctgaat ccaatctctg acctttgggt caagttgtgg tgggaagaag cctaggtcta 1681 gaggagctgc caaaaaagtt ggtggctatg tagcacttgc cctggaccca tttctcctct 1741 ctcgcctctt cacgggaact ctccggaaga ctagcttttc taagctacca cttcttccca 1801 ggaaactttg ctatttttac tgcttcttcc cctactttat ggaaaccaag gtattcactg
```

```
1861 acatgtgctc ccttgcaagg gtacagccag aaaagtgcta ttttaaaata catccttaaa 1921 aaatgcatcc cttataactt caagacactg tggatttagt caccaacttc tatcttgttc 1981 acctgttcct gaatgtctgt ctacagaggc caggacaact ttctgtctgg agtctgctca 2041 atgttttaga gcaacagctc aatctgatcc cttgggccca cacagaaatc tcattggttc 2101 aacctagaca ggacagtgga attagacttt gaactgagcc tctgtttttt gttttatttt 2161 attgctgggg tttgaaccca gagcttcaca cagcttcttt aggcttccaa gtagcttgag 2221 ctaccaggcc cagctgagct aaacctcctg acctgagctc ttcaaaggaa tactcttgct 2281 ctgaggccct tggccttctc taaattacgt gacttccccc ttcctctgac tcctggggga 2341 gctgtggcct cagtcccctg gcagattcct ttcagtctgt gcctttccta gtccaaaccc 2401 cttcactatt ttataaccct ttgtgatcag aggttcagaa tatctacaaa gactataagc 2461 ttcctctcct ggggttaagg ggagaacagg ggtcctgatt ttaatgatgg ctaggaacaa 2521 aactttccag agatgagagg attgggtgta ttctcttctg aataaacgtg atgagtgaaa 2581 atgatgtaat taaattgatg atgaaatatt tgatgtggcc c
```

By "cMyc polypeptide" is meant a protein or fragment thereof having at least 85% homology to the sequence provided at NCBI Ref: NP_002458.2 (human) or NP_001170823.1 (murine).

An exemplary human amino acid sequence is provided below:

MDFFRVVENQQPPATMPLNVSFTNRNYDLDYDSVQPYFYCDEEENFYQQQ
QQSELQPPAPSEDIWKKFELLPTPPLSPSRRSGLCSPSYVAVTPFSLRGD
NDGGGGSFSTADQLEMVTELLGGDMVNQSFICDPDDETFIKNIIIQDCMW
SGFSAAAKLVSEKLASYQAARKDSGSPNPARGHSVCSTSSLYLQDLSAAA
SECIDPSVVFPYPLNDSSSPKSCASQDSSAFSPSSDSLLSSTESSPQGSP
EPLVLHEETPPTTSSDSEEEQEDEEEIDVVSVEKRQAPGKRSESGSPSAG
GHSKPPHSPLVLKRCHVSTHQHNYAAPPSTRKDYPAAKRVKLDSVRVLRQ
ISNNRKCTSPRSSDTEENVKRRTHNVLERQRRNELKRSFFALRDQIPELE
NNEKAPKVVILKKATAYILSVQAEEQKLISEEDLLRKRREQLKHKLEQLR
NSCA

An exemplary murine amino acid sequence is provided below:

MPLNVNFTNRNYDLDYDSVQPYFICDEEENFYHQQQQSELQPPAPSEDIW
KKFELLPTPPLSPSRRSGLCSPSYVAVATSFSPREDDDGGGGNFSTADQL
EMMTELLGGDMVNQSFICDPDDETFIKNIIIQDCMWSGFSAAAKLVSEKL
ASYQAARKDSTSLSPARGHSVCSTSSLYLQDLTAAASECIDPSVVFPYPL
NDSSSPKSCTSSDSTAFSPSSDSLLSSESSPPASPEPLVLHEETPPTTSS
DSEEEQEDEEEIDVVSVEKRQTPAKRSESGSSPSRGHSKPPHSPLVLKRC
HVSTHQHNYAAPPSTRKDYPAAKRAKLDSGRVLKQISNNRKCSSPRSSDT
EENDKRRTHNVLERQRRNELKRSFFALRDQIPELENNEKAPKVVILKKAT
AYILSIQADEHKLTSEKDLLRKRREQLKHKLEQLRNSGA

By "cMyc" is meant a nucleic acid molecule encoding a cMyc polypeptide. An exemplary human cMyc polynucleotide sequence is provided at NM_002467.4, the sequence of which is reproduced below:

```
  1 gaccccgag  ctgtgctgct cgcggccgcc accgccgggc cccggccgtc cctggctccc 61 ctcctgcctc gagaagggca gggcttctca gaggcttggc gggaaaaaga acggagggag 121 ggatcgcgct gagtatataaaa gccggttttc ggggctttat ctaactcgct gtagtaattc 181 cagcgagagg cagaggagc gagcgggcgg ccggctaggg tggaagagcc gggcgagcag 241 agctgcgctg cgggcgtcct gggaagggag atccggagcg aatagggggc ttcgcctctg 301 gcccagccct ccgctgatcc cccagccag cggtccgcaa cccttgccgc atccacgaaa 361 ctttgcccat agcagcgggc gggcactttg cactggaact tacaacaccc gagcaaggac 421 gcgactctcc cgacgcgggg aggctattct gcccatttgg ggacacttcc ccgccgctgc 481 caggacccgc ttctctgaaa ggctctcctt gcagctgctt agacgctgga ttttttcgg 541 gtagtggaaa accagcagcc tcccgcgacg atgcccctca acgttagctt caccaacagg 601 aactatgacc tcgactacga ctcggtgcag ccgtatttct actgcgacga ggaggagaac
```

-continued

```
 661 ttctaccagc agcagcagca gagcgagctg cagcccccgg cgcccagcga ggatatctgg 721 aagaaattcg agctgctgcc cacccogccc ctgtccccta gccgccgctc cgggctctgc 781 tcgccctcct acgttgcggt cacacccttc tccottcggg gagacaacga cggcggtggc 841 gggagcttct ccacggccga ccagctggag atggtgaccg agctgctggg aggagacatg 901 gtgaaccaga gtttcatctg cgacccggac gacgagacct tcatcaaaaa catcatcatc 961 caggactgta tgtggagcgg cttctcggcc gccgccaagc tcgtctcaga gaagctggcc 1021 tcctaccagg ctgcgcgcaa agacagcggc agcccgaacc ccgccgcgg ccacagcgtc 1081 tgctccacct ccagcttgta cctgcaggat ctgagcgccg ccgcctcaga gtgcatcgac 1141 ccctcggtgg tcttccccta ccctctcaac gacagcagct cgcccaagtc ctgcgcctcg 1201 caagactcca gcgccttctc tccgtcctcg gattctctgc tctcctcgac ggagtcctcc 1261 ccgcagggca gcoccgagcc cctggtgctc catgaggaga caccgccac caccagcagc 1321 gactctgagg aggaacaaga agatgaggaa gaaatcgatg ttgtttctgt ggaaaagagg 1381 caggctcctg gcaaaaggtc agagtctgga tcaccttctg ctggaggcca cagcaaacct 1441 cctcacagcc cactggtcct caagaggtgc cacgtctcca cacatcagca caactacgca 1501 gcgcctccct ccactcggaa ggactatcct gctgccaaga gggtcaagtt ggacagtgtc 1561 agagtcctga cacagatcag caacaaccga aaatgcacca gccccaggtc ctcggacacc 1621 gaggagaatg tcaagaggcg aacacacaac gtcttggagc gccagaggag gaacgagcta 1681 aaacggagct ttttgccct gcgtgaccag atcccggagt tggaaaacaa tgaaaaggcc 1741 cccaaggtag ttatccttaa aaaagccaca gcatacatcc tgtccgtcca agcagaggag 1801 caaaagctca tttctgaaga ggacttgttg cggaaacgac gagaacagtt gaaacacaaa 1861 cttgaacagc tacggaactc ttgtgcgtaa ggaaaagtaa ggaaaacgat tccttctaac 1921 agaaatgtcc tgagcaatca cctatgaact tgtttcaaat gcatgatcaa atgcaacctc 1981 acaaccttgg ctgagtcttg agactgaaag atttagccat aatgtaaact gcctcaaatt 2041 ggactttggg cataaaagaa cttttttatg cttaccatct ttttttttc tttaacagat 2101 ttgtatttaa gaattgtttt taaaaaattt taagatttac acaatgtttc tctgtaaata 2161 ttgccattaa atgtaaataa ctttaataaa acgtttatag cagttacaca gaatttcaat 2221 cctagtatat agtacctagt attataggta ctataaaccc taattttttt tatttaagta 2281 cattttgctt tttaaagttg atttttttct attgttttta gaaaaaataa aataactggc 2341 aaatatatca ttgagccaaa tcttaaaaaa aaaaaaaaa
```

An exemplary murine cMyc polynucleotide sequence is provided at NM_001177352.1, the sequence of which is reproduced below:

```
   1 cccgcccacc cgccctttat attccggggg tctgcgcggc cgaggacccc tgggctgcgc 61 tgctctcagc tgccgggtcc gactcgcctc actcagctcc cctcctgcct cctgaagggc 121 agggcttcgc cgacgcttgg cgggaaaaag aagggagggg agggatcctg agtcgcagta 181 taaaagaagc ttttcgggcg ttttttttctg actcgctgta gtaattccag cgagagacag 241 agggagtgag cggacggttg aagagccgt gtgtgcagag ccgcgctccg gggcgaccta 301 agaaggcagc tctggagtga gaggggcttt gcctccgagc ctgccgccca ctctccccaa 361 ccctgcgact gacccaacat cagcggccgc aaccctcgcc gccgctggga aactttgccc 421 attgcagcgg gcagacactt ctcactggaa cttacaatct gcgagccagg acaggactcc
```

-continued

```
 481 ccaggctccg gggagggaat ttttgtctat ttggggacag tgttctctgc ctctgcccgc
 541 gatcagctct cctgaaaaga gctcctcgag ctgtttgaag gctggatttc ctttgggcgt
 601 tggaaacccc gcagacagcc acgacgatgc ccctcaacgt gaacttcacc aacaggaact
 661 atgacctcga ctacgactcc gtacagccct atttcatctg cgacgaggaa gagaatttct
 721 atcaccagca acagcagagc gagctgcagc cgcccgcgcc cagtgaggat atctggaaga
 781 aattcgagct gcttcccacc ccgcccctgt ccccgagccg ccgctccggg ctctgctctc
 841 catcctatgt tgcggtcgct acgtccttct ccccaaggga agacgatgac ggcggcggtg
 901 gcaacttctc caccgccgat cagctggaga tgatgaccga gttacttgga ggagacatgg
 961 tgaaccagag cttcatctgc gatcctgacg acgagacctt catcaagaac atcatcatcc
1021 aggactgtat gtggagcggt ttctcagccg ctgccaagct ggtctcggag aagctggcct
1081 cctaccaggc tgcgcgcaaa gacagcacca gcctgagccc cgcccgcggg cacagcgtct
1141 gctccacctc cagcctgtac ctgcaggacc tcaccgccgc cgcgtccgag tgcattgacc
1201 cctcagtggt cttccctac ccgctcaacg acagcagctc gcccaaatcc tgtacctcgt
1261 ccgattccac ggccttctct ccttcctcgg actcgctgct gtcctccgag tcctccccac
1321 gggccagccc tgagcccta gtgctgcatg aggagacacc gcccaccacc agcagcgact
1381 ctgaagaaga gcaagaagat gaggaagaaa ttgatgtggt gtctgtggag aagaggcaaa
1441 cccctgccaa gaggtcggag tcgggctcat ctccatcccg aggccacagc aaacctccgc
1501 acagcccact ggtcctcaag aggtgccacg tctccactca ccagcacaac tacgccgcac
1561 cccctccac aaggaaggac tatccagctg ccaagagggc caagttggac agtggcaggg
1621 tcctgaagca gatcagcaac aaccgcaagt gctccagccc caggtcctca gacacggagg
1681 aaaacgacaa gaggcggaca cacaacgtct tggaacgtca gaggaggaac gagctgaagc
1741 gcagcttttt tgccctgcgt gaccagatcc ctgaattgga aaacaacgaa aaggccccca
1801 aggtagtgat cctcaaaaaa gccaccgcct acatcctgtc cattcaagca gacgagcaca
1861 agctcacctc tgaaaaggac ttattgagga aacgacgaga acagttgaaa cacaaactcg
1921 aacagcttcg aaactctggt gcataaactg acctaactcg aggaggagct ggaatctctc
1981 gtgagagtaa ggagaacggt tccttctgac agaactgatg cgctggaatt aaaatgcatg
2041 ctcaaagcct aacctcacaa ccttggctgg ggctttggga ctgtaagctt cagccataat
2101 tttaactgcc tcaaacttaa atagtataaa agaactttt tttatgcttc ccatcttttt
2161 tcttttttcct tttaacagat ttgtatttaa ttgttttttt aaaaaaatct taaaatctat
2221 ccaattttcc catgtaaata gggccttgaa atgtaaataa ctttaataaa acgtttataa
2281 cagttacaaa agattttaag acatgtacca taatttttt tatttaaaga cattttcatt
2341 tttaaagttg attttttct attgttttta gaaaaaaata aaataattgg aaaaaatac
```

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include diseases associated with a deficiency in cell number. Such diseases include but are not limited to neurodegenerative disorders, heart disease, and diabetes.

By "effective amount" is meant the amount of a cell of the invention required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "estrogen related receptor (ERR) alpha polypeptide is meant a protein having at least 85% amino acid sequence identity to an estrogen-related receptor alpha sequence provided at NCBI Ref No. NP_001269379 or NP_031979.2, or a fragment thereof having transcriptional regulatory activity.

The sequence of human ERR alpha also termed "ERR1" is provided below:

```
Err1_HUMAN Estrogen-related receptor
alpha OS = Homo sapiens GN
mssqvvgiep lyikaepasp dspkgssete teppvalapg paptrclpgh keeedgegag pgeqgggklv lsslpkrlcl vcgdvasgyh ygvasceack affkrtiqgs ieyscpasne ceitkrrrka cqacrftkcl rvgmlkegvr ldrvrggrqk ykrrpevdpl pfpgpfpagp lavaggprkt aapvnalvsh llvvepekly ampdpagpdg hlpavatlcd lfdreivvti swaksipgfs slslsdqmsv lqsvwmevlv lgvaqrslpl qdelafaedl vldeegaraa glgelgaall qlvrrlqalr lereeyvllk alalansdsv hiedaeaveq lrealheall
``` eyeagragpg ggaerrragr llltlpllrq tagkvlahfy gvklegkvpm hklflemlea mmd

The sequence of a murine ERR alpha (NCBI Ref No. NP_031979.2) polypeptide also termed "ERR1" is provided below:

MSSQVVGIEPLYIKAEPASPDSPKGSSETETEPPVTLASGPAPARCLPG

HKEEEDGEGAGSGEQGSGKLVLSSLPKRLCLVCGDVASGYHYGVASC

EACKAFFKRTIQGSIEYSCPASNECEITKRRRKACQACRFTKCLRVGML

KEGVRLDRVRGGRQKYKRRPEVDPLPFPGPFPAGPLAVAGGPRKTAP

VNALVSHLLVVEPEKLYAMPDPASPDGHLPAVATLCDLFDREIVVTI

SWAKSIPGFSSLSLSDQMSVLQSVWMEVLVLGVAQRSLPLQDELAFA

EDLVLDEEGARAAGLGDLGAALLQLVRRLQALRLEREEYVLLKALALA

NSDSVHIEDAEAVEQLREALHEALLEYEAGRAGPGGGAERR

RAGRLLLTLPLLRQTAGKVLAHFYGVKLEGKVPMHKLFLEMLEAMMD

By "ERR alpha polynucleotide" is meant any nucleic acid sequence encoding an ERR alpha polypeptide or fragment thereof. An exemplary human ERR alpha nucleic acid sequence is provided at NCBI Ref: NM_001282450 and reproduced below:

```
   1 tagaggtctc ccgcgggcgg ggaggggggag gcgtagcaac tttaggcaac ttcccaaagg
  61 tgtgcgcagg ttgggggcgg gacgcggcgc cccgggaggt ggcggcctct gcgacagcgg
 121 gagtataaga gtggacctgc aggctggtcg cgaggaggtg gagcggcgcc cgccgtgtgc
 181 ctgggaccgg catgctgggg caggagggca gccgcgtgtc aggtgaccag cgccatgtcc
 241 agccaggtgg tgggcattga gcctctctac atcaaggcag agccggccag ccctgacagt
 301 ccaaagggtt cctcggagac agagaccgag cctcctgtgg ccctggcccc tggtccagct
 361 cccactcgct gcctcccagg ccacaaggaa gaggaggatg ggaggggggc tgggcctggc
 421 gagcagggcg gtgggaagct ggtgctcagc tccctgccca agcgcctctg cctggtctgt
 481 ggggacgtgg cctccggcta ccactatggt gtggcatcct gtgaggcctg caaagccttc
 541 ttcaagagga ccatccaggg gagcatcgaa tacagctgtc cggcctccaa cgagtgtgag
 601 atcaccaagc ggagacgcaa ggcctgccag gcctgccgct tcaccaagtg cctgcgggtg
 661 ggcatgctca aggagggagt gcgcctggac cgcgtccggg gtgggcggca gaagtacaag
 721 cggcggccgg aggtggaccc actgcccttc ccgggcccct tccctgctgg gcccctggca
 781 gtcgctggag gccccggaa gacagcagcc ccagtgaatg cactggtgtc tcatctgctg
 841 gtggttgagc ctgagaagct ctatgccatg cctgaccccg caggccctga tgggcacctc
 901 ccagccgtgg ctaccctctg tgacctcttt gaccgagaga ttgtggtcac catcagctgg
 961 gccaagagca tcccaggctt ctcatcgctg tcgctgtctg accagatgtc agtactgcag
1021 agcgtgtgga tggaggtgct ggtgctgggt gtggcccagc gctcactgcc actgcaggat
1081 gagctggcct tcgctgagga cttagtcctg gatgaagagg gggcacgggc agctggcctg
1141 ggggaactgg gggctgccct gctgcaacta gtgcggcggc tgcaggccct gcggctggag
1201 cgagaggagt atgttctact aaaggccttg gcccttgcca attcagactc tgtgcacatc
1261 gaagatgccg aggctgtgga gcagctgcga gaagctctgc acgaggccct gctggagtat
```

-continued

```
1321 gaagccggcc gggctggccc cggaggggggt gctgagcggc ggcgggcggg caggctgctg 1381 ctcacgctac cgctcctccg ccagacagcg ggcaaagtgc tggcccattt ctatggggtg 1441 aagctggagg gcaaggtgcc catgcacaag ctgttcttgg agatgctcga ggccatgatg 1501 gactgaggca aggggtggga ctggtggggg ttctggcagg acctgcctag catgggtca 1561 gccccaaggg ctgggcgga gctgggtct gggcagtgcc acagcctgct ggcagggcca 1621 gggcaatgcc atcagcccct gggaacaggc cccacgccct ctcctccccc tcctagggg 1681 tgtcagaagc tgggaacgtg tgtccaggct ctgggcacag tgctgcccct tgcaagccat 1741 aacgtgcccc cagagtgtag ggggccttgc ggaagccata gggggctgca cgggatgcgt 1801 gggaggcaga aacctatctc agggagggaa ggggatggag gccagagtct cccagtgggt 1861 gatgcttttg ctgctgctta atcctacccc ctcttcaaag cagagtggga cttggagagc 1921 aaaggcccat gccccttcg ctcctcctct catcatttgc attgggcatt agtgtcccc 1981 cttgaagcaa taactccaag cagactccag cccctggacc cctggggtgg ccagggcttc 2041 cccatcagct cccaacgagc ctcctcaggg ggtaggagag cactgcctct atgccctgca 2101 gagcaataac actatattta tttttgggtt tggccaggga ggcgcaggga catggggcaa 2161 gccagggccc agagcccttg gctgtacaga gactctattt taatgtatat ttgctgcaaa 2221 gagaaaccgc ttttggtttt aaacctttaa tgagaaaaaa atatataata ccgagctcaa 2281 aaaaaaaaaa aaa
```

An exemplary murine ERR alpha nucleic acid sequence is provided at NCBI Ref No. NM_007953.2:

```
   1 tggaggaagc ggagtaggaa gcagccgcga tgtcctttg tgtcctacaa gcagccagcg 61 gcgccgccga gtgagggggg acgcagccgcg gcgggggcggt gcggccggag gaggcggccc 121 ccgctcaccc cggcgctccg ggccgctcgg cccccatgcc tgcccgccag ccctgccgga 181 gcccaaggtg accagcacca tgtccagcca ggtggtgggc atcgagcctc tctacatcaa 241 ggcagagcca gccagtcctg acagtccaaa gggttcctca gagactgaga ctgaaccccc 301 ggtgaccctg gcctctggtc cagctccagc ccgctgcctt ccagggcaca aggaggagga 361 ggatggggag ggggcagggt ctggtgagca gggcagtggg aagctagtgc tcagctctct 421 acccaaacgc ctctgcctgg tctgtgggga tgtggcctct ggctaccact acggtgtggc 481 atcctgtgag gcctgcaaag ccttcttcaa gaggaccatc caggggagca tcgagtacag 541 ctgtccggcc tccaatgagt gtgagatcac caagcggaga cgcaaggcct gtcaggcctg 601 ccgcttcacc aagtgcctgc gggtgggcat gctcaaggag ggtgtgcgtc tggaccgtgt 661 ccgcggcgga cggcagaagt acaaacggcg gccagaggtg gaccctttgc ctttcccggg 721 ccccttccct gctggacctc tggcagtagc tggaggaccc aggaagacag ccccagtgaa 781 cgctctggtg tcgcatctgc tggtggttga acctgagaag ctgtacgcca tgcctgaccc 841 agcaagcccc gatggcacc tccccgctgt ggccactctc tgtgaccttt ttgatcgaga 901 gatagtggtc accatcagct gggccaagag catcccaggc ttctcctcac tgtcactgtc 961 tgaccagatg tcagtactgc agagtgtgtg gatggaagtg ctggtgctgg gtgtggccca 1021 gcgctcactg ccactgcagg atgagctggc ctttgctgag gacctggtcc tagatgaaga 1081 ggggcacgg gcagctggcc tggggatct ggggcagcc ctgctgcagc tggttcggcg 1141 actgcaagct cttcggctgg agcgggagga gtacgtcctg ctgaaagctc tggcccttgc 1201 caattctgac tctgtgcaca ttgaagatgc tgaggctgtg gagcagctgc gcgaagccct
```

-continued

```
1261 gcatgaggcc ctgctggagt atgaagctgg ccgggctggc cctggagggg gtgctgagcg 1321 gaggcgtgca ggcaggctgc tgcttacgct gccactcctc cgccagacag caggcaaagt 1381 cctggcccat ttctatgggg tgaagctgga gggcaaggtg cccatgcaca agctgttttt 1441 ggaaatgctt gaggccatga tggactgagg caaggggtgg gacagggtgg ggtggctggc 1501 aggatctgcc cagcataggg tgttagcccc aaaggggcaa agctggagtc tgggcagtgc 1561 catagcctgc tggcagggcc agggcaatgc catccgcccc tgggagaagg cttcatgccc 1621 ttccctcccc actttgtgtg tgtggggat tgtcagaagc caggaaagtg aatgcccagg 1681 tgtgggcaca gtgctgcccc ttgcaagcca taacgtgccc cccaagagtg ttgggggcct 1741 cgcggaagcc ataggggggct gcaggggatg tgcaggaggc agacactgat ctcagggagg 1801 gaagggatgg aggccgccgg ctcccactgg gtgatgcttt tgctgctgct taatccgatc 1861 tcctctccgg agcagagggg ggcttggaaa gcaaaggccc cgtcccttcg ctcctctcct 1921 catccgcatt gggcattatt gccccccctt gaagcaataa ctccaagcag gctccagccc 1981 ctggacccca ggggtggcca gggcccccta tcagctccca cctcaagggg tgggggacag 2041 cactgcctct atgccctgca gagcaataac actatattta tttttgggtt tggccaggga 2101 ggcgcagggc catgggcaa gccagggccc agagcccttg gctgtacaga gactctattt 2161 taatgtatat ttgctgcaaa gagaaaccgc ttttggtttt gaacctttaa tgagaaaaaa 2221 aatatactat ggagctcaag taaaaaaaaa aaaaaaaaa aaaa
```

By "estrogen-related receptor (ERR) gamma polypeptide" also termed "ERR3" is meant a protein having at least 85% amino acid sequence identity to an estrogen-related receptor gamma sequence provided at NCBI Ref No. P62508 (human), NP_001230721.1 (murine), or a fragment thereof having transcriptional regulatory activity.

The sequence of human ERR gamma is provided below:
sp|P62508|ERR3_HUMAN Estrogen-related receptor gamma OS=Homo sapiens GN

```
MDSVELCLPE SFSLHYEEEL LCRMSNKDRH IDSSCSSFIK

TEPSSPASLT DSVNHHSPGG SSDASGSYSS TMNGHQNGLD

SPPLYPSAPI LGGSGPVRKL YDDCSSTIVE DPQTKCEYML

NSMPKRLCLV CGDIASGYHY GVASCEACKA FFKRTIQGNI

EYSCPATNEC EITKRRRKSC QACRFMKCLK VGMLKEGVRL

DRVRGGRQKY KRRIDAENSP YLNPQLVQPA KKPYNKIVSH

LLVAEPEKIY AMPDPTVPDS DIKALTTLCD LADRELVVII

GWAKHIPGFS TLSLADQMSL LQSAWMEILI LGVVYRSLSF

EDELVYADDY IMDEDQSKLA GLLDLNNAIL QLVKKYKSMK

LEKEEFVTLK AIALANSDSM HIEDVEAVQK LQDVLHEALQ

DYEAGQHMED PRRAGKMLMT LPLLRQTSTK AVQHFYNIKL

EGKVPMHKLF LEMLEAKV
```

A murine estrogen-related receptor gamma sequence is provided at NCBI Ref No. NP_001230721.1. The sequence of murine ERR gamma is provided below:

```
MSNKDRHIDSSCSSFIKTEPSSPASLTDSVNHHSPGGSSDASGSYSSTM

NGHQNGLDSPPLYPSAPILGGSGPVRKLYDDCSSTIVEDPQTKCEYMLN

SMPKRLCLVCGDIASGYHYGVASCEACKAFFKRTIQGNIEYSCPATNEC

EITKRRRKSCQACRFMKCLKVGMLKEGVRLDRVGGRQKYKRRIDAEN

SPYLNPQLLQSAWMEILILGVVYRSLSFEDELVYADDYIMDEDQSKLAG

LLDLNNAILQLVKKYKSMKLEKEEFVTLKAIALANSDSMHIEDVEAVQK

LQDVLHEALQDYEAGQHMEDPRRAGKMLMTLPLLRQTSTKAVQHFYNI

KLEGKVPMHKLFLEMLEAKV
```

By "ERR gamma polynucleotide" is meant any nucleic acid sequence encoding an ERR gamma polypeptide or fragment thereof. An exemplary human ERR gamma nucleic acid sequence is provided at NCBI Ref: NM_001438.3

```
aagctccaat cggggctttta agtccttgat taggagagtg tgagagcttt ggtcccaact    61
ggctgtgcct ataggcttgt cactaggaga acatttgtgt taattgcact gtgctctgtc   121
aaggaaactt tgatttatag ctggggtgca caaataatgg ttgccggtcg cacatggatt   181
cggtagaact ttgccttcct gaatcttttt ccctgcacta cgaggaagag cttctctgca   241
gaatgtcaaa caaagatcga cacattgatt ccagctgttc gtccttcatc aagacggaac   301
```

-continued

```
cttccagccc agcctccctg acggacagcg tcaaccacca cagccctggt ggctcttcag    361
acgccagtgg gagctacagt tcaaccatga atggccatca gaacggactt gactcgccac    421
ctctctaccc ttctgctcct atcctgggag gtagtgggcc tgtcaggaaa ctgtatgatg    481
actgctccag caccattgtt gaagatcccc agaccaagtg tgaatacatg ctcaactcga    541
tgcccaagag actgtgttta gtgtgtggtg acatcgcttc tgggtaccac tatggggtag    601
catcatgtga agcctgcaag gcattcttca gaggacaat  tcaaggcaat atagaataca    661
gctgccctgc cacgaatgaa tgtgaaatca caaagcgcag acgtaaatcc tgccaggctt    721
gccgcttcat gaagtgttta aaagtgggca tgctgaaaga aggggtgcgt cttgacagag    781
tacgtggagg tcggcagaag tacaagcgca ggatagatgc ggagaacagc ccatacctga    841
accctcagct ggttcagcca gccaaaaagc catataacaa gattgtctca catttgttgg    901
tggctgaacc ggagaagatc tatgccatgc ctgaccctac tgtccccgac agtgacatca    961
aagccctcac tacactgtgt gacttggccg accgagagtt ggtggttatc attggatggg   1021
cgaagcatat tccaggcttc tccacgctgt ccctggcgga ccagatgagc cttctgcaga   1081
gtgcttggat ggaaattttg atccttggtg tcgtataccg gtctctttcg tttgaggatg   1141
aacttgtcta tgcagacgat tatataatgg acgaagacca gtccaaatta gcaggccttc   1201
ttgatctaaa taatgctatc ctgcagctgg taaagaaata caagagcatg aagctggaaa   1261
aagaagaatt tgtcaccctc aaagctatag ctcttgctaa ttcagactcc atgcacatag   1321
aagatgttga agccgttcag aagcttcagg atgtcttaca tgaagcgctg caggattatg   1381
aagctggcca gcacatggaa gaccctcgtc gagctggcaa gatgctgatg acactgccac   1441
tcctgaggca gacctctacc aaggccgtgc agcatttcta caacatcaaa ctagaaggca   1501
aagtcccaat gcacaaactt tttttggaaa tgttggaggc caaggtctga ctaaaagctc   1561
cctgggcctt cccatccttc atgttgaaaa agggaaaata aacccaagag tgatgtcgaa   1621
gaaacttaga gtttagttaa caacatcaaa aatcaacaga ctgcactgat aatttagcag   1681
caagactatg aagcagcttt cagattcctc cataggttcc tgatgagttt ctttctactt   1741
tctccatcat cttctttcct cttcttccc  acatttctct ttctctttat ttttttctcct   1801 tttcttcttt cacctcccct  atttctttgc ttctttcatt cctagttccc attctccttt   1861
attttcttcc cgtctgcctg ccttctttct tttctttacc tactctcatt cctctctttt   1921
ctcatccttc ccctttttc  taaatttgaa atagctttag tttaaaaaaa aatcctccct   1981
tccccctttc ctttccctt  ctttcctttt tccctttcct tttcccttc  ctttcctttc   2041 ctcttgacct tctttccatc tttctttttc ttccttctgc tgctgaactt ttaaaagagg   2101
tctctaactg aagagagatg gaagccagcc ctgccaaagg atggagatcc ataatatgga   2161
tgccagtgaa cttattgtga accatactgt ccccaatgac taaggaatca aagagagaga   2221
accaacgttc ctaaaagtac agtgcaacat atacaaattg actgagtgca gtattagatt   2281
tcatgggagc agcctctaat tagacaactt aagcaacgtt gcatcggctg cttcttatca   2341
ttgcttttcc atctagatca gttacagcca tttgattcct taattgtttt ttcaagtctt   2401
ccaggtattt gttagtttag ctactatgta acttttcag  ggaatagttt aagctttatt   2461
cattcatgca atactaaaga gaaataagaa tactgcaatt ttgtgctggc tttgaacaat   2521
tacgaacaat aatgaaggac aaatgaatcc tgaaggaaga ttttaaaaa  tgttttgttt   2581 cttcttacaa atgagatttt ttttgtacca gctttaccac ttttcagcca tttattaata   2641
tgggaattta acttactcaa gcaatagttg aagggaaggt gcatattatc acggatgcaa   2701
```

-continued

```
tttatgttgt gtgccagtct ggtcccaaac atcaatttct taacatgagc tccagtttac   2761
ctaaatgttc actgacacaa aggatgagat tacacctaca gtgactctga gtagtcacat   2821
atataagcac tgcacatgag atatagatcc gtagaattgt caggagtgca cctctctact   2881
tgggaggtac aattgccata tgatttctag ctgccatggt ggttaggaat gtgatactgc   2941
ctgtttgcaa agtcacagac cttgcctcag aaggagctgt gagccagtat tcatttaaga   3001
ggcaataagg caaatgccag aattaaaaaa aaaatcatc aaagacagaa aatgcctgac    3061
caaattctaa aacctaatcc atataagttt attcatttag gaatgttcgt ttaaattaat    3121
ctgcagtttt taccaagagc taagccaata tatgtgcttt tcaaccagta ttgtcacagc    3181
atgaaagtca agtcaggttc cagactgtta agaggtgtaa tctaatgaag aaatcaatta   3241
gatgccccga aatctacagt cgctgaataa ccaataaaca gtaacctcca tcaaatgcta   3301
taccaatgga ccagtgttag tagctgctcc ctgtattatg tgaacagtct tattctatgt   3361
acacagatgt aattaaaatt gtaatcctaa caaacaaaag aaatgtagtt cagcttttca   3421
atgtttcatg tttgctgtgc ttttctgaat tttatgttgc attcaaagac tgttgtcttg   3481
ttcttgtggt gtttggattc ttgtggtgtg tgcttttaga cacagggtag aattagagac   3541
aatattggat gtacaattcc tcaggagact acagtagtat attctattcc ttaccagtaa   3601
taaggttctt cctaataata attaagagat tgaaactcca acaagtatt cattatgaac     3661 agatacacat caaaatcata ataatatttt caaaacaagg aataatttct ctaatggttt    3721
attatagaat accaatgtat agcttagaaa taaaactttg aatatttcaa gaatatagat    3781
aagtctaatt tttaaatgct gtatatatgg ctttcactca atcatctctc agatgttgtt    3841
attaactcgc tctgtgttgt tgcaaaactt tttggtgcag attcgtttcc aaaactattg    3901
ctactttgtg tgctttaaac aaaataccct tggttgatga acatcaacc cagtgctagg     3961 aatactgtgt atctatcatt agctatatgg gactatattg tagattgtgg tttctcagta    4021
gagaagtgac tgtagtgtga ttctagataa atcatcatta gcaattcatt cagatggtca    4081
ataacttgaa atttatagct gtgataggag ttcagaaatt ggcacatccc tttaaaaata    4141
acaacagaaa atacaactcc tgggaaaaaa ggtgctgatt ctataagatt atttatatat   4201
gtaagtgttt aaaaagatta ttttccagaa agtttgtgca gggtttaagt tgctactatt    4261 caactcacact atatataaat aaaatatata caatatatac attgtttca ctgtatcaca    4321 ttaaagtact tgggcttcag aagtaagagc caaccaactg aaaacctgag atggagatat    4381
gttcaaagaa tgagatacaa ttttttagtt ttcagtttaa gtaactctca gcattacaaa    4441
agagtaagta tctcacaaat aggaaataaa actaaaacgt ggatttaaaa agaactgcac   4501 gggcttagg gtaaatgctc atcttaaacc tcactagagg gaagtcttct caagtttcaa    4561
gcaagaccat ttacttaatg tgaagttttg gaaagttata aaggtgtatg ttttagccat   4621 atgatttaa ttttaatttt gcttctttta ggttcgttct tatttaaagc aatatgattg    4681
tgtgactcct tgtagttaca cttgtgtttc aatcagatca gattgttgta tttattccac    4741 tatttttgcat ttaaatgata acataaaaga tataaaaaat ttaaaactgc tatttttctt   4801
atagaagaga aaatgggtgt tggtgattgt atttttaatta tttaagcgtc tctgtttacc   4861
tgcctaggaa aacattttat ggcagtctta tgtgcaaaga tcgtaaaagg acaaaaaatt    4921
taaactgctt ataataatcc aggagttgca ttatagccag tagtaaaaat aataataata   4981
ataataaaac catgtctata gctgtagatg ggcttcacat ctgtaaagca atcaattgta    5041 tattttgtg atgtgtacca tactgtgtgc tccagcaaat gtccatttgt gtaaatgtat    5101
ttattttata ttgtatatat tgttaaatgc aaaaaggaga tatgattctg taactccaat   5161
```

```
cagttcagat gtgtaactca aattattatg cctttcagga tgatggtaga gcaatattaa   5221 acaagcttcc
```

By "ERR gamma polynucleotide" is meant any nucleic acid sequence encoding an ERR gamma polypeptide or fragment thereof. An exemplary murine ERR gamma nucleic acid sequence is provided at NCBI Ref: NM_001243792.1 and reproduced below:

```
   1 agcccgaacc ccgtgcccga ttcctggtgc ggagtgcgag aggttcccgc ggcgcctggc
  61 ggacagtctc gctggcctcc ggtgacttgt tttgtgttgg ttttcccctc ttgcagccgg
 121 cgaccaagcg gacatcctcg ggaccccca aagccaccca ctcccgagag ctcggagagc
 181 ggctctgcac gagggacctt agctacttgc tggttcatca atgaagcaac ccgaagtgat
 241 gaagatgtaa ggaacgcatc ctacgctagc actgttgcag ttggaaaggc ttctctgcag
 301 aatgtcaaac aaagatcgac acattgattc cagctgttcg tccttcatca agacggaacc
 361 ctccagccca gcctccctga cggacagcgt caaccaccac agccctggtg ggtcttccga
 421 cgccagtggg agttacagtt caaccatgaa tggccatcag aacggactgg actcgccacc
 481 tctctacccc tctgctccga tcctgggagg cagcgggcct gtccggaaac tgtatgatga
 541 ctgctccagc accatcgtag aggatcccca gaccaagtgt gaatatatgc tcaactccat
 601 gcccaagaga ctgtgcttag tgtgtggcga catcgcctct gggtaccact atggggttgc
 661 atcatgtgaa gcctgcaagg cattcttcaa gaggacgatt caaggtaaca tagagtacag
 721 ctgcccagcc acgaatgaat gtgagatcac aaagcgcaga cgcaaatcct gccaggcctg
 781 ccgcttcatg aagtgtctca agtgggcat gctgaaagaa ggggtccgtc ttgacagagt
 841 gcgtggaggt cggcagaagt acaagcgcag aatagatgct gagaacagcc catacctgaa
 901 ccctcagctg gtgcagccag ccaaaaagcc atataacaag attgtctcgc atttgttggt
 961 ggctgaacca gagaagatct atgccatgcc tgaccctact gtccccgaca gtgacatcaa
1021 agccctcacc acactctgtg acttggctga ccgagagttg gtggttatca ttggatgggc
1081 aaaacatatt ccaggcttct ccacactgtc cctggcagac cagatgagcc tcctccagag
1141 tgcatggatg gagattctga tcctcggcgt tgtgtaccga tcgctttcgt ttgaggatga
1201 acttgtctat gcagacgatt ataatggga tgaagaccag tctaaattag caggccttct
1261 tgacctaaat aatgctatcc tgcagctggt gaagaagtac aagagcatga agctagagaa
1321 ggaagaattc gtcaccctca aagcaatagc tcttgctaat tcagattcca tgcatataga
1381 agatgtggaa gctgtgcaga aacttcagga tgtgttacat gaggccctgc aggattacga
1441 ggctggccag cacatggaag accctcgccg tgcaggcaag atgctgatga cgctgccgct
1501 gctgaggcag acctccacca aggcagtcca gcacttctac aacatcaaac tcgaaggcaa
1561 agtgcccatg cacaaacttt ttttggaaat gctggaggcc aaggtctgac taaaagcccc
1621 ccctgggccc tcccatcctg cacgttgaaa agggaagata aacccaagaa tgatgtcgaa
1681 gaatcttaga gttagtgaa caacattaaa aatcaacaga ctgcactgat attttagcag
1741 ccacagtacg atgcagcctg cggattccgc tacatcttcc tgataggttt cctctacttt
1801 atcccacgat cctctggcca catccctgca ttcctccact cttccttgtt ctattattat
1861 gtttggcttc tttcactaat agttcatttt ccctcctccc ctcccttctc ttctccctcc
1921 ctcctctgtc tcccccttcc ttcctttctc ttcctttcca caatcttctc ctcttgcctt
1981 gctctcacct ctcttcgctt tctcacatct cctcccactc tgcgtacata gtcaatacct
```

-continued

```
2041 ctgattgtat ggaacatttc ttttacctct tgcatctctt ctccgtctct tccttcccca
2101 cttttttttg tttgtttgtt tgtttccttt ccttccttct gctgctgaac tcttaatagc
2161 agtctctaac tggagagaga aagagagaga gatggaagcc agccctgcca aaggacagag
2221 atccatacta tggatgccag tgaacttgtc atgaaccatg acatccccag tgagtaagga
2281 atcaaagaga gaaccgtacc taaagtacat tgcaacgcaa acggatcaac ttagtgcagt
2341 attagattct accgggcagc cttcgatcag acaacctaag tggcggcatt ggctgcttct
2401 ccttgctttc tcatctagat cagttacagc catttgattc cttaattctt ttgtcaagtc
2461 ttccaggtgt tggttagttt agctactatg taacttttc agggaatcct ttaagcttta
2521 ttcattcatg caatactaga gaggggtaag gataccgcaa cctcgtgctg gctttgaaca
2581 attgaacact aatgaaggac aaatgaaccc tgaaggaaga tttttaaaaa tgtttcgttt
2641 cttcttacaa atggagattt ttttgtacca gctttaccac ttttcagcca tttattaata
2701 tggggattta acttactcaa gcaatagttg aagggaaggt gcatattacc acggatgcaa
2761 tttatgttgt gtgccagtct ggtcccaaac atcagtttct tacatgagct ccagtttgcc
2821 taaatgttca ctgacaccaa ggattagatg atacctgccg tgacaccgag tggtcccatc
2881 cacgagcact gcacatggga tccctatctg tagaattagc accagtacac ctccctgccg
2941 ggagggacag tcgccatacg gtttctagct gccctcgtgg ttaggaacaa gatgctgcct
3001 gtatacaaac tctgtctcag aaggagctgt gagccaatac catttcagag gcaataaagg
3061 ctaagtgcca gaattcaaac caaccaacca tcaaagacag cagacgcctg accaaattct
3121 aaagtcctga tccataggag tcgattcact taggaatggt tgtttaaatt aacctgcagg
3181 tttgttttgt ttccttgttt gtttttttac caaaagctaa gccaatagat gtgcttttc
3241 aacaagtatg gtcacagcac gaaggtcagt caggtttcag actgtaacca ggtgtaatct
3301 aatgaagaaa tcaaatgtcc cctcccgaaa cctacagtcg ccgaataacc agaaaccagt
3361 aacctccgta gaacgcttta ccaatggacc agtgttagta gctgctctct gtattctgtg
3421 gacagtctta ttctatgtac acagatgtaa ttaaagttgt actcctaaca aacaaaagaa
3481 tagttcagct tcaatgttcc atgtttgctg cgcttttctg aactttatgt tgcattcaga
3541 aactgtcgtc ttgttctcgt ggtgtttgga ttcttgtggt gtgtgctttt agacacaggg
3601 tagaattaga gacagtattg gatgtatact tcctcaggag actacagtag tatattctac
3661 tccttaccag taataactaa gagattgaaa ctccaaaaca gtattcatta cgatcagaca
3721 cacatcaaaa tcataataat atttttcaaaa aagggataat ttctctaatg gtttattata
3781 gaataccaat gtatagctta gacataaaac tttgaatatt caagaatata gataagtcta
3841 attttttaaat gctgtatata aggcttccac ctgatcatct ctcagatgtt gttattaact
3901 cgctctgtgt tgttgcaaac cttttggtg cggacttgct tccaaaacta ttgctacttt
3961 gtgtgcgtta agcaaaatac cttggactga gggtgtctca gccctgtgct aggaatactg
4021 tgtatctatc attagctata tgggaatata tcgtagattg tggttctcag tagagaaagt
4081 gactgtagtg tgactctagg taaatcatca ttagcaattc attcggatgg tcaataactt
4141 gaaattgata gctgtgataa gttttaaaaa attggcaaat ccctgactaa acatcaacag
4201 aaaatacaac tcctgggggg gaaaggtgct catcctgtaa gattctttca tcatgtaagt
4261 gtttgaaaca ttactttgca gaaggtttat gcagggttta agttactacc gctcaataat
4321 gctatatata cacaaatgga atatagacaa tgtatgtacc caccgtttca ctgagtcgca
4381 gagaagaatc tgagcttcag aagccagagc ccacaagtga tcaggtgaga cagaggcaca
```

```
4441 tttaaggaag gaggtacaat gtgtagttct ccgtttaaaa gacttggcct tttaaaacaa 4501 caaatatctc acaactatgg tgaaaacaac aacagcttca agtgtggatc taaaggaaac 4561 gcacaggttt agggtaaata ccatttgtac cttgctcgag caaagtttat tgttttgttt 4621 tttttttgttt tgttttgttt tgttttcaag tttccagcaa gaccgtttag ttaatgccag 4681 ctgtcaggaa gataccaagg tgtatgtttt agccatgcaa tttgcagttt tattttccttt 4741 ttaggtttgt ccttatttaa ggcagtgcga ttgttttggc ttcttgtagt gactctcgtg 4801 ttttaatcaa gccagattgt tgtatttatt ccactatttt gcatttaaat gatgacataa 4861 aagatataaa aaatttaaaa ctgctatttt tcttatagaa gagaaaatgg atgttggtga 4921 ttgtatttta attatttaag catctctgtt tacctgcctg ggacaacatt ttatggcagt 4981 cttatgtgca aagatcgtga atggacaaaa caaaaaatta aactgcttac aatgatccag 5041 gagttgcatt atagccagta gtaaaaataa taatgataat taataataat taataataat 5101 aatgaaacca tgtctatagc tgtaggtggg catcacatct gtaaagcaat caattgtata 5161 tttttgtgat gtgtaccata ctgtgtgctc cagcaaatgt ccatttgtgt aaatgtattt 5221 attttatatt gtatatattg ttaaatgcaa aaaggagcta tgattctgtg actccaatca 5281 gttcagatat gtaactcaaa ttattatgcc tttcaggagg atggtagaac aatattaaac 5341 aagcttccac ttttaaaaaa aaaaaaaaaa aaaa
```

The invention provides for the use of other estrogen-related receptors, such as ERRbeta. The amino acid sequence of *Homo sapiens* estrogen-related receptor beta (ESRRbeta) is provided, for example, at NCBI Accession No. NP_004443, which is reproduced below:

```
  1 mssddrhlgs scgsfiktep sspssgidal shhspsgssd asggfglalg thangldspp 61 mfagaglggt pcrksyedca sgimedsaik ceymlnaipk rlclvcgdia sgyhygvasc 121 eackaffkrt iqgnieyscp atneceitkr rrkscqacrf mkclkvgmlk egvrldrvrg 181 grqkykrrld sesspylslq isppakkplt kivsyllvae pdklyamppp gmpegdikal 241 ttlcdladre lvviigwakh ipgfsslslg dqmsllqsaw meililgivy rslpyddklv 301 yaedyimdee hsrlagllel yrailqlvrr ykklkvekee fvtlkalala nsdsmyiedl 361 eavqklqdll healqdyels qrheepwrtg kllltlpllr qtaakavqhf ysvklqgkvp 421 mhklflemle akvgqeqlrg spkdermssh dgkcpfqsaa ftsrdqsnsp gipnprpssp 481 tplnergrqi spstrtpggq gkhlwltm
```

A polynucleotide sequence encoding an ERRbeta is provided, for example, at NCBI Accession No. NM_004452, which is reproduced below:

```
  1 ccgcagagag gtgtggtcag ggacatttcc cctggccggg agcccatgga gcactgtcct 61 cagagatgcg caggttaggc tcactgtcta ggccaggccc accttagtca ctgtggactg 121 gcaatggaag ctcttcctgg acacacctgc cctagccctc accctggggt ggaagagaaa 181 tgagcttggc ttgcaactca gaccattcca cggaggcatc ctcccttcc tgggctggtg 241 aataaaagtt tcctgaggtc aaggacttcc ttttccctgc caaatggtg tccagaactt 301 tgaggccaga ggtgatccag tgatttggga gctgcaggtc acacaggctg ctcagagggc 361 tgctgaacag gatgtcctcg gacgacaggc acctgggctc cagctgcggc tccttcatca 421 agactgagcc gtccagcccg tcctcgggca tcgatgccct cagccaccac agccccagtg
```

-continued

```
 481 gctcgtccga cgccagcggc ggctttggcc tggccctggg cacccacgcc aacggtctgg
 541 actcgccacc catgtttgca ggcgccgggc tgggaggcac cccatgccgc aagagctacg
 601 aggactgtgc cagcggcatc atggaggact cggccatcaa gtgcgagtac atgctcaacg
 661 ccatccccaa gcgcctgtgc ctcgtgtgcg ggacattgc ctctggctac cactacggcg
 721 tggcctcctg cgaggcttgc aaggccttct tcaagaggac tatccaaggg aacattgagt
 781 acagctgccc ggccaccaac gagtgcgaga tcaccaaacg gaggcgcaag tcctgccagg
 841 cctgccgctt catgaaatgc ctcaaagtgg ggatgctgaa ggaaggtgtg cgccttgatc
 901 gagtgcgtgg aggccgtcag aaatacaagc gacggctgga ctcagagagc agcccatacc
 961 tgagcttaca aatttctcca cctgctaaaa agccattgac caagattgtc tcatacctac
1021 tggtggctga gccggacaag ctctatgcca tgcctccccc tggtatgcct gaggggaca
1081 tcaaggccct gaccactctc tgtgacctgg cagaccgaga gcttgtggtc atcattggct
1141 gggccaagca catcccaggc ttctcaagcc tctccctggg ggaccagatg agcctgctgc
1201 agagtgcctg gatggaaatc ctcatcctgg gcatcgtgta ccgctcgctg ccctatgacg
1261 acaagctggt gtacgctgag gactacatca tggatgagga gcactcccgc ctcgcggggc
1321 tgctggagct ctaccgggcc atcctgcagc tggtacgcag gtacaagaag ctcaaggtgg
1381 agaaggagga gtttgtgacg ctcaaggccc tggccctcgc caactccgat tccatgtaca
1441 tcgaggatct agaggctgtc cagaagctgc aggacctgct gcacgaggca ctgcaggact
1501 acgagctgag ccagcgccat gaggagccct ggaggacggg caagctgctg ctgacactgc
1561 cgctgctgcg gcagacggcc gccaaggccg tgcagcactt ctatagcgtc aaactgcagg
1621 gcaaagtgcc catgcacaaa ctcttcctgg agatgctgga ggccaaggtt ggccaagagc
1681 agcttagagg atctcccaag gatgaaagaa tgtcaagcca tgatggaaaa tgccccttcc
1741 aatcagctgc cttcacaagc agggatcaga gcaactcccc ggggatcccc aatccacgcc
1801 cttctagtcc aacccccctc aatgagagag cacggcagat ctcacccagc actaggacac
1861 caggaggcca gggaaagcat ctctggctca ccatgtaaca tctggcttgg agcaagtggg
1921 tgttctgcac accaggcagc tgcacctcac tggatctagt gttgctgcga gtgacctcac
1981 ttcagagccc ctctagcaga gtggggcgga agtcctgatg gttggtgtcc atgaggtgga
2041 agctgctttt atacttaaaa ctcagatcac aacaggaaat gtgtcagtaa caatggaact
2101 ccatccaatg ggaaagttcc tggtactgaa ggggtccatt ggacactcag aaaagaagtt
2161 caggggccaa cttcttagct ggaatcctgg ccagatgagg accctctccg gggaagggag
2221 aggactgact tagtggaagg tggtgaagtg aggagagttt aggggaacct tcccccagtg
2281 gaacagatct caagtttacc ctaaacctgc catttctgga aaatctgtaa agaggaaaca
2341 gcctgtctca gctgtactct catgatacag gtcatttgaa atgaaccaag aaataaaaca
2401 tgaaaatcca accatggaga aggtggtatg gctgggtttt gtttggtccc cttgtcctta
2461 tacgttctaa agtttccaga ctggctttgt cactttgtga actcgtcatg tgtgaaaacc
2521 aatctttgca tatagggaac ttcctcgggc cacactttaa gaaccaagta agaggctctc
2581 aagactccag cagagtcggg aggccatggc agcgccttag aggagctgga acctgcaccc
2641 acctgtgtcg gtgggggggg cctcctttcc ccatagactc tgccctccct ctgtgcagat
2701 ggaagtggca gggagggtg accagcttgt gacaagaaga ctgaagggtc cagagtccat
2761 gctcacggaa cagcaccaaa gaaaagcact atgtggaaag attgttttat tttctaataa
```

```
-continued
2821 tgataatatg gctggaatgg cttcttaaga tgtatatatt ttttaaaatg gcagttcccc 2881 attgcagcat cacctacttg tatgtctttc tgcctctgta tatgttctcc cagaaacccc 2941 catgtaaatc aaatgcccta ggatgcttcc atcctggtcc catgtatctg gaatctaata 3001 aataaggaaa ggaaaaaaaa aaaaaaaaa
```

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "increases or decreases" is meant a positive or negative alteration. Such alterations are by 5%, 10%, 25%, 50%, 75%, 85%, 90% or even by 100% of a reference value. The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated cell" is meant a cell that is separated from the molecular and/or cellular components that naturally accompany the cell. In particular embodiments, the cell is a Sca1–CD34-cell isolated from a population expressing Sca1 and/or CD34. In other embodiments, the cell is isolated from a population expressing Oct4, Sox2, Klf4 and cMyc.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "Klf4 polypeptide" is meant a protein or fragment thereof having at least 85% homology to the sequence provided at NCBI Ref NP_004226.3 (human) or NP_034767.2 (mouse). An exemplary human Klf4 amino acid sequence is provided below:

MRQPPGESDMAVSDALLPSFSTFASGPAGREKTLRQAGAPNNRWREELS

HMKRLPPVLPGRPYDLAAATVATDLESGGAGAACGGSNLAPLPRRETEE

FNDLLDLDFILSNSLTHPPESVAATVSSSASASSSSSPSSSGPASAPST

CSFTYPIRAGNDPGVAPGGTGGGLLYGRESAPPPTAPFNLADINDVSPS

GGFVAELLRPELDPVYIPPQQPQPPGGGLMGKFVLKASLSAPGSEYGS

PSVISVSKGSPDGSHPVVVAPYNGGPPRTCPKIKQEAVSSCTHLGAGP

PLSNGHRPAAHDFPLGRQLPSRTTPTLGLEEVLSSRDCHPALPLPPGF

HPHPGPNYPSFLPDQMQPQVPPLHYQELMPPGSCMPEEPKPKRGRRSW

PRKRTATHTCDYAGCGKTYTKSSHLKAHLRTHTGEKPYHCDWDGCGWKF

ARSDELTRHYRKHTGHRPFQCQKCDRAFSRSDHLALHMKRHF"

An exemplary Klf4 murine amino acid sequence is provided below:

MRQPPGESDMAVSDALLPSFSTFASGPAGREKTLRPAGAPTNRWREELS

HMKRLPPLPGRPYDLAATVATDLESGGAGAACSSNNPALLARRETEEFN

DLLDLDFILSNSLTHQESVAATVTTSASASSSSSPASSGPASAPSTCSF

SYPIRAGGDPGVAASNTGGGLLYSRESAPPPTAPFNLADINDVSPSGGF

VAELLRPELDPVYIPPQQPQPPGGGLMGKFVLKASLTTPGSEYSSPSVI

SVSKGSPDGSHPVVVAPYSGGPPRMCPKIKQEAVPSCTVSRSLEAHLS

AGPQLSNGHRPNTHDFPLGRQLPTRTTPTLSPEELLNSRDCHPGLPLP

PGFHPHPGPNYPPFLPDQMQSQVPSLHYQELMPPGSCLPEEPKPKRGR

RSWPRKRTATHTCDYAGCGKTYTKSSHLKAHLRTHTGEKPYHCDWDGC

GWKFARSDELTRHYRKHTGHRPFQCQKCDRAFSRSDHLALHMKRHF

By "Klf4" is meant a nucleic acid molecule encoding a Klf4 polypeptide. An exemplary human Klf4 polynucleotide sequence is provided at NM_004235.4 below:

```
   1 agtttcccga ccagagagaa cgaacgtgtc tgcgggcgcg cggggagcag aggcggtggc
  61 gggcggcggc ggcaccggga gccgccgagt gaccctcccc cgcccctctg gcccccacc
 121 ctcccacccg cccgtggccc gcgcccatgg ccgcgcgcgc tccacacaac tcaccggagt
 181 ccgcgccttg cgccgccgac cagttcgcag ctccgcgcca cggcagccag tctcacctgg
 241 cggcaccgcc cgcccaccgc cccggccaca gcccctgcgc ccacgcagc actcgaggcg
 301 accgcgacag tggtggggga cgctgctgag tggaagagag cgcagccgg ccaccggacc
 361 tacttactcg ccttgctgat tgtctatttt tgcgtttaca acttttctaa gaacttttgt
 421 atacaaagga acttttttaaa aaagacgctt ccaagttata tttaatccaa agaagaagga
 481 tctcggccaa tttggggttt tgggttttgg cttcgtttct tctcttcgtt gactttgggg
 541 ttcaggtgcc ccagctgctt cgggctgccg aggaccttct gggcccccac attaatgagg
 601 cagccacctg gcgagtctga catggctgtc agcgacgcgc tgctcccatc tttctccacg
 661 ttcgcgtctg gccggcggg aagggagaag acactgcgtc aagcaggtgc cccgaataac
 721 cgctggcggg aggagctctc ccacatgaag cgacttcccc cagtgcttcc cggccgcccc
 781 tatgacctgg cggcggcgac cgtggccaca gacctggaga gcggcggagc cggtgcggct
 841 tgcggcggta gcaacctggc gcccctacct cggagagaga ccgaggagtt caacgatctc
 901 ctggacctgg actttattct ctccaattcg ctgacccatc ctccggagtc agtggccgcc
 961 accgtgtcct cgtcagcgtc agcctcctct tcgtcgtcgc cgtcgagcag cggccctgcc
1021 agcgcgccct ccacctgcag cttcacctat ccgatccggg ccgggaacga cccgggcgtg
1081 gcgccgggcg gcacgggcgg aggcctcctc tatggcaggg agtccgctcc ccctccgacg
1141 gctcccttca acctggcgga catcaacgac gtgagcccct cggcggctt cgtggccgag
1201 ctcctgcggc cagaattgga cccggtgtac attccgccgc agcagccgca gccgccaggt
1261 ggcgggctga tgggcaagtt cgtgctgaag gcgtcgctga gcgcccctgg cagcgagtac
1321 ggcagcccgt cggtcatcag cgtcagcaaa ggcagccctg acggcagcca cccggtggtg
1381 gtggcgccct acaacggcgg gccgccgcgc acgtgcccca agatcaagca ggaggcggtc
1441 tcttcgtgca cccacttggg cgctggaccc cctctcagca atggccaccg gccggctgca
1501 cacgacttcc ccctggggcg gcagctcccc agcaggacta ccccgaccct gggtcttgag
1561 gaagtgctga gcagcaggga ctgtcaccct gccctgccgc ttcctcccgg cttccatccc
1621 cacccggggc ccaattaccc atccttcctg cccgatcaga tgcagccgca agtcccgccg
1681 ctccattacc aagagctcat gccacccggt tcctgcatgc cagaggagcc caagccaaag
1741 aggggaagac gatcgtggcc ccggaaaagg accgccaccc acacttgtga ttacgcgggc
1801 tgcggcaaaa cctacacaaa gagttcccat ctcaaggcac acctgcgaac ccacacaggt
1861 gagaaacctt accactgtga ctgggacggc tgtggatgga attcgcccg ctcagatgaa
1921 ctgaccaggc actaccgtaa acacacgggg caccgcccgt tccagtgcca aaaatgcgac
1981 cgagcatttt ccaggtcgga ccacctcgcc ttacacatga gaggcattt ttaaatccca
2041 gacagtggat atgacccaca ctgccagaag agaattcagt attttttact tttcacactg
2101 tcttcccgat gagggaagga gcccagccag aaagcactac aatcatggtc aagttcccaa
2161 ctgagtcatc ttgtgagtgg ataatcagga aaaatgagga atccaaaaga caaaaatcaa
2221 agaacagatg gggtctgtga ctggatcttc tatcattcca attctaaatc cgacttgaat
2281 attcctggac ttacaaaatg ccagggggt gactggaagt tgtggatatc agggtataaa
2341 ttatatccgt gagttggggg agggaagacc agaattccct tgaattgtgt attgatgcaa
2401 tataagcata aaagatcacc ttgtattctc tttaccttct aaaagccatt attatgatgt
```

-continued

```
2461 tagaagaaga ggaagaaatt caggtacaga aaacatgttt aaatagccta aatgatggtg
2521 cttggtgagt cttggttcta aaggtaccaa acaaggaagc caaagttttc aaactgctgc
2581 atactttgac aaggaaaatc tatatttgtc ttccgatcaa catttatgac ctaagtcagg
2641 taatatacct ggtttacttc tttagcattt ttatgcagac agtctgttat gcactgtggt
2701 ttcagatgtg caataatttg tacaatggtt tattcccaag tatgccttaa gcagaacaaa
2761 tgtgttttc tatatagttc cttgccttaa taaatatgta atataaattt aagcaaacgt
2821 ctattttgta tatttgtaaa ctacaaagta aaatgaacat tttgtggagt ttgtattttg
2881 catactcaag gtgagaatta agttttaaat aaacctataa tattttatct gaaaaaaaaa
2941 aaaaaaaaa
```

An exemplary murine Klf4 polynucleotide sequence is provided at NM_010637.3 below:

```
   1 agttccccgg ccaagagagc gagcgcggct ccgggcgcgc ggggagcaga ggcggtggcg
  61 ggcggcggcg gcacccggag ccgccgagtg cccctccccg cccctccagc cccccaccca
 121 gcaacccgcc cgtgacccgc gcccatggcc gcgcgcaccc ggcacagtcc ccaggactcc
 181 gcaccccgcg ccaccgccca gctcgcagtt ccgcgccacc gcggccattc tcacctggcg
 241 gcgccgcccg cccaccgccc ggaccacagc ccccgcgccg ccgacagcca cagtggccgc
 301 gacaacggtg ggggacactg ctgagtccaa gagcgtgcag cctggccatc ggacctactt
 361 atctgccttg ctgattgtct attttttataa gagtttacaa cttttctaag aattttttgta
 421 tacaaaggaa cttttttaaa gacatcgccg gtttatattg aatccaaaga agaaggatct
 481 cgggcaatct gggggttttg gtttgaggtt ttgtttctaa agttttaat cttcgttgac
 541 tttggggctc aggtacccct ctctcttctt cggactccgg aggaccttct gggcccccac
 601 attaatgagg cagccacctg gcgagtctga catggctgtc agcgacgctc tgctcccgtc
 661 cttctccacg ttcgcgtccg gcccggcggg aagggagaag acactgcgtc cagcaggtgc
 721 cccgactaac cgttggcgtg aggaactctc tcacatgaag cgacttcccc cacttcccgg
 781 ccgcccctac gacctggcgg cgacggtggc cacagacctg gagagtggcg gagctggtgc
 841 agcttgcagc agtaacaacc cggccctcct agcccggagg gagaccgagg agttcaacga
 901 cctcctggac ctagacttta tccttttccaa ctcgctaacc caccaggaat cggtggccgc
 961 caccgtgacc acctcggcgt cagcttcatc ctcgtcttcc ccggcgagca gcggccctgc
1021 cagcgcgccc tccacctgca gcttcagcta tccgatccgg gccgggggtg acccgggcgt
1081 ggctgccagc aacacaggtg gagggctcct ctacagccga gaatctgcgc cacctcccac
1141 ggccccctc aacctggcgg acatcaatga cgtgagcccc tcgggcggct cgtggctga
1201 gctcctgcgg ccggagttgg acccagtata cattccgcca cagcagcctc agccgccagg
1261 tggcgggctg atgggcaagt ttgtgctgaa ggcgtctctg accacccctg cagcgagta
1321 cagcagccct tcggtcatca gtgttagcaa aggaagccca gacggcagcc accccgtggt
1381 agtggcgccc tacagcggtg gccgccgcg catgtgcccc aagattaagc aagaggcggt
1441 cccgtcctgc acgtcagcc ggtccctaga ggcccatttg agcgctggac cccagctcag
1501 caacggccac cggcccaaca cacacgactt cccctgggg cggcagctcc ccaccaggac
1561 tacccctaca ctgagtcccg aggaactgct gaacagcagg gactgtcacc ctggcctgcc
1621 tcttcccca ggattccatc cccatccggg gcccaactac cctccttttcc tgccagacca
```

-continued

```
1681 gatgcagtca caagtcccct ctctccatta tcaagagctc atgccaccgg gttcctgcct 1741 gccagaggag cccaagccaa agaggggaag aaggtcgtgg ccccggaaaa gaacagccac 1801 ccacacttgt gactatgcag gctgtggcaa aacctatacc aagagttctc atctcaaggc 1861 acacctgcga actcacacag gcgagaaacc ttaccactgt gactgggacg gctgtgggtg 1921 gaaattcgcc cgctccgatg aactgaccag gcactaccgc aaacacacag ggcaccggcc 1981 ctttcagtgc cagaagtgtg acagggcctt ttccaggtcg gaccaccttg ccttacacat 2041 gaagaggcac ttttaaatcc cacgtagtgg atgtgaccca cactgccagg agagagagtt 2101 cagtattttt ttttctaacc tttcacactg tcttcccacg aggggaggag cccagctggc 2161 aagcgctaca atcatggtca agttcccagc aagtcagctt gtgaatggat aatcaggaga 2221 aaggaagagt tcaagagaca aaacagaaat actaaaaaca aacaaacaaa aaaacaaaca 2281 aaaaaaacaa gaaaaaaaaa tcacagaaca gatggggtct gatactggat ggatcttcta 2341 tcattccaat accaaatcca acttgaacat gcccggactt acaaaatgcc aagggggtgac 2401 tggaagtttg tggatatcag ggtatacact aaatcagtga gcttgggggg agggaagacc 2461 aggattccct tgaattgtgt ttcgatgatg caatacacac gtaaagatca ccttgtatgc 2521 tctttgcctt cttaaaaaaa aaaaaagcca ttattgtgtc ggaggaagag gaagcgattc 2581 aggtacagaa catgttctaa cagcctaaat gatggtgctt ggtgagtcgt ggttctaaag 2641 gtaccaaacg ggggagccaa agttctccaa ctgctgcata cttttgacaa ggaaaatcta 2701 gttttgtctt ccgatctaca ttgatgacct aagccaggta aataagcctg gtttatttct 2761 gtaacatttt tatgcagaca gtctgttatg cactgtggtt tcagatgtgc aataatttgt 2821 acaatggttt attcccaagt atgcctttaa gcagaacaaa tgtgtttttc tatatagttc 2881 cttgccttaa taaatatgta atataaattt aagcaaactt ctattttgta tatttgtaaa 2941 ctacaaagta aaaaaaaatg aacatttttgt ggagtttgta ttttgcatac tcaaggtgag 3001 aaataagttt taaataaacc tataatattt tatctgaacg acaaaaaaaa aaaaaaa
```

By "marker" is meant any protein or polynucleotide having an alteration in expression level or activity that is associated with a disease or disorder.

By "negative" is meant that a cell expresses an undetectable level of a marker or a reduced level of marker, such that the cell can be distinguished in a negative selection from a population of unselected cells.

By "Oct4 polypeptide" is meant a protein or fragment thereof having at least 85% homology to the sequence provided at NCBI Ref: NP_001167002.1 (human) or NP_001239381.1 (murine) and having transcriptional regulatory activity.

An exemplary Oct4 human amino acid sequence is provided below:

MGVLFGKVFSQTTICRFEALQLSFKNMCKLRPLLQKWVEEADNNENLQEI

CKAETLVQARKRKRTSIENRVRGNLENLFLQCPKPTLQQISHIAQQLGLE

KDVVRVWFCNRRQKGKRSSSDYAQREDFEAAGSPFSGGPVSFPLAPGPHF

GTPGYGSPHFTALYSSVPFPEGEAFPPVSVTTLGSPMHSN

An exemplary Oct4 murine amino acid sequence (NCBI Ref: NP_001239381.1) is provided below:

MKALQKELEQFAKLLKQKRITLGYTQADVGLTLGVLFGKVFSQTTICRFE

ALQLSLKNMCKLRPLLEKWVEEADNNENLQEICKSETLVQARKRKRTSIE

NRVRWSLETMFLKCPKPSLQQITHIANQLGLEKDVVRVWFCNRRQKGKRS

SIEYSQREEYEATGTPFPGGAVSFPLPPGPHFGTPGYGSPHFTTLYSVPF

PEGEAFPSVPVTALGSPMHSN

By "Oct4 polynucleotide" is meant a nucleic acid molecule encoding a Oct4 polypeptide. An exemplary human Oct4 polynucleotide sequence is provided at NM_001173531.2 and reproduced below:

```
  1 ggaaaaaagg aaagtgcact tggaagagat ccaagtgggc aacttgaaga acaagtgcca 61 aatagcactt ctgtcatgct ggatgtcagg gctctttgtc cactttgtat agccgctggc 121 ttatagaagg tgctcgataa atctcttgaa tttaaaaatc aattaggatg cctctatagt 181 gaaaaagata cagtaaagat gagggataat caatttaaaa aatgagtaag tacacacaaa
```

```
241 gcactttatc cattcttatg acacctgtta cttttttgct gtgtttgtgt gtatgcatgc
301 catgttatag tttgtgggac cctcaaagca agctggggag agtatatact gaatttagct
361 tctgagacat gatgctcttc cttttttaatt aacccagaac ttagcagctt atctatttct
421 ctaatctcaa aacatcctta aactgggggt gatacttgag tgagagaatt ttgcaggtat
481 taaatgaact atcttctttt ttttttttct ttgagacaga gtcttgctct gtcacccagg
541 ctggagtgca gtggcgtgat ctcagctcac tgcaacctcc gcctcccggg ttcaagtgat
601 tctcctgcct cagcctcctg agtagctggg attacagtcc caggacatca aagctctgca
661 gaaagaactc gagcaatttg ccaagctcct gaagcagaag aggatcaccc tgggatatac
721 acaggccgat gtgggctca ccctgggggt tctatttggg aaggtattca gccaaacgac
781 catctgccgc tttgaggctc tgcagcttag cttcaagaac atgtgtaagc tgcggccctt
841 gctgcagaag tgggtggagg aagctgacaa caatgaaaat cttcaggaga tatgcaaagc
901 agaaaccctc gtgcaggccc gaaagagaaa gcgaaccagt atcgagaacc gagtgagagg
961 caacctggag aatttgttcc tgcagtgccc gaaacccaca ctgcagcaga tcagccacat
1021 cgcccagcag cttgggctcg agaaggatgt ggtccgagtg tggttctgta accggcgcca
1081 gaagggcaag cgatcaagca gcgactatgc acaacgagag gattttgagg ctgctgggtc
1141 tcctttctca gggggaccag tgtcctttcc tctggcccca gggccccatt ttggtacccc
1201 aggctatggg agccctcact tcactgcact gtactcctcg gtccctttcc ctgaggggga
1261 agcctttccc cctgtctccg tcaccactct gggctctccc atgcattcaa actgaggtgc
1321 ctgcccttct aggaatgggg gacaggggga ggggaggagc tagggaaaga aaacctggag
1381 ttttgtgccag ggttttttggg attaagttct tcattcacta aggaaggaat tgggaacaca
1441 aagggtgggg gcaggggagt ttggggcaac tggttggagg gaaggtgaag ttcaatgatg
1501 ctcttgattt taatcccaca tcatgtatca ctttttttctt aaataaagaa gcctgggaca
1561 cagtagatag acacacttaa aaaaaaaaa
```

An exemplary murine Oct4 polynucleotide sequence is provided at NM_001252452.1 and reproduced below:

```
   1 gcagccttaa aacttcttca gaatagggtg acattttgtc ctcagtgggg cggttttgag
  61 taatctgtga gcagatagga acttgctggg tcccaggaca tgaaagccct gcagaaggag
 121 ctagaacagt ttgccaagct gctgaagcag aagaggatca ccttggggta cacccaggcc
 181 gacgtggggc tcaccctggg cgttctcttt ggaaaggtgt tcagccagac caccatctgt
 241 cgcttcgagg ccttgcagct cagccttaag aacatgtgta agctgcggcc cctgctggag
 301 aagtgggtgg aggaagccga caacaatgag aaccttcagg agatatgcaa atcggagacc
 361 ctggtgcagg cccggaagag aaagcgaact agcattgaga ccgtgtgag gtggagtctg
 421 gagaccatgt ttctgaagtg cccgaagccc tccctacagc agatcactca catcgccaat
 481 cagcttgggc tagagaagga tgtggttcga gtatggttct gtaaccggcg ccagaagggc
 541 aaaagatcaa gtattgagta ttcccaacga gaagagtatg aggctacagg gacacctttc
 601 ccaggggggg ctgtatcctt tcctctgccc ccaggtcccc actttggcac cccaggctat
 661 ggaagccccc acttcaccac actctactca gtccttttc ctgagggcga ggcctttccc
 721 tctgttcccg tcactgctct gggctctccc atgcattcaa actgaggcac cagccctccc
 781 tggggatgct gtgagccaag gcaagggagg tagacaagag aacctggagc tttggggtta
```

```
841 aattcttta ctgaggaggg attaaaagca caacaggggt gggggtggg atggggaaag 901 aagctcagtg atgctgttga tcaggagcct ggcctgtctg tcactcatca ttttgttctt 961 aaataaagac tgggacacac agtagatagc t
```

By "PGC1 alpha polypeptide" is meant a protein or fragment thereof having at least 85% identity to the amino acid sequence provided at NCBI Ref: NP_037393.1 or UniProt Ref: Q9UBK2 (human), NCBI Ref: NP_032930.1 (mouse) and having transcriptional coactivating activity. An exemplary PGC1 alpha human amino acid sequence is provided below:

```
>sp|Q9UBK2|PRGC1_HUMAN Peroxisome proliferator-
activated receptor gamma coactivator 1-alpha OS =
Homo sapiens GN = PPARGC1A PE = 1 SV = 1
MAWDMCNQDSESVWSDIECAALVGEDQPLCPDLPELDLSELDVNDLDTDS

FLGGLKWCSDQSEIISNQYNNEPSNIFEKIDEENEANLLAVLTETLDSLP

VDEDGLPSFDALTDGDVTTDNEASPSSMPDGTPPPQEAEEPSLLKKLLLA

PANTQLSYNECSGLSTQNHANHNHRIRTNPAIVKTENSWSNKAKSICQQQ

KPQRRPCSELLKYLTTNDDPPHTKPTENRNSSRDKCTSKKKSHTQSQSQH

LQAKPTTLSLPLTPESPNDPKGSPFENKTIERTLSVELSGTAGLTPPTTP

PHKANQDNPFRASPKLKSSCKTVVPPPSKKPRYSESSGTQGNNSTKKGPE

QSELYAQLSKSSVLTGGHEERKTKRPSLRLFGDHDYCQSINSKTEILINI

SQELQDSRQLENKDVSSDWQGQICSSTDSDQCYLRETLEASKQVSPCSTR

KQLQDQEIRAELNKHFGHPSQAVFDDEADKTGELRDSDFSNEQFSKLPMF

INSGLAMDGLFDDSEDESDKLSYPWDGTQSYSLFNVSPSCSSFNSPCRDS

VSPPKSLFSQRPQRMRSRSRSFSRHRSCSRSPYSRSRSRSPGSRSSSRSC

YYYESSHYRHRTHRNSPLYVRSRSRSPYSRRPRYDSYEEYQHERLKREEY

RREYEKRESERAKQRERQRQKAIEERRVIYVGKIRPDTTRTELRDRFEVF

GEIEECTVNLRDDGDSYGFITYRYTCDAFAALENGYTLRRSNETDFELYF

CGRKQFFKSNYADLDSNSDDFDPASTKSKYDSLDFDSLLKEAQRSLRR
```

An exemplary murine PGC1 alpha amino acid sequence is provided below:

```
MAWDMCSQDSVWSDIECAALVGEDQPLCPDLPELDLSELDVNDLDTDSFL

GGLKWCSDQSEIISNQYNNEPANIFEKIDEENEANLLAVLTETLDSLPVD

EDGLPSFDALTDGAVTTDNEASPSSMPDGTPPPQEAEEPSLLKKLLLAPA

NTQLSYNECSGLSTQNHAANHTHRIRTNPAIVKTENSWSNKAKSICQQQK

PQRRPCSELLKYLTTNDDPPHTKPTENRNSSRDKCASKKKSHTQPQSQHA

QAKPTTLSLPLTPESPNDPKGSPFENKTIERTLSVELSGTAGLTPPTTPP

HKANQDNPFKASPKLKPSCKTVVPPPTKRARYSECSGTQGSHSTKKGPEQ

SELYAQLSKSSGLSRGHEERKTKRPSLRLFGDHDYCQSLNSKTDILINIS

QELQDSRQLDFKDASCDWQGHICSSTDSGQCYLRETLEASKQVSPCSTRK

QLQDQEIRAELNKHFGHPCQAVFDDKSDKTSELRDGDFSNEQFSKLPVFI

NSGLAMDGLFDDSEDESDKLSYPWDGTQPYSLFDVSPSCSSFNSPCRDSV

SPPKSLFSQRPQRMRSRSRSFSRHRSCSRSPYSRSRSRSPGSRSSSRSCY

YYESSHYRHRTHRNSPLYVRSRSRSPYSRRPRYDSYEAYEHERLKRDEYR

KEHEKRESERAKQRERQKQKAIEERRVIYVGKIRPDTTRTELRDRFEVFG

EIEECTVNLRDDGDSYGFITYRYTCDAFAALENGYTLRRSNETDFELYFC

GRKQFFKSNYADLDTNSDDFDPASTKSKYDSLDFDSLLKEAQRSLRR
```

By "PGC1 alpha polynucleotide" is meant a nucleic acid molecule encoding a PGC1 alpha polypeptide. An exemplary human PGC1 alpha polynucleotide sequence is provided at NM_013261:

```
         tagtaagaca ggtgccttca gttcactctc agtaaggggc tggttgcctg catgagtgtg    61
tgctctgtgt cactgtggat tggagttgaa aaagcttgac tggcgtcatt caggagctgg   121
atggcgtggg acatgtgcaa ccaggactct gagtctgtat ggagtgacat cgagtgtgct   181
gctctggttg gtgaagacca gcctctttgc ccagatcttc ctgaacttga tctttctgaa   241
ctagatgtga acgacttgga tacagacagc tttctgggtg gactcaagtg gtgcagtgac   301
caatcagaaa taatatccaa tcagtacaac aatgagcctt caaacatatt tgagaagata   361
gatgaagaga atgaggcaaa cttgctagca gtcctcacag agacactaga cagtctccct   421
gtggatgaag acggattgcc ctcatttgat gcgctgacag atggagacgt gaccactgac   481
aatgaggcta gtccttcctc catgcctgac ggcacccctc caccccagga ggcagaagag   541
ccgtctctac ttaagaagct cttactggca ccagccaaca ctcagctaag ttataatgaa   601
tgcagtggtc tcagtaccca gaaccatgca aatcacaatc acaggatcag aacaaaccct   661
gcaattgtta agactgagaa ttcatggagc aataaagcga agagtatttg tcaacagcaa   721
aagccacaaa gacgtccctg ctcggagctt ctcaaatatc tgaccacaaa cgatgaccct   781
```

-continued

```
cctcacacca aacccacaga gaacagaaac agcagcagag acaaatgcac ctccaaaaag    841
aagtcccaca cacagtcgca gtcacaacac ttacaagcca aaccaacaac tttatctctt    901
cctctgaccc cagagtcacc aaatgacccc aagggttccc catttgagaa caagactatt    961
gaacgcacct taagtgtgga actctctgga actgcaggcc taactccacc caccactcct    1021
cctcataaag ccaaccaaga taacccttt agggcttctc caaagctgaa gtcctcttgc    1081
aagactgtgg tgccaccacc atcaaagaag cccaggtaca gtgagtcttc tggtacacaa    1141
ggcaataact ccaccaagaa agggccggag caatccgagt tgtatgcaca actcagcaag    1201
tcctcagtcc tcactggtgg acacgaggaa aggaagacca agcggcccag tctgcggctg    1261
tttggtgacc atgactattg ccagtcaatt aattccaaaa cagaaatact cattaatata    1321
tcacaggagc tccaagactc tagacaacta gaaataaag atgtctcctc tgattggcag    1381
gggcagattt gttcttccac agattcagac cagtgctacc tgagagagac tttggaggca    1441
agcaagcagg tctctccttg cagcacaaga aaacagctcc aagaccagga aatccgagcc    1501
gagctgaaca agcacttcgg tcatcccagt caagctgttt ttgacgacga agcagacaag    1561
accggtgaac tgagggacag tgatttcagt aatgaacaat tctccaaaact acctatgttt    1621 ataaattcag gactagccat ggatggcctg tttgatgaca gcgaagatga aagtgataaa    1681
ctgagctacc cttgggatgg cacgcaatcc tattcattgt tcaatgtgtc tccttcttgt    1741
tcttctttta actctccatg tagagattct gtgtcaccac ccaaatcctt attttctcaa    1801 agacccaaa ggatgcgctc tcgttcaagg tccttttctc gacacaggtc gtgttcccga    1861
tcaccatatt ccaggtcaag atcaaggtct ccaggcagta gatcctcttc aagatcctgc    1921
tattactatg agtcaagcca ctacagacac cgcacgcacc gaaattctcc cttgtatgtg    1981
agatcacgtt caagatcgcc ctacagccgt cggcccaggt atgacagcta cgaggaatat    2041
cagcacgaga ggctgaagag ggaagaatat cgcagagagt atgagaagcg agagtctgag    2101
agggccaagc aaagggagag gcagaggcag aaggcaattg aagagcgccg tgtgatttat    2161
gtcggtaaaa tcagacctga cacaacacg acagaactga gggaccgttt tgaagttttt    2221
ggtgaaattg aggagtgcac agtaaatctg cgggatgatg agacagcta tggtttcatt    2281 acctaccgtt atacctgtga tgcttttgct gctcttgaaa atggatacac tttgcgcagg    2341
tcaaacgaaa ctgactttga gctgtacttt tgtggacgca agcaattttt caagtctaac    2401
tatgcagacc tagattcaaa ctcagatgac tttgaccctg cttccaccaa gagcaagtat    2461
gactctctgg attttgatag tttactgaaa gaagctcaga gaagcttgcg caggtaacat    2521
gttccctagc tgaggatgac agagggatgg cgaatacctc atgggacagc gcgtccttcc    2581
ctaaagacta ttgcaagtca tacttaggaa tttctcctac tttacactct ctgtacaaaa    2641
acaaaacaaa acaacaacaa tacaacaaga acaacaacaa caataacaac aatggtttac    2701
atgaacacag ctgctgaaga ggcaagagac agaatgatat ccagtaagca catgtttatt    2761
catgggtgtc agctttgctt ttcctggagt ctcttggtga tggagtgtgc gtgtgtgcat    2821
gtatgtgtgt gtgtatgtat gtgtgtggtg tgtgtgcttg gtttagggga agtatgtgtg    2881
ggtacatgtg aggactgggg gcacctgacc agaatgcgca agggcaaacc atttcaaatg    2941
gcagcagttc catgaagaca cgcttaaaac ctagaacttc aaaatgttcg tattctattc    3001
aaaaggaaat atatatatat atatatatat atatatatat atatataaat taaaaaggaa    3061
agaaaactaa caaccaacca accaaccaac caaccacaaa ccaccctaaa atgacagccg    3121
ctgatgtctg ggcatcagcc tttgtactct gttttttaa gaaagtgcag aatcaacttg    3181
```

```
aagcaagctt tctctcataa cgtaatgatt atatgacaat cctgaagaaa ccacaggttc   3241
catagaacta atatcctgtc tctctctctc tctctctctc tctctttttt ttttcttttt   3301 cctttttgcca tggaatctgg gtgggagagg atactgcggg caccagaatg ctaaagtttc   3361
ctaacatttt gaagtttctg tagttcatcc ttaatcctga cacccatgta aatgtccaaa   3421
atgttgatct tccactgcaa atttcaaaag ccttgtcaat ggtcaagcgt gcagcttgtt   3481
cagcggttct ttctgaggag cggacaccgg gttacattac taatgagagt tgggtagaac   3541
tctctgagat gtgttcagat agtgtaattg ctacattctc tgatgtagtt aagtatttac   3601
agatgttaaa tggagtattt ttattttatg tatatactat acaacaatgt tcttttttgt   3661
tacagctatg cactgtaaat gcagccttct tttcaaaact gctaaattt tcttaatcaa   3721 gaatattcaa atgtaattat gaggtgaaac aattattgta cactaacata tttagaagct   3781
gaacttactg cttatatata tttgattgta aaaacaaaaa gacagtgtgt gtgtctgttg   3841
agtgcaacaa gagcaaaatg atgctttccg cacatccatc ccttaggtga gcttcaatct   3901
aagcatcttg tcaagaaata tcctagtccc ctaaggtat taaccacttc tgcgatattt   3961
ttccacattt tcttgtcgct tgttttttctt tgaagttta tacactggat ttgttagggg   4021
aatgaaattt tctcatctaa aatttttcta gaagatatca tgattttatg taaagtctct   4081
caatgggtaa ccattaagaa atgtttttat tttctctatc aacagtagtt ttgaaactag   4141
aagtcaaaaa tctttttaaa atgctgtttt gttttaattt ttgtgatttt aatttgatac   4201
aaaatgctga ggtaataatt atagtatgat ttttacaata attaatgtgt gtctgaagac   4261
tatctttgaa gccagtattt cttttcccttg gcagagtatg acgatggtat ttatctgtat   4321
tttttacagt tatgcatcct gtataaatac tgatatttca ttcctttgtt tactaaagag   4381
acatatttat cagttgcaga tagcctattt attataaatt atgagatgat gaaaataata   4441
aagccagtgg aaattttcta cctaggatgc atgacaattg tcaggttgga gtgtaagtgc   4501
ttcatttggg aaattcagct tttgcagaag cagtgtttct acttgcacta gcatggcctc   4561
tgacgtgacc atggtgttgt tcttgatgac attgcttctg ctaaatttaa taaaaacttc   4621
agaaaaacct ccatttttgat catcaggatt tcatctgagt gtggagtccc tggaatggaa   4681
ttcagtaaca tttggagtgt gtattcaagt ttctaaattg agattcgatt actgtttggc   4741
tgacatgact tttctggaag acatgataca cctactactc aattgttctt ttcctttctc   4801
tcgcccaaca cgatcttgta agatggattt cacccccagg ccaatgcagc taattttgat   4861
agctgcattc atttatcacc agcatatgt gttctgagtg aatccactgt ttgtcctgtc   4921
ggatgcttgc ttgatttttt ggcttcttat ttctaagtag atagaaagca ataaaatac   4981 tatgaaatga aagaacttgt tcacaggttc tgcgttacaa cagtaacaca tctttaatcc   5041
gcctaattct tgttgttctg taggttaaat gcaggtattt taactgtgtg aacgccaaac   5101
taaagtttac agtctttctt tctgaatttt gagtatcttc tgttgtagaa taataataaa   5161
aagactatta agagcaataa attatttta agaaatcgag atttagtaaa tcctattatg   5221
tgttcaagga ccacatgtgt tctctatttt gcctttaaat ttttgtgaac caattttaaa   5281
tacattctcc tttttgccct ggattgttga catgagtgga atacttggtt tcttttctta   5341
cttatcaaaa gacagcacta cagatatcat attgaggatt aatttatccc cctaccccc   5401 agcctgacaa atattgttac catgaagata gttttcctca atggacttca aattgcatct   5461
agaattagtg gagcttttgt atcttctgca gacactgtgg gtagcccatc aaaatgtaag   5521
ctgtgctcct ctcattttta tttttatttt tttgggagaa atatttcaa atgaacacgt   5581 gcaccccatc atcactggag gcaaatttca gcatagatct gtaggatttt tagaagaccg   5641
```

-continued

```
tgggccattg ccttcatgcc gtggtaagta ccacatctac aattttggta accgaactgg    5701
tgctttagta atgtggattt ttttcttttt taaaagagat gtagcagaat aattcttcca    5761
gtgcaacaaa atcaatttt tgctaaacga ctccgagaac aacagttggg ctgtcaacat     5821
tcaaagcagc agagagggaa ctttgcacta ttggggtatg atgtttgggt cagttgataa    5881
aaggaaacct tttcatgcct ttagatgtga gcttccagta ggtaatgatt atgtgtcctt    5941
tcttgatggc tgtaatgaga acttcaatca ctgtagtcta agacctgatc tatagatgac    6001
ctagaatagc catgtactat aatgtgatga ttctaaattt gtacctatgt gacagacatt    6061
ttcaataatg tgaactgctg atttgatgga gctactttaa gatttgtagg tgaaagtgta    6121
atactgttgg ttgaactatg ctgaagaggg aaagtgagcg attagttgag cccttgccgg    6181
gccttttttc cacctgccaa ttctacatgt attgttgtgg ttttattcat tgtatgaaaa    6241
ttcctgtgat ttttttttaaa tgtgcagtac acatcagcct cactgagcta ataaagggaa   6301
acgaatgttt caaatcta
```

An exemplary murine PGC1 alpha polynucleotide sequence is provided at NM_008904.2:

```
   1 gtcatgtgac tggggactgt agtaagacag gtgccttcag ttcactctca gtaaggggct 61 ggttgcctgc atgagtgtgt gctgtgtgtc agagtggatt ggagttgaaa aagcttgact 121 ggcgtcattc gggagctgga tggcttggga catgtgcagc caagactctg tatggagtga 181 catagagtgt gctgctctgg ttggtgagga ccagcctctt tgcccagatc ttcctgaact 241 tgaccttct gaacttgatg tgaatgactt ggatacagac agctttctgg gtggattgaa 301 gtggtgtagc gaccaatcgg aaatcatatc caaccagtac aacaatgagc ctgcgaacat 361 atttgagaag atagatgaag agaatgaggc aaacttgcta gcggttctca cagagacact 421 ggacagtctc cccgtggatg aagacggatt gccctcattt gatgcactga cagatggagc 481 cgtgaccact gacaacgagg ccagtccttc ctccatgcct gacggcaccc ctcccccta 541 ggaggcagaa gagccgtctc tacttaagaa gctcttactg gcaccagcca acactcagct 601 cagctacaat gaatgcagcg gtcttagcac tcagaaccat gcagcaaacc acacccacag 661 gatcagaaca aaccctgcca ttgttaagac cgagaattca tggagcaata aagcgaagag 721 catttgtcaa cagcaaaagc cacaaagacg tccctgctca gagcttctca agtatctgac 781 cacaaacgat gaccctcctc acaccaaacc cacagaaaac aggaacagca gcagagacaa 841 atgtgcttcg aaaaagaagt cccatacaca accgcagtcg caacatgctc aagccaaacc 901 aacaacttta tctcttcctc tgaccccaga gtcaccaaat gaccccaagg gttccccatt 961 tgagaacaag actattgagc gaaccttaag tgtggaactc tctggaactg caggcctaac 1021 tcctcccaca actcctcctc ataaagccaa ccaagataac cctttcaagg cttcgccaaa 1081 gctgaagccc tcttgcaaga ccgtggtgcc accgccaacc aagagggccc ggtacagtga 1141 tgttctggt acccaaggca gccactccac caagaaaggg cccgagcaat ctgagttgta 1201 cgcacaactc agcaagtcct cagggctcag ccgaggacac gaggaaagga agactaaacg 1261 gcccagtctc cggctgtttg gtgaccatga ctactgtcag tcactcaatt ccaaaacgga 1321 tatactcatt aacatatcac aggagctcca agactctaga caactagact tcaaagatgc 1381 ctcctgtgac tggcaggggc acatctgttc ttccacagat tcaggccagt gctacctgag 1441 agagactttg gaggccagca agcaggtctc tccttgcagc accagaaaac agctccaaga
```

-continued

```
1501 ccaggaaatc cgagcggagc tgaacaagca cttcggtcat ccctgtcaag ctgtgtttga
1561 cgacaaatca gacaagacca gtgaactaag ggatggcgac ttcagtaatg aacaattctc
1621 caaactacct gtgtttataa attcaggact agccatggat ggcctatttg atgacagtga
1681 agatgaaagt gataaactga gctacccttg ggatggcacg cagccctatt cattgttcga
1741 tgtgtcgcct tcttgctctt cctttaactc tccgtgtcga gactcagtgt caccaccgaa
1801 atccttattt tctcaaagac cccaaaggat gcgctctcgt tcaagatcct tttctcgaca
1861 caggtcgtgt tcccgatcac catattccag gtcaagatca aggtccccag gcagtagatc
1921 ctcttcaaga tcctgttact actatgaatc aagccactac agacaccgca cacaccgcaa
1981 ttctcccttg tatgtgagat cacgttcaag gtcaccctac agccgtaggc ccaggtacga
2041 cagctatgaa gcctatgagc acgaaaggct caagagggat gaataccgca aagagcacga
2101 gaagcgggag tctgaaaggg ccaaacagag agagaggcag aagcagaaag caattgaaga
2161 gcgccgtgtg atttacgttg gtaaaatcag acctgacaca acgcggacag aattgagaga
2221 ccgctttgaa gtttttggtg aaattgagga atgcaccgta atctgcggg atgatggaga
2281 cagctatggt ttcatcacct accgttacac ctgtgacgct ttcgctgctc ttgagaatgg
2341 atatactta cgcaggtcga acgaaactga cttcgagctg tacttttgtg acggaagca
2401 atttttcaag tctaactatg cagacctaga taccaactca gacgattttg accctgcttc
2461 caccaagagc aagtatgact ctctggattt tgatagttta ctgaaggaag ctcagagaag
2521 cttgcgcagg taacgtgttc ccaggctgag gaatgacaga gagatggtca atacctcatg
2581 ggacagcgtg tcctttccca agactcttgc aagtcatact taggaatttc tcctactta
2641 cactctctgt acaaaaataa aacaaaacaa aacaacaata acaacaacaa caacaacaat
2701 aacaacaaca accataccag aacaagaaca acggtttaca tgaacacagc tgctgaagag
2761 gcaagagaca gaatgataat ccagtaagca cacgtttatt cacgggtgtc agctttgctt
2821 tccctggagg ctcttggtga cagtgtgtgt gcgtgtgtgt gtgtgggtgt gcgtgtgtgt
2881 atgtgtgtgt gtgtacttgt ttggaaagta catatgtaca catgtgagga cttgggggca
2941 cctgaacaga acgaacaagg gcgaccccct caaatggcag catttccatg aagacacact
3001 taaaacctac aacttcaaaa tgttcgtatt ctatacaaaa ggaaaataaa taaatataaa
3061 ttaaaaggaa agaaaactca caaccaccc taaaatgaca ctgctgatgc ctgttgtcag
3121 cctccggtac cgtcttttca gaaagtgcaa aacccagaaa gtgcaaaacc aacctgcagc
3181 aagctctctc tctctcttaa tgtaatcatt acgtgacaat cccgaagaca ctacaggttc
3241 catagaactc atatccacct ctctctctct ctctctctct ctctctctct ctctctctct
3301 cctctctcct ctctcctctc tccctcccctt ctttgccatt gaatctgggt gggagaggat
3361 actgcaggca ccagatgcta aactttccta acatttgaa gtttctgtag tttgtcctt
3421 gtcctgacac ctatgtatat gttcaaaatg ttgatcttcc actgcagatt ttgaaaagcc
3481 ttgttattgg tcaagcgggg agtgtgttca gtggctcctt ctgaggagca gacgcggtgt
3541 tacatgagta ctgagagttg agtagaactc tctggatgtg ttcagatagt gtaattgcta
3601 cattctctga tgtagttaag tatttacaga tgttaaatgg agtattttta ttttatgtac
3661 atactctaca actatgttct tttttgttac agctatgcac tgtaaatgca gccttctttt
3721 caaaactgct aaatttttct taatcaagaa tattcaaatg taattatgag gtgaaacaat
3781 tattgtacac taacatattt agaagctaaa cttactgctt atatatattt gattgtaaaa
3841 aaaaaaaaaa acaaaaccaa caaaacaaaa gacagtgtgt gtgtgtgtgt ccgttgagtg
3901 caagtccaac aaaatggcgc ttcacgcaca tccatcccct cttaggtgag cttcaatcta
```

-continued

```
3961 agcatcttgt caacaacaac aaaaatccta ggccctcaa ggtattaacc acttctgcaa
4021 tatttttcca cattttcttg ttgcttgttt ttctttgaag ttttatacac tggatttgtt
4081 agggaatga aattttctca tctaaaattt ttctagacaa tatcatgatt ttatgtaaag
4141 tctctcaatg gggaaccatt aagaaatgtt tttattttct ctatcaacag tagatttgaa
4201 actagaggtc aaaaaaaatc ttttttaaaat gctgttttgt tttaattttt gtgattttaa
4261 tttgatacaa aatgctgagg taataattac agtatgattt ttacaatagt caatgtgtgt
4321 ctgaagacta tctttgaagc cagtatctct ttcccttggc agagtatgat gatggtattt
4381 aatctgtatt ttttacagtt atacatcctg taaaatactg atatttcatt cctttgttta
4441 ctaaagagac atatttatca gttgcagata gcctatttat tataaattaa gagatgatga
4501 aaataataag gtcagtggag actttctacc cagggtgcat ggcagttgtc aggctggagt
4561 gtaccttctt cgtttgggaa actcagctct cgcagaagca gtgttccatc tttcactagc
4621 atggcctctg atacgaccat ggtgttgttc ttggtgacat tgcttctgct aaatttaata
4681 ttaataataa taaatgtcag aaaaaaaacc ctccattttg agcatcagga tttcatctga
4741 gtatggagtc gctgccatgg gagtcactaa actttggagt atgtatttca tttccaaatt
4801 gagatgcatt tactgtttgg ctgacatgaa ttttctggaa gatatgatag acctactact
4861 taaccgtttt tgtttgtttt ttttttcttg ttgttgttgt tttgttttt gttttttgt
4921 ttttctctct cacccaacac tatcttacaa aatgggtttc accccaggc caatgcagct
4981 aattttgaca gctgcattca tttatccacca gcatattgtg ttctgagtga atccactgtc
5041 tgtcctgtcg aatgcttgct caagtgtttg gcttattatt tctaagtaga tagaaagcaa
5101 taaataacta tgaaataaaa aagaattgtg ttcacaggtt ctgcgttaca acagtaacac
5161 atctttaatc cgcctaattc ttgttctgta ggataaatgc aggtattta actctttgtg
5221 aacgccaaac taaagtttac agtctttctt tctgaattt gagtatcttc tgttgtagaa
5281 taataataaa aagactatta agagcaataa attatttta agaaatcaat atttagtaaa
5341 tcctgttatg tgtttaagga ccagatgcgt tctctatttt gcctttaaat ttttgtgatc
5401 caactttaaa aacatacgtt gtcttgtttg ccctggatca tggacatgac taaaattttg
5461 tggtttcttt tcttacttat caaaagacaa cactacagat ttcatgttga ggattcattg
5521 agctctcacc ctctggcctg acaaatcttg ttaccatgaa gatagttttc ctccgtggac
5581 ttcaaattgc atctaaaatt agtgaagctt gtgtatctta tgcagacact gtgggtagcc
5641 catcaaaata taagctgtaa gctttgttcc tttcattttt tttttttac ttcttttggg
5701 agagaatatt tccaacaaac acatgcaccc caccaacagg ggaggcaaat ttcagcatag
5761 atctataaga ctttcagatg accatgggcc attgccttca tgctgtggta agtactacat
5821 ctacaatttt ggtacccgaa ctggtgcttt agaaatgcgg ggttttatt aaaaaaaaa
5881 aaaagaaatg tagcagaata attctttag tgcagcaact cagttttgt aaaggactct
5941 gagaacactt gggctgtgaa cattcaaagc agcagagagg gaacctggca ctattggggt
6001 aaagtgtttg ggtcagttga aaaaaaggaa accttttcat gcctttagat gtgagctaac
6061 agtaggtaat gatcatgtgt ccctttttga tggctgtacg aagaacttca atcactgtag
6121 tctaagatct gatctataga tgacctagaa tagccatgta atataatgtg atgattctaa
6181 atttgtacct atgtgacaga catttcaat aatgtgaaaa ctgcagattt gatggagcta
6241 ctttaagatt tgtaggtgaa agtgtgctac tgttggttga actatgctga agagggaaag
```

```
6301 tgagtgatta gtttgagccc ttgctggctc ttttccacct gccaattcta catgtattgt 6361 tgtggtttta ttcattgtat gaaaattcct gtgattttt tttaaatgtg cagtacacat 6421 cagcctcact gagctaataa agggaaaaga atgtttcaaa tcta
```

By "PGC1 beta polypeptide" is meant a protein or fragment thereof having at least 83% homology to the sequence provided at NCBI Ref: NP_001166169 or NCBI Ref: NP_573512.1 and having coactivating activity. An exemplary human PGC1 beta amino acid sequence is provided below:

```
peroxisome proliferator-activated receptor gamma coactivator 1-beta
isoform 2 [Homo sapiens]:
magndcgall deelssffln yladtqgggs geeqlyadfp eldlsqldas dfdsatcfge lqwcpenset epnqyspdds elfqidsene allaeltktl ddipeddvgl aafpaldggd alsctsaspa pssappspap ekpsapapev delsladstq dkkapmmqsq srsctelhkh ltsaqcclqd rglqppclqs prlpakedke pgedcpspqp apasprdsla lgradpgapv sqedmqamvq lirymhtycl pqrklppqtp eplpkacsnp sqqvrsrpws rhhskaswae fsilrellaq dvlcdvskpy rlatpvyasl tprsrprppk dsqaspgrps sveevriaas pkstgprpsl rplrlevkre vrrparlqqq eeedeeeeee eeeeekeeee ewgrkrpgrg lpwtklgrkl essvcpvrrs rrlnpelgpw ltfadeplvp sepqgalpsl clapkaydve relgsptded sgqdqqllrg pqipalespc esgcgdmded pscpqlpprd sprclmlals qsdptfgkks feqtltvelc gtagltpptt ppykpteedp fkpdikhslg keialslpsp eglslkatpg aahklpkkhp ersellshlr hataqpasqa gqkrpfscsf gdhdycqvlr pegvlqrkvl rswepsgvhl edwpqqgapw aeaqapgree drscdagapp kdstllrdhe irasltkhfg lletaleeed lasckspeyd tvfedssssss gessflpeee eeegeeeeed deeedsgvsp tcsdhcpyqs ppskanrqlc srsrsssgss pchswspatr rnfrcesrgp csdrtpsirh arkrrekaig egrvvyiqnl ssdmssrelk rrfevfgeie ecevltrnrr gekygfityr csehaalslt kgaalrkrne psfqlsyggl rhfcwprytd ydsnseealp asgkskyeam dfdsllkeaq qslh
```

An exemplary murine PGC1 beta polypeptide amino acid sequence is provided below:

```
MAGNDCGALLDEELSSFFLNYLSDTQGGDSGEEQLCADLPELDLSQLDAS

DFDSATCFGELQWCPETSETEPSQYSPDDSELFQIDSENEALLAALTKTL

DDIPEDDVGLAAFPELDEGDTPSCTPASPAPLSAPPSPTLERLLSPASDV

DELSLLQKLLLATSSPTASSDALKDGATWSQTSLSSRSQRPCVKVDGTQD

KKTPTLRAQSRPCTELHKHLTSVLPCPRVKACSPTPHPSPRLLSKEEEEE

VGEDCPSPWPTPASPQDSLAQDTASPDSAQPPEEDVPAMVQLIRYMHTYC

LPQRKLPQRAPEPIPQACSSLSRQVQPRSRHPPKAFWTEFSILRELLAQD

ILCDVSKPYRLAIPVYASLTPQSRPRPPKDSQASPAHSAMAEEVRITASP

KSTGPRPSLRPLRLEVKRDVNKPTRQKREEDEEEEEEEEEEEKEEEEE

EWGRKRPGRGLPWTKLGRKMDSSVCPVRRSRRLNPELGPWLTFTDEPLGA

LPSMCLDTETHNLEEDLGSLTDSSQGRQLPQGSQIPALESPCESGCGDTD

EDPSCPQPTSRDSSRCLMLALSQSDSLGKKSFEESLTVELCGTAGLTPPT

TPPYKPMEEDPFKPDTKLSPGQDTAPSLPSPEALPLTATPGASHKLPKRH

PERSELLSHLQHATTQPVSQAGQKRPFSCSFGDHDYCQVLRPEAALQRKV

LRSWEPIGVHLEDLAQQGAPLPTETKAPRREANQNCDPTHKDSMQLRDHE

IRASLTKHFGLLETALEGEDLASCKSPEYDTVFEDSSSSSGESSFLLEEE

EEEEEGGEEDDEGEDSGVSPPCSDHCPYQSPPSKASRQLCSRSRSSSGSS

SCSSWSPATRKNFRRESRGPCSDGTPSVRHARKRREKAIGEGRVVYIRNL

SSDMSSRELKKRFEVFGEIVECQVLTRSKRGQKHGFITFRCSEHAALSVR

NGATLRKRNEPSFHLSYGGLRHFRWPRYTDYDPTSEESLPSSGKSKYEAM

DFDSLLKEAQQSLH
```

By "PGC1 beta polynucleotide" is meant a nucleic acid molecule encoding a PGC1 beta polypeptide. An exemplary human PGC1 beta polynucleotide sequence is provided at NM_001172698:

```
   1 ctcctccctc ctcccttgct cgctcgctgg ctccctcccc ccgggccggc tcggcgttga
  61 ctccgccgca cgctgcagcc gcggctggaa gatggcgggg aacgactgcg gcgcgctgct
 121 ggacgaagag ctctcctcct tcttcctcaa ctatctcgct gacacgcagg gtggagggtc
 181 cggggaggag caactctatg ctgactttcc agaacttgac ctctcccagc tggatgccag
 241 cgactttgac tcggccacct gctttgggga gctgcagtgg tgcccagaga actcagagac
 301 tgaacccaac cagtacagcc ccgatgactc cgagctcttc agattgaca gtgagaatga
 361 ggccctcctg gcagagctca ccaagaccct ggatgacatc cctgaagatg acgtgggtct
 421 ggctgccttc ccagccctgg atggtggaga cgctctatca tgcacctcag cttcgcctgc
 481 ccctcatct gcaccccca gccctgcccc ggagaagccc tcggccccag ccctgaggt
 541 ggacgagctc tcactggcgg acagcaccca agacaagaag gctcccatga tgcagtctca
 601 gagccgaagt tgtacagaac tacataagca cctcacctcg gcacagtgct gcctgcagga
 661 tcggggtctg cagccaccat gcctccagag tccccggctc cctgccaagg aggacaagga
 721 gccgggtgag gactgcccga gccccagcc agctccagcc tctccccggg actccctagc
 781 tctgggcagg gcagaccccg gtgccccggt ttcccaggaa gacatgcagg cgatggtgca
 841 actcatacgc tacatgcaca cctactgcct cccccagagg aagctgcccc cacagacccc
 901 tgagccactc cccaaggcct gcagcaaccc ctcccagcag gtcagatccc ggccctggtc
 961 ccggcaccac tccaaagcct cctgggctga gttctccatt ctgagggaac ttctggctca
1021 agacgtgctc tgtgatgtca gcaaacccta ccgtctggcc acgcctgttt atgcctccct
1081 cacacctcgg tcaaggccca ggcccccaa agacagtcag gcctcccctg gtcgcccgtc
1141 ctcggtggag gaggtaagga tcgcagcttc acccaagagc accgggccca gaccaagcct
1201 gcgcccactg cggctggagg tgaaaaggga ggtccgccgg cctgccagac tgcagcagca
1261 ggaggaggaa gacgaggaag aagaggagga ggaagaggaa gaagaaaaag aggaggagga
1321 ggagtggggc aggaaaaggc caggccgagg cctgccatgg acgaagctgg ggaggaagct
1381 ggagagctct gtgtgccccg tgcggcgttc tcggagactg aaccctgagc tgggcccctg
1441 gctgacattt gcagatgagc cgctggtccc ctcggagccc caaggtgctc tgccctcact
1501 gtgcctggct cccaaggcct acgacgtaga gcgggagctg ggcagcccca cggacgagga
1561 cagtggccaa gaccagcagc tcctacgggg accccagatc cctgccctgg agagcccctg
1621 tgagagtggg tgtggggaca tggatgagga ccccagctgc ccgcagctcc ctcccagaga
1681 ctctcccagg tgcctcatgc tggccttgtc acaaagcgac ccaacttttg gcaagaagag
1741 ctttgagcag accttgacag tggagctctg tggcacagca ggactcaccc cacccaccac
1801 accaccgtac aagcccacag aggaggatcc cttcaaacca gacatcaagc atagtctagg
1861 caaagaaata gctctcagcc tcccctcccc tgagggcctc tcactcaagg ccaccccagg
1921 ggctgcccac aagctgccaa agaagcaccc agagcgaagt gagctcctgt cccacctgcg
1981 acatgccaca gcccagccag cctcccaggc tggccagaag cgtcccttct cctgttcctt
2041 tggagaccat gactactgcc aggtgctccg accagaaggc gtcctgcaaa ggaaggtgct
2101 gaggtcctgg gagccgtctg gggttcacct tgaggactgg ccccagcagg tgccccttg
2161 ggctgaggca caggcccctg gcaggaggagg agacagaagc tgtgatgctg cgcgccccacc
2221 caaggacagc acgctgctga gagaccatga gatccgtgcc agcctcacca aacactttgg
2281 gctgctggag accgccctgg aggaggaaga cctggcctcc tgcaagagcc ctgagtatga
2341 cactgtcttt gaagacagca gcagcagcag cggcgagagc agcttcctcc cagaggagga
2401 agaggaagaa ggggaggagg aggaggagga cgatgaagaa gaggactcag gggtcagccc
```

-continued

```
2461  cacttgctct gaccactgcc cctaccagag cccaccaagc aaggccaacc ggcagctctg
2521  ttcccgcagc cgctcaagct ctggctcttc accctgccac tcctggtcac cagccactcg
2581  aaggaacttc agatgtgaga gcagagggcc gtgttcagac agaacgccaa gcatccggca
2641  cgccaggaag cggcgggaaa aggccattgg ggaaggccgc gtggtgtaca ttcaaaatct
2701  ctccagcgac atgagctccc gagagctgaa gaggcgcttt gaagtgtttg gtgagattga
2761  ggagtgcgag gtgctgacaa gaataggag aggcgagaag tacggcttca tcacctaccg
2821  gtgttctgag cacgcggccc tctctttgac aaagggcgct gccctgagga agcgcaacga
2881  gccctccttc cagctgagct acggagggct ccggcacttc tgctggccca gatacactga
2941  ctacgattcc aattcagaag aggcccttcc tgcgtcaggg aaaagcaagt atgaagccat
3001  ggattttgac agcttactga agaggccca gcagagcctg cattgataac agccttaacc
3061  ctcgaggaat acctcaatac ctcagacaag gcccttccaa tatgtttacg ttttcaaaga
3121  aatcaagtat atgaggagag cgagcgagcg tgagagaaca cccgtgagag agacttgaaa
3181  ctgctgtcct ttaaaaaaaa aaaaaatcaa tgtttacatt gaacaaagct gcttctgtct
3241  gtgagttttcc atggtgttga cgttccactg ccacattagt gtcctcgctt ccaacgggtt
3301  gtcccgggtg cacctcgaag tgccgggtcc gtcacccatc gcccttcct tcccgactga
3361  cttcctctcg tagacttgca gctgtgttca ccataacatt tcttgtctgt agtgtgtgat
3421  gatgaaattg ttacttgtga atagaatcag gactataaac ttcatttta attgaaaaaa
3481  aaagtatatc cttaaaataa tgtatttatg gctcagatgt actgtgcctg ggattattgt
3541  attgcttcct tgatttttta actatgcact gtcatgaggt gtttgccact gagctgccct
3601  gctccccttg ccagattgcc ctggaggtgc tgggtggccg ctaggctggt ctgcaggaaa
3661  gcgcggcctg ccgtttccgg gccgtatctg ccaagccctg ccttgtctct tactgagcaa
3721  gtttggctca aattatagga gccccatct tgtgcccagc tcatgctcca agtgtgtgtc
3781  tatccatttg tactcagact cttgagtacc ttgtaaggaa ggcggggcaa gctgcatcat
3841  tcctgttttc caggggaggc tggcagctcc tcaagaggcg aaatgactgt gggaggtccg
3901  gttaccagtg aggaggcaga gcggtgaccc agaccaggcc ttctggttct tggtcccgtg
3961  cttccgtagt agctggggta aagacaccgt ttcagggact ggtagaggtg agttcggcta
4021  aattgggcac cgggctagaa gcctaagggc tcattttagg ggttacatta ggtgttgatt
4081  caccagcatc aggtgaattc aagccctggc atgtgtcttg gatgcaccat cagctttgat
4141  cctgagtggt cctgcggttt gtctgtgcct gtggacacac tgtcagaact tcagtgacac
4201  ccctggcagc ggtacagaca ggtggtctgg gagcagtcat ctttttggg ccagccacca
4261  gcccatccta ctccctcagg tagtccttcg tctttacctt gtccttgtct gtaaagttgt
4321  tttggtggct ggggcagggg agccaggagg agggagtgaa ggttgggaat agataggaca
4381  atctcctagc tctcctccaa ttgagaaaac actccaattg ggctttgctt taaactttgt
4441  gttcttaagt gatgtcaaag ccatttccag cttaatgttc tgtgggtacc ttgggggcca
4501  ttcatgcagg gagcatggcc aggcagggta tgagtacatt gtttctgatt tctttcatac
4561  atcagggttc ctcgggaaat ttttgtattt tttttttaag tcctgctgct ttaaaaattt
4621  gaaagtggct cattaaacta aacaggctaa tgtaatttgt tgcttatgcc aagcctagac
4681  tgttgagaat tgacgttttt aaagattatc aaatacctca gtaggtaaaa tgagcccatg
4741  atcttccact gagtggtgag catactccca gcccatggac aaggccggaa gagacaggct
4801  ttagtagggg tagggaattt gaactgttgt gtgtcacagc agttgacctc tctggactcc
```

-continued

```
4861 aatttccttt cctgtgaaat gaactgatta gacatgtttc aacattgtta gcttctgctg 4921 aggcagtgtc tagcccaaga tggcaaatac atagctcatg tgccactact cccacctcct 4981 tgaccaatac agacataact aatcaatcac accactcagg ttccctgagc ctggatgtgc 5041 tataagaatc ctgaaatcag tgctctggta agtcattact aattgattag agttcaatct 5101 atttgacatc ttgggctaat ctttggaagg tttccaacaa tcacacaaaa ccatatgctg 5161 gctgggtttc atgctggcct atccctgtct gtgatgttcc gttccatgag agaaaactcc 5221 cctaatgcta ttccatggcg taacactccc aatactattt tgacgcccac gtccccttgc 5281 agagggtgca gggggcggta gacgaatgac agacaggaac atatttgggg aaggcagggc 5341 ttaggaagat ggaccaaaaa gggacttccc acagcacaga cctgatcatt cggatttcct 5401 ctttagctat tcactgccta gcacatagta ggcacacaat aaatgattat ggaatgggat 5461 aaaatttaga tctttctgct gcctccacta agttaagtcc tgatttacat caaggagaga 5521 actgagatag gaaagaacac tagattccaa gtctggagag ttgggggagt ccagattcta 5581 ccaagaattt cctttgtaac tttggtaagt ccctttttact ccctggcacc ccggtgtgct 5641 gaaaggagtt ggtccatata tgatctctta gcccctccta tttgcttctt ccttgattgc 5701 tcttggtcaa agggtcagcc ttgggctggt gatactttag agtaaagaaa tggagagttt 5761 tagcaaagga ccagtctgtc cctccctgct ttggggtcag ctaaagctgt cctttcatgt 5821 cagattaacc taggacactt gtagttagct tagacgttgg cccttgagca gagacctgag 5881 cgtggcattg ggacatgaca tacctaaagt cagggctagg ggacgctgcc tgccaagggc 5941 atcgagtagt ctctacttgc tatcccgtac ataaaatgct acaagttcta aaatttaccg 6001 accctgcaga caacctctat cccgaaggac tcattcggtg ctgtgtatta tttagggcaa 6061 ctccaaggtc tattcagaaa aacgagtgaa ccttggtctc tttcccacca aattgaggag 6121 taacccagag ggagcagctg ccattggcaa ccatctcgtt gtagctctgt cctagtgttt 6181 gctcttgatg atgtttacat gtgatcgcca taaagcttgc tgtagactgt gtcgatagcc 6241 gcccgcacag ggcaggtcgt actgtccgtt tctgtgccgt gctggtgttt tccaaaaatg 6301 tctgatccaa ccactaagtg gaattcttcc atctccttcc tcagtctgta caaggctgaa 6361 tcagaatccc cattctcggg ggctctggtt accgaaggaa aatgcatcaa agagttaaag 6421 aatatgagtg gatggagtgc agctaaggcc cccacccccct gctccgtcac aacttgcccc 6481 ctcaaccaaa aagctgcttt gagtcaaaaa gcacccataa gatacctgca tctgccttga 6541 aatcttgcag catggagtgt catatgtact caggagagag gcagggcttt gcgggcagga 6601 gaaggaaggg aggaatgctc tgagctgcaa agacccagta ctcaagttct gacgtgggag 6661 gagatgcagt gagacgtctc ttgttgccta agcctgttc ctgttggttt tcttagagtg 6721 atttctccta gacatgtgca gtaggcccac tggggctgct gtgcagtggt gagtaaaagg 6781 gcagggaagg catggacagc ctggtccttc tgcatggaca gctcagtcca tggcccatcc 6841 caggtataga gttcagttaa tcccatttga gcctgcagct taagagatgg ctcatcctaa 6901 ctgtgaagca aaatcagccc cagaggatgt attgatctga ctcactgatg tcaaaattgc 6961 agtatttttt tagcatttga gatttagcag ctgccttcag tttggggtta cccacatccc 7021 agcatcagat atgattaagg aaagaaattg gatgtacaac agcaaagaaa gtgaatgtca 7081 tggtttccct ggccaaagaa gagggaccct gtcatcctta ccaatgggga agaagaaaac 7141 tagtgcatgt gcaatatgtc aaagttagtc ccctagtccc tgaggggttt ttacacacag 7201 atgggctcca ggtctgctcg tcaagtttgg aggtaccggg taaatggagg ggagctgcag 7261 agttggaaac ccacatgcat ggatgtgtcc ttggcccaga accaccatgg gatgggggag
```

-continued

```
7321  gccctgagcc ggctacaaga cacccaggaa gtaggcaaag gctgactttg cattaaacaa
7381  taaaagcact ttgagaaaac cccaacactt cagcctgggt ccgtgtttct acactggaaa
7441  atacgagtct cctttggctg tgtgaagtga tcttctagag actgggacag ggagtttggg
7501  aatggggctg ctgtcaggta ggagagagca gagatgcctt tggagatgtc agcagcagga
7561  gagccagtgc tggggccaac cctttgctgg ccttttgttg aagcccttg aaacagggag
7621  ccatgggttt agatcttggt acctacctt acagaaagat gaaaacagcc cagctgagtg
7681  aaatgagttt gtagagtaag tcacttaact gtaagccatc tcagaatcag aaaccctaat
7741  gtttcttact tgctatgtga ccttgggccc ctgtttcctc atctaccaaa tgagaatgtt
7801  gaatatgagc attaaagtcc ctttcacctc tgagaggctc agatccccaa ccaggagcat
7861  tgggaatcca tcactcctcc ttgaaactga ttccattctc tgacttgacc cagctcctgt
7921  tcagggtgag ggttctctgc aagaaccaac cagcagtagg ttcaatccca ctgtgtcctg
7981  gctgagttgc cttatccaag aagaccagct ccccgggaca gatctaagcc atagtttcta
8041  gtggggacag taaggaatta aacccccaac ttggctaggt aacgatgtca aatctcacat
8101  taaccttgtc tttgtcccca ctggatagct gttaatccga atgttgtgac catttggctg
8161  tttctctctt gttctcagac aatactagca atacactttt ttttttttt tttaaagaaa
8221  aacagcttag gagcttttca cacatttctt tcaaatgatt gtaaaacata tggggcaaca
8281  ggaggcattg atcgcgctgc atatgtttag ggcagctttt gttttttgtt tctttaatgg
8341  tatagcagca gtgactgagc cttcgtgatt cctggggaca gcttttcaga tactctgttt
8401  catcagtatg ctttgcacat ccggaaggag tacaaaaatc caactgccca aatttggggc
8461  ttggaaaata ggttttatag gtggtcggtc cctggctgt gcaacaactc ctcaaagagg
8521  ggtttatata actagaaccc ccctgggctg tattttggt caaaggagtc tccaaggcgg
8581  cttacaaaag cttccttttt cacttgacca cccttgctca ttggttactt gtgaagggaa
8641  ttggtcagtt tccacctcag cactttgcct tatcaacatg cggtcgccat ctagtggcca
8701  aaggttgtct ccaccagcta cccagatgga aggcaaataa atcctttcgg ccaccctgct
8761  gtccatcgtg aactttggga atgaaatata atggcctgaa cgaactgcct ttgtgttcag
8821  agatcagtgc aacactaggg tcagaagact ccagaagcag ccacttagta gactctcacg
8881  cagaactgag aaatgcacta gctgtcctgt gggcagaaga gacaggagtg gaccaggaga
8941  ggtccaggtg cccggggaagg gtttactgta actgcaatac tggcagccca gctgctgacc
9001  ttgttaagta aacctttgct gggtggtccg aattctgccc tcaaggcaag ataagaagtt
9061  gggtgtaagg attttgtggg gggcctggcc atgatctttg atatgatccc cgaatagcca
9121  aatagttttt tttgttcaat ttttttgttc tgtattttgt atttttaaaa tcttgtcaaa
9181  tgttttgtg ttaggaataa aaagtcataa actattccca actttgtttc ttgagggatg
9241  ttctgattcc aatggaaaca ggtgggaaat ctcaagggga gcgtggacaa ggtggtatgt
9301  gcagcagggg aatagactgc ttggatttcc aaatggtttc tggggaagat gaccatccag
9361  aagtccagct tagtgcagtc tgctctggaa ttcacaccca cccctcgcc tccttgtgcc
9421  atgttgttag cattggcttg gagcatctgc ttcttccaga ggcagctgct aatgttgaaa
9481  ccaacacgag ccctctcccc aaccccaggt ttctaaagaa ggtgtctgta gccagcctta
9541  atcaactggg caaggtggtc cctatggtcc tttccagcat ttccaaatct tggactcaaa
9601  ttattttctc ttggtgtgac cacacagcct agagaattct gagcaatagg agccagggct
9661  ttccctgact ctgcgacagg gtcaaaccaa ggaatggcta aacctgtgag gttttgtcat
```

-continued

```
 9721 ccccgggggt actactgtag ggggcattat ttattaggaa gcttaacaag gtaactacgg 9781 cctgagtgcg tgagtgtaag gctgtgtttg tggtgggggt gtgtgtgtgt gtatctgtgc 9841 acacatacac acgtctgtgc ctgtgtgtgt gtgtttgtgt gtgtgtgtgt gtgtggaatt 9901 acattgatgc atttattgag aaaggtgcaa gaatttcacc tacacagagg gacacatctg 9961 ctttgttatt tataatagaa agctaaattt taattttttta aaggacactg ctaatgattg 10021 agaatcaagt ttttagtttt gctatttttt ttaattggta gaggattttt atatattttt 10081 tccattttgt tgggttgtgt ccttatttat ataaatactt tatccgtaag aggcaaggag 10141 gaaaccttct ttgcttttac atattgtggt tgtcatcgtc cctattttat ttctggtgtg 10201 atttctctgt cttaccttct aaatgagaaa atgttttctt gtatttgtac attgtcagat 10261 tctatagttt cctagataat ttaaccaaat tgctctatgt attattattc tgtgagtata 10321 aagttctatt ttaatgtctg taaatacttc agaactggct tcttttctca aactcccact 10381 gtggggttat tgtttacatc acagaaactg tagaatctct atgctcatgt actgtaaata 10441 gtgaagtgat ctgcttataa ataaacttaa caaatacact atggagatta aaaacaaaat 10501 accacccaca aaaaaaaaaa aaaaa
```

An exemplary murine PGC1 beta polynucleotide sequence is provided at NM_133249.2:

```
   1 ctcgctccct ccccccgggcg ggctcggcgc tgactccgcc gcacgctgca gccgcggctg 61 gaagatggcg gggaacgact gcggcgcgct gctggatgaa gagctctcgt ccttcttcct 121 caactatctc tctgacacgc agggtgggga ctctggagag gaacagctgt gtgctgactt 181 gccagagctt gacctctccc agctggacgc cagtgacttt gactcagcca cgtgctttgg 241 ggagctgcag tggtgcccgg agacctcaga gacagagccc agccagtaca gccccgatga 301 ctccgagctc ttccagattg acagtgagaa tgaagctctc ttggctgcgc ttacgaagac 361 cctggatgac atccccgaag acgatgtggg gctggctgcc ttcccagaac tggatgaagg 421 cgacacacca tcctgcaccc cagcctcacc tgcccccttg tctgcacccc cagccccac 481 cctggagagg cttctgtccc cagcgtctga cgtggacgag cttttcactgc tacagaagct 541 cctcctggcc acatcctccc aacagcaag ctctgacgct ctgaaggacg gggccacctg 601 gtcccagacc agcctcagtt ccagaagtca gcggccttgt gtcaaggtgg atggcaccca 661 ggataagaag accccccacac tgcgggctca gagccggcct tgtacggaac tgcataagca 721 cctcacttcg gtgctgccct gtcccagagt gaaagcctgc tccccaactc cgcacccgag 781 cccctcggctc ctctccaaag aggaggagga ggaggtgggg gaggattgcc caagcccttg 841 gccgactcca gcctcgcccc aagactccct agcacaggac acggccagcc ccgacagtgc 901 ccagcctccc gaggaggatg tgagggccat ggtacagctc attcgctaca tgcatacccta 961 ctgcctgcct cagaggaagc tgccccaacg ggccccagag ccaatccccc aggcctgcag 1021 cagcctctcc aggcaggttc aaccccgatc ccggcatccc cccaaagcct tctggactga 1081 gttctctatc ctaagggaac ttctggccca agatatcctc tgtgatgtta gcaagcccta 1141 ccgcctggcc atacctgtct atgcttccct cacacctcag tccaggccca gccccccaa 1201 ggacagtcag gcctcccctg cccactctgc catggcagaa gaggtgagaa tcactgcttc 1261 ccccaagagc accgggccta gacccagcct gcgtcctctg aggctggagg tgaaacggga 1321 tgttaacaag cctacaaggc aaaagcggga ggaagatgag gaggaggagg aggaagaaga 1381 agaagaggaa gaagaaaaag aagaggaaga agaggagtgg ggcaggaaga gaccaggtcg
```

-continued

```
1441 tggcctgcca tggaccaaac tagggaggaa gatggacagc tccgtgtgcc ccgtgcggcg
1501 ctccaggaga ctgaatccag agctgggtcc ctggctgaca ttcactgatg agcccttagg
1561 tgctctgccc tcgatgtgcc tggatacaga gacccacaac ctggaggaag acctgggcag
1621 cctcacagac agtagtcaag gccggcagct cccccaggga tcccagatcc ccgccctgga
1681 aagcccctgt gagagtgggt gcggagacac agatgaagat ccaagctgcc cacagcccac
1741 ttccagagac tcctccaggt gcctcatgct ggccttgtca caaagcgact ctcttggcaa
1801 gaagagcttt gaggagtccc tgacggtgga gctttgcggc acggcaggac tcacgccacc
1861 caccacacct ccatacaagc caatggagga ggaccccttc aagccagaca ccaagctcag
1921 cccaggccaa gacacagctc ccagccttcc ctcccccgag gctcttccgc tcacagccac
1981 cccaggagct tcccacaagc tgcccaagag gcacccagag cgaagcgagc tcctgtccca
2041 tttgcagcat gccacaaccc aaccagtctc acaggctggc cagaagcgcc ccttctcctg
2101 ctccttttgga gaccacgact actgccaggt gctcaggcca gaggctgccc tgcagaggaa
2161 ggtgctgcgg tcctgggagc caatcggggt ccaccttgaa gacttggccc agcagggtgc
2221 ccctctgcca acggaaacaa aggcccctag cagggaggca aaccagaact gtgaccctac
2281 ccacaaggac agcatgcagc taagagacca tgagatccgt gccagtctca caaagcactt
2341 tgggctgctg gagactgctc tggaaggtga agacctggcg tcctgtaaaa gcccggagta
2401 tgacaccgta tttgaggaca gcagcagcag cagtggcgag agtagcttcc tgcttgagga
2461 ggaggaggaa gaggaggagg gaggggaaga ggacgatgaa ggagaggact caggggtcag
2521 ccctccctgc tctgatcact gcccctacca gagcccaccc agtaaggcca gtcggcagct
2581 ctgctcccga agccgctcca gttccggctc ctcgtcctgc agctcctggt caccagccac
2641 ccggaagaac ttcagacgtg agagcagagg gccctgttca gatggaaccc caagcgtccg
2701 gcatgccagg aagcggcggg aaaaggccat cggtgaaggc cgtgtggtat acattcgaaa
2761 tctctccagt gacatgagct ctcgggaact aaagaagcgc tttgaggtgt cggtgagat
2821 tgtagagtgc caggtgctga cgagaagtaa aagaggccag aagcacggtt ttatcacctt
2881 ccggtgttca gagcacgctg ccctgtccgt gaggaacggc gccaccctga aaagcgcaa
2941 tgagcccctcc ttccacctga gctatggagg gctccggcac ttccgttggc cagatacac
3001 tgactatgat cccacatctg aggagtccct tccctcatct gggaaaagca agtacgaagc
3061 catggatttt gacagcttac tgaaagaggc ccagcagagc ctgcattgat atcagcctta
3121 accttcgagg aatacctcaa tacctcagac aaggcccttc caatatgttt acgttttcaa
3181 agaaaagagt atatgagaag gagagcgagc gagcgagcga gcgagcgagt gagcgtgaga
3241 gatcacacag gagagagaaa gacttgaatc tgctgtcgtt tcctttaaaa aaaaaaaac
3301 gaaaaacaaa aacaaatcaa tgtttacatt gaacaaagct gcttccgtcc gtctgtccgt
3361 ccgtccgtcc gtccgtgagt ttccatgctg ttgatgttcc actgccacgt tagcgtcgtc
3421 ctcgcttcca gcggatcgtc ctgggtgcgc ctccaagtgc tgtcagtcgt cctctgcccc
3481 tcccacccga ctgacttcct tctgttagac ttgagctgtg ttcacataac atcttctgtc
3541 tgtagagtgt gatgatgaca ttgttacttg tgaatagaat caggagttag aaactcattt
3601 ttaattgaag aaaaaaaaag tatatcctta aaagaaaaa aaaaaaaaca aatgta
```

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "positive" is meant that a cell expresses a detectable level of a marker.

By "promoter" is meant a polynucleotide sufficient to direct transcription.

By "reference" is meant a standard or control condition. In one embodiment, a reference cell is a cell that expresses Sca1 and/or CD34. In another embodiment, the reference cell expresses Sca1 and/or CD34 and also expresses Oct4, Sox2, Klf4 and cMyc (OSKM).

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "reprogramming" is meant altering a cell such that at least one protein product is produced in the reprogrammed cell that is not produced in the cell prior to reprogramming or that is not expressed in a corresponding control cell. Typically, the reprogrammed cell has an altered transcriptional or translational profile, such that the reprogrammed cell expresses a set of proteins not expressed in the cell prior to reprogramming (or in a corresponding control cell).

By "regenerate" is meant capable of contributing at least one cell to the repair or de novo construction of a tissue or organ.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "SOX2 polypeptide" is meant a protein or fragment thereof having at least 85% homology to the sequence provided at NCBI Ref: NP_003097.1 (human) or NP_035573.3 (murine). An exemplary human amino acid sequence is provided below:

MYNMMETELKPPGPQQTSGGGGGNSTAAAAGGNQKNSPDRVKRPMNAFMV

WSRGQRRKMAQENPKMHNSEISKRLGAEWKLLSETEKRPFIDEAKRLRAL

HMKEHPDYKYRPRRKTKTLMKKDKYTLPGGLLAPGGNSMASGVGVGAGLG

-continued

AGVNQRMDSYAHMNGWSNGSYSMMQDQLGYPQHPGLNAHGAAQMQPMHRY

DVSALQYNSMTSSQTYMNGSPTYSMSYSQQGTPGMALGSMGSVVKSEASS

SPPVVTSSSHSRAPCQAGDLRDMISMYLPGAEVPEPAAPSRLHMSQHYQS

GPVPGTAINGTLPLSHM

An exemplary murine amino acid sequence is provided below:

MYNMMETELKPPGPQQASGGGGGGGNATAAATGGNQKNSPDRVKRPMNAF
MVWSRGQRRKMAQENPKMHNSEISKRLGAEWKLLSETEKRPFIDEAKRLR

-continued

ALHMKEHPDYKYRPRRKTKTLMKKDKYTLPGGLLAPGGNSMASGVGVGAG

LGAGVNQRMDSYAHMNGWSNGSYSMMQEQLGYPQHPGLNAHGAAQMQPMH

RYDVSALQYNSMTSSQTYMNGSPTYSMSYSQQGTPGMALGSMGSVVKSEA

SSSPPVVTSSSHSRAPCQAGDLRDMISMYLPGAEVPEPAAPSRLHMAQHY

QSGPVPGTAINGTLPLSHM

By "SOX2 polynucleotide" is meant a nucleic acid molecule encoding a SOX2 polypeptide. An exemplary human SOX2 polynucleotide sequence is provided at NM_003106:

```
   1 ggatggttgt ctattaactt gttcaaaaaa gtatcaggag ttgtcaaggc agagaagaga
  61 gtgtttgcaa aaggggggaaa gtagtttgct gcctctttaa gactaggact gagagaaaga
 121 agaggagaga gaaagaaagg gagagaagtt tgagcccag gcttaagcct ttccaaaaaa
 181 taataataac aatcatcggc ggcggcagga tcggccagag gaggagggaa gcgcttttt
 241 tgatcctgat tccagtttgc ctctctcttt ttttcccca aattattctt cgcctgattt
 301 tcctcgcgga gccctgcgct cccgacaccc ccgcccgcct cccctcctcc tctcccccg
 361 cccgcgggcc cccaaagtc ccggccgggc cgagggtcgg cggccgccgg cgggccgggc
 421 ccgcgcacag cgcccgcatg tacaacatga tggagacgga gctgaagccg ccgggccccgc
 481 agcaaacttc gggggggcggc ggcggcaact ccaccgcggc ggcggccggc ggcaaccaga
 541 aaaacagccc ggaccgcgtc aagcggccca tgaatgcctt catggtgtgg tcccgcgggc
 601 agcggcgcaa gatggcccag gagaacccca agatgcacaa ctcggagatc agcaagcgcc
 661 tgggcgccga gtggaaactt ttgtcggaga cggagaagcg gccgttcatc gacgaggcta
 721 agcggctgcg agcgctgcac atgaaggagc cccggatta taaataccgg ccccggcgga
 781 aaaccaagac gctcatgaag aaggataagt acacgctgcc cggcgggctg ctggcccccg
 841 gcggcaatag catggcgagc ggggtcgggg tgggcgccgg cctgggcgcg ggcgtgaacc
 901 agcgcatgga cagttacgcg cacatgaacg gctggagcaa cggcagctac agcatgatgc
 961 aggaccagct gggctacccg cagcacccgg gcctcaatgc gcacggcgca gcgcagatgc
1021 agccccatgca ccgctacgac gtgagcgccc tgcagtacaa ctccatgacc agctcgcaga
1081 cctacatgaa cggctcgccc acctacagca tgtcctactc gcagcagggc acccctggca
1141 tggctcttgg ctccatgggt tcggtggtca agtccgaggc cagctccagc ccccctgtgg
1201 ttacctcttc ctcccactcc agggcgccct gccaggccgg ggacctccgg acatgatca
1261 gcatgtatct ccccggcgcc gaggtgccgg aacccgccgc ccccagcaga cttcacatgt
1321 cccagcacta ccagagcggc ccggtgcccg gcacggccat taacggcaca ctgcccctct
1381 cacacatgtg agggccggac agcgaactgg aggggggaga aattttcaaa gaaaaacgag
1441 ggaaatggga ggggtgcaaa agaggagagt aagaaacagc atggagaaaa cccggtacgc
1501 tcaaaaagaa aaaggaaaaa aaaaaatccc atcacccaca gcaaatgaca gctgcaaaag
1561 agaacaccaa tcccatccac actcacgcaa aaaccgcgat gccgacaaga aaactttat
1621 gagagagatc ctggacttct ttttgggga ctattttgt acagagaaaa cctggggagg
1681 gtggggaggg cgggggaatg gaccttgtat agatctggag gaaagaaagc tacgaaaaac
1741 ttttttaaaag ttctagtggt acggtaggag ctttgcagga agtttgcaaa agtctttacc
1801 aataatattt agagctagtc tccaagcgac gaaaaaatg ttttaatatt tgcaagcaac
```

-continued

```
1861 ttttgtacag tatttatcga gataaacatg gcaatcaaaa tgtccattgt ttataagctg 1921 agaatttgcc aatattttc aaggagaggc ttcttgctga attttgattc tgcagctgaa 1981 atttaggaca gttgcaaacg tgaaagaag aaaattattc aaatttggac atttaattg 2041 tttaaaaatt gtacaaaagg aaaaattag aataagtact ggcgaaccat ctctgtggtc 2101 ttgtttaaaa agggcaaaag ttttagactg tactaaattt tataacttac tgttaaaagc 2161 aaaaatggcc atgcaggttg acaccgttgg taatttataa tagcttttgt tcgatcccaa 2221 ctttccattt tgttcagata aaaaaaacca tgaaattact gtgtttgaaa tatttcta 2281 tggtttgtaa tatttctgta aatttattgt gatattttaa ggttttcccc cctttatttt 2341 ccgtagttgt attttaaaag attcggctct gtattatttg aatcagtctg ccgagaatcc 2401 atgtatatat ttgaactaat atcatcctta taacaggtac attttcaact taagttttta 2461 ctccattatg cacagtttga gataaataaa tttttgaaat atggacactg aaaaaaaaaa
```

An exemplary murine SOX2 polynucleotide sequence is provided at NM 011443.3:

```
   1 ctattaactt gttcaaaaaa gtatcaggag ttgtcaaggc agagaagaga gtgtttgcaa 61 aaagggaaaa gtactttgct gcctctttaa gactagggct gggagaaaga agaggagaga 121 gaaagaaagg agagaagttt ggagcccgag gcttaagcct ttccaaaaac taatcacaac 181 aatcgcggcg gcccgaggag gagagcgcct gttttttcat cccaattgca cttcgcccgt 241 ctcgagctcc gcttcccccc aactattctc cgccagatct ccgcgcaggg ccgtgcacgc 301 cgaggccccc gcccgcggcc cctgcatccc ggccccgag cgcggccccc acagtcccgg 361 ccgggccgag ggttggcggc cgccggcggg ccgcgcccgc ccagcgcccg catgtataac 421 atgatggaga cggagctgaa gccgccgggc ccgcagcaag cttcgggggg cggcggcgga 481 ggaggcaacg ccacggcggc ggcgaccggc ggcaaccaga gaacagccc ggaccgcgtc 541 aagaggccca tgaacgcctt catggtatgg tcccgggggc agcggcgtaa gatgcccag 601 gagaacccca agatgcacaa ctcggagatc agcaagcgcc tgggcgcgga gtggaaactt 661 ttgtccgaga ccgagaagcg gccgttcatc gacgaggcca agcggctgcg cgctctgcac 721 atgaaggagc acccggatta taatacccgg ccgcggcgga aaaccaagac gctcatgaag 781 aaggataagt acacgcttcc cggaggcttg ctggcccccg gcgggaacag catggcgagc 841 ggggttgggg tgggcgccgg cctgggtgcg ggcgtgaacc agcgcatgga cagctacgcg 901 cacatgaacg gctggagcaa cggcagctac agcatgatgc aggagcagct gggctacccg 961 cagcacccgg gcctcaacgc tcacggcgcg gcacagatgc aaccgatgca ccgctacgac 1021 gtcagcgccc tgcagtacaa ctccatgacc agctcgcaga cctacatgaa cggctcgccc 1081 acctacagca tgtcctactc gcagcagggc accccggta tggcgctggg ctccatgggc 1141 tctgtggtca gtccgaggc cagctccagc ccccccgtgg ttacctcttc ctcccactcc 1201 agggcgccct gccaggccgg ggacctccgg gacatgatca gcatgtacct ccccggcgcc 1261 gaggtgccgg agcccgctgc gcccagtaga ctgcacatgg cccagcacta ccagagcggc 1321 ccggtgcccg gcacggccat taacggcaca ctgcccctgt cgcacatgtg agggctggac 1381 tgcgaactgg agaaggggag agattttcaa agagatacaa gggaattggg aggggtgcaa 1441 aaagaggaga gtaggaaaaa tctgataatg ctcaaaagga aaaaaatct ccgcagcgaa 1501 acgacagctc cggaaaaaaa ccaccaatcc catccaaatt aacgcaaaaa ccgtgatgcc 1561 gactagaaaa ctttttatgag agatcttggg acttcttttt gggggactat ttttgtacag
```

```
1621 agaaaacctg agggcggcgg ggagggcggg ggaatcggac catgtataga tctggaggaa 1681 aaaaactacg caaaactttt ttttaaagtt ctagtggtac gttaggcgct tcgcagggag 1741 ttcgcaaaag tctttaccag taatatttag agctagactc cgggcgatga aaaaaaagtt 1801 ttaatatttg caagcaactt ttgtacagta tttatcgaga taaacatggc aatcaaatgt 1861 ccattgttta taagctgaga atttgccaat attttttcgag gaaagggttc ttgctgggtt 1921 ttgattctgc agcttaaatt taggaccgtt acaaacaagg aaggagttta ttcggatttg 1981 aacattttag ttttaaaatt gtacaaaagg aaaacatgag agcaagtact ggcaagaccg 2041 ttttcgtggt cttgtttaag gcaaacgttc tagattgtac taaattttta acttactgtt 2101 aaaggcaaaa aaaaaatgtc catgcaggtt gatatcgttg gtaatttata atagcttttg 2161 ttcaatccta cccttcatt ttgttcacat aaaaaatatg gaattactgt gtttgaaata 2221 ttttcttatg gtttgtaata tttctgtaaa ttgtgatatt ttaaggtttt tccccccttt 2281 tattttccgt agttgtattt taaaagattc ggctctgtta ttggaatcag gctgccgaga 2341 atccatgtat atatttgaac taataccatc cttataacag ctacattttc aacttaagtt 2401 tttactccat tatgcacagt ttgagataaa taaattttttg aaatatggac actgaaa
```

By "IDH3α polypeptide" is meant a protein or fragment thereof having at least 85% homology to the sequence provided at NCBI Ref: NP_005521.1 (human) or NP_083849.1 (murine). IDH3α may also be termed IDH3a. An exemplary human amino acid sequence is provided below:

```
MAGPAWISKVSRLLGAFHNPKQVTRGFTGGVQTVTLIPGDGIGPEISAAV
MKIFDAAKAPIQWEERNVTAIQGPGGKWMIPSEAKESMDKNKMGLKGPLK
TPIAAGHPSMNLLLRKTFDLYANVRPCVSIEGYKTPYTDVNIVTIRENTE
GEYSGIEHVIVDGVVQSIKLITEGASKRIAEFAFEYARNNHRSNVTAVHK
ANIMRMSDGLFLQKCREVAESCKDIKFNEMYLDTVCLNMVQDPSQFDVLV
MPNLYGDILSDLCAGLIGGLGVTPSGNIGANGVAIFESVHGTAPDIAGKD
MANPTALLLSAVMMLRHMGLFDHAARIEAACFATIKDGKSLTKDLGGNAK
CSDFTEEICRRVKDLD
```

An exemplary murine amino acid sequence is provided below:

```
MAGSAWVSKVSRLLGAFHNTKQVTRGFAGGVQTVTLIPGDGIGPEISASV
MKIFDAAKAPIQWEERNVTAIQGPGGKWMIPPEAKESMDKNKMGLKGPLK
TPIAAGHPSMNLLLRKTFDLYANVRPCVSIEGYKTPYTDVNIVTIRENTE
GEYSGIEHVIVDGVVQSIKLITEEASKRIAEFAFEYARNNHRSNVTAVHK
ANIMRMSDGLFLQKCREVAENCKDIKFNEMYLDTVCLNMVQDPSQFDVLV
MPNLYGDILSDLCAGLIGGLGVTPSGNIGANGVAIFESVHGTAPDIAGKD
MANPTALLLSAVMMLRHMGLFDHAAKIEAACFATIKDGKSLTKDLGGNAK
CSDFTEEICRRVKDLD
```

By "IDH3α polynucleotide" is meant a nucleic acid molecule encoding a IDH3α polypeptide. An exemplary human IDH3α polynucleotide sequence is provided at NM_005530:

```
  1 gttgctgcgg agccaggagg ggaagcgatg gctgggcccg cgtggatctc taaggtctct 61 cggctgctgg gggcattcca caacccaaaa caggtgacca gaggttttac tggtggtgtt 121 cagacagtaa ctttaattcc aggagatggt attggcccag aaatttcagc tgcagttatg 181 aagattttg atgctgccaa agcacctatt cagtgggagg agcggaacgt cactgccatt 241 caaggacctg gaggaaagtg gatgatccct tcagaggcta aagagtccat ggataagaac 301 aagatgggct tgaaaggccc tttgaagacc ccaatagcag ccggtcaccc atctatgaat 361 ttactgctgc gcaaaacatt tgacctttac gcgaatgtcc gaccatgtgt ctctatcgaa 421 ggctatgaaa ccccttacac cgatgtaaat attgtgacca ttcgagagaa cacagaagga 481 gaatacagtg gaattgagca tgtgattgtt gatggagtcg tgcagagtat caagctcatc 541 accgaggggg cgagcaagcg cattgctgag tttgcctttg agtatgcccg gaacaaccac 601 cggagcaacg tcacggcggt gcacaaagcc aacatcatgc ggatgtcaga tgggcttttt 661 ctacaaaaat gcagggaagt gcagaaagc tgtaaagata ttaaatttaa tgagatgtac
```

-continued

```
 721 cttgatacag tatgtttgaa tatggtacaa gatccttccc aatttgatgt tcttgttatg
 781 ccaaatttgt atggagacat ccttagtgac ttgtgtgcag gattgatcgg aggtctcggt
 841 gtgacaccaa gtggcaacat tggagccaat ggggttgcaa tttttgagtc ggttcatggg
 901 acggctccag acattgcagg caaggacatg gcgaatccca cagccctcct gctcagtgcc
 961 gtgatgatgc tgcgccacat gggacttttt gaccatgctg caagaattga ggctgcgtgt
1021 tttgctacaa ttaaggacgg aaagagcttg acaaaagatt tgggaggcaa tgcaaaatgc
1081 tcagacttca cagaggaaat ctgtcgccga gtaaaagatt tagattaaca cttctacaac
1141 tggcatttac atcagtcact ctaaatggac accacatgaa cctctgttta gaatacctac
1201 gtatgtatgc attggtttgc ttgtttcttg acagtacatt tttagatctg gccttttctt
1261 aacaaaatct gtgcaaaaga tgcaggtgga tgtccctagg tctgtttttca aagaactttt
1321 tccaagtgct tgttttattt attaagtgtc tacctggtaa atgttttttt tgtaaactct
1381 gagtggactg tatcatttgc tattctaaac cattttacac ttaagttaaa atagtttctc
1441 ttcagctgta aataacagga tacagaatta acaagagaaa atgtctaact ttttaagaaa
1501 aaccttattt tcttcggttt ttgaaaaaca taatggaaat aaaacaggat attgacataa
1561 tagcacaaaa tgacactctt ctaaaactaa atgggcacaa gagaattttc ctgggaaagt
1621 tcacatcaaa aagagtgaat gtggtatatt tctaaatgat atggaaaata gagacagatt
1681 tgtcctttac agaaattact gagtgtgaat aaaaacttca gatccaagaa atatataatg
1741 agagatataa ttttttgttaa taagacaaag gtaatatatt ggatacaaag acacaaatgt
1801 attgtgtgtt caattatttt gttgtcttga gatttaatat tctttccaag agcttttaat
1861 gaagcagaga gctagtactt cattttcact ggatacattt tcagcatcat gagttgtcac
1921 agcctctgag cccctgatct gaagccagaa gggctgagtg tattgtaaac ttattcttgc
1981 atgttgctgt ctgggaatgg accacactac agcaggtagt tctgggggcg atactgccga
2041 aaggcccgaa cacatgtatt ttggctgcaa ttgaggaact tgggatgcta ttaattttgt
2101 atttcagcaa ctgccccttc tcctatccca aagcaccaat tactgccctc tgcctcagca
2161 gtaccagtat aagatgacat tccaaagact ggaggcaact cagcctgagt taattcacaa
2221 aattatgcca tgctggggct tgagcttgag cttgggctta ggcttgggct cagcttttga
2281 ccctcaggca tctcctttcc cttcctgtct tcctctccct tctcctctgc tgcagcatga
2341 ttttcttaat cttcagacac tcactatttt catgaacagt taccctctgt ccccacaacc
2401 aaagacaact catggcctcc tttggcccctt gtgtaacatt gcaaacctgt ggctttgcaa
2461 aatgtaccca ggtcacaagg ggatttttttt tttttttagca atgatatccc tgtctgggtc
2521 acttttttaag cttgtaaccg ccccccccaga cttataatct taaatgtatt ttcctttgtt
2581 taagctgctg cttcctctgt ttcattggat tgtgccagtt atcagtggct cttgggttca
2641 aagtaataaa gaattccaaa actgaaaaaa aaaaaaaaaa aaaaaaaaaa aaaaaaaaaa
2701 a
```

An exemplary murine IDH3α polynucleotide sequence is provided at NM_029573:

```
  1 gacgcgatgg ccgggtccgc gtgggtgtcc aaggtctctc ggctgctggg tgcattccac
 61 aacacaaaac aggtgacaag aggttttgct ggtggtgttc agacagtaac tttaattcct
121 ggagatggaa ttggcccaga aatttcagcc tcagtcatga agattttga tgctgccaaa
```

```
181 gcacctattc agtgggagga gcgcaatgtc acagcaattc aaggaccagg aggaaagtgg 241 atgatccctc cagaagccaa ggagtccatg gataagaaca agatgggctt gaaaggccca 301 ctaaagaccc caatagccgc tggccatcca tctatgaatc tgttgcttcg taagacattt 361 gacctttatg ccaatgtccg gccatgtgtc tcaattgaag gttataaaac cccttacacg 421 gatgtaaata tcgtcaccat ccgagagaac acggaaggag aatacagtgg aattgagcat 481 gtgatcgttg atggggttgt gcagagcatc aagctcatca ccgaagaagc aagcaagcgc 541 attgcagagt ttgccttcga gtacgctcgg aacaaccacc ggagcaacgt cacagctgtg 601 cacaaagcta acatcatgag gatgtcagat gggctctttc tgcaaaaatg cagggaagtt 661 gcggagaact gtaaagacat taaatttaac gagatgtacc ttgatactgt atgtttaaat 721 atggtacaag acccatccca gtttgatgtt cttgtcatgc caaatttata cggagacatc 781 cttagtgatc tgtgtgcagg actgattgga ggtcttgggg tgactccaag tggcaatatt 841 ggagccaacg gtgttgccat ctttgaatcg gttcatggaa cagccccgga cattgcaggc 901 aaggacatgg ccaaccccac ggccctcctg cttagtgctg tgatgatgct tcgccacatg 961 ggacttttg accatgcagc aaaaatcgag gctgcatgtt ttgctacaat taaggatgga 1021 aagagcttaa caaaagatct gggaggcaac gcgaagtgct ctgacttcac agaagaaatc 1081 tgtcgtagag tcaaagactt agattagcac tcctgctggt ggatttgctg cagtcagtca 1141 atcactccaa aaggataccc tgtaatcctc cttgagggcg cccaccattg gtttgcttgc 1201 ttcttgacag agtacgtttt ttgaatctgg ccttttctta acaaaaccct tgcaatggat 1261 gcacatgatg gccccaggcc ttcattcaaa gggttttccc aagtgctggt tgtatttatt 1321 gtccgtctgg taaaccttat tttgtaaact gtaagtgaac tgtatcattt atcattgtta 1381 acccatttta cacttcaggc aaaatcattt tcctcaactg taaatattct gatacagaat 1441 taataagaga agatatttaa cttttttaaca aaagccctgg atttttggtt tatgaaaaac 1501 aaactgggaa taaaacaggg ttttaacaat cgcacaagat aacattattc taatactaat 1561 gggtacaaaa gaaatttact gggaaagttc acagcaaaaa aatggtatat ttcttaaaaa 1621 tatggaaata aagtatttgt cctatacatg aattactatt aataaaaatg taagctccaa 1681 gaaatccata atgaatgatg taattttgtt actacatcgg taatccttgt caaggccccg 1741 gatgctctct gtgtatttga ttcttttgtt accttgagat tcactatttt ggggggaagag 1801 ctttcagata agggagatca ctcctcacta gacagatcgt cagcattgcg agctgtcagc 1861 catgagagcc agccactgca gatcccctcc cacgtggcca cactccagcc agtgctgcag 1921 gtgaccctgg aaaggcctgg ctgcccctttg actttcccta aagcaaccag tcactgcctt 1981 ctgccccagt agcacccatt acagacttaa ttgccgaggt ggagctgact cagcccacgc 2041 tcatacaaat caggccaagc gggggcctgt gttaccagct gctgaccatc aggttctgcc 2101 cctcattctt cccacagcct ctgctccaca gcatgaacct agcctttggc ccacaccaaa 2161 gccaagctgt cttcccttag cccttgcact agtttgcaaa ctcgtggctt tgcataatgt 2221 accctggtcc caagggggatt tcttaacaac agatgtccct gtctgggtca ttttttaaa 2281 gcttttattt ggacttacaa tcttctgtgt attttacttt aaaactgctg ctttccctgt 2341 ctcactggat tgttctggtt agcagtggct ttgggttcac agtaataaag aacttaagaa 2401 ctgaaaaaaa aaaaaaaa
```

By "IDH3β polypeptide" is meant a protein or fragment thereof having at least 85% homology to the sequence provided at NCBI Ref: NP_008830.2 (human) or NP_570954.1 (murine). IDH3β may also be termed IDH3b. An exemplary human amino acid sequence is provided below:

MAALSGVRWLTRALVSAGNPGAWRGLSTSAAAHAASRSQAEDVRVEGSFP
VTMLPGDGVGPELMHAVKEVFKAAAVPVEFQEHHLSEVQNMASEEKLEQV
LSSMKENKVAIIGKIHTPMEYKGELASYDMRLRRKLDLFANVVHVKSLPG
YMTRHNNLDLVIIREQTEGEYSSLEHESARGVIECLKIVTRAKSQRIAKF
AFDYATKKGRGKVTAVHKANIMKLGDGLFLQCCEEVAELYPKIKFETMII
DNCCMQLVQNPYQFDVLVMPNLYGNIIDNLAAGLVGGAGVVPGESYSAEY
AVFETGARHPFAQAVGRNIANPTAMLLSASNMLRHLNLEYHSSMIADAVK
KVIKVGKVRTRDMGGYSTTTDFIKSVIGHLQTKGS

An exemplary murine amino acid sequence is provided below:

MAALSNVRWLTRAVLAARNSGAWRGLGTSTAHAASQSQAQDVRVEGAFPV
TMLPGDGVGPELMHAVKEVFKAAAVPVEFKEHHLSEVQNMASEEKLEQVL
SSMKENKVAIIGKIYTPMEYKGELASYDMQLRRKLDLFANVVHVKSLPGY
KTRHNNLDLVIIREQTEGEYSSLEHESAKGVIECLKIVTRTKSQRIAKFA
FDYATKKGRSKVTAVHKANIMKLGDGLFLQCCEEVAELYPKIKFETMIID
NCCMQLVQNPYQFDVLVMPNLYGNIIDNLAAGLVGGAGVVPGESYSAEYA
VFETGARHPFAQAVGRNIANPTAMLLSATNMLRHLNLEYHSSMIADAVKK
VIKAGKVRTRDMGGYSTTTDFIKSVIGHLHPHGG

By "IDH3β polynucleotide" is meant a nucleic acid molecule encoding a IDH3β polypeptide. An exemplary human IDH3β polynucleotide sequence is provided at NM_006899:

```
   1 gtcacttccc acgcgacttc ctgcgggaaa catggcggca ttgagcggag tccgctggct
  61 gacccgagcg ctggtctccg ccgggaaccc tggggcatgg agaggtctga gtacctcggc
 121 cgcggcgcac gctgcatcgc ggagccaggc cgaggacgtg agggtggagg gctcctttcc
 181 cgtgaccatg cttccgggag acggtgtggg gcctgagctg atgcacgccg tcaaggaggt
 241 gttcaaggct gccgctgtcc cagtggagtt ccaggagcac cacctgagtg aggtgcagaa
 301 tatggcatct gaggagaagc tggagcaggt gctgagttcc atgaaggaga caaagtggc
 361 catcattgga aagattcata ccccgatgga gtataagggg gagctagcct cctatgatat
 421 gcggctgagg cgtaagttgg acttatttgc aacgtagtc catgtgaagt cacttcctgg
 481 gtatatgact cggcacaaca atctagacct ggtgatcatt cgagagcaga cagaagggga
 541 gtacagctct ctggaacatg agagtgcaag gggtgtgatt gagtgtttga agattgtcac
 601 acgagccaag tctcagcgga ttgcaaagtt cgcctttgac tatgccacca agaaggggcg
 661 gggcaaggtc actgctgtcc acaaggccaa catcatgaaa cttggggatg ggttgttcct
 721 gcagtgctgt gaggaagttg ctgaactgta ccccaaaatc aaatttgaga caatgatcat
 781 agacaactgc tgcatgcagc tggtgcagaa tccttaccag tttgatgtgc ttgtgatgcc
 841 caatctctat gggaacatta ttgacaatct ggctgctggc ctggttgggg gagctggtgt
 901 ggtccctggt gagagctata gtgcagaata cgcagtcttt gagacgggtg cccggcaccc
 961 atttgcccag gcagtgggca ggaatatagc caatcccacg gccatgctgc tgtcggcttc
1021 caacatgctg cggcatctta atcttgagta tcactccagc atgatcgcag atgcggtgaa
1081 gaaggtgatc aaagttggca aggtgcggac tcgagacatg ggcggctaca gcaccacaac
1141 cgacttcatc aagtctgtca tcggtcacct gcagactaaa gggagctaga gcccttatt
1201 tcttccaacc ttgcaaggac cacactcccc atacccttca gtgcagtgta ccagggaaga
1261 gaccttgtgc ctctaagcag tggaccatgg tcaccttgct gggtagagcc taggttgtcc
1321 ttgggccggc ttccttaggg gacagactgt tgggtggtga tggggattgt taggatggag
1381 cccaggccac atggatgatg atgattctcc cccacaggtt cgaacctctg acatgggtgg
1441 ctatgctact tgccatgact tcactgaggc tgtcattgct gccttgcccc acccataggc
1501 cctgtccata cccatgtaag gtgttcaata aagaacatga accaaaaaaa aaaaaaaaa
1561 a
```

An exemplary murine IDH3β polynucleotide sequence is provided at NM_130884:

```
   1 ggcgtcactt cccccgcgac ttcctcggcc gaacatggca gcgctgagca atgtccgctg
  61 gctgacccga gcggtgctcg ccgctcggaa ctccggggca tggagaggtc tcggaacatc
 121 tacggctcac gccgcttccc agagccaggc acaagatgtg agggtggagg gtgcctttcc
 181 tgtgaccatg ctgcctggag acggcgtggg gccagagctc atgcatgctg tcaaggaagt
 241 gttcaaggct gctgctgtcc ctgtggaatt taaggagcat catctgagcg aggtgcagaa
 301 tatggcttct gaggagaagc tggagcaggt gctgagttcc atgaaggaga caaagttgc
 361 catcattgga aagatctata ccccaatgga gtataagggt gaactagcct cctatgatat
 421 gcagctgagg cgtaagttgg atttgtttgc caacgtagtc cacgtgaagt cacttcctgg
 481 atacaagact cggcacaaca atctagacct ggttatcatt cgagagcaga cagaagggga
 541 gtatagctct ctggaacatg agagcgccaa gggtgtcatt gagtgcctga agatcgtcac
 601 tcgcaccaag tctcagagga ttgcaaagtt tgcgttcgac tatgccacca agaaagggcg
 661 gagcaaggtc acagccgtcc ataaagccaa catcatgaaa ctaggggatg gcttgttctt
 721 gcagtgctgt gaggaagttg ctgaactgta ccctaaaatc aagtttgaaa ccatgatcat
 781 agacaactgc tgcatgcagc tggtgcagaa cccttaccag tttgatgtgc tcgtgatgcc
 841 caatctctat ggcaacataa ttgacaatct ggctgctggc cttgttgggg gagctggcgt
 901 ggttcctggg gagagctaca gtgcagagta tgcagttttt gagacgggtg ctcggcaccc
 961 atttgcccag gcagtgggca ggaatatagc caacccccaca gccatgctgc tgtcggccac
1021 caacatgctg cggcatctca atcttgagta tcactccagc atgattgcag atgcagtgaa
1081 gaaagtgatc aaagctggca aggtacggac tcgagacatg ggaggctaca gcaccacaac
1141 tgacttcatc aagtctgtca tcggccacct gcaccccat gggggctaga gcccttactc
1201 cctccaattt caaaaggacc atgcttcgta tacatccctt cagtacaatg gaccagaaga
1261 gaacatctag acagtagact ataatagctt ttctgaggct aggctgtcct gggggctggt
1321 gttaagggta tctcaaaggg tgggttgttg cgacaaggcc cagaccctaa gatgataact
1381 ttttcccaca ggttcgaacc tcagatatgg gtggttatgc cacatgtcat gacttcactg
1441 aagctgtcat tactgccctg tcataaatcc tatacatgcc catgaaaaaa atagtcaata
1501 aacaaaatac acacatacta
```

By "IDH3γ polypeptide" is meant a protein or fragment thereof having at least 85% homology to the sequence provided at NCBI Ref: NP_004126.1 (human) or NP_032349.1 (murine). IDH3γ may also be termed IDH3g. An exemplary human amino acid sequence is provided below:

```
MALKVATVAGSAAKAVLGPALLCRPWEVLGAHEVPSRNIFSEQTIPPSAK
YGGRHTVTMIPGDGIGPELMLHVKSVFRHACVPVDFEEVHVSSNADEEDI
RNAIMAIRRNRVALKGNIETNHNLPPSHKSRNNILRTSLDLYANVIHCKS
LPGVVTRHKDIDILIVRENTEGEYSSLEHESVAGVVESLKIITKAKSLRI
AEYAFKLAQESGRKKVTAVHKANIMKLGDGLFLQCCREVAARYPQITFEN
MIVDNTTMQLVSRPQQFDVMVMPNLYGNIVNNVCAGLVGGPGLVAGANYG
HVYAVFETATRNTGKSIANKNIANPTATLLASCMMLDHLKLHSYATSIRK
AVLASMDNENMHTPDIGGQGTTSEAIQDVIRHIRVINGRAVEA
```

An exemplary murine amino acid sequence is provided below:

```
MALKVAIAAGGAAKAMLKPTLLCRPWEVLAAHVAPRRSISSQQTIPPSAK
YGGRHTVTMIPGDGIGPELMLHVKSVFRHACVPVDFEEVHVSSNADEEDI
RNAIMAIRRNRVALKGNIETNHNLPPSHKSRNNILRTSLDLYANVIHCKS
LPGVVTRHKDIDILIVRENTEGEYSSLEHESVAGVVESLKIITKAKSLRI
AEYAFKLAQESGRKKVTAVHKANIMKLGDGLFLQCCREVAAHYPQITFDS
MIVDNTTMQLVSRPQQFDVMVMPNLYGNIVNNVCAGLVGGPGLVAGANYG
HVYAVFETATRNTGKSIANKNIANPTATLLASCMMLDHLKLHSYATSIRK
AVLASMDNENMHTPDIGGQGTTSQAIQDIIRHIRIINGRAVEA
```

By "IDH3γ polynucleotide" is meant a nucleic acid molecule encoding a IDH3γ polypeptide. An exemplary human IDH3γ polynucleotide sequence is provided at NM_004135:

```
   1 ggggcccagc tggtcgcggt ccccccctca acatggcggc agcggtgctc taggcgccgg
  61 aaggggggcgt gaatcggtgc gaccgcgcgc gtgcgcagta ccgggtccgc gcctgtcccc
 121 gaaacttcgc accccgtcga actctcgcga gagcggtatc tgcgtgtcgg gacgtgcgga
 181 ggctctcact ttccgtcatg gcgctgaagg tagcgaccgt cgccggcagc gccgcgaagg
 241 cggtgctcgg gccagccctt ctctgccgtc cctgggaggt tctaggcgcc cacgaggtcc
 301 cctcgaggaa catcttttca gaacaaacaa ttcctccgtc cgctaagtat ggcgggcggc
 361 acacggtgac catgatccca ggggatggca tcgggccaga gctcatgctg catgtcaagt
 421 ccgtcttcag gcacgcatgt gtaccagtgg actttgaaga ggtgcacgtg agttccaatg
 481 ctgatgaaga ggacattcgc aatgccatca tggccatccg ccggaaccgc gtggccctga
 541 agggcaacat cgaaaccaac cataacctgc caccgtcgca caaatctcga acaacatcc
 601 ttcgcaccag cctggacctc tatgccaacg tcatccactg taagagcctt ccaggcgtgg
 661 tgacccggca aaggacata gacatcctca ttgtccggga aacacagag ggcgagtaca
 721 gcagcctgga gcatgagagt gtggcgggag tggtggagag cctgaagatc atcaccaagg
 781 ccaagtccct gcgcattgcc gagtatgcct tcaagctggc gcaggagagc gggcgcaaga
 841 aagtgacggc cgtgcacaag gccaacatca tgaaactggg cgatgggctt ttcctccagt
 901 gctgcaggga ggtggcagcc cgctaccctc agatcacctt cgagaacatg attgtggata
 961 acaccaccat gcagctggtg tcccggcccc agcagtttga tgtcatggtg atgcccaatc
1021 tctatggcaa catcgtcaac aatgtctgcg cgggactggt cggggccca ggccttgtgg
1081 ctggggccaa ctatggccat gtgtacgcgg tgtttgaaac agctacgagg aacaccggca
1141 agagtatcgc caataagaac atcgccaacc ccacggccac cctgctggcc agctgcatga
1201 tgctggacca cctcaagctg cactcctatg ccacctccat ccgtaaggct gtcctggcat
1261 ccatggacaa tgagaatatg cacactccgg acatcggggg ccagggcaca acatctgaag
1321 ccatccagga cgtcatccgc cacatccgcg tcatcaacgg ccgggccgtg gaggcctagg
1381 ctggccctag gaccttcttg gtttgctcct tggattcccc ttcccactcc agcacccag
1441 ccagcctggt acgcagatcc cagaataaag caccttctcc ctagaaaaaa aaaaaaaaa
1501 aa
```

An exemplary murine IDH3γ polynucleotide sequence is provided at NM_008323:

```
   1 ggtgcttaat gttttgacct gtagaggtcc tcactttcg tcatggcgct gaaggtggcg
  61 atagctgctg gcggtgctgc aaaggcaatg ctcaagccaa ctctcctctg ccgtccttgg
 121 gaggttctgg ctgcccatgt ggccccccga aggagcattt cctcacaaca aacaattcct
 181 ccatctgcta agtatggtgg gcggcataca gtgactatga tcccagggga tggcatcggc
 241 ccagagctca tgttgcatgt taagtctgta ttcaggcatg catgtgtgcc ggtggacttt
 301 gaagaggtgc atgtaagctc caacgctgat gaggaggaca tccgcaatgc catcatggcc
 361 atccgccgga accgtgtggc cctgaagggc aacattgaaa caaatcataa cctgccacca
 421 tcccacaaat ctcgaaacaa catccttcgc accagcctag acctctatgc caacgtcatc
 481 cactgtaaga gcctgccagg agtggtgacc cggcacaagg acatagacat cctcattgta
 541 cgggaaaaca cagaaggcga gtacagcagc ctggagcatg agcgtagc aggagtggtg
 601 gagagcttga agattatcac caaagccaag tccctgcgca ttgctgaata tgcttttcaag
 661 ctggcccagg agagtgggcg taagaaagtg acggctgtgc acaaggccaa catcatgaaa
```

```
 721 ctgggtgatg gactcttcct ccagtgctgc agggaagtag cagcccacta ccctcagatc 781 acctttgaca gcatgattgt agacaacaca acaatgcagc tggtatcccg gcctcagcag 841 tttgatgtca tggtgatgcc taatctctat ggtaacattg tcaacaacgt ctgtgcaggg 901 ctagttggag gcccaggcct tgtggctggg gccaactatg gccatgtgta tgcagtattc 961 gagacagcta caaggaacac aggcaaaagt attgccaata agaacattgc taacccgact 1021 gccacactgc tagcaagctg catgatgcta gaccacctca agctccactc ctatgccact 1081 tccatccgca aagctgtctt agcatccatg gacaatgaaa atatgcatac cccagatatt 1141 ggaggccagg gcaccacatc ccaagccatc caggacatca ttcgtcatat ccgcatcatt 1201 aatggacggg ctgtggaggc ttagctatcc ctacagtttt gctcagcttg tctgtaggac 1261 tctcttctca ctttagcact ccagctagct tgggggacag gacccagaat aaagccactt 1321 ctgttccaga aaaaa
```

By "IDH3 polynucleotide" is meant a nucleic acid molecule encoding a IDH3 polypeptide.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST®, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST® program may be used, with a probability score between e-3 and e-100 indicating a closely related sequence.

By "subject" is meant a mammal, including, but not limited to, a human or non-human mammal, such as a bovine, equine, canine, murine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating, treatment, and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1T (related to FIG. 2) are bar graphs, images and two schematics showing that ERRs and PGC1α/β were direct targets of reprogramming factors during early reprogramming FIGS. 1A-1D depict bar graphs showing that mouse ERRα/γ and PGC1α/β were activated in retroviral reprogramming mouse embryonic fibroblasts (MEFs) at day 3, shown by qPCR results (n=3, *p<0.01, error bars show standard error of the mean (s.e.m.)). FIGS. 1K-1M are bar graphs of qPCR showing relative expression of ERRα, PGC-1α and PGC-1β in single factor infected cells (n=3, error bars show s.e.m.). FIG. 1N is a schematic representation of ERRα, PGC-1α and PGC-1β induction by Oct3/4, Sox2, Klf4 or c-Myc. FIG. 1O is a bar graph showing relative reprogramming efficiencies of doxycycline-inducible reprogramming MEFs with and without ERRγ over expression (Ad-ERRγ and Ad-GFP, respectively). Reprogramming efficiency based on alkaline phosphatase staining at day 21 (n=6, error bars show s.d. **p<0.01). FIG. 1P is a schematic design of the lentiviral reporter which recapitulates the human ERRα enhancer activity. A 974 bp enhancer sequence (chr11: 64072402-64073375) which covers the upstream and 5UTR of the human ERRα gene was cloned into a lentiviral reporter which contains green fluorescence protein (GFP) and luciferase. A separate constitutive active promoter EF1a drove the expression of Neomycin resistance gene, which allowed the selection in cells with low expression of endogenous ERRα. FIG. 1Q is a schematic design of isolation of a sub-population of reprogramming cells which has high ERRα expression. Human fibroblasts were transduced with lentiviral reprogramming factors which overexpress Oct4, Sox2, Klf4, cMyc, Nanog and Lin28. The fibroblasts were transduced with ERRα reporter at the same time. GFP was not observed at day 1-2, but started to appear and reach its peak around day 4-6. Cells were sorted by GFP intensity at this stage to isolate the top 5% GFP positive cells. FIG. 1R is a fluorescence image showing that the ERRα reporter could be observed in day 5 reprogramming fibroblast, whereas the control which only transduced with reporter but not the reprogramming factors remained GFP negative. FIG. 1S shows fluorescence activated cell sorting (FACS) results of reprogramming cells with ERRα reporter. P4 represent the GFP positive population. FIG. 1T shows gene expression comparing ERRα and its targets in normal fibroblasts (control), fibroblasts transduced with reporter only (GF only), and GFP+ and GFP- population at reprogramming day 6. ERRα and its targets were highly enriched in GFP+ population, compared to other samples, indicating that the ERRα reporter could fully capture the endogenous ERRα expression pattern.

FIG. 2A is a bar graph showing mouse embryonic fibroblasts (MEFs) undergoing retroviral reprogramming with OSKM were transduced with control, ERRα, ERRγ, PGC-1α or PGC-1β shRNA. Depletion of ERRα/γ and PGC-1α/β significantly reduced reprogramming efficiency. (n=3, error bars show s.d.). FIGS. 2B-2F depict images of cell cultures and graphs showing ERRγlox/lox and ERRγlox/loxCreERT mouse MEFs infected with a doxycycline-inducible OSKM lentivirus that were treated with 4-Hydroxytamoxifen (4-OHT) 3 days after OSKM induction. FIG. 2B-E are bright field images and graphs showing that ERRγ depletion reduced the clusters of early reprogramming cells (FIG. 2B), significantly reduced AP colonies (FIGS. 2C and 2D), and reduced Nanog-positive colonies (FIGS. 2E and 2F) (n=3, *p<0.01, error bars show s.d.). FIG. 2G is a bar graph showing that ERRα and PGC-1α/β were important for reprogramming of IMR90 (n=3, *p<0.01, error bars show standard deviation (s.d)).

FIGS. 2H and 2I are bar graphs depicting qPCR results showing that depletion of p53 lead to increased expression of human ERRα during reprogramming of IMR90 cells (n=3, *p<0.01, error bars show s.e.m). FIG. 2J are two images of cell cultures showing Nanog staining of retroviral OSKM-infected MEFs with p53 (left), or p53 and ERRγ (right) shRNA vectors, demonstrating that loss of ERRγ resulted in complete collapse of reprogramming even with p53 depletion.

FIG. 3A is a graph showing that the time course of oxygen consumption rate (OCR) and extracellular acidification rate (ECAR) in Dox-induced reprogramming mouse embryonic fibroblasts (MEFs), isolated from the single gene transgenic mouse, revealed that the reprogramming population experienced an early oxidative phosphorylation (OXPHOS) burst. FIG. 3B is a graph showing that mitostress test of early reprogramming MEFs in FIG. 3A showed increased basal OCR and maximal OXPHOS capacity. FIG. 3C is a graph showing that relative gene expression of ERRα, coactivators PGC-1α and PGC-1β, and Nanog after retroviral OSKM infection of IMR90 cells, measured by qPCR, indicated that the expression pattern of ERRs and their cofactors coincide with the metabolic switch in early reprogramming (n=3, *p<0.01, error bars show s.e.m.). FIG. 3D is a heat map showing temporal expression of metabolic genes during retroviral OSKM induced IMR90 reprogramming FIG. 3E is a graph showing OCR and extracellular acidification rate (ECAR) measurements of control and ERRα knockdown retroviral reprogramming IMR90 cells demonstrating that ERRα was important for the early OXPHOS burst in human cells. FIG. 3F. is a graph showing that OCR and ECAR measurements of control and ERRγ knockdown retroviral reprogramming MEF cells demonstrated that ERRγ is important for the early OXPHOS burst in mouse cells. FIG. 3G is a graph showing that rotenone treatment, which inhibits the OXPHOS burst, resulted in significant reduction of retroviral reprogramming efficiency in IMR90, indicating that the metabolic switch was important. (n=3, *p<0.05, error bars show s.d.).

FIG. 4A is a bar graph showing kinetics of maximal oxidative phosphorylation (OXPHOS) capacity in doxycycline-inducible reprogramming mouse embryonic fibroblasts (MEFs). Reprogramming cells at days 2 to 5 have higher OXPHOS capacity than MEFs and iPSCs. FIGS. 4B and 4C are linear graphs showing that time course measurements of oxygen consumption rate (OCR, FIG. 4B) and extracellular acidification rate (ECAR, FIG. 4C) in retroviral reprogramming IMR90 cells showed an up-regulated metabolic profile in early reprogramming human fibroblasts. FIGS. 4D-4F are bar graphs showing that in early retroviral reprogramming of IMR90 cells, NADH, ATP and NAD+/NADH levels were changed (n=5, error bars show s.d. *p<0.01). FIG. 4G is a heat map showing that metabolic genes listed in FIG. 4D showed a similar expression pattern between various human ES and iPS lines, in contrast to fibroblast (hFib) lines. FIG. 4H is a linear graph showing the dynamic expression pattern of ROS genes SOD2, NOX4 and CAT during retroviral reprogramming of IMR90 cells (n=3, error bars show s.e.m. *p<0.01).

FIGS. 5A-5G are images, graphs and a table showing that ERRγ enriched sub-population in early reprogramming represented bona fide reprogramming cells with significantly enhanced reprogramming efficiency. FIG. 5A depicts two images showing Sca1 and CD34 labeled bona fide reprogramming cells. Retroviral OSKM-infected mouse embryonic fibroblasts (MEFs) stained for Sca1 (green) and CD34

(red) expression, and phase contrast image (right). Sca1−CD34− double negative (DN) cells were demarcated by white dashed lines from phase contrast images. FIG. 5B shows six representative phase contrast images of Sca1−CD34− cells during retroviral reprogramming. Arrowheads indicate a representative DN colony. FIGS. 5C and 5D are bar graphs of qPCR demonstrating that ERRγ and PGC-113 were enriched in the DN population (n=3, error bars show s.e.m. *p<0.01). FIGS. 5E and 5F are bar graphs showing that fluorescence-activated cell sorting (FACS)-isolated DN population exhibited higher extracellular acidification rate (ECAR, FIG. 5E) and oxygen consumption rate (OCR, FIG. 5F) than double positive (DP) or single positive (SP) population (n=4, *p<0.05, error bars show s.d.). FIG. 5G is a table showing that DN cells demonstrated significantly higher reprogramming efficiency (n=7, *p<0.05, **p<0.01).

FIG. 6A is a group of graphs showing flow cytometry analysis of Sca1 and CD34 expression in WT mouse embryonic fibroblasts (MEFs), retroviral OSKM-infected MEFs, iPSCs and embryonic stem cells (ESCs). FIG. 6B is a bar graph showing that Sca1− MEFs had similar reprogramming efficiencies to Sca1+ MEFs (n=6, error bars show s.d.). FIG. 6C shows an alkaline phosphatase staining and phase contrast image of iPSCs from DN population. FIG. 6D shows three images of immunofluorescence of SSEA1 (PE), Nanog (FITC) and DNA (DAPI) in iPSCs originating from Sca1−CD34− cells. FIGS. 6E and 6F are bar graphs showing q-PCR analysis of pluripotent marker genes (FIG. 6E) and differentiation marker genes (FIG. 6F) in undifferentiated and differentiated mouse ESCs and iPSCs. The scale for Cardiac a-actin and Mtap2 corresponded with y-axis shaded in gray on the right. FIG. 6G is an image that shows an adult chimeric mouse obtained from an iPSC line derived from DN cell population sorted 5 days after OSKM infection. FIG. 6H is an image that shows offspring of chimera crossed with a C56BL/6N female (asterisk) showing pups with black coats (green arrows) originating from iPSC cells.

FIGS. 7A-7G depict a table, graph, heat maps and a schematic of transcriptome analysis that revealed that ERRs orchestrated the up-regulation of a panel of oxidative phosphorylation (OXPHOS) related genes and promoted the metabolic switch during early reprogramming FIGS. 7A and 7B are a matrix and a graph showing RNA-Seq analysis that revealed that the genome-wide expression pattern of various cell types could be grouped into pluripotent stem cells, mouse embryonic fibroblasts (MEFs) and intermediate retroviral reprogramming cells, demonstrated by distance matrix (FIG. 7A) and clustering analysis (FIG. 7B). FIGS. 7C and 7D are heat maps showing the RNA-Seq patterns of a subset of key pluripotency markers (FIG. 7C) and cell cycle genes (FIG. 7D) that revealed similarity between double negative (DN) cells and ESCs, indicating that the DN population represented bona fide early reprogramming cells which were in the process of adopting induced pluripotency. FIG. 7E is an expression heat map from RNA-Seq data that showed that DN cells had a unique pattern in metabolic genes that represents a hyperenergetic state. FIG. 7F is a heat map of gene expression from microarray in IMR90 cells after ERRα depletion, showing that a significant portion of the OXPHOS program was directly influenced by ERRα in human fibroblast reprogramming FIG. 7G is a schematic representation of the role of ERRs and PGC1α/β in inducing the early OXPHOS burst and transition to induced pluripotency. The OXPHOS burst was important for somatic cell reprogramming and transient activation of ERRs and their co-factors were epistatic to the roadblock of p53/p21-induced senescence in reprogramming.

FIGS. 8A-8C (related to FIG. 7) are two pie charts and a table showing that ERRα depletion affected oxidative phosphorylation (OXPHOS) burst during reprogramming FIGS. 8A and 8B are a pie chart and a table of KEGG PATHWAY analysis, a process that maps molecular datasets, which revealed a panel of OXPHOS related genes in DN population at 5 days after infection, indicating up-regulation of ERRγ in bona fide reprogramming cells induced the transcription of OXPHOS program. Gene selection was based on a Bonferroni error threshold of αBonf=0.01. FIG. 8C is a table of enrichment analysis on gene sets generated using GO ANALYSIS, that shows that ERRα depletion in IMR90 cells induced widespread changes of genes involved in metabolic processes.

FIG. 9A is a schematic to demonstrate the function of ERRs in reprogramming IDH3 gene encodes isocitrate dehydrogenase, which catalyzes the oxidation of isocitrate to α-ketoglutarate. H3K4Me2 stands for H3 histone (H3) with its lysine at the fourth (4th) amino acid position from the N-terminal of the protein (K4) dimethylated (Me2). H3K4Me3 stands for histone 3 with its lysine at the fourth (4th) amino acid position from the N-terminal of the protein (K4) trimethylated (Me3). H3K4Me1 stands for H3 histone with its lysine at the fourth (4th) amino acid position from the N-terminal of the protein (K4) monomethylated (Me1). H3K4 stands for H3 histone with its lysine at the fourth (4th) amino acid position from the N-terminal of the protein (K4) unmethylated.

FIG. 9B is a bar graph showing the NAD+/NADH ratio change during reprogramming, corresponding with the surge of ERR expression. FIG. 9C is a bar graph showing that IDH3 genes regulation in various reprogramming populations. WT fibroblast stands for wild type filbroblast, which was not infected by lentivirus. Mock infection was included as a control. ERRα-GFP describes a lentivirus encoding GFP protein under the control of the ERRα promoter. Cells were either untreated (WT fibroblasts), mock infected or infected with the ERRα-GFP lentivirus. ERRα-GFP infected cells were FACS stored based on GFP activity (ERRα-GFP+ and ERRα-GFP−). The relative expression of IDH3 genes in the various cell populations was determined by qPCR. FIG. 9D is a bar graph showing α-ketoglutarate level in early reprogramming (day 5) without (control) and with treatment with a small hairpin RNA (shRNA) designed to reduce the expression of ERRγ (ERRg shRNA). α-KG stands for α-ketoglutarate. FIG. 9E shows representative images of iPS colonies after treatment of D-2-hydroxyglutarate (D-2-HG) or L-2-hydroxyglutarate (L-2-HG). FIG. 9F is a bar graph showing that reprogramming efficiency after D-2-HG or L-2-HG treatment of the cells. The image and the bar labelled with "Veh" in FIGS. 9E and 9F represents the iPS colonies after negative control treatment, in which the cells were treated with the solvent for D-2-HG and L-2-HG only.

FIGS. 10A-10B depict a schematic and a table showing that ERRα expression labels a metabolically active cell subpopulation during early reprogramming FIG. 10A is schematic presentation of experimental design. IMR90 cells are transduced with lentivirus expressing reprogramming factors Oct4, Sox2, Klf4, Myc, Lin28, and Nanog, together with a lentiviral GFP reporter which reflect the endogenous ERRα activity. Lenti-OSKMLN stands for lentivirus expressing Oct4, Sox2, Klf4, Myc, Lin28, and Nanog GF-hEERa-III stands for a lentiviral GFP reporter in which the GFP activity is a measure of the endogenous ERRα expression pattern. Cells are sorted based on GFP expression in Day 2 to Day 6 and RNA sequencing was performed for the cells in all sub-populations. FIG. 10B is a table to show the results of KEGG gene ontology analysis of the genes enriched in GFP+ population.

FIG. 11A are graphs showing the H3K4Me2 level in the enhancer/promoter regions of of genes that function in fibroblast identity, such as SNAI1 and ZEB2, in ERRα+ and ERRα− population. FIG. 11B are graphs showing the H3K4Me2 level in the enhancer/promoter of genes that function in reprogramming, such as Oct4 and Sox2. H3K4Me2 stands for H3 histone with the lysine at the fourth (4th) position from the N-terminal of the protein which is dimethylated.

DETAILED DESCRIPTION OF THE INVENTION

Figure 1A:
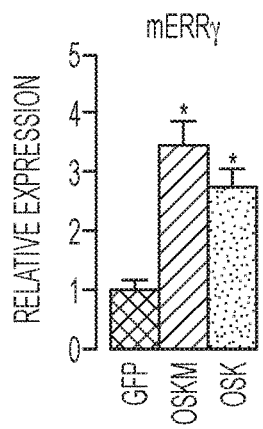
Figure 1B:
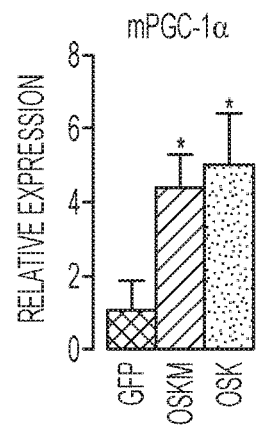
Figure 1C:
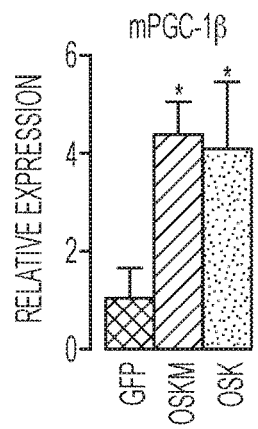
Figure 1D:
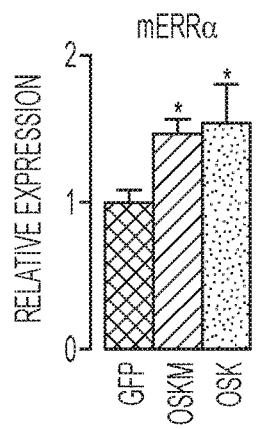

As described below, the invention generally features compositions comprising induced pluripotent stem cell progenitors (also termed reprogramming progenitor cells) and methods of isolating such cells. The invention also provides compositions comprising induced pluripotent stem cells (iPSCs) derived from such progenitor cells. Induced pluripotent stem cell progenitors generate iPSCs at high efficiency.

Cell metabolism is adaptive to extrinsic demands. However, the intrinsic metabolic demands that drive the induced pluripotent stem cell (iPSC) program remain unclear. While glycolysis increases throughout the reprogramming process, here it was demonstrated that the estrogen related nuclear receptors (ERRα and γ) and their partnered co-factors PGC-1α and β, were transiently induced at an early stage resulting in a burst of oxidative phosphorylation (OXPHOS) activity. Up-regulation of ERRα or γ was important for both the OXPHOS burst in human and mouse cells, respectively, as well as in iPSC generation itself. Failure to induce this metabolic switch collapsed the reprogramming process. The invention is based, at least in part, on the discovery of a rare pool of Sca1-/CD34− sortable cells that is highly enriched in bona fide reprogramming progenitors. Transcriptional profiling confirmed that these progenitors are ERRγ and PGC-1β positive and have undergone extensive metabolic reprogramming. These studies characterize a previously unrecognized, ERR-dependent metabolic gate prior to establishment of induced pluripotency.

Accordingly, the invention provides compositions comprising reprogramming progenitors or their descendants (i.e., IPSCs), and methods of using such compositions for the treatment of conditions associated with a deficiency in cell number.

Induced Pluripotent Stem Cells

An understanding of the molecular mechanisms that influence the generation, maintenance, and differentiation of human pluripotent stem cells is key to advancing their use in a therapeutic setting. Whereas the transcriptional and epigenetic dynamics have been extensively documented, temporal changes in metabolic states during the induction of pluripotency remain largely unknown. Distinct from somatic cells, pluripotent stem cells have unique metabolic pathways (Zhang et al., 2012, Cell stem cell 11, 589-595), which influence their cellular behavior and epigenetic status. Indeed, factors involved in metabolic functions such as mitochondrial proteins are among the first to be up-regulated in cells undergoing reprogramming. Therefore, delineating the molecular mechanisms governing the dynamic regulation of cellular metabolism is crucial to understanding the connections between metabolic and epigenetic reprogramming.

Nuclear receptors (NRs) are pleiotropic regulators of organ physiology controlling broad aspects of glucose and fatty acid metabolism and overall energy homeostasis (Mangelsdorf et al., 1995, Cell 83, 835-839, Yang et al., 2006, Cell 126, 801-810). While orphan receptors such as the Estrogen Related Receptors (ERRs) are ligand-independent, they nonetheless are capable of directing dramatic changes in both glycolytic and oxidative metabolism in tissues with high energy. ERRs switch between various oxidative states by associating preferentially with their co-activators PGC-1α/β. The ERR family member ERRβ (also known as Esrrb) is glycolytic in the absence of PGC-1α and plays a key role in establishing pluripotency (Buganim et al., 2012, Cell 150, 1209-1222; Feng et al., 2009, Nature cell biology 11, 197-203; Festuccia et al., 2012, Cell stem cell 11, 477-490; Martello et al., 2012, Cell stem cell 11, 491-504). In contrast, ERRα and ERRγ, which are expressed in oxidative tissues such as skeletal muscle and heart (Narkar et al., 2011, Cell Metab 13, 283-293), have not previously been linked to iPSC generation. As described in detail below, transient up-regulation of ERRα and γ in the early stages of reprogramming induced a unique energetic state. Furthermore, it was shown that the transient OXPHOS burst and increased glycolysis initiated by this metabolic switch were important for epigenetic reprogramming. Mechanistically, ERRα and γ were enriched in bona fide reprogramming progenitors and induced widespread changes in metabolic gene networks. These results indicate that an ERR-mediated metabolic transition is important for induced pluripotency.

Accordingly, the invention provides methods for generating a reprogramming progenitor that is capable of giving rise to induced pluripotent stem cells at high efficiency. In one embodiment, a Sca1−CD34− reprogramming progenitor is approximately 50-fold more efficient at generating iPSCs than a reference cell. In other embodiments, nearly 75% of the iPSC colonies in a population were generated by Sca1−CD34− reprogramming progenitors which were less than 5% of the OSKM infected cells. Surprisingly, Sca1−CD34− reprogramming progenitors exhibited a 1500% increased colony formation frequency (CFF) relative to a reference cell.

Cellular Compositions

Compositions of the invention comprising purified reprogramming progenitors or induced pluripotent stem cells derived from those progenitors can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the reprogramming progenitors or their progeny utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the reprogramming progenitors or their descendants.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the reprogramming progenitors or their descendants (i.e., IPSCs) as described in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of reprogramming progenitors or their descendants (i.e., IPSCs) of the invention is the quantity of cells necessary to achieve an optimal effect. The quantity of cells to be administered will vary for the subject being treated. In a one embodiment, between 104 to 108, between 105 to 107, or between 106 and 107 cells of the invention are administered to a human subject. In preferred embodiments, at least about $1 \times 10^7$, $2 \times 10^7$, $3 \times 10^7$, $4 \times 10^7$, and $5 \times 10^7$ cells of the invention are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active stem cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.03 wt. % or about 0.001 to about 20 wt. %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Administration of Cellular Compositions

Compositions comprising reprogramming progenitors or their descendants (i.e., IPSCs) are described herein. In particular, the invention provides for the administration of an induced pluripotent stem cell derived from a reprogramming progenitor that expresses ERRalpha or gamma and optionally PGC1 alpha or beta. Such cells can be provided systemically or locally to a subject for the treatment or prevention of a disease or condition associated with a decrease in cell number (e.g., neurodegenerative diseases, heart disease, autoimmune diseases, type I diabetes, type II diabetes, pre-diabetes, metabolic disorders, and the treatment of other diseases or disorders associated with a deficiency in cell division, differentiation and cell death (e.g., a reduction in the number of pancreatic cells, a reduction of T-cells, a loss of neuronal cells or myocytes). In one embodiment, cells of the invention are directly injected into an organ or tissue of interest (e.g., pancreas, thymus, brain, muscle, or heart). Alternatively, compositions comprising cells of the invention are provided indirectly to the organ of interest, for example, by administration into the circulatory system (e.g., the cardio or pancreatic vasculature). Expansion and differentiation agents can be provided prior to, during or after administration of the cells to increase production of cells having, for example neurotransmitter, or insulin producing potential in vitro or in vivo. The cells can be administered in any physiologically acceptable vehicle, normally intravascularly, although they may also be introduced into another convenient site where the cells may find an appropriate site for regeneration and differentiation.

In one approach, at least 100,000, 250,000, or 500,000 cells are injected. In other embodiments, 750,000, or 1,000,000 cells are injected. In other embodiments, at least about $1\times10^5$ cells will be administered, 1×106, 1×107, or even as many as 1×108 to $1\times10^{10}$, or more are administered. Selected cells of the invention comprise a purified population of cells that express ERRalpha or gamma and PGC1 alpha or beta. Preferable ranges of purity in populations comprising selected cells are about 50 to about 55%, about 55 to about 60%, and about 65 to about 70%. More preferably the purity is at least about 70%, 75%, or 80% pure, more preferably at least about 85%, 90%, or 95% pure. In some embodiments, the population is at least about 95% to about 100% selected cells. Dosages can be readily adjusted by those skilled in the art (e.g., a decrease in purity may require an increase in dosage). The cells can be introduced by injection, catheter, or the like.

Compositions of the invention include pharmaceutical compositions comprising reprogramming progenitors or their descendants (i.e., IPSCs) and a pharmaceutically acceptable carrier. Administration can be autologous or heterologous. For example, somatic cells can be obtained from one subject, and administered to the same subject or a different, compatible subject.

Selected cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a selected cell), it will generally be formulated in a unit dosage injectable form (solution, suspension, emulsion).

Accordingly, the invention also relates to a method of treating a subject having, for example, a disease or condition characterized by a deficiency in cell number, including but not limited to neurodegenerative diseases, cancer, heart disease, autoimmune diseases, type I diabetes, type II diabetes, pre-diabetes, metabolic disorders, and the treatment of other diseases or disorders associated with a deficiency in cell division, differentiation and cell death (e.g., a reduction in the number of pancreatic cells, a reduction of T-cells, a loss of neuronal cells or myocytes). This method comprises administering to the subject an effective amount either of a reprogramming progenitor or descendant thereof (i.e., IPSCs) isolated as explained herein.

Kits

The invention provides kits comprising an effective amount of reprogramming progenitors or their descendants (i.e., IPSCs). In one embodiment, the invention provides a reprogramming progenitor derived from an embryonic fibroblasts (MEFs) or a lung fibroblast that expresses ERRalpha or gamma. Optionally, the cells also express PGC1α or β. The cells are provided in unit dosage form. In some embodiments, the kit comprises a sterile container which contains a therapeutic or prophylactic cellular composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired a cell of the invention is provided together with instructions for administering the cell to a subject having or at risk of developing a condition characterized by a deficiency in cell number, such as a neurodegenerative disease, heart disease, autoimmune disease, type I diabetes, type II diabetes, pre-diabetes, other metabolic disorders, or other diseases or disorders associated with a deficiency in cell division, differentiation and cell death (e.g., a reduction in the number of pancreatic cells, a reduction of T-cells, a loss of neuronal cells or myocytes). The instructions will generally include information about the use of the composition for the treatment or prevention of a neurodegenerative disease, cancer, heart disease, autoimmune disease, type I diabetes, type II diabetes, pre-diabetes, other metabolic disorders, or other diseases or disorders associated with a deficiency in cell division, differentiation and cell death (e.g., a reduction in the number of pancreatic cells, a reduction of T-cells, a loss of neuronal cells or myocytes). In other embodiments, the instructions include at least one of the following: description of the cells; dosage schedule and administration for treatment or prevention of a neurodegenerative disease, cancer, heart disease, autoimmune disease, type I diabetes, type II diabetes, pre-diabetes, other metabolic disorders, or other diseases or disorders associated with a deficiency in cell division, differentiation and cell death or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: ERRα/γ are Important for Somatic Cell Reprogramming

Figure 1E:
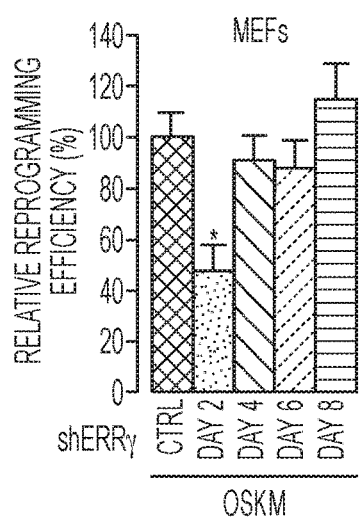
FIG. 1E is a bar graph showing that depleting ERRγ in retroviral reprogramming MEFs after day 4 did not influence reprogramming efficiency (n=3, error bars show standard deviation (s.d.).).
Figure 1F:
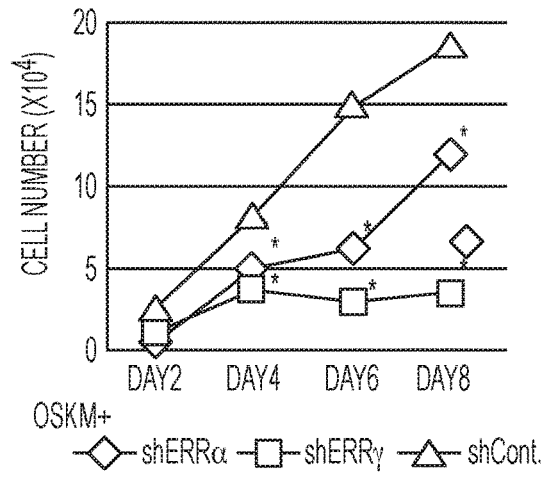
FIG. 1F is a linear graph showing that reprogramming cells with ERRα or ERRγ depletion by lentiviral shRNA showed a reduced proliferation rate.
Figure 1G:
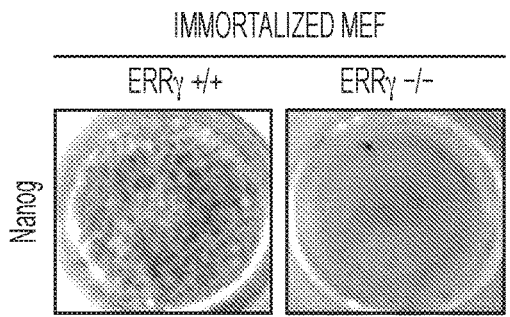
FIG. 1G shows two images of cell cultures of Nanog staining of immortalized MEFs from wild-type (ERRγ+/+) or ERRγ knockout (ERR γ−/−) embryos after retroviral OSKM reprogramming
Figure 2A:
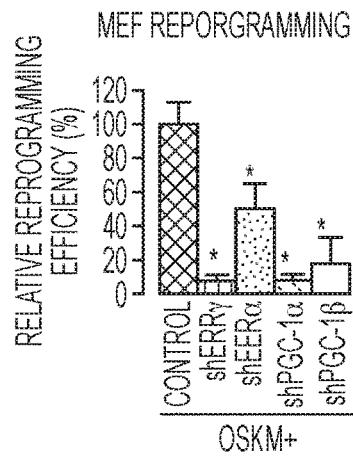
FIGS. 2A-2J are bar graphs and images showing ERRα/γ and PGC1α/β were important for induced pluripotency in both mouse and human cells.
Figure 2D:
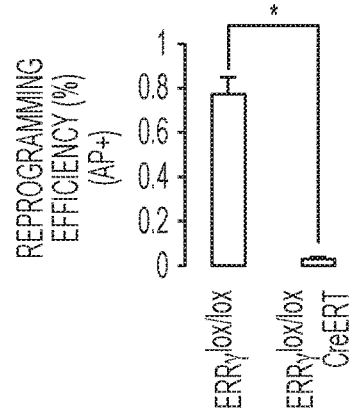
Figure 2F:
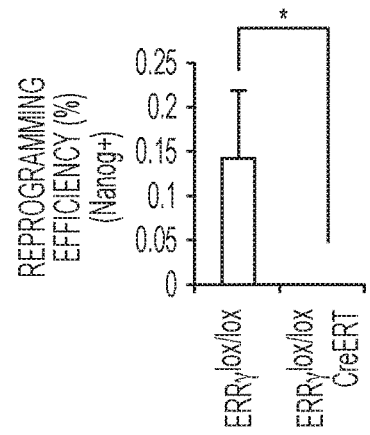
Figure 2B:
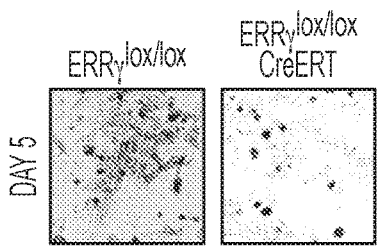

Temporal gene expression studies in mouse embryonic fibroblasts (MEFs) after reprogramming with Oct4, Sox2, Klf4 and cMyc (OSKM) or OSK revealed transient increases in the expression of ERRγ, PGC-1α, PGC-1β, and to a lesser extent, ERRα, 3 days after infection (FIGS. 1A-1D). Furthermore, depletion of ERRγ, PGC-1α or PGC-1β by shRNA knockdown coincident with OSKM induction significantly reduced reprogramming efficiency in MEFs (FIG. 2A), whereas ERRγ depletion later in reprogramming had little effect (FIG. 1E). To further explore the timing of gene induction in early reprogramming, OSKM expression was induced in MEFs isolated from ERRγlox/lox and ERRγlox/lox CreERT mice via doxycycline-inducible lentiviruses (Wei et al., 2009, Stem cells (Dayton, Ohio) 27, 2969-2978). While tamoxifen-treated ERRγlox/lox MEFs (ERRγ control cells) exhibited multiple foci of reprogramming cells 5 days after doxycycline-induced OSKM expression, ERRγlox/lox CreERT MEFs treated with tamoxifen at day 3 (ERRγ iKO cells) displayed fibroblast-like morphology (FIG. 2B). Consistent with a failure of the ERRγ iKO cells to reprogram, few alkaline phosphatase (AP) or Nanog-positive colonies were observed after 3 weeks of OSKM infection, whereas control cells showed normal reprogramming efficiency (FIGS. 2C-2F). As depletion of ERRγ or ERRα in reprogramming cells lead to a reduction in cell proliferation (FIG. 1F), the reprogramming efficiencies of immortalized MEFs generated from ERRγ knockout (ERRγ-/-) or wildtype (ERRγ+/+) mouse embryos were also compared. No Nanog-positive cells were detected in (ERRγ-/-) cells after OSKM infection (FIG. 1G). Reprogramming efficiencies of doxycycline-inducible reprogramming MEFs with and without ERRγ over expression (Ad-ERRγ and Ad-GFP, respectively) were also compared indicating that ERRγ over expression significantly increased reprogramming efficiency (FIG. 1O) Together, these findings indicate that the induction of ERRγ early in reprogramming was important for iPSC generation from efficiency in MEFs.

Figure 1H:
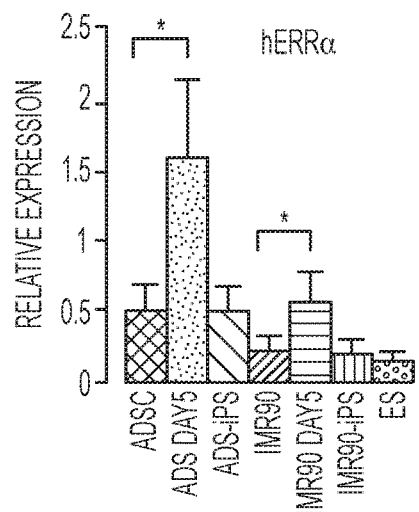
FIGS. 1H-1J are bar graphs showing that human ERRα and PGC1α/β were up-regulated in retroviral reprogramming human lung fibroblast IMR90 cells at day 5, but not in adipose stem cells (ADSCs), IMR90, or pluripotent stem cells (n=3, *p<0.01, error bars show s.e.m.).
Figure 1I:
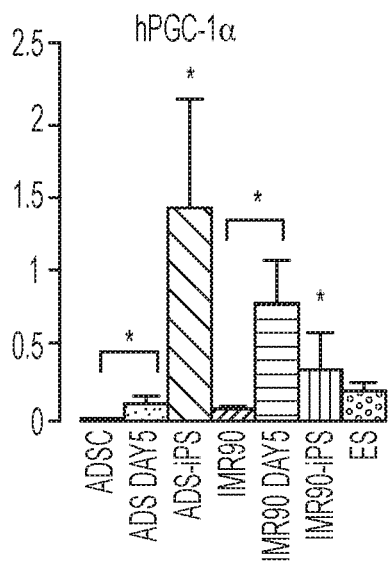
Figure 1J:
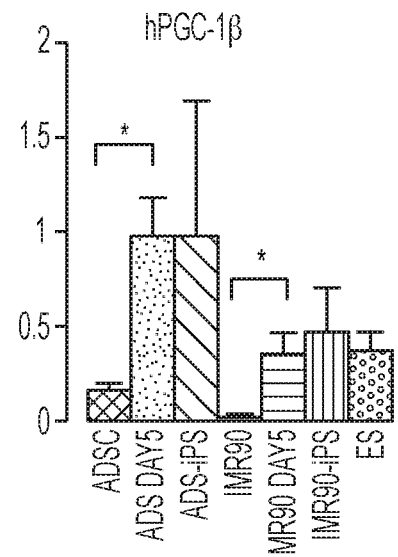
Figure 2G:
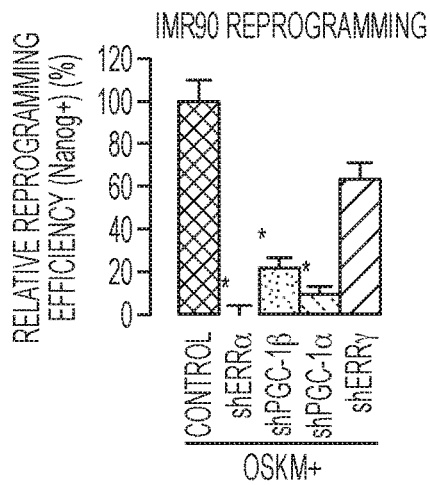
Figure 2H:
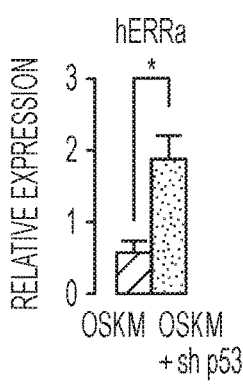
Figure 2C:
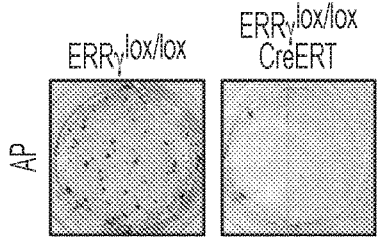
Figure 2I:
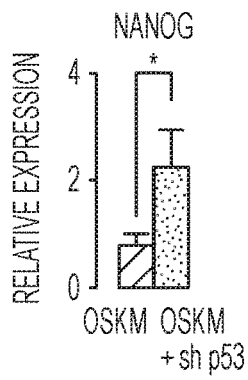
Figure 2E:
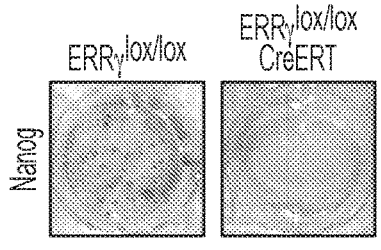
Figure 2J:
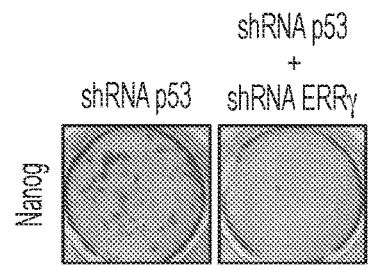

Similar gene expression patterns were observed during the reprogramming of human lung fibroblast IMR90 cells and adipose-derived stem cells (ADSCs), with the distinction that ERRα, rather than ERRγ, was up-regulated (FIGS. 1H-1J). Parallel shRNA knockdown studies in the human IMR90 cells revealed a strong dependence on ERRα expression, alongside PGC-1α and β expression, whereas depletion of ERRγ was partially tolerated (~40% reduction in Nanog+ colonies, FIG. 2G), further indicating that ERRα rather than ERRγ was important for iPSC generation in human fibroblasts. Furthermore, knockdown of p53, previously shown to increase iPSC generation (Kawamura et al., 2009, Nature 460, 1140-1144), resulted in the hyper-induction of ERRα and Nanog during IMR90 cell reprogramming (FIGS. 2H and 2I). Notably, the coincident knockdown of ERRγ and p53 blocked iPSC generation in MEFs (FIG. 2J), indicating that the ERR signaling pathway was epistatic to p53-induced senescence in iPSC reprogramming.

Figure 1K:
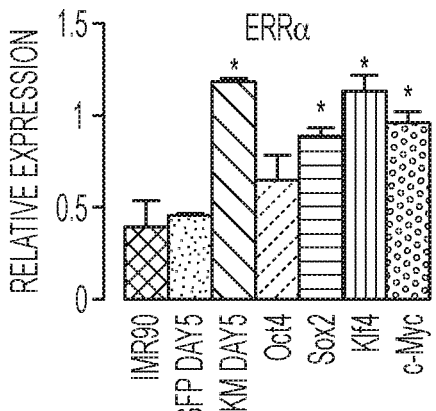
Figure 1L:
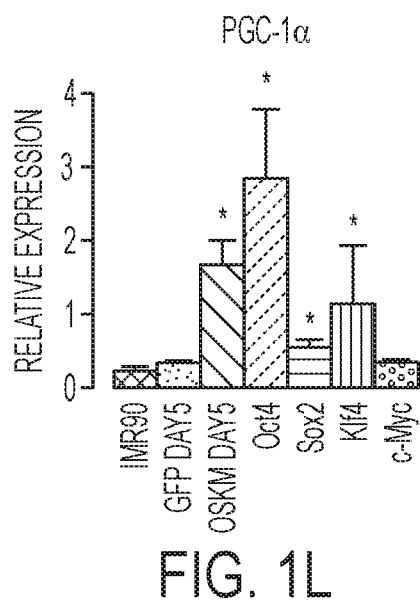

To decipher the molecular mechanisms driving ERR/PGC-1 induction, IMR90 cells were infected with each of the four factors individually. Distinctive expression patterns for ERRα, PGC-1α and -1β were observed 5 days after infection. Klf4, c-Myc and Sox2 were each able to efficiently induce ERRα, Oct3/4 and Klf4 both induced the expression of PGC-1α, while c-Myc efficiently induced PGC-1β expression (FIGS. 1K-1M). These patterns of gene induction indicate that all four reprogramming factors contributed in complementary ways to produce the operational ERRα transcriptional complex at day 5 (FIG. 1N).

Further, the human ERRα gene was cloned into a lentiviral reporter which contained green fluorescent protein (GFP) and luciferase (FIG. 1P). A separate constitutive active promoter EF1a drove the expression of Neomycin resistance gene, which allowed the selection in cells with low expression of endogenous ERRα (FIG. 1P). A sub-population of reprogramming cells which had high ERRα expression were isolated (FIG. 1Q). Human fibroblasts were transduced with lentiviral reprogramming factors which overexpressed Oct4, Sox2, Klf4, cMyc, Nanog and Lin28 (FIG. 1Q). The fibroblasts were transduced with ERRα reporter at the same time. GFP was not observed at day 1-2, but started to appear and reach its peak around day 4-6 (FIG. 1Q). Cells were sorted by GFP intensity at that stage to isolate the top 5% GFP positive cells (FIG. 1Q). ERRα reporter could be observed in day 5 reprogramming fibroblast, whereas the control which only transduced with reporter but not the reprogramming factors remained GFP negative (FIG. 1R). Reprogramming cells with ERRα reporter were analyzed by fluorescence activated cell sorting (FACS), P4 representing the GFP positive population (FIG. 1S). Gene expression between ERRα and its targets in normal fibroblasts (control), fibroblasts transduced with reporter only (GF only), and GFP+ and GFP- population at reprogramming day 6 was compared (FIG. 1T). ERRα and its targets were highly enriched in GFP+ population, compared to other samples, indicating that the ERRα reporter could fully capture the endogenous ERRα expression pattern (FIG. 1T).

Figure 3A:
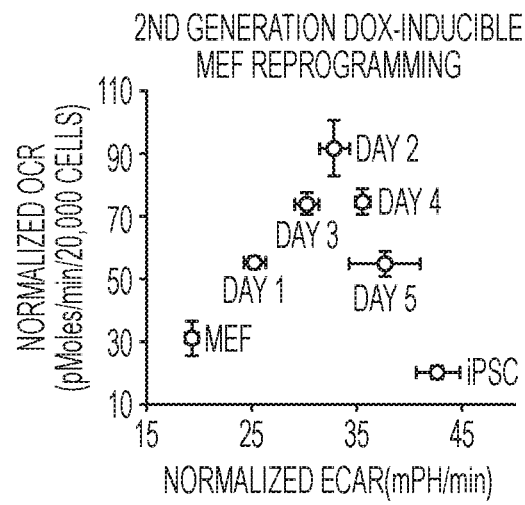
FIGS. 3A-3G are graphs and a heat map showing that ERRα/γ induced a metabolic transition in early reprogramming, which is important to induced pluripotency.
Figure 3B:
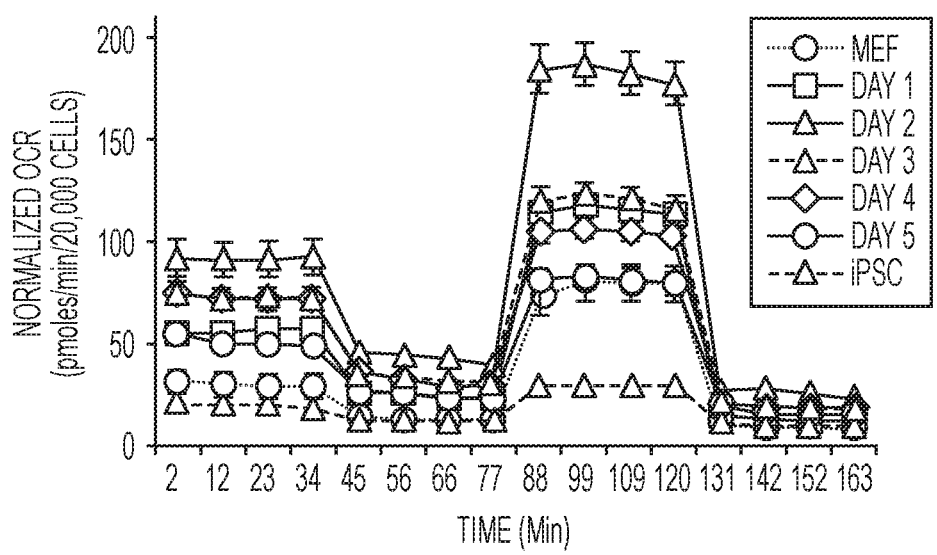
Figure 3C:
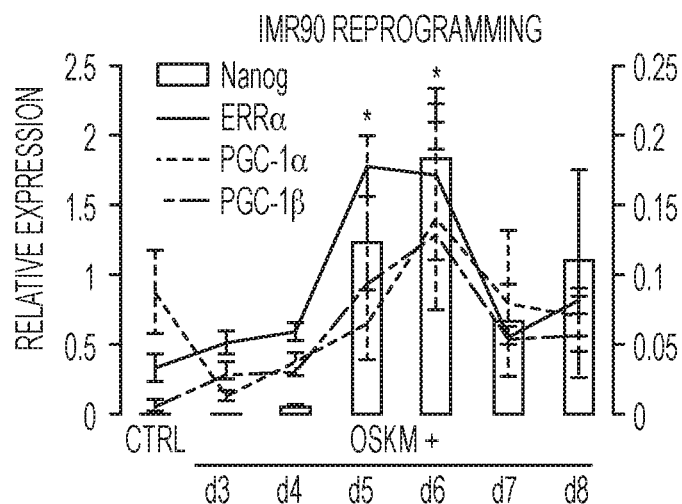
Figure 3D:
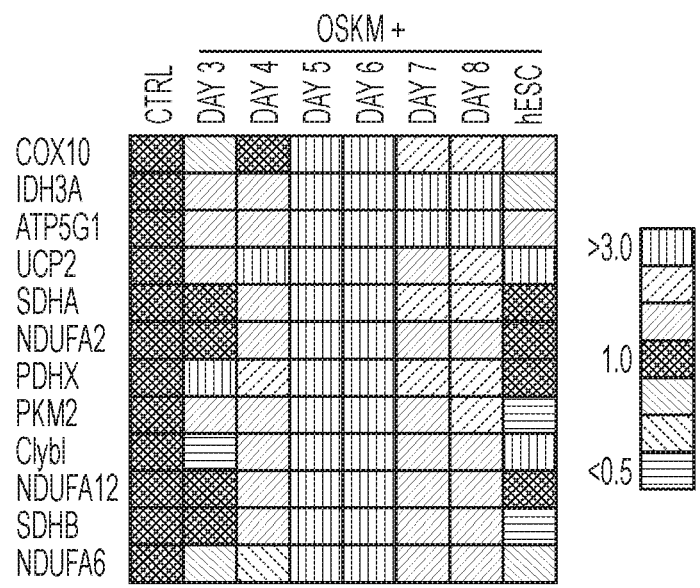
Figure 4A:
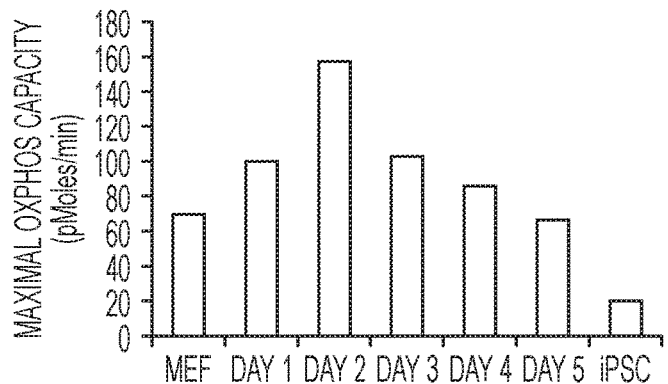
FIGS. 4A-4H (related to FIG. 3) are graphs and a heat map showing changes in metabolic activity and protooncogene tyrosine-protein kinase (ROS) genes during reprogramming
Figure 4B:
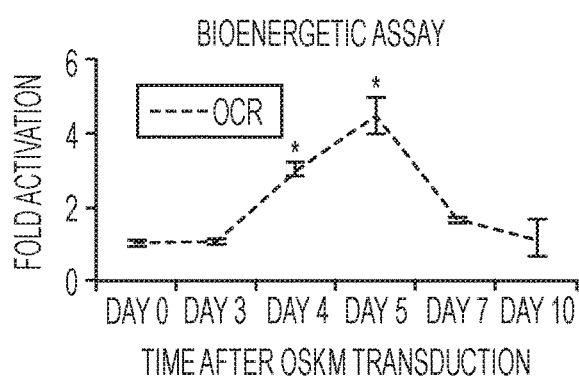
Figure 4C:
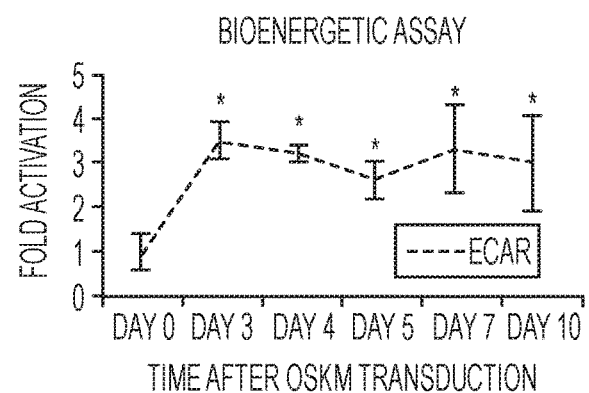
Figure 4D:
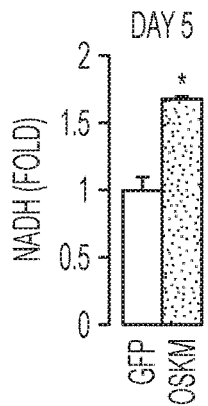
Figure 4E:
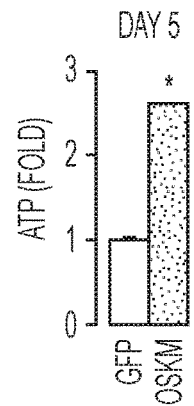
Figure 4F:
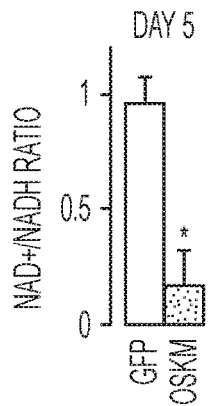
Figure 4G:
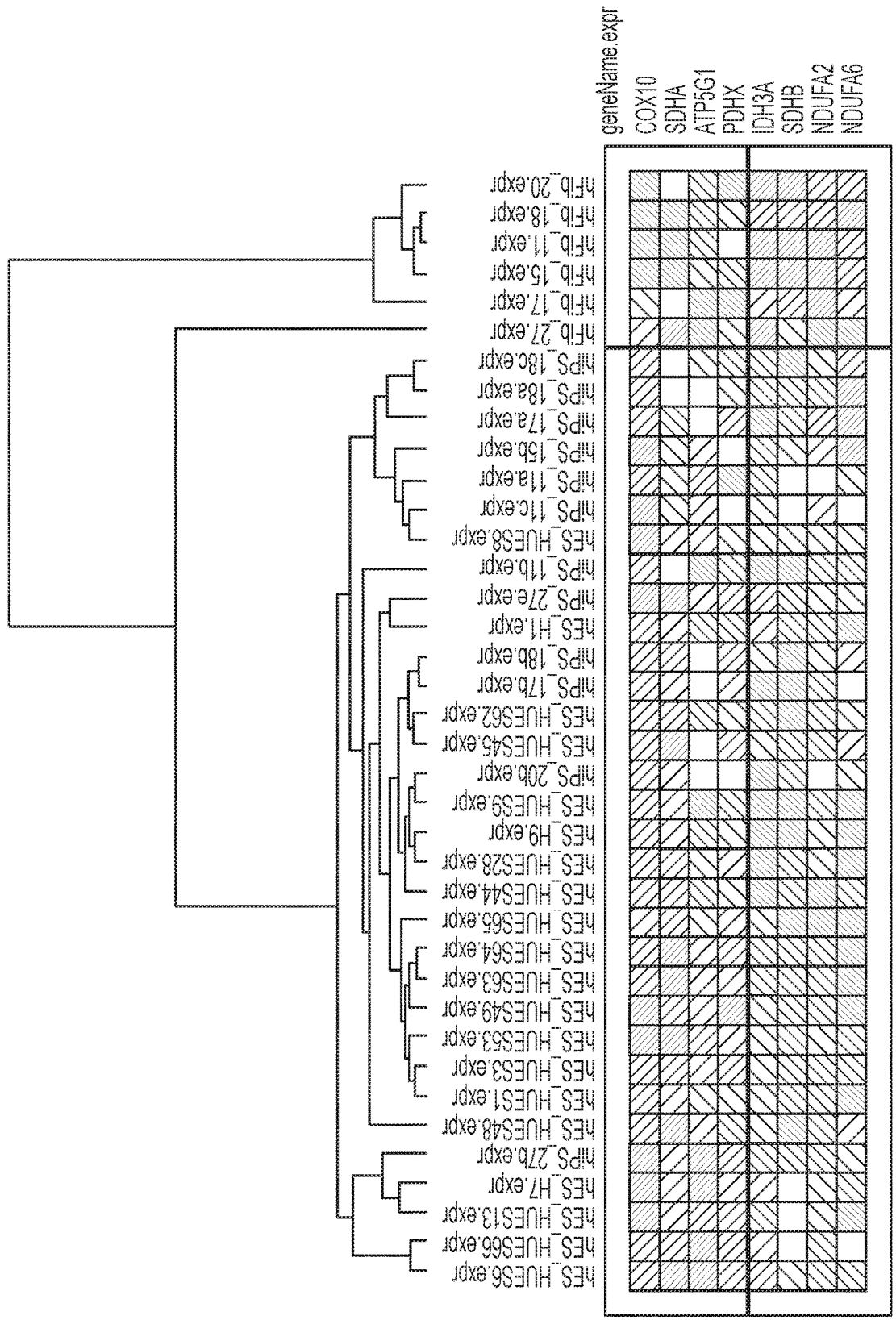
Figure 4H:
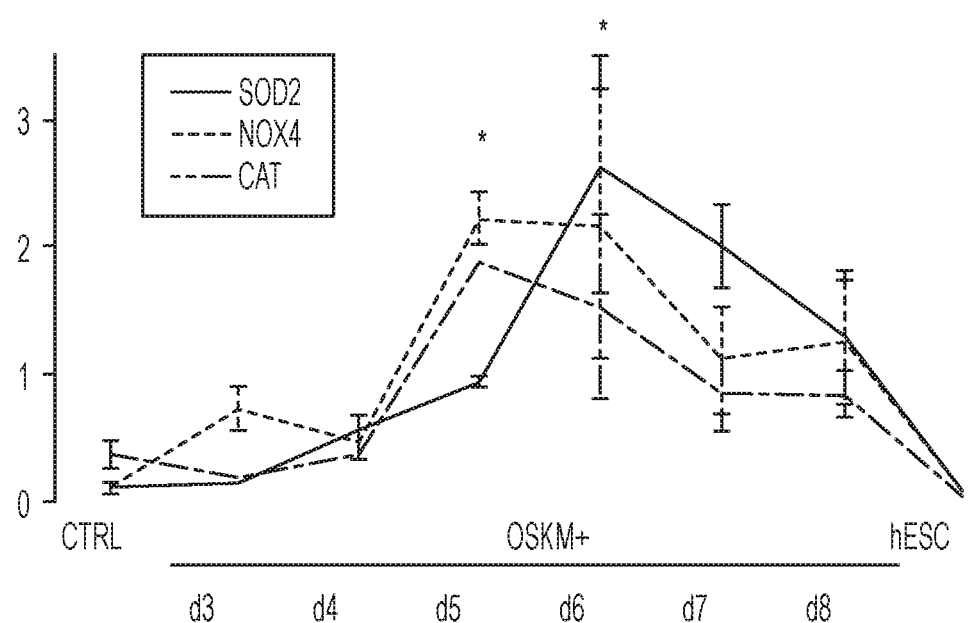

Example 2: ERRs Directed a Transient Hyper-Energetic State that Functions in Reprogramming The increased expression of ERRs and their co-activators led to the question of whether acutely altered energy flux in the mitochondria may be fueling reprogramming. Mouse embryonic fibroblasts (MEFs) from the reprogramming factor doxycycline-inducible mouse (Carey et al., 2010, Nature methods 7, 56-59) reached an oxidative phosphorylation (OXPHOS) peak around days 2-4 after induction (FIG. 3A). Importantly, the maximal OXPHOS capacity was also significantly increased in early reprogramming MEFs (FIGS. 3B and 4A). A similar bioenergetics time course recorded on days 3 to 10 after OSKM infection in human IMR90 cells revealed a transient increase in mitochondrial OXPHOS that peaked 5 days after infection (2.5-5.0 fold increase in oxygen consumption rates (OCR)) accompanied by a sustained increase in glycolysis (2.5-3.5 fold increase in the extra-cellular acidification rates (ECAR)) (FIGS. 4B and 4C). Corresponding with the increased expression of energy regulators, the levels of both nicotinamide adenine dinucleotide (NADH) and cellular ATP were increased in IMR90 cells 5 days after infection, while the NAD+/NADH ratio decreased (FIGS. 4D-4F). Together, these results indicated that early reprogramming cells were in a hyper-energetic state. Closer examination of human lung fibroblast IMR90 cells revealed remarkably coincident temporal expression patterns of ERRα, PGC-1α and β during the early stages of reprogramming that are consistent with the known role of PCG1α/β as an ERR cofactor (days 3 to 8, FIG. 3C). ERRs and PGC-1s directly regulate an extensive network of genes controlling energy homeostasis including proteins involved in fatty acid oxidation, the tricarboxylic acid (TCA) cycle and OXPHOS. Therefore, the temporal expression pattern of various known regulators of cellular energy homeostasis during the reprogramming of IMR90 cells was examined. Remarkably, multiple key players in energy metabolism, including ATP synthase in mitochondria (AIP3GI), succinate dehydrogenase (SDHB), isocitrate dehydrogenase (IDH3A) and NADH dehydrogenase (NDUFA2), reached peak expression at day 5 (FIGS. 3D and 4G). In addition, the induction of superoxide dismutase 2 (SOD2), NADPH oxidase 4 (NOX4) and catalase (CAT) by OSKM infection (FIG. 4H), indicated that the antioxidant program was being triggered coordinately with the ERRα-PGC-1 surge.

Pluripotent stem cells are known to mainly rely on glycolysis to produce energy. Previous studies have focused on the changes in glycolytic activity during reprogramming, as elevated glycolysis was linked to a faster cell cycle and iPSC generation (Folmes et al., 2011, Cell metabolism 14, 264-271; Panopoulos et al., 2012, Cell research 22, 168-177; Shyh-Chang et al., 2013b, Science, New York, N.Y., 339, 222-226). However, the present findings indicate that iPSC precursors underwent a transient increase in oxidative phosphorylation activity. The dynamics of ECAR support previous work showing that the glycolytic activity of the cells was gradually enhanced and maintained during reprogramming to a level similar to iPSCs (FIGS. 3A and 4C). In contrast, the transient burst of OXPHOS during reprogramming of both human and mouse cells had not been previously documented (FIGS. 3A, 3B and 4B). This led to the investigation of the potential influence of the ERRα/γ surge on cell plasticity during reprogramming.

Figure 3E:
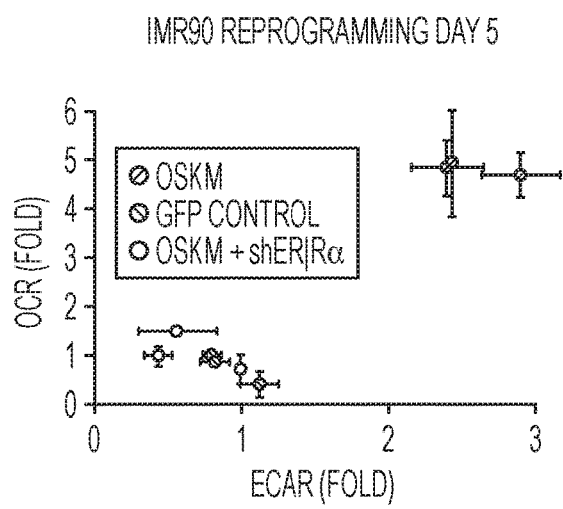
Figure 3F:
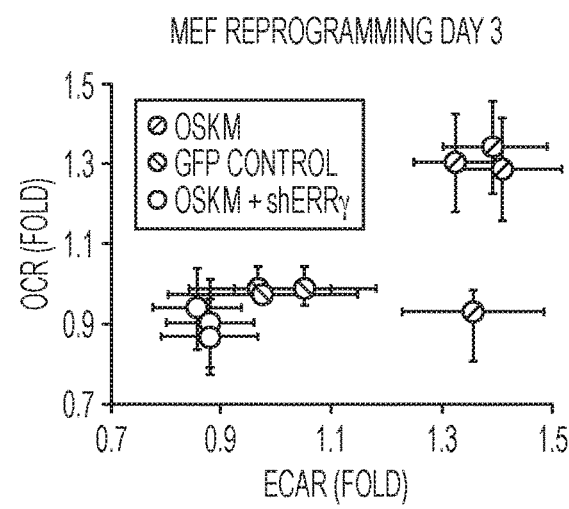
Figure 3G:
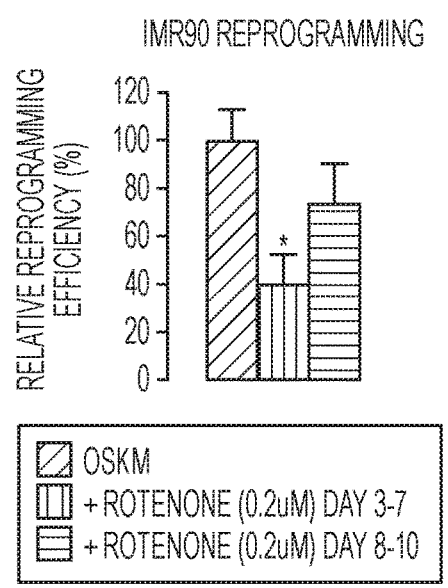

To examine a potential causal relationship between ERR expression and the induction of the hyper-energetic state, the metabolic activities of partially reprogrammed cells before and after targeted shRNA knockdowns were compared. Notably, the increase in OXPHOS and glycolysis was completely abrogated in cells depleted of ERRs (ERRα in IMR90 cells at day 5, and ERRγ in MEFs at day 3; FIGS. 3E and 3F). Furthermore, the mitochondrial inhibitor Rotenone significantly reduced iPSC generation, though only when treatment was coincident with the observed hyper-energetic state, consistent with the OXPHOS burst being necessary for reprogramming (FIG. 3G). Together these data indicate that ERRα and γ regulate iPSC generation through the induction of a transient enhanced metabolic state that is important for somatic cell reprogramming.

Example 3: Bona Fide iPSC Progenitors were Enriched for ERRγ Expression

Figure 6A:
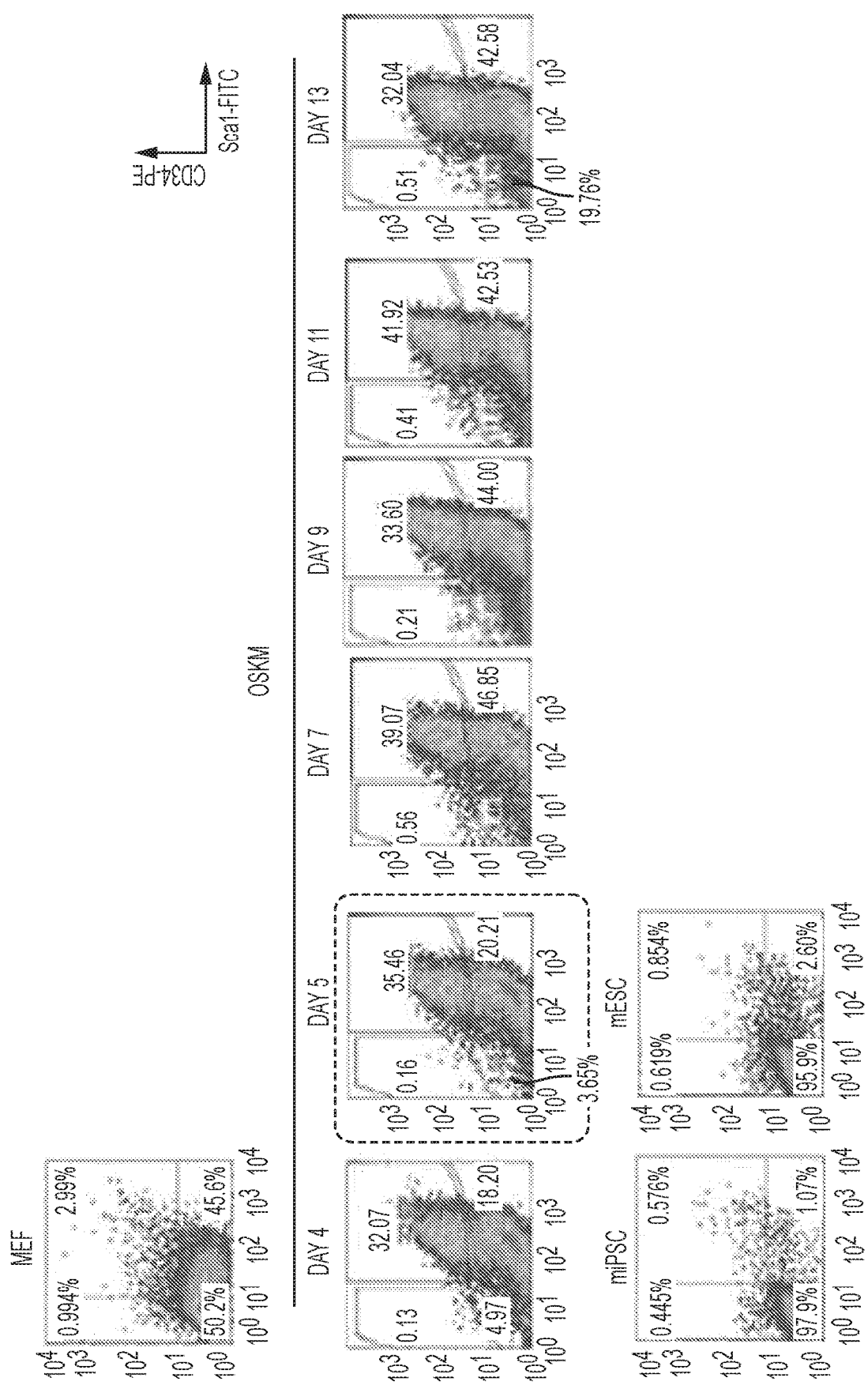
FIGS. 6A-6H (related to FIG. 5) are graphs and images showing pluripotency assays and germline transmission of iPSCs from double negative (DN) population.
Figure 6B:
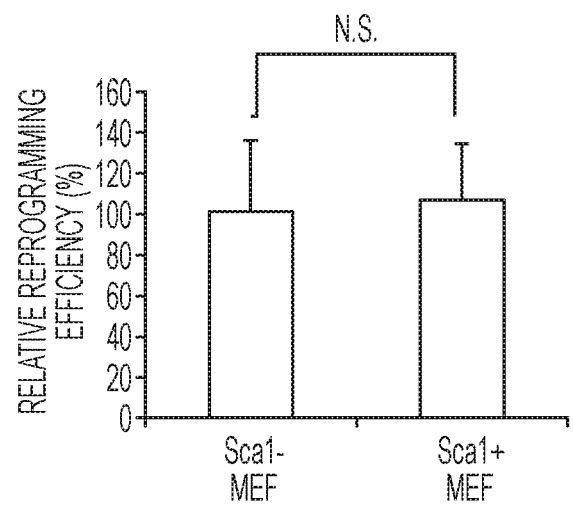
Figure 6C:
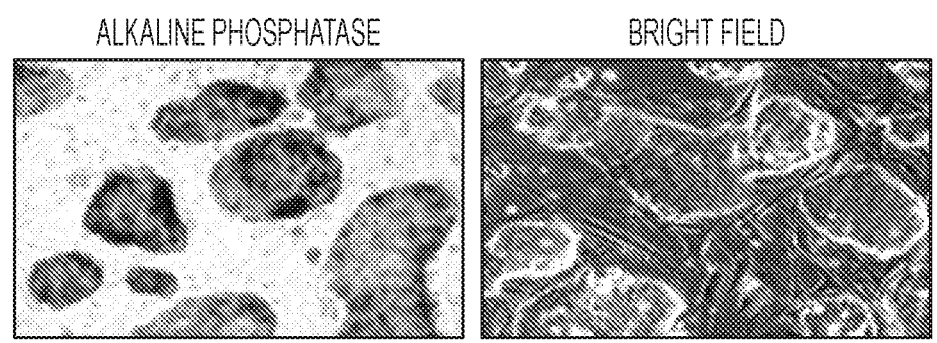
Figure 6D:
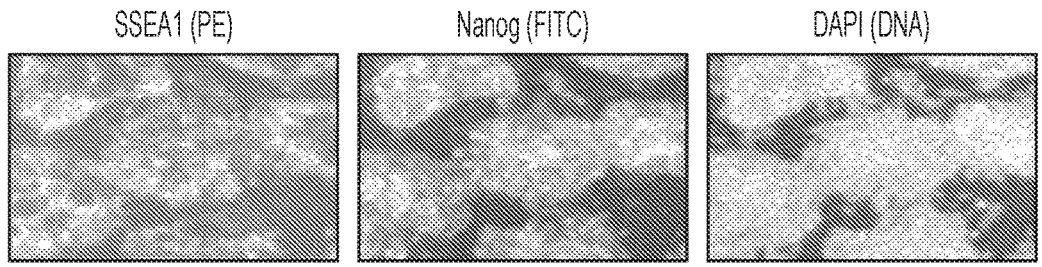
Figure 6F:
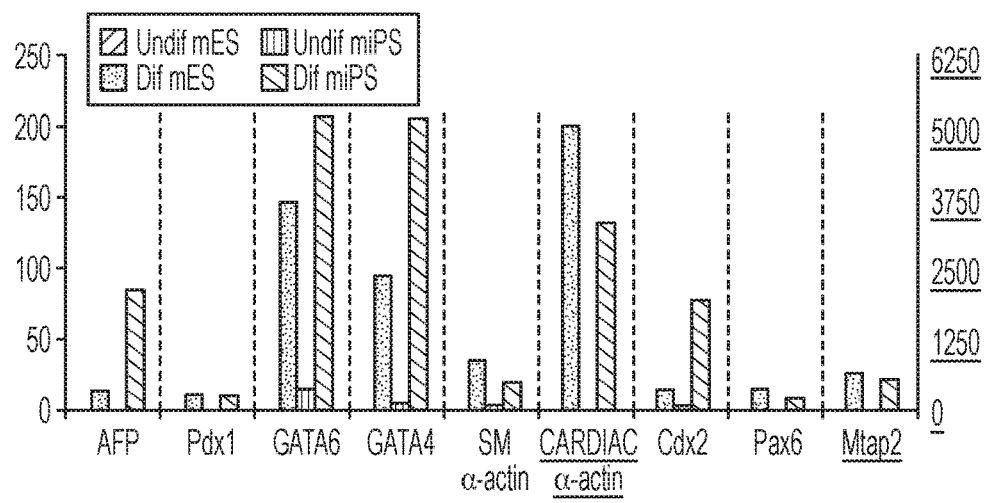
Figures 6E, 6G, 6H:
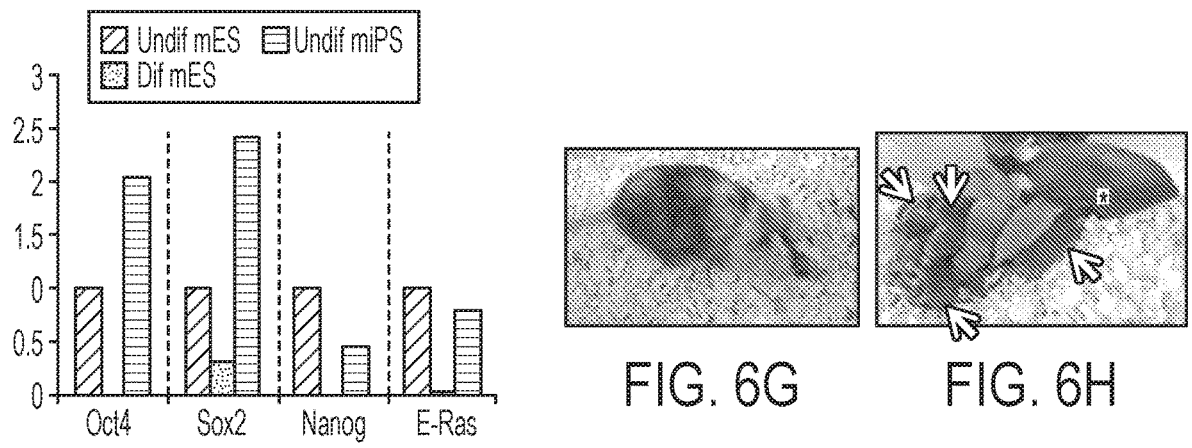

Under standard conditions, only a small percentage of cells are successfully reprogrammed into iPSCs. Given the observation of a metabolic switch in the heterogeneous cell populations present in the early stages of reprogramming, it was hypothesized that the sub-population of bona fide iPSC progenitors might be enriched for the ERR-mediated hyper-energetic burst. Analysis of cell surface markers differentially expressed during mouse embryonic fibroblasts (MEFs) reprogramming revealed that early clusters of reprogramming cells lacked the expression of stem cell antigen 1 (Sca1) and cluster of differentiation gene 34 (CD34) expression (FIGS. 5A and 5B). Upon OSKM induction, CD34 expression was promptly up-regulated, resulting in three distinct cell sub-populations in early reprogramming cells; Sca1−CD34− double negative (DN), Sca1+CD34+ double positive (DP), and Sca1+CD34− single positive (SP) (FIG. 6A). Correlating with immunofluorescence staining (FIG. 5A), only a minor fraction (~3-5%) of early reprogramming cells were Sca1−CD34− (FIG. 6A). Strikingly, ERRγ and PGC-1β expression were ~10- and ~7-fold higher, respectively, in the early reprogramming DN cells compared to DP or SP cells, as determined by qPCR analysis (FIGS. 5C and 5D). Importantly, these early reprogramming DN cells exhibited significantly elevated extracellular acidification rate (ECAR) and oxygen consumption rate (OCR) compared to DP or SP populations (FIGS. 5E and 5F), consistent with Sca1−CD34− labeling a subpopulation of hyper-energetic cells. Notably, Sca1−CD34− cells present in non-infected MEFs did not show elevated reprogramming efficiency (FIG. 6B). To test the hypothesis that this hyper-energetic state is important for reprogramming, the number of iPS colonies generated from isolated DN, SP and DP cells was compared. While DN cells comprised only ~5% of the infected cells, they were approximately 50-fold more efficient at generating iPSCs than the DP or SP populations, based on Nanog staining (FIG. 5G; 35.5% (DN) vs 0.6% (DP) or 0.8% (SP)). That is, nearly 75% of the iPSC colonies generated were derived from less than 5% of the infected cells, corresponding to a 1500% increased colony formation frequency (CFF). The iPSCs derived from the DN population showed ESC-like morphology and expressed high levels of alkaline phosphatase activity as well as pluripotency markers (FIGS. 6C-6E). In addition, embryoid body differentiation of the DN-derived iPSCs produced markers from each of the three germ layers (FIG. 6F). Moreover, iPSCs generated from DN cells contributed to the formation of chimeric mice with subsequent crosses demonstrating germline-competency (FIGS. 6G and 6H). Collectively, these data indicate that the hyper-energetic cells identified in early reprogramming represented by the DN population, were bona fide reprogramming precursors that generate iPSCs at high efficiency.

Example 4: Reprogramming Cells Underwent an ERR-Mediated OXPHOS Burst

Figure 7E:
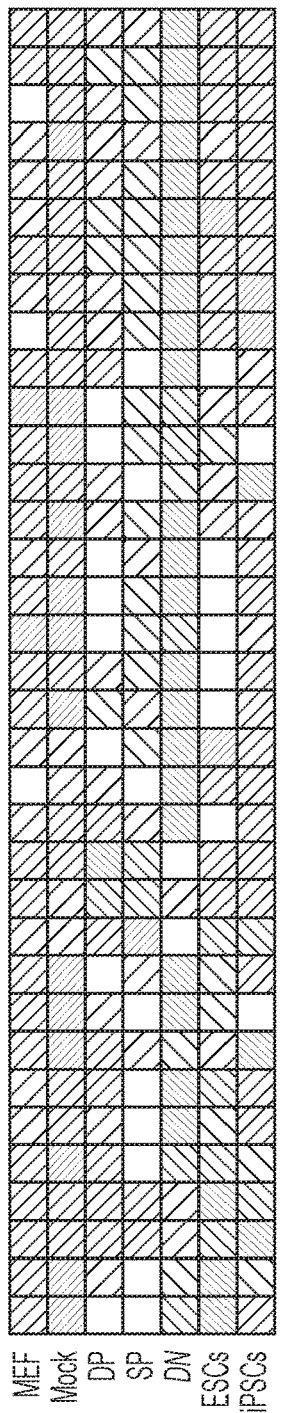

To better understand the molecular underpinnings of cell reprogramming and cell fate determination, the complete transcriptomes, determined by RNA-Sequencing, of somatic fibroblasts (non-infected mouse embryonic fibroblasts (MEFs), mock infected MEFs at day 5), intermediate reprogramming cell populations (DN, DP, SP, unsorted day 5 cells) and pluripotent stem cells (iPSCs generated from the DN population and mESCs) were compared. Not unexpectedly, distance matrix and clustering analyses grouped the cell types into the above 3 categories (FIGS. 7A and 7B). The clear separation of the DN population from the pluripotent stem cells indicated that these transitional cells have yet to adopt a durable pluripotency fate. Furthermore, the more subtle separation of the DN population from the other intermediate reprogramming cells in the cluster analysis indicated that they should express a unique gene signature associated with enhanced reprogramming efficiency (FIG. 7B). Indeed, the expression of selected pluripotency markers and key cell cycle genes in the DN population more closely resembled that observed in ESCs and iPSCs than found in the DP and SP populations (FIGS. 7C and 7D). However, a majority of other stem cell markers including ERRβ and Nanog were not enriched in the DN population. Thus, the DN cell population is in a definable transcriptional and metabolic state that appeared to facilitate efficient progression toward pluripotency.

Pivotal pathways controlling the enhanced reprogramming efficiency of DN cells were identified by comparing transcriptomes between DN, DP or SP populations. Interestingly, KEGG PATHWAY analysis, a process that maps molecular datasets, of the differentially regulated genes identified (oxidative phosphorylation) OXPHOS as the most significantly altered pathway in DN cells (FIGS. 8A and 8B). Furthermore, a comparison of the expression levels of genes involved in cellular energy metabolism revealed that the majority were upregulated in the DN population (FIG. 7E), consistent with the DN population comprising the most hyper-energetic cells. This supported the idea that a key feature of bona fide reprogramming is directing progenitors to enter a hyper-energetic state.

Figure 7F:
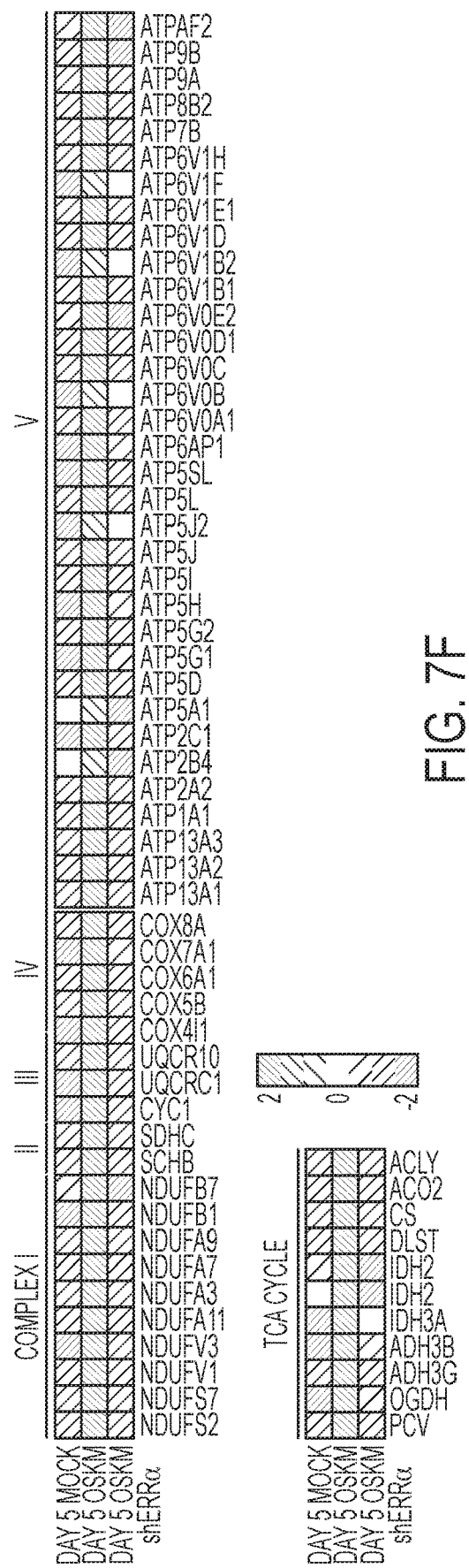
Figure 7G:
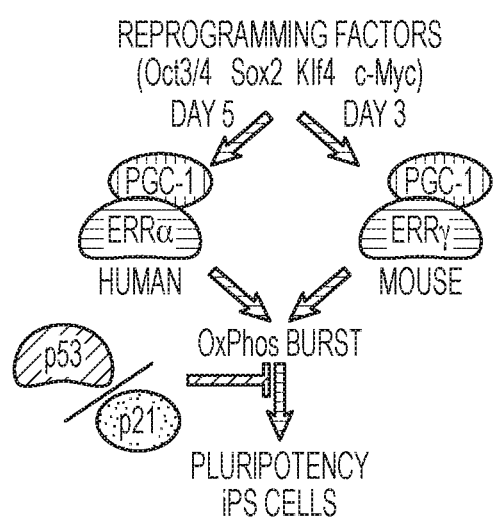

Finally, to determine if a causal association exists between the ERR surge and the increased expression of energy metabolism genes, the transcriptional consequences of ERRα knockdown in reprogramming IMR90s were examined. The expression of a large number (1061) of metabolic genes was significantly affected by ERRα depletion (FIG. 8C). In particular, dramatic decreases in the expression of regulators of cellular energy homeostasis including NADH dehydrogenases (NDUF), succinate dehydrogenases (SDH), mitochondrial respiratory chains (COX), ATPase, and ATP synthases in mitochondria were seen (FIG. 7F). The fact that ERRα depletion influenced the expression of a plethora of mitochondrial genes, including a variety of genes in Complex I-V, and the TCA cycle (FIG. 7F), further supported the conclusion that transient ERRα/γ expression induced an equally transient OXPHOS burst, facilitating reprogramming and enabling the transition from the somatic to pluripotent state (FIG. 7G).

Recent single-cell expression analyses revealed a requirement for early expression of ERRβ (Buganim et al., 2012), previously demonstrated by Feng et al. to be a 'Myc substitute' (Feng et al., 2009). In this model, Sox2 and ERRβ mutually enhanced each other's expression and initiated the reprogramming process, presumably in all transfected cells (Buganim et al., 2012). Here a downstream requirement for other ERR family members, ERRα and ERRγ, together with their coactivators PGC-1α/β, that define a distinct subpopulation of cells with dramatically enhanced efficiency for iPSC generation was revealed. A transient surge in ERRα/γ and PGC1α/β expression during reprogramming induced an early metabolic switch epitomized by a transient OXPHOS burst and sustained enhanced glycolysis. These findings complement a recent study demonstrating stage-specific roles for HIF1α and HIF2α in the early increase in glycolytic metabolism (Mathieu et al., 2014, Haematologica 99, e112-114). The surprising functional divergence between ERRα/γ and ERRβ adds a new dimension to the model for reprogramming, in which transient ERRα/γ expression is important to drive an early hyper-energetic metabolic state characterized by increased OXPHOS and glycolysis, whereas ERRβ is important for establishing induced pluripotency at later reprogramming stages (Chen et al., 2008, Cell 133, 1106-1117; Martello et al., 2012, Cell stem cell 11, 491-504; Zhang et al., 2008, The Journal of biological chemistry 283, 35825-35833). The fact that metabolic reprogramming is a prerequisite of induced pluripotency revealed the functional relevance of a unique metabolic state to achieving cell plasticity. Furthermore, via cell sorting of Sca1/CD34 double negative cells it was demonstrated that ERRγ and PGC-1β are early markers of a newly defined sub-group of reprogramming progenitors. In summary, these studies characterize a previously unrecognized, ERR/PGC-1 dependent metabolic switch prior to establishment of induced pluripotency in both human and mouse cells (FIG. 7G).

Figure 9A:
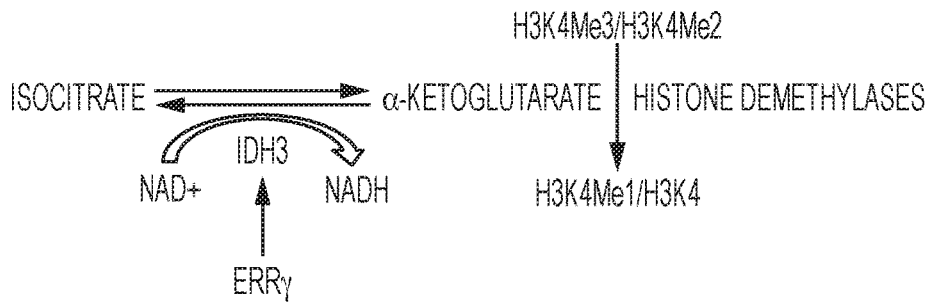
FIGS. 9A-9F depict a schematic, graphs, and an image that revealed that ERRs function through IDH and α-ketoglutarate to regulate reprogramming
Figure 9B:
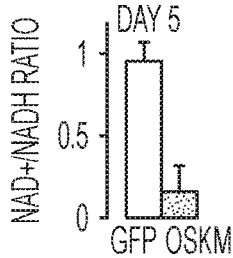

Example 5: ERRs Function Through IDH and α-Ketoglutarate to Regulate Reprogramming ERRα/γ regulate IDH gene expression and control the NAD+/NADH level in the cells during reprogramming (FIG. 9A). As a key co-enzyme of histone demethylase, α-ketoglutarate regulates the enzyme activity of several histone demethylases, such as KDM2 and KDM5, which act on H3K4Me2/3 and H3K9Me3. KDM stands for lysine (K) specific demethylase. As shown in FIG. 9A, ERRγ activates IDH3, which in turn catalyzes the oxidation of isocitrate to α-ketoglutarate. During the reaction, NAD+, as electron donor, is converted to NADH, thus decreasing the amount of NAD+ and increasing the amount of NADH and decreasing the NAD+/NADH ratio (increasing NADH/NAD+ ratio) (FIG. 9B). Under the regulation of α-ketoglutarate, histone demethylases demethylate histones at the lysine site. For example, H3K4Me3 is demethylated to H3K4Me1. The demethylation of the histone leads to global changes in enhancer and promoter landscape, and subsequently transcriptome dynamics.

Figure 9C:
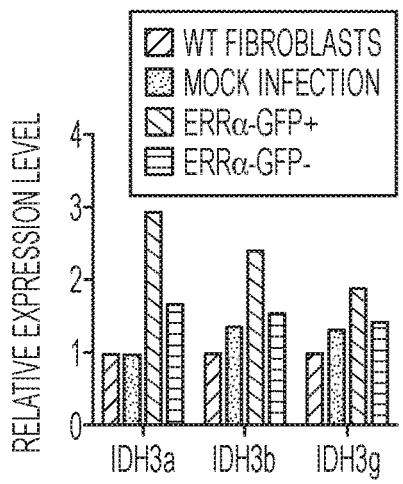

IDH3 gene expression was upregulated during reprogramming of a cell population (FIG. 9C). On day six of reprogramming, the relative expression levels of IDH3α, IDH3β, and IDH3γ genes were measured. To evaluate the IDH3 gene expression in response to ERRα expression level, fibroblast cells were infected with a lentivirus expressing GFP under the control of human ERRα promter. GFP expression was used to mark infected cells and was subsequently used to FACS sort the cells into those with high infection (ERRα–GFP+) and low infection (ERRα–GFP–). IDH3α, β and γ gene expression was upregulated in cells expressing high levels of ERRα (GFP+ cells) relative to corresponding control cells. Wild type (WT) fibroblasts, which are not infected, and cells with mock infection (infected with vector only) serve as controls.

Figure 9D:
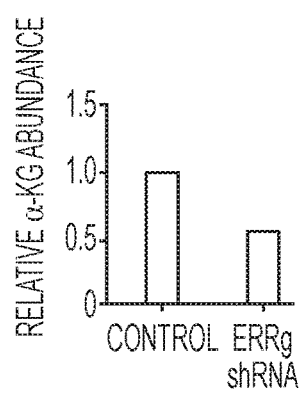

The α-ketoglutarate level in early reprogramming (day 5) depends on ERRγ level in mouse reprogramming cells. In cells where ERRγ expression level was reduced through shRNA silencing, the relative abundance of α-ketoglutarate was lower (FIG. 9D).

Figure 9E:
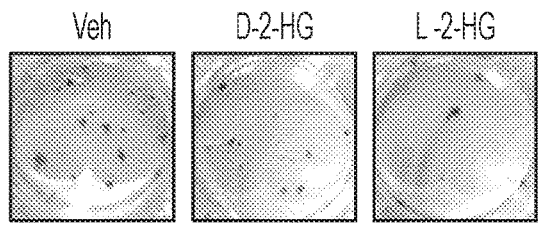
Figure 9F:
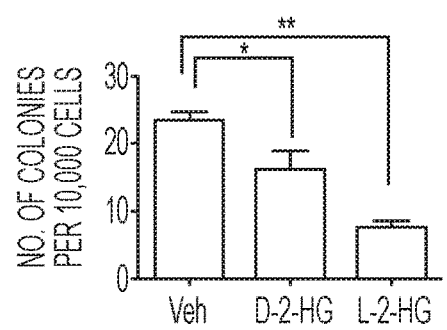
Figure 11A:
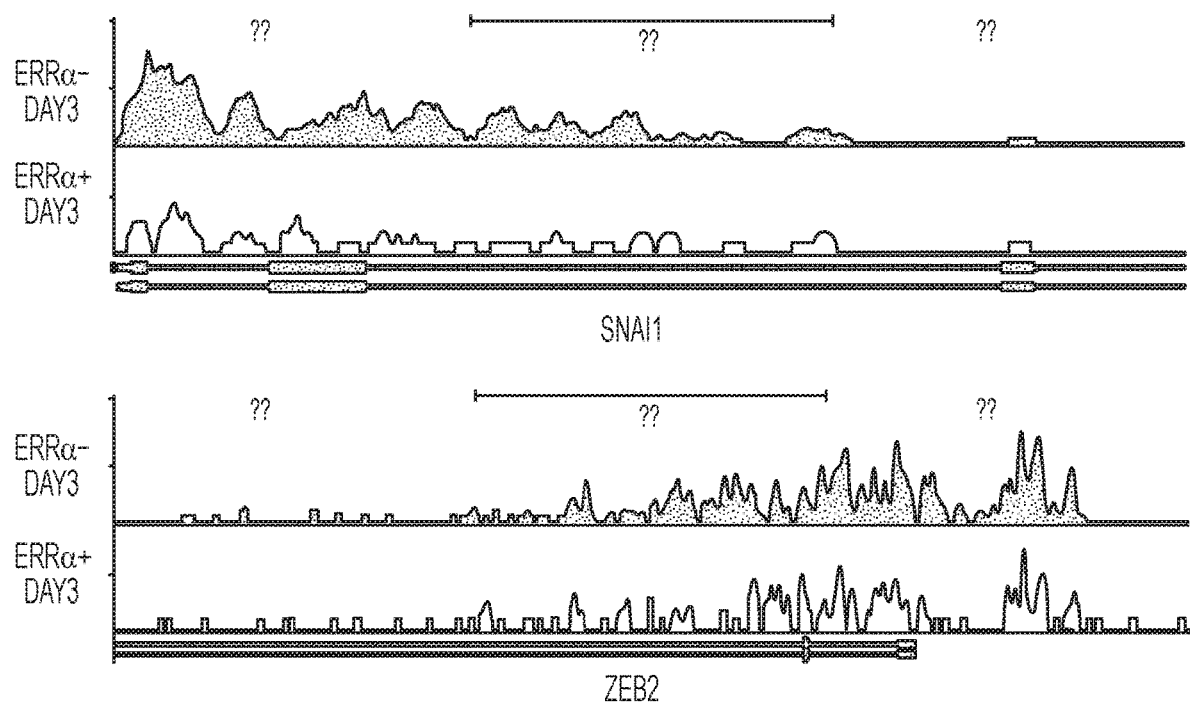
FIGS. 11A-11B are graphs showing the promoter/enhancer landscapes in ERRα+ and ERRα− reprogramming populations.
Figure 11B:
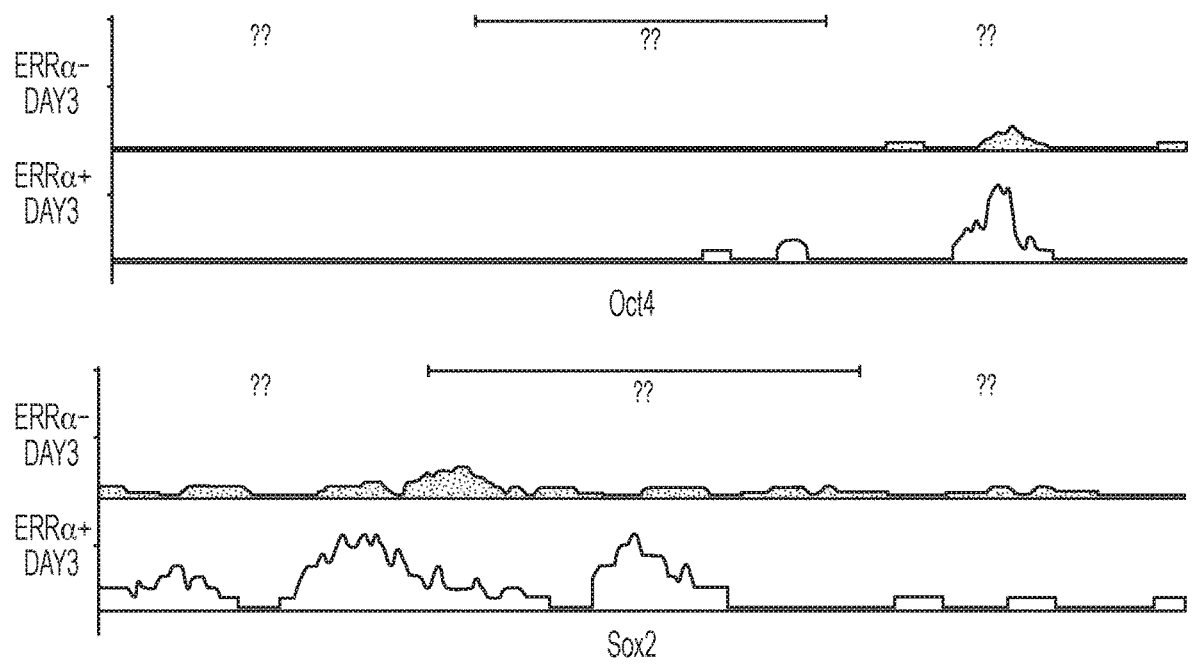

Inhibition of α-ketoglutarate-dependent histone demethylases led to reduced reprogramming efficiency (FIGS. 9E and 9F). Fewer iPS colonies were formed after treatment of D-2-hydroxyglutarate (D-2-HG) or L-2-hydroxyglutarate (L-2-HG), which competitively inhibit α-ketoglutarate-dependent histone demethylases. Reprogramming efficiency was significantly decreased after D-2-HG or L-2-HG treatment. L-2-HG is known to be a more potent competitor than D-2-HG. Correspondingly, L-2-HG treatment led to more significant decrease of reprogramming (n=4-6, *P<0.05, *P<0.01) (FIGS. 9E and 9F). The determination of the abundance of α-ketoglutarate is well known to those skilled in the art. For example, commercial kits are available to quantify α-ketoglutarate. See, e.g., http://www.biovision.com/alpha-ketoglutarate-colorimetric-fluorometric-assay-kit-2943.html, the content of which is incorporated by reference.

Example 6: ERRα Labels a Metabolically Active Subpopulation During Early Reprogramming During early reprogramming, ERRα expressing cells and ERRα non-expressing cells were separated by GFP-based FACS analysis and RNA-seq was performed on each cell population (FIG. 10A). KEGG gene ontology analysis was performed to identify the genes enriched in the ERRα expressing population. The highly expressed genes in GFP+ cells were associated with oxidative phosphorylation and other metabolic processes, which correlate with the known function of ERRα. The KEGG gene ontology analysis is well known to those skilled in the art. See, e.g., Mao et al., Automated genome annotation and pathway identification using the KEGG Orthology (KO) as a controlled vocabulary, Bioinformatics, 2005, 21(19): 3787-93, the content of which is incorporated by reference.

Example 7: The Promoter/Enhancer Landscapes are Different Between ERRα+ and ERRα− Reprogramming Population The promoter/enhancer landscapes were characterized in reprogramming populations. In ERRα+ populations, H3 histone lysine 4 dimethylated (H3K4Me2) levels were decreased in the enhancer/promoter region of genes that function in fibroblast identity, such as SNAI1 and ZEB2, compared with levels in cells that did not express detectable ERRα. This suggests that ERRα may be involved in the silencing of fibroblast specific epigenetic modifications.

The opposite changes were observed in genes that function in reprogramming, such as Oct4 and Sox2. That is, the H3K4Me2 level was increased in the enhancer/promoter region of these genes, suggesting that ERRα+ population contains cells whose pluripotency circuitry are poised to be activated.

Methods for characterizing the promoter/enhancer landscape measurement is well known to those skilled in the art. One example is to use Chromatin Immunoprecipitation assays (ChIP assays) to identify a polynucleotide associated with a histone with a modified amino acid, such as methylated lysine and quantify the level of the modification of the amino acid in a cell population. See, e.g., Chromatin Assembly and Analysis, Current Protocols in Molecular Biology, Chapter 21 (Ausubel et al. eds., 2011), the content of which is incorporated by reference. The experiments described above were performed with the following methods and materials.

Methods

Mouse embryonic fibroblasts (MEFs) were isolated from embryonic day (E) 13.3 embryos obtained from wild-type and ERRγ-deficient mice (Alaynick et al., 2007). Retroviruses and lentiviruses were produced in HEK293T cells, and 12 to 14 days after infection MEFs were fixed for staining. Reprogramming of MEFs and human lung fibroblast IMR90s was done as previously described (Kawamura et al., 2009, Nature 460, 1140-1144; Sugii et al., 2010, Proceedings of the National Academy of Sciences of the United States of America 107, 3558-3563; Takahashi et al., 2007, Cell 126, 663-676; Wei et al., 2013, Cell stem cell 2013 Jul. 3; 13(1):36-47; Yu et al., 2007, Science, New York, N.Y., 318, 1917-1920).

Reprogramming

Mouse reprogramming was performed as previously described, with modifications (Kawamura et al., 2009, Nature 460, 1140-1144; Sugii et al., 2010, Proceedings of the National Academy of Sciences of the United States of America 107, 3558-3563; Takahashi and Yamanaka, 2006, Cell 126, 663-676; Yu et al., 2007, Science, New York, N.Y., 318, 1917-1920). For retroviral reprogramming, pMX-based retroviral vectors harboring each of the mouse reprogramming genes (c-Myc, Klf4, Oct4, or Sox2; Addgene) were transfected along with gag/pol and VSV-G envelope genes into HEK293T cells using Lipofectamine (Invitrogen). For lentivirus production, tet-inducible lentiviral vectors containing OSKM (Wei et al., 2009) were transfected together with pspax2 and pMD2.G (Addgene). Two days after transfection, supernatants containing viruses were collected and filtered through a 0.45-μm filter. For retroviral reprogramming, a total of $1 \times 10^4$ (MEFs (passages 2-4) were infected with retroviral mixtures in 12-well plates (day 0). One well was used to quantify cell numbers for each group. Control cells were transduced with GFP retrovirus alone to determine infection efficiencies. On day 2, one-fifth of the cells were passaged onto gelatin-coated plates with MEF feeder layers (Millipore) and cultured in Knockout (KO)-DMEM containing L-glutamine (2 mM), nucleosides (1×), NEAA (nonessential amino acid; 1×), β-mercaptoethanol (1×), and LIF (1,000 units/mL), with 15% knockout serum replacement (KSR, Millipore or Invitrogen). Media was changed every other day. On days 7-10, cells were either immunostained for assessing efficiencies or derived into individual colonies for downstream analyses.

For reprogramming of IMR90 fibroblasts, cells were infected with the combination of human reprogramming retroviruses (c-Myc, Klf4, Oct4, or Sox2 in pMXs; Addgene) that had been produced in 293T cells cotransfected with gag/pol and VSV-G as described above. EGFP retrovirus was included at 1/40 volume as internal controls for transduction efficiencies. One well from each group was reserved for quantifying cell numbers. On day 2, cells were passaged onto 12-well plates containing MEF feeder cells (for generating iPSCs) or onto 6-cm dishes without MEF (for collecting mRNAs at day 5). Cells were cultured in Knockout (KO)-DMEM plus 20% knockout serum replacement (KSR) supplemented with β-mercaptoethanol (0.1%), NEAA (1×), Glutamax (1%), and 10 ng/mL FGF2. Media was changed every day. Reprogramming of MEFs using an inducible lentiviral system was performed as previously described (Wei et al., 2009). Doxycyme-inducible MEFs were isolated from Gt(ROSA)26Sortm1(rtTA*M2)Jae Col1altm4(tetO-Pou5f1,-Sox2,-K1f4,-Myc)Jae/J mice (Jackson Labs) and reprogramming was performed as previously described (Carey et al., 2010). ERRγ-iKO mice were generated by crossing ERRγlox/lox (generously provided by Johan Auwerx) and B6.Cg-Tg(CAG-cre/Esr1)5Amc/j (Jackson Labs, Cat. No. 004682) and ERRγ-iKO MEFs were isolated from Embryonic Day 14.5 embryos. The ERRγ-iKO MEFs were reprogrammed using the inducible lentiviral system (Wei et al., 2009) and were treated by 4-hydroxytamoxifen (4-OHT) at final concentration 50 nM from reprogramming day 0 to day 2. All procedures involving hiPS/hES cells were approved by the Embryonic Stem Cell Research Oversight Committee at the Salk Institute.

Microarray Analysis

RNA was extracted from OSKM-induced MEFsat days 3, 4, 5, 6, 7 with shERRα and GFP-infected IMR90 cells at day 5 using RNEASY® (QIAGEN). RNA was DNASE® (AMBION) treated, reverse transcribed to first-strand cDNA using a SUPERSCRIPT® II kit (Invitrogen), and then treated with RNase. Global gene expression analysis was performed as described (Narkar et al., 2011, Cell Metab 13, 283-293.).

RNA-Seq Library Generation

Total RNA was isolated from cell pellets treated with RNALATER® using the RNA mini kit (Qiagen) and treated with DNASEI® (Qiagen) for 30 min at room temperature. Sequencing libraries were prepared from 100-500 ng total RNA using the TRUSEQ® RNA Sample Preparation Kit v2 (Illumina) according to the manufacturer's protocol. Briefly, mRNA was purified, fragmented, and used for first-, then second-strand cDNA synthesis followed by adenylation of 3' ends. Samples were ligated to unique adapters and subjected to PCR amplification. Libraries were then validated using the 2100 BIOANALYZER® (Agilent), normalized, and pooled for sequencing. RNA-Seq libraries prepared from two biological replicates for each experimental condition were sequenced on the Illumina HISEQ® 2000 using barcoded multiplexing and a 100 bp read length.

High-Throughput Sequencing and Analysis

Image analysis and base calling were performed with Illumina CASAVA®-1.8.2. This yielded a median of 29.9M usable reads per sample. Short read sequences were mapped to a UCSC mm9 reference sequence using the RNA-sequence aligner STAR® (Dobin et al., 2013, Bioinformatics. 29(1):15-21). Known splice junctions from mm9 were supplied to the aligner and de novo junction discovery was also permitted. Differential gene expression analysis, statistical testing and annotation were performed using CUFFDIFF® 2 (Trapnell et al., 2013, Nat Biotechnol. 31(1):46-53). Transcript expression was calculated as gene-level relative abundance in fragments per kilobase of exon model per million mapped fragments and employed correction for transcript abundance bias (Roberts et al., 2011, Genome biology 12, R22). RNA-Seq results for genes of interest were also explored visually using the UCSC Genome Browser.

Gene Expression Analysis by qPCR

Samples were run in triplicate and expression was normalized to the levels of the housekeeping controls Rplp0 (36b4) for human and mouse. Samples were analyzed by qPCR, using SYBR® Green dye (Invitrogen). Endogenous versus exogenous reprogramming gene expression was performed as previously reported (Yang et al., 2006, Cell 126, 801-810). Statistical comparisons were made using Student's t test. Error bars are mean±SEM.

Immunohistochemistry and Cell Staining

Cells grown on dishes were immunostained using the VectaStain ABC kit and IMMPACT® DAB substrate (Vector Lab) with rabbit anti-mouse Nanog (Calbiochem), anti-human Nanog (Abcam).

Bioenergetic Assay

Measurements were made with a SEAHORSE® XF instrument. Adherent cells were seeded in 96-well SEAHORSE® cell culture microplates at 20,000 per well 16 hours before measurement. Approximately 60 minutes prior to the assay, culture media was exchanged with a low-buffered DMEM assay media with 20 mM glucose and 1 mM sodium pyruvate. For measurement of maximal oxidative phosphorylation (OXPHOS) capacity, Oligomycin (final concentration 1.204), Carbonyl cyanide-4 (trifluoromethoxy)phenylhydrazone (FCCP, final concentration 4 µM), Antimycin A (final concentration 1 µM) and Rotenone (final concentration 2 µM) were added per manufacturer's instruction. The oxygen consumption rate (OCR) and extracellular acidification rate (ECAR) value were further normalized by measuring the cell number in each well using HOECHST® 33342 staining followed by quantification of fluorescence at 355 excitation and 460 emission. The baseline OCR was defined by the average value for the first 4 measurements. The maximal OXPHOS capacity was defined by the difference between average OCR after addition of Carbonyl cyanide-4 (trifluoromethoxy)phenylhydrazone (FCCP, minute 88-120) and OCR after addition of antimycin A and rotenone (minute 131-163).

shRNA Knockdown shRNA constructs for mouse and human ERRα/γ and PGC-1α/β, as well as control shRNA, were purchased from OPENBIOSYSTEMS®. Lentiviral shRNA were produced in 293T cells and polybrene (6 µg/ml) was used in transduction. For reprogramming experiments, cells were transduced with lentiviral shRNA at day 0 of reprogramming.

Live Cell Staining, Alkaline Phosphatase Staining, and Cell Sorting

Cells were incubated with culture media containing FITC-conjugated anti-Sca1 (1:50, Biolegend) and Phycoerythrin (PE)-conjugated anti-CD34 (1:100, Biolegend) antibodies for 30 minutes, washed, then maintained in culture. Alkaline phosphatase staining was performed on formaldehyde-fixed cells using 4-Nitro blue tetrazolium chloride (450 mg/ml) and 5-Bromo-4-chloro-3-indolyl phosphate (175 mg/ml) in NTMT solution (0.1M NaCl, 0.1M Tris PH9.5, 50 mM MgCl2, and 0.1% TWEEN®20). OSKM-infected cells were fluorescence-activated cell sorted (FACS, FACSAria, BD Biosciences) 5 days after infection using FITC-conjugated anti-Sca1 (1:100) and phycoerythrin (PE)-conjugated anti-CD34 antibodies (1:200), and subsequently cultured for iPS cell formation.

In Vitro Differentiation iPS cells were differentiated in vitro by embryoid body formation (Kawamura et al., 2009, Nature 460, 1140-1144) with some modification. Briefly, hanging droplets (1500 single cells at 60 cells/µl in mouse ES cell media without LIF) were suspended on petri-dish lids for two or three days prior to suspension culture. Six days after differentiation, embryoid bodies were plated on gelatinized dishes for 1-2 weeks. Gene expression of pluripotency markers (Oct4, Sox2, Nanong, and E-Ras) and germ-layer markers (AFP, Pdx1, and GATA6 for endoderm; GATA4, SM α-actin, and Cardiac α-actin for mesoderm; Cdx2, Pax6, and Mtap2 for ectoderm) was determined by QPCR. Values were standardized to GAPDH and normalized to undifferentiated mouse ES cells.

Blastocyst Injections for Chimeric Mice

Mouse iPS cells (derived from C57BL/6N MEFs) were injected into BALB/c host blastocysts and transferred into 2.5 dpc ICR pseudopregnant recipient females. Chimerism was ascertained after birth by the appearance of black coat color (from iPS cell) in albino host pups. High-contribution chimeras were crossed to C57BL/6N mice to test for germline transmission.

NAD+/NADH Assay

Intracellular NAD+ and NADH levels were measured by NAD+/NADH Assay Kit (Abcam, San Francisco, Calif.) as per manufacturer's instructions. Briefly, 2×105 cells were washed with cold PBS and extracted with NADH/NAD Extraction Buffer by two freeze/thaw cycles (20 min on dry ice, then 10 min at room temperature). Total NAD (NADt) and NADH were detected in 96-well plates and color was developed and read at 450 nm. NAD/NADH Ratio is calculated as: [NADt−NADH]/NADH.

Measurement of ATP

Intracellular ATP was measured by ATP assay kit (Sigma-Aldrich) according to manufacturer's directions. Briefly, 1×104 cells were washed with cold PBS and ATP extracted with ATP extraction buffer. Amounts of ATP were detected in 384-well plates and measured with a luminometer.

ChIP-Seq Library Construction, Sequencing and Data Analysis.

ChIP-Seq libraries were constructed using standard Illumina protocols, validated using the 2100 BioAnalyzer (Agilent), normalized and pooled for sequencing. Libraries were sequenced on the Illumina HiSeq 2500 using barcoded multiplexing and a 50-bp read length. Short DNA reads were demultiplexed using Illumina CASAVA v1.8.2. Reads were aligned against the mouse mm9 using the Bowtie aligner allowing up to 2 mismatches in the read. Only tags that map uniquely to the genome were considered for further analysis. Subsequent peak calling and motif analysis were conducted using HOMER, a software suite for ChIP-Seq analysis. The methods for HOMER, which are described below, have been implemented and are freely available at http://biowhat.ucsd.edu/homer/. One tag from each unique position was considered to eliminate peaks resulting from clonal amplification of fragments during the ChIP-Seq protocol. Peaks were identified by searching for clusters of tags within a sliding 200 bp window, requiring adjacent clusters to be at least 1 kb away from each other. The threshold for the number of tags that determine a valid peak was selected for a false discovery rate of <0.01, as empirically determined by repeating the peak finding procedure using randomized tag positions. Peaks are required to have at least 4-fold more tags (normalized to total count) than input or IgG control samples and 4-fold more tags relative to the local background region (10 kb) to avoid identifying regions with genomic duplications or non-localized binding. Peaks are annotated to gene products by identifying the nearest RefSeq transcriptional start site. Visualization of ChIP-Seq results was achieved by uploading custom tracks onto the UCSC genome browser.

RNA-Seq and Data Analysis

Total RNA was isolated using Trizol (Invitrogen) and the RNeasy mini kit (Qiagen). RNA purity and integrity were confirmed using an Agilent Bioanalyzer. Libraries were prepared from 100 ng total RNA (TrueSeq v2, Illumina) and singled-ended sequencing performed on the Illumina HiSeq 2500, using bar-coded multiplexing and a 100 bp read length, yielding a median of 34.1M reads per sample. Read alignment and junction finding was accomplished using STAR and differential gene expression with Cuffdiff 2 utilizing UCSC mm9 as the reference sequence.

Chromatin Immunoprecipitation

Cells were then harvested for ChIP assay. Briefly, after fixation, nuclei were isolated, lysed and sheared with a Diagenode Bioruptor to yield DNA fragment sizes of 200-1000 base pairs followed by immunoprecipitation using H3K4Me2 antibodies (Abcam ab32356).

ChIP-Seq Data Analysis

The procedure was as previously described (Barish et al., 2010; Ding et al., 2013). Briefly, short DNA reads were demultiplexed using Illumina CASAVA v1.8.2. Reads were aligned against the human hg18 (NCBI Build 36.1) using the Bowtie aligner allowing up to 2 mismatches in the read. Only tags that map uniquely to the genome were considered for further analysis. Subsequent peak calling and motif analysis were conducted using HOMER, a software suite for ChIP-Seq analysis. The methods for HOMER, which are described below, have been implemented and are freely available at http://biowhat.ucsd.edu/homer/. One tag from each unique position was considered to eliminate peaks resulting from clonal amplification of fragments during the ChIP-Seq protocol. Peaks were identified by searching for clusters of tags within a sliding 200 bp window, requiring adjacent clusters to be at least 1 kb away from each other. The threshold for the number of tags that determine a valid peak was selected for a false discovery rate of <0.01, as empirically determined by repeating the peak finding procedure using randomized tag positions. Peaks are required to have at least 4-fold more tags (normalized to total count) than input or IgG control samples and 4-fold more tags relative to the local background region (10 kb) to avoid identifying regions with genomic duplications or non-localized binding. Peaks are annotated to gene products by identifying the nearest RefSeq transcriptional start site. Visualization of ChIP-Seq results was achieved by uploading custom tracks onto the UCSC genome browser.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of obtaining a reprogrammed murine induced pluripotent stem cell, the method comprising: (a) transducing mouse embryonic fibroblast progenitor cells with one or more viral vectors comprising polynucleotides encoding expressing Oct4, Sox2, Klf4 and cMyc reprogramming factors; (b) inducing in the cells a transient oxidative burst comprising an at least 2-fold increase in oxidative phosphorylation and metabolicactivity and an increased level of at least one analyte selected from nicotinamide adenine dinucleotide (NADH), a ketoglutarate, cellular ATP, ATP synthase in mitochondria (ATP5G1), succinate dehydrogenase (SDHB), isocitrate dehydrogenase (IDH3), NADH dehydrogenase (NDUFA2), superoxide dismutase 2 (SOD2), NADPH oxidase 4 (NOX4), or catalase (CAT) by transducing the mouse embryonic fibroblast progenitor cells with a viral vector comprising a polynucleotide encoding estrogen related receptor gamma (ERRγ) and expressing ERRγ in the cells 3-5 days following step (a), wherein the expression of ERRγ in the cells results in the upregulation of at least one ERRγ cofactor selected from Peroxisome proliferator-activated receptor Gamma Coactivator 1 alpha (PGC-1α) or Peroxisome proliferator-activated receptor Gamma Coactivator 1 beta (PGC-1β) in the cells, thereby facilitating reprogramming and inducing pluripotency in the cells; (c) obtaining a reprogrammed murine induced pluripotent stem cell; and, (d) optionally, isolating said reprogrammed murine induced pluripotent stem cell from the culture.

2. A method of obtaining a reprogrammed human induced pluripotent stem cell, the method comprising: (a) transducing human fibroblast progenitor cells or human adipose stem cell progenitor cells with one or more viral vectors comprising polynucleotides encoding Oct4, Sox2, Klf4 and cMyc reprogramming factors; (b) inducing in the cells a transient oxidative burst comprising an at least 2-fold increase in oxidative phosphorylation and metabolic activity and an increased level of at least one analyte selected from nicotinamide adenine dinucleotide (NADH), a-ketoglutarate, cellular ATP, ATP synthase in mitochondria (ATP5G1), succinate dehydrogenase (SDHB), isocitrate dehydrogenase (IDH3), NADH dehydrogenase (NDUFA2), superoxide dismutase 2 (SOD2), NADPH oxidase 4 (NOX4), or catalase (CAT) by transducing the human fibroblast progenitor cells or the human adipose stem cell progenitor cells with a viral vector comprising a polynucleotide encoding estrogen related receptor alpha (ERRα) and expressing ERRα in the cells 3-5 days following step (a), wherein the expression of ERRα in the cells results in the upregulation of at least one ERRα cofactor selected from Peroxisome proliferator activated receptor Gamma Coactivator 1 alpha (PGC-1α) or Peroxisome proliferator-activated receptor Gamma Coactivator 1 beta (PGC-1β), in the cells, thereby facilitating reprogramming and inducing pluripotency in the cells; (c) obtaining a reprogrammed human induced pluripotent stem cell; and, (d) optionally, isolating said reprogrammed human induced pluripotent stem cell from the culture.

3. A method of generating a reprogrammed human induced pluripotent stem cell, the method comprising:
(a) transducing human fibroblast progenitor cells or human adipose stem cell progenitor cells with one or more viral vectors comprising polynucleotides encoding recombinant Oct4, Sox2, Klf4 and cMyc reprogramming factors;
(b) inducing in the cell a transient oxidative burst comprising an at least 2-fold increase in oxidative phosphorylation and metabolic activity and an increased level of at least one analyte selected from nicotinamide adenine dinucleotide (NADH), a-ketoglutarate, cellular ATP, ATP synthase in mitochondria (ATP5G1), succinate dehydrogenase (SDHB), isocitrate dehydrogenase (IDH3), NADH dehydrogenase (NDUFA2), superoxide dismutase 2 (SOD2), NADPH oxidase 4 (NOX4), or catalase (CAT) by transducing the human fibroblast progenitor cells or the human adipose stem cell progenitor cells with a viral vector comprising a polynucleotide encoding estrogen related receptor alpha (ERRa) and expressing ERRα in the cells 3-5 days following step (a), wherein the expression of ERRα in the cells results in the upregulation of at least one ERRα cofactor selected from Peroxisome proliferator-activated receptor Gamma Coactivator 1 alpha PGC-1α) or Peroxisome proliferator-activated receptor Gamma Coactivator 1 beta (PGC-1β) in the cells; and
(c) culturing the human cells, thereby generating a reprogrammed human induced pluripotent stem cell.

4. A method of generating a reprogrammed mammalian induced pluripotent stem cell, the method comprising:
(a) transducing mammalian fibroblast progenitor cells or mammalian adipose stem cell progenitor cells with one or more viral vectors comprising polynucleotides encoding Oct4, Sox2, Klf4 and cMyc-reprogramming factors;
(b) inducing in the cells a transient oxidative burst comprising an at least 2-fold increase in oxidative phosphorylation and metabolic activity and increased levels of at least one analyte selected from nicotinamide adenine dinucleotide (NADH), a-ketoglutarate, cellular ATP, ATP synthase in mitochondria (ATP5G1), succinate dehydrogenase (SDHB), isocitrate dehydrogenase (IDH3), NADH dehydrogenase (NDUFA2), superoxide dismutase 2 (SOD2), NADPH oxidase 4 (NOX4), or catalase (CAT) by transducing the mammalian fibroblast progenitor cells or mammalian adipose stem cell progenitor cells with a viral vector comprising a polynucleotide encoding at least one of estrogen related receptor (ERR) alpha (ERRα) and estrogen related receptor gamma (ERRγ) and expressing at least one of ERRα or ERRγ in the cells 3-5 days following step (a), wherein the expression of the at least one of ERRα and ERRγ in the cells results in the upregulation of an ERRα or ERRγ cofactor selected from Peroxisome proliferator-activated receptor Gamma Coactivator 1 alpha (PGC-1α) or Peroxisome proliferator-activated receptor Gamma Coactivator 1 beta (PGC-1β) in the cells, thereby generating a reprogrammed mammalian induced pluripotent stem cell; and
(c) culturing said reprogrammed mammalian induced pluripotent stem cell.

5. The method of claim 4, further comprising isolating the mammalian induced pluripotent stem cell from the culture.

6. The method of claim 1, wherein the one or more viral vectors in step (a) and step (b) is a lentivirus vector.

7. The method of claim 2, wherein the one or more viral vectors in step (a) and step (b) is a lentivirus vector.

8. The method of claim 3, wherein the one or more viral vectors in step (a) and step (b) is a lentivirus vector.

9. The method of claim 4, wherein the one or more viral vectors in step (a) and step (b) is a lentivirus vector.

10. The method of claim 3, further comprising isolating the reprogrammed human induced pluripotent stem cell from the culture.

11. The method of claim 8, wherein the mouse embryonic fibroblast progenitor cell expressing Oct4, Sox2, Klf4 and cMyc reprogramming factors in step (a) has an undetectable level of at least one of stem cell antigen 1 (Sca1) and CD34 protein.

12. The method of claim 2, wherein the human fibroblast progenitor cells or human adipose stem cell progenitor cells expressing Oct4, Sox2, Klf4 and cMyc reprogramming factors in step (a) have an undetectable level of at least one of stem cell antigen 1 (Sca1) and CD34 protein.

13. The method of claim 3, wherein the human fibroblast progenitor cells or adipose stem cell progenitor cells expressing Oct4, Sox2, Klf4 and cMyc reprogramming factors in step (a) have an undetectable level of at least one of stem cell antigen 1 (Sca1) and CD34 protein.

14. The method of claim 4, wherein the mammalian fibroblast progenitor cell or adipose stem cell progenitor cell expressing the Oct4, Sox2, Klf4 and cMyc reprogramming factors in step (a) has an undetectable level of at least one of stem cell antigen 1 (Sca1) and CD34 protein.

* * * * *

UNITED STATES PATENT AND TRADEMARK OFFICE
CERTIFICATE OF CORRECTION

PATENT NO.         : 10,920,199 B2
APPLICATION NO.    : 15/552476
DATED              : February 16, 2021
INVENTOR(S)        : Ronald Evans et al.

It is certified that error appears in the above-identified patent and that said Letters Patent is hereby corrected as shown below:

On the Title Page

Item (54) In the title, please delete "Therefore" and insert -- Thereof --.

In the Specification

At Column 1, Line 29, under STATEMENT OF RIGHTS TO INVENTIONS MADE UNDER FEDERALLY SPONSORED RESEARCH, please delete "under HD105278" and insert -- under HL105278 -- therefor.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 52

<210> SEQ ID NO 1
<211> LENGTH: 134
<212> TYPE: PRT
<213> ORGANISM: Mus musculus

<400> SEQUENCE: 1

Met Asp Thr Ser His Thr Thr Lys Ser Cys Leu Leu Ile Leu Leu Val
1               5                   10                  15

Ala Leu Leu Cys Ala Glu Arg Ala Gln Gly Leu Glu Cys Tyr Gln Cys
            20                  25                  30

Tyr Gly Val Pro Phe Glu Thr Ser Cys Pro Ser Ile Thr Cys Pro Tyr
        35                  40                  45

Pro Asp Gly Val Cys Val Thr Gln Glu Ala Ala Val Ile Val Asp Ser
    50                  55                  60

Gln Thr Arg Lys Val Lys Asn Asn Leu Cys Leu Pro Ile Cys Pro Pro
65                  70                  75                  80

Asn Ile Glu Ser Met Glu Ile Leu Gly Thr Lys Val Asn Val Lys Thr
                85                  90                  95

Ser Cys Cys Gln Glu Asp Leu Cys Asn Val Ala Val Pro Asn Gly Gly
```

```
                100                 105                 110
Ser Thr Trp Thr Met Ala Gly Val Leu Leu Phe Ser Leu Ser Ser Val
            115                 120                 125

Leu Leu Gln Thr Leu Leu
        130
```

<210> SEQ ID NO 2
<211> LENGTH: 982
<212> TYPE: DNA
<213> ORGANISM: Mus musculus

<400> SEQUENCE: 2

```
cttaaccaat aaacatgatg gcctggaaaa ggttaagtac tgaaacccct ccctcttcag    60
gatgccagct gggaggagct gaaggaaatt aaagtacttc agtccacatc tgacagaact   120
tgccactgtg cctgcaacct tgtctgagag gaagtaagga ctggtgtgag gagggagctc   180
ccttctctga ggatggacac ttctcacact acaaagtcct gtttgctgat tcttcttgtg   240
gccctactgt gtgcagaaag agctcaggga ctggagtgtt accagtgcta tggagtccca   300
tttgagactt cttgcccatc aattacctgc ccctaccctg atggagtctg tgttactcag   360
gaggcagcag ttattgtgga ttctcaaaca aggaaagtaa agaacaatct ttgcttaccc   420
atctgccctc ctaatattga aagtatggag atcctgggta ctaaggtcaa cgtgaagact   480
tcctgttgcc aggaagacct ctgcaatgta gcagttccca atggaggcag cacctggacc   540
atggcagggg tgcttctgtt cagcctgagc tcagtcctcc tgcagacctt gctctgatgg   600
tcctcccaat gacctccacc cttgtccttt tatcctcatg tgcaacaatt cttcctggag   660
ccctctagtg atgaattatg agttatagaa gctccaaggt gggagtagtg tgtgaaatac   720
catgttttgc ctttatagcc cctgctgggt aggtaggtgc tctaatcctc tctagggctt   780
tcaagtctgt acttcctaga atgtcatttt gttgtggatt gctgctcatg accctggagg   840
cacacagcca gcacagtgaa gaggcagaat tccaaggtat tatgctatca ccatccacac   900
ataagtatct ggggtcctgc aatgttccca catgtatcct gaatgtcccc ctgttgagtc   960
caataaaccc tttgttctcc ca                                            982
```

<210> SEQ ID NO 3
<211> LENGTH: 385
<212> TYPE: PRT
<213> ORGANISM: Homo sapiens

<400> SEQUENCE: 3

```
Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
        35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
            100                 105                 110
```

Gln Thr Ser Val Ile Ser Thr Val Phe Thr Thr Pro Ala Asn Val Ser
            115                 120                 125

Thr Pro Glu Thr Thr Leu Lys Pro Ser Leu Ser Pro Gly Asn Val Ser
130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
        195                 200                 205

Gly Leu Ala Arg Val Leu Cys Gly Glu Glu Gln Ala Asp Ala Asp Ala
210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270

Leu Asp Phe Thr Glu Gln Asp Val Ala Ser His Gln Ser Tyr Ser Gln
        275                 280                 285

Lys Thr Leu Ile Ala Leu Val Thr Ser Gly Ala Leu Leu Ala Val Leu
    290                 295                 300

Gly Ile Thr Gly Tyr Phe Leu Met Asn Arg Arg Ser Trp Ser Pro Thr
305                 310                 315                 320

Gly Glu Arg Leu Gly Glu Asp Pro Tyr Tyr Thr Glu Asn Gly Gly Gly
                325                 330                 335

Gln Gly Tyr Ser Ser Gly Pro Gly Thr Ser Pro Glu Ala Gln Gly Lys
            340                 345                 350

Ala Ser Val Asn Arg Gly Ala Gln Glu Asn Gly Thr Gly Gln Ala Thr
        355                 360                 365

Ser Arg Asn Gly His Ser Ala Arg Gln His Val Val Ala Asp Thr Glu
    370                 375                 380

Leu
385

<210> SEQ ID NO 4
<211> LENGTH: 325
<212> TYPE: PRT
<213> ORGANISM: Mus musculus

<400> SEQUENCE: 4

Met Gln Val His Arg Asp Thr Arg Ala Gly Leu Leu Leu Pro Trp Arg
1               5                   10                  15

Trp Val Ala Leu Cys Leu Met Ser Leu Leu His Leu Asn Asn Leu Thr
            20                  25                  30

Ser Ala Thr Thr Glu Thr Ser Thr Gln Gly Ile Ser Pro Ser Val Pro
        35                  40                  45

Thr Asn Glu Ser Val Glu Glu Asn Ile Thr Ser Ser Ile Pro Gly Ser
    50                  55                  60

Thr Ser His Tyr Leu Ile Tyr Gln Asp Ser Ser Lys Thr Thr Pro Ala
65                  70                  75                  80

Ile Ser Glu Thr Met Val Asn Phe Thr Val Thr Ser Gly Ile Pro Ser
                85                  90                  95

Gly Ser Gly Thr Pro His Thr Phe Ser Gln Pro Gln Thr Ser Pro Thr
            100                 105                 110

Gly Ile Leu Pro Thr Thr Ser Asp Ser Ile Ser Thr Ser Glu Met Thr
        115                 120                 125

Trp Lys Ser Ser Leu Pro Ser Ile Asn Val Ser Asp Tyr Ser Pro Asn
130                 135                 140

Asn Ser Ser Phe Glu Met Thr Ser Pro Thr Glu Pro Tyr Ala Tyr Thr
145                 150                 155                 160

Ser Ser Ser Ala Pro Ser Ala Ile Lys Gly Glu Ile Lys Cys Ser Gly
                165                 170                 175

Ile Arg Glu Val Arg Leu Ala Gln Gly Ile Cys Leu Glu Leu Ser Glu
            180                 185                 190

Ala Ser Ser Cys Glu Glu Phe Lys Lys Glu Lys Gly Glu Asp Leu Ile
        195                 200                 205

Gln Ile Leu Cys Glu Lys Glu Glu Ala Glu Ala Asp Ala Gly Ala Ser
    210                 215                 220

Val Cys Ser Leu Leu Leu Ala Gln Ser Glu Val Arg Pro Glu Cys Leu
225                 230                 235                 240

Leu Met Val Leu Ala Asn Ser Thr Glu Leu Pro Ser Lys Leu Gln Leu
                245                 250                 255

Met Glu Lys His Gln Ser Asp Leu Arg Lys Leu Gly Ile Gln Ser Phe
            260                 265                 270

Asn Lys Gln Asp Ile Gly Ser His Gln Ser Tyr Ser Arg Lys Thr Leu
        275                 280                 285

Ile Ala Leu Val Thr Ser Val Leu Leu Ala Ile Leu Gly Thr Thr
    290                 295                 300

Gly Tyr Phe Leu Met Asn Arg Arg Ser Trp Ser Pro Thr Gly Glu Arg
305                 310                 315                 320

Leu Glu Leu Glu Pro
                325

<210> SEQ ID NO 5
<211> LENGTH: 2621
<212> TYPE: DNA
<213> ORGANISM: Homo sapiens

<400> SEQUENCE: 5 cctttttttgg cctcgacggc ggcaacccag cctccctcct aacgccctcc gcctttggga      60
ccaaccaggg gagctcaagt tagtagcagc caaggagagg cgctgccttg ccaagactaa     120
aaagggaggg gagaagagag gaaaaaagca agaatccccc acccctctcc cgggcggagg     180
gggcgggaag agcgcgtcct ggccaagccg agtagtgtct tccactcggt gcgtctctct     240
aggagccgcg cgggaaggat gctggtccgc aggggcgcgc gcgcagggcc caggatgccg     300
cggggctgga ccgcgctttg cttgctgagt ttgctgcctt ctgggttcat gagtcttgac     360
aacaacggta ctgctacccc agagttacct acccagggaa cattttcaaa tgtttctaca     420
aatgtatcct accaagaaac tacaacacct agtaccttg gaagtaccag cctgcaccct     480
gtgtctcaac atggcaatga ggccacaaca aacatcacag aaacgacagt caaattcaca     540
tctacctctg tgataacctc agtttatgga aacacaaact cttctgtcca gtcacagacc     600
tctgtaatca gcacagtgtt caccacccca gccaacgttt caactccaga gacaaccttg     660
aagcctagcc tgtcacctgg aaatgtttca gacctttcaa ccactagcac tagccttgca     720
acatctccca ctaaacccta tcatcatct tctcctatcc taagtgacat caaggcagaa     780

```
atcaaatgtt caggcatcag agaagtgaaa ttgactcagg gcatctgcct ggagcaaaat      840
aagacctcca gctgtgcgga gtttaagaag gacaggggag agggcctggc ccgagtgctg      900
tgtggggagg agcaggctga tgctgatgct ggggcccagg tatgctccct gctccttgcc      960
cagtctgagg tgaggcctca gtgtctactg ctggtcttgg ccaacagaac agaaatttcc     1020
agcaaactcc aacttatgaa aaagcaccaa tctgacctga aaaagctggg gatcctagat     1080
ttcactgagc aagatgttgc aagccaccag agctattccc aaaagaccct gattgcactg     1140
gtcacctcgg gagccctgct ggctgtcttg ggcatcactg gctatttcct gatgaatcgc     1200
cgcagctgga gccccacagg agaaaggctg gcgaagacc cttattacac ggaaaacggt      1260
ggaggccagg gctatagctc aggacctggg acctcccctg aggctcaggg aaaggccagt     1320
gtgaaccgag gggctcagga aaacgggacc ggccaggcca cctccagaaa cggccattca     1380
gcaagacaac acgtggtggc tgataccgaa ttgtgactcg gctaggtggg gcaaggctgg     1440
gcagtgtccg agagagcacc cctctctgca tctgaccacg tgctacccccc atgctggagg    1500 tgacatctct tacgcccaac ccttccccac tgcacacacc tcagaggctg ttcttggggc     1560
cctacacctt gaggaggggc aggtaaactc ctgtccttta cattcggc tccctggagc       1620 cagactctgg tcttctttgg gtaaacgtgt gacggggaa agccaaggtc tggagaagct      1680
cccaggaaca atcgatggcc ttgcagcact cacacaggac cccttcccc tacccccctcc    1740 tctctgccgc aatacaggaa ccccccagggg aaagatgagc ttttctaggc tacaattttc   1800
tcccaggaag ctttgatttt taccgttctct tccctgtatt ttctttctct actttgagga   1860
aaccaaagta acctttttgca cctgctctct tgtaatgata tagccagaaa aacgtgttgc   1920
cttgaaccac ttccctcatc tctcctccaa gacactgtgg acttggtcac cagctcctcc    1980
cttgttctct aagttccact gagctccatg tgccccctct accattttgca gagtcctgca   2040 cagttttctg gctggagcct agaacaggcc tcccaagttt taggacaaac agctcagttc    2100
tagtctctct ggggccacac agaaaactctt tttgggctcc tttttctccc tctggatcaa   2160
agtaggcagg accatgggac caggtcttgg agctgagcct ctcacctgta ctcttccgaa    2220
aaatcctctt cctctgaggc tggatcctag ccttatcctc tgatctccat ggcttcctcc    2280
tccctcctgc cgactcctgg gttgagctgt tgcctcagtc ccccaacaga tgcttttctg    2340
tctctgcctc cctcaccctg agccccttcc ttgctctgca cccccatatg gtcatagccc    2400
agatcagctc ctaacccta tcaccagctg cctcttctgt gggtgaccca ggtccttgtt     2460
tgctgttgat ttcttttccag aggggttgag cagggatcct ggtttcaatg acggttggaa   2520
atagaaattt ccagagaaga gagtattggg tagatatttt ttctgaatac aaagtgatgt    2580
gtttaaatac tgcaattaaa gtgatactga aacacaaaaa a                        2621
```

<210> SEQ ID NO 6
<211> LENGTH: 2621
<212> TYPE: DNA
<213> ORGANISM: Mus musculus

<400> SEQUENCE: 6

```
ggggataagc cagcatcccc cacccactcc ggacagggag caggggagga gagccaatat       60
cccccacccc tgcgcagggc ggaggagcgc gtcccgcgcc gggccgcctc ctgcaccgag      120
cgcatctccg gagcggtaca ggagaatgca ggtccacagg gacacgcgcg cggggctcct      180
gctgccatgg cgctgggtag ctctctgcct gatgagtctg ctgcatctaa ataacttgac      240
```

```
ttctgctacc acggagactt ctacacaagg aatatcccca tcagttccta ccaatgagtc    300
tgttgaggaa aatatcacat ctagcatccc tggaagtacc agccactact tgatctatca    360
ggacagcagt aagaccacac cagccatctc agagactatg gtcaacttta cagttacctc    420
tgggatccct tcaggctctg gaactccaca cactttttca caaccacaga cttccccaac    480
tggcatactg cctactactt cagacagtat ttccacttca gagatgacct ggaagtccag    540
cctgccatct ataaatgttt ctgattattc gcctaataat agcagctttg agatgacatc    600
acccaccgag ccatatgctt acacatcatc ttctgctccg agtgccatta agggagaaat    660
caaatgctct ggaatccgag aagtgaggtt ggcccaggt atctgcctgg aactaagtga     720
agcatctagt tgtgaggagt ttaagaagga aaagggagaa gatctaattc aaatactgtg    780
tgaaaaggag gaggctgagg ctgatgctgg tgctagtgtc tgctccctgc ttctagccca    840
gtctgaggtt aggcctgagt gtttgctgat ggtcttggcc aatagcacag aacttcccag    900
caaactccag cttatggaaa agcaccaatc tgacttgaga aagctgggga tccaaagctt    960
caataaacaa gatatcggga gccaccagag ctattcccga aagactctta ttgcattggt    1020
cacctctgga gttctgctgg ccatcttggg caccactggt tatttcctga tgaaccgtcg    1080
cagttggagc cctacaggag aaaggctgga gctggaacct tgatggctgt tgggaagaaa    1140
agaggctgca catgtagctg tacctgctct gcccccccc cactcctact tcctttgtgc     1200
tctcctcaca gtacctcaca accctgctta ccagataatg ctactttatt tctatactgt    1260
ccagggtgaa gacccttatt acacggagaa tggtggaggc cagggctata gctcaggacc    1320
tggggcctcc cctgagactc agggaaaggc caatgtgacc cgaggggctc aggagaacgg    1380
gaccggccag gccacttcca gaaacggcca ttcagcaaga caacatgtgg tggctgacac    1440
agaactgtga tttggttggg tggcaactg ggtggtatgc aggaaagtgg catctcttgt     1500
ctctgacttc atgctgcctt cagctcatgt ccggccttct cctattacat acacttctga    1560
aactgttcct gggactcttc acctttggga aggcagataa actgccttct gcacattcaa    1620
cttcctgaat ccaatctctg accttgggtt caagttgtgg tgggaagaag cctaggtcta    1680
gaggagctgc caaaaagtt ggtggctatg tagcacttgc cctggaccca tttctcctct     1740
ctcgcctctt cacgggaact ctccggaaga ctagcttttc taagctacca cttcttccca    1800
ggaaactttg ctatttttac tgcttcttcc cctactttat ggaaaccaag gtattcactg    1860
acatgtgctc ccttgcaagg gtacagccag aaaagtgcta ttttaaaata catccttaaa    1920
aaatgcatcc cttataactt caagacactg tggatttagt caccaacttc tatcttgttc    1980
acctgttcct gaatgtctgt ctacagaggc caggacaact ttctgtctgg agtctgctca    2040
atgttttaga gcaacagctc aatctgatcc cttgggccca cacagaaatc tcattggttc    2100
aacctagaca ggacagtgga attagacttt gaactgagcc tctgtttttt gttttatttt    2160
attgctgggg tttgaaccca gagcttcaca cagcttcttt aggcttccaa gtagcttgag    2220
ctaccaggcc cagctgagct aaacctcctg acctgagctc ttcaaaggaa tactcttgct    2280
ctgaggccct tggccttctc taaattacgt gacttccccc ttcctctgac tcctggggga    2340
gctgtggcct cagtccctg gcagattcct ttcagtctgt gcctttccta gtccaaaccc     2400
cttcactatt ttataaccct ttgtgatcag aggttcagaa tatctacaaa gactataagc    2460
ttcctctcct gggggttaagg ggagaacagg ggtcctgatt ttaatgatgg ctaggaacaa   2520
aactttccag agatgagagg attgggtgta ttctcttctg aataaacgtg atgagtgaaa    2580
atgatgtaat taaattgatg atgaaatatt tgatgtggcc c                        2621
```

<210> SEQ ID NO 7
<211> LENGTH: 454
<212> TYPE: PRT
<213> ORGANISM: Homo sapiens

<400> SEQUENCE: 7

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Asn Phe Tyr Gln
            35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65              70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
                100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu

```
                370                 375                 380
Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
                420                 425                 430

Asp Leu Leu Arg Lys Arg Glu Gln Leu Lys His Lys Leu Glu Gln
                435                 440                 445

Leu Arg Asn Ser Cys Ala
            450

<210> SEQ ID NO 8
<211> LENGTH: 439
<212> TYPE: PRT
<213> ORGANISM: Mus musculus

<400> SEQUENCE: 8

Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Asn Phe Tyr
            20                  25                  30

His Gln Gln Gln Gln Ser Glu Leu Gln Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Ala Thr Ser
65                  70                  75                  80

Phe Ser Pro Arg Glu Asp Asp Asp Gly Gly Gly Asn Phe Ser Thr
                85                  90                  95

Ala Asp Gln Leu Glu Met Met Thr Glu Leu Leu Gly Gly Asp Met Val
                100                 105                 110

Asn Gln Ser Phe Ile Cys Asp Pro Asp Asp Glu Thr Phe Ile Lys Asn
                115                 120                 125

Ile Ile Ile Gln Asp Cys Met Trp Ser Gly Phe Ser Ala Ala Ala Lys
    130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ser Glu Cys Ile Asp Pro
            180                 185                 190

Ser Val Val Phe Pro Tyr Pro Leu Asn Asp Ser Ser Ser Pro Lys Ser
                195                 200                 205

Cys Thr Ser Ser Asp Ser Thr Ala Phe Ser Pro Ser Ser Asp Ser Leu
    210                 215                 220

Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Thr
                260                 265                 270

Pro Ala Lys Arg Ser Glu Ser Gly Ser Ser Pro Ser Arg Gly His Ser
            275                 280                 285
```

```
            Lys  Pro  Pro  His  Ser  Pro  Leu  Val  Leu  Lys  Arg  Cys  His  Val  Ser  Thr
                 290                 295                 300

His  Gln  His  Asn  Tyr  Ala  Ala  Pro  Pro  Ser  Thr  Arg  Lys  Asp  Tyr  Pro
            305                 310                 315                      320

Ala  Ala  Lys  Arg  Ala  Lys  Leu  Asp  Ser  Gly  Arg  Val  Leu  Lys  Gln  Ile
                           325                 330                      335

Ser  Asn  Asn  Arg  Lys  Cys  Ser  Ser  Pro  Arg  Ser  Ser  Asp  Thr  Glu  Glu
                      340                 345                      350

Asn  Asp  Lys  Arg  Arg  Thr  His  Asn  Val  Leu  Glu  Arg  Gln  Arg  Arg  Asn
                           355                 360                 365

Glu  Leu  Lys  Arg  Ser  Phe  Phe  Ala  Leu  Arg  Asp  Gln  Ile  Pro  Glu  Leu
                 370                 375                 380

Glu  Asn  Asn  Glu  Lys  Ala  Pro  Lys  Val  Val  Ile  Leu  Lys  Lys  Ala  Thr
            385                 390                 395                      400

Ala  Tyr  Ile  Leu  Ser  Ile  Gln  Ala  Asp  Glu  His  Lys  Leu  Thr  Ser  Glu
                                405                 410                 415

Lys  Asp  Leu  Leu  Arg  Lys  Arg  Arg  Glu  Gln  Leu  Lys  His  Lys  Leu  Glu
                           420                 425                      430

Gln  Leu  Arg  Asn  Ser  Gly  Ala
                      435
```

<210> SEQ ID NO 9
<211> LENGTH: 2379
<212> TYPE: DNA
<213> ORGANISM: Homo sapiens

<400> SEQUENCE: 9

```
gaccccgag ctgtgctgct cgcggccgcc accgccgggc cccggccgtc cctggctccc     60
ctcctgcctc gagaagggca gggcttctca gaggcttggc gggaaaaaga acggagggag    120
ggatcgcgct gagtataaaa gccggttttc ggggctttat ctaactcgct gtagtaattc    180
cagcgagagg cagagggagc gagcgggcgg ccggctaggg tggaagagcc gggcgagcag    240
agctgcgctg cgggcgtcct gggaagggag atccggagcg aataggggc ttcgcctctg     300 gcccagccct cccgctgatc ccccagccag cggtccgcaa cccttgccgc atccacgaaa    360 cttttgcccat agcagcgggc gggcactttg cactggaact acaacacccc gagcaaggac    420
gcgactctcc cgacgcgggg aggctattct gcccatttgg ggacacttcc ccgccgctgc    480
caggacccgc ttctctgaaa ggctctcctt gcagctgctt agacgctgga tttttttcgg    540
gtagtggaaa accagcagcc tcccgcgacg atgcccctca acgttagctt caccaacagg    600
aactatgacc tcgactacga ctcggtgcag ccgtatttct actgcgacga ggaggagaac    660
ttctaccagc agcagcagca gagcgagctg cagcccccgg cgcccagcga ggatatctgg    720
aagaaattcg agctgctgcc caccccgccc ctgtccccta gccgccgctc cgggctctgc    780
tcgccctcct acgttgcggt cacacccttc tcccttcggg gagacaacga cggcggtggc    840
gggagcttct ccacggccga ccagctggag atggtgaccg agctgctggg aggagacatg    900
gtgaaccaga gtttcatctg cgacccggac gacgagacct tcatcaaaaa catcatcatc    960
caggactgta tgtggagcgg cttctcggcc gccaagctc gtctcagag aagctggcc     1020 tcctaccagg ctgcgcgcaa agacagcggc agcccgaacc ccgccgcgg ccacagcgtc     1080 tgctccacct ccagcttgta cctgcaggat ctgagcgccg ccgcctcaga gtgcatcgac    1140
ccctcggtgg tcttccccta ccctctcaac gacagcagct cgcccaagtc ctgcgcctcg    1200
caagactcca gcgccttctc tccgtcctcg gattctctgc tctcctcgac ggagtcctcc    1260
```

| | |
|---|---:|
| ccgcagggca gccccgagcc cctggtgctc catgaggaga caccgcccac caccagcagc | 1320 |
| gactctgagg aggaacaaga agatgaggaa gaaatcgatg ttgtttctgt ggaaaagagg | 1380 |
| caggctcctg gcaaaaggtc agagtctgga tcaccttctg ctggaggcca cagcaaacct | 1440 |
| cctcacagcc cactggtcct caagaggtgc cacgtctcca cacatcagca caactacgca | 1500 |
| gcgcctccct ccactcggaa ggactatcct gctgccaaga gggtcaagtt ggacagtgtc | 1560 |
| agagtcctga gacagatcag caacaaccga aaatgcacca gccccaggtc ctcggacacc | 1620 |
| gaggagaatg tcaagaggcg aacacacaac gtcttggagc gccagaggag gaacgagcta | 1680 |
| aaacggagct ttttgcccct gcgtgaccag atcccggagt tggaaaacaa tgaaaaggcc | 1740 |
| cccaaggtag ttatccttaa aaaagccaca gcatacatcc tgtccgtcca agcagaggag | 1800 |
| caaaagctca tttctgaaga ggacttgttg cggaaacgac gagaacagtt gaaacacaaa | 1860 |
| cttgaacagc tacggaactc ttgtgcgtaa ggaaagtaa ggaaaacgat tccttctaac | 1920 |
| agaaatgtcc tgagcaatca cctatgaact tgtttcaaat gcatgatcaa atgcaacctc | 1980 |
| acaaccttgg ctgagtcttg agactgaaag atttagccat aatgtaaact gcctcaaatt | 2040 |
| ggactttggg cataaaagaa cttttttatg cttaccatct tttttttttc tttaacagat | 2100 |
| ttgtatttaa gaattgtttt taaaaaattt taagatttac acaatgtttc tctgtaaata | 2160 |
| ttgccattaa atgtaaataa ctttaataaa acgtttatag cagttacaca gaatttcaat | 2220 |
| cctagtatat agtacctagt attataggta ctataaaccc taattttttt tatttaagta | 2280 |
| catttttgctt tttaaagttg attttttttct attgttttta gaaaaaataa aataactggc | 2340 |
| aaatatatca ttgagccaaa tcttaaaaaa aaaaaaaaa | 2379 |

<210> SEQ ID NO 10
<211> LENGTH: 2399
<212> TYPE: DNA
<213> ORGANISM: Mus musculus

<400> SEQUENCE: 10

| | |
|---|---:|
| cccgcccacc cgcccttat attccggggg tctgcgcggc cgaggacccc tgggctgcgc | 60 |
| tgctctcagc tgccgggtcc gactcgcctc actcagctcc cctcctgcct cctgaagggc | 120 |
| agggcttcgc cgacgcttgg cgggaaaaag aagggagggg agggatcctg agtcgcagta | 180 |
| taaaagaagc ttttcgggcg ttttttttctg actcgctgta gtaattccag cgagagacag | 240 |
| agggagtgag cggacggttg gaagagccgt gtgtgcagag ccgcgctccg gggcgaccta | 300 |
| agaaggcagc tctggagtga gaggggctt gcctccgagc ctgccgccca ctctccccaa | 360 |
| ccctgcgact gacccaacat cagcggccgc aaccctcgcc gccgctggga aactttgccc | 420 |
| attgcagcgg gcagacactt ctcactggaa cttacaatct gcgagccagg acaggactcc | 480 |
| ccaggctccg gggagggaat ttttgtctat ttggggacag tgttctctgc ctctgcccgc | 540 |
| gatcagctct cctgaaaaga gctcctcgag ctgtttgaag gctggatttc ctttgggcgt | 600 |
| tggaaacccc gcagacagcc acgacgatgc ccctcaacgt gaacttcacc aacaggaact | 660 |
| atgacctcga ctacgactcc gtacagcccct atttcatctg cgacgaggaa gagaatttct | 720 |
| atcaccagca acagcagagc gagctgcagc cgccgcgcc cagtgaggat atctggaaga | 780 |
| aattcgagct gcttcccacc ccgcccctgt ccccgagccg ccgctccggg ctctgctctc | 840 |
| catcctatgt gcggtcgct acgtccttcc ccccaaggga agacgatgac ggcggcggtg | 900 |
| gcaacttctc caccgccgat cagctggaga tgatgaccga gttacttgga ggagacatgg | 960 |

```
tgaaccagag cttcatctgc gatcctgacg acgagacctt catcaagaac atcatcatcc   1020
aggactgtat gtggagcggt ttctcagccg ctgccaagct ggtctcggag aagctggcct   1080
cctaccaggc tgcgcgcaaa gacagcacca gcctgagccc cgcccgcggg cacagcgtct   1140
gctccacctc cagcctgtac ctgcaggacc tcaccgccgc cgcgtccgag tgcattgacc   1200
cctcagtggt ctttccctac ccgctcaacg acagcagctc gcccaaatcc tgtacctcgt   1260
ccgattccac ggccttctct ccttcctcgg actcgctgct gtcctccgag tcctccccac   1320
gggccagccc tgagccccta gtgctgcatg aggagacacc gcccaccacc agcagcgact   1380
ctgaagaaga gcaagaagat gaggaagaaa ttgatgtggt gtctgtggag aagaggcaaa   1440
ccccctgcca gaggtcggag tcgggctcat ctccatcccg aggccacagc aaacctccgc   1500
acagcccact ggtcctcaag aggtgccacg tctccactca ccagcacaac tacgccgcac   1560 cccctccac aaggaaggac tatccagctg ccaagagggc caagttggac agtggcaggg   1620
tcctgaagca gatcagcaac aaccgcaagt gctccagccc caggtcctca gacacggagg   1680
aaaacgacaa gaggcggaca cacaacgtct tggaacgtca gaggaggaac gagctgaagc   1740
gcagcttttt tgccctgcgt gaccagatcc ctgaattgga aaacaacgaa aaggccccca   1800
aggtagtgat cctcaaaaaa gccaccgcct acatcctgtc cattcaagca gacgagcaca   1860
agctcacctc tgaaaaggac ttattgagga aacgacgaga acagttgaaa cacaaactcg   1920
aacagcttcg aaactctggt gcataaactg acctaactcg aggaggagct ggaatctctc   1980
gtgagagtaa ggagaacggt tccttctgac agaactgatg cgctggaatt aaaatgcatg   2040
ctcaaagcct aacctcacaa ccttggctgg ggctttggga ctgtaagctt cagccataat   2100
tttaactgcc tcaaacttaa atagtataaa agaacttttt tttatgcttc ccatcttttt   2160 tcttttcct tttaacagat ttgtatttaa ttgttttttt aaaaaaatct taaaatctat   2220
ccaattttcc catgtaaata gggccttgaa atgtaaataa ctttaataaa acgtttataa   2280
cagttacaaa agattttaag acatgtacca taatttttt tatttaaaga cattttcatt   2340
tttaaagttg atttttttct attgttttta gaaaaaaata aaataattgg aaaaaatac   2399
```

<210> SEQ ID NO 11
<211> LENGTH: 423
<212> TYPE: PRT
<213> ORGANISM: Homo sapiens

<400> SEQUENCE: 11

```
Met Ser Ser Gln Val Val Gly Ile Glu Pro Leu Tyr Ile Lys Ala Glu
1               5                   10                  15

Pro Ala Ser Pro Asp Ser Pro Lys Gly Ser Ser Glu Thr Glu Thr Glu
                20                  25                  30

Pro Pro Val Ala Leu Ala Pro Gly Pro Ala Pro Thr Arg Cys Leu Pro
            35                  40                  45

Gly His Lys Glu Glu Glu Asp Gly Glu Gly Ala Gly Pro Gly Glu Gln
        50                  55                  60

Gly Gly Gly Lys Leu Val Leu Ser Ser Leu Pro Lys Arg Leu Cys Leu
65                  70                  75                  80

Val Cys Gly Asp Val Ala Ser Gly Tyr His Tyr Gly Val Ala Ser Cys
                85                  90                  95

Glu Ala Cys Lys Ala Phe Phe Lys Arg Thr Ile Gln Gly Ser Ile Glu
                100                 105                 110

Tyr Ser Cys Pro Ala Ser Asn Glu Cys Glu Ile Thr Lys Arg Arg Arg
            115                 120                 125
```

```
Lys Ala Cys Gln Ala Cys Arg Phe Thr Lys Cys Leu Arg Val Gly Met
            130                 135                 140

Leu Lys Glu Gly Val Arg Leu Asp Arg Val Arg Gly Gly Arg Gln Lys
145                 150                 155                 160

Tyr Lys Arg Arg Pro Glu Val Asp Pro Leu Pro Phe Pro Gly Pro Phe
                165                 170                 175

Pro Ala Gly Pro Leu Ala Val Ala Gly Gly Pro Arg Lys Thr Ala Ala
            180                 185                 190

Pro Val Asn Ala Leu Val Ser His Leu Leu Val Glu Pro Glu Lys
        195                 200                 205

Leu Tyr Ala Met Pro Asp Pro Ala Gly Pro Asp Gly His Leu Pro Ala
210                 215                 220

Val Ala Thr Leu Cys Asp Leu Phe Asp Arg Glu Ile Val Val Thr Ile
225                 230                 235                 240

Ser Trp Ala Lys Ser Ile Pro Gly Phe Ser Ser Leu Ser Leu Ser Asp
                245                 250                 255

Gln Met Ser Val Leu Gln Ser Val Trp Met Glu Val Leu Val Leu Gly
            260                 265                 270

Val Ala Gln Arg Ser Leu Pro Leu Gln Asp Glu Leu Ala Phe Ala Glu
            275                 280                 285

Asp Leu Val Leu Asp Glu Glu Gly Ala Arg Ala Ala Gly Leu Gly Glu
290                 295                 300

Leu Gly Ala Ala Leu Leu Gln Leu Val Arg Arg Leu Gln Ala Leu Arg
305                 310                 315                 320

Leu Glu Arg Glu Glu Tyr Val Leu Leu Lys Ala Leu Ala Leu Ala Asn
                325                 330                 335

Ser Asp Ser Val His Ile Glu Asp Ala Glu Ala Val Glu Gln Leu Arg
            340                 345                 350

Glu Ala Leu His Glu Ala Leu Leu Glu Tyr Glu Ala Gly Arg Ala Gly
            355                 360                 365

Pro Gly Gly Gly Ala Glu Arg Arg Ala Gly Arg Leu Leu Leu Thr
370                 375                 380

Leu Pro Leu Leu Arg Gln Thr Ala Gly Lys Val Leu Ala His Phe Tyr
385                 390                 395                 400

Gly Val Lys Leu Glu Gly Lys Val Pro Met His Lys Leu Phe Leu Glu
                405                 410                 415

Met Leu Glu Ala Met Met Asp
            420

<210> SEQ ID NO 12
<211> LENGTH: 422
<212> TYPE: PRT
<213> ORGANISM: Mus musculus

<400> SEQUENCE: 12

Met Ser Ser Gln Val Val Gly Ile Glu Pro Leu Tyr Ile Lys Ala Glu
1               5                   10                  15

Pro Ala Ser Pro Asp Ser Pro Lys Gly Ser Ser Glu Thr Glu Thr Glu
            20                  25                  30

Pro Pro Val Thr Leu Ala Ser Gly Pro Ala Pro Ala Arg Cys Leu Pro
        35                  40                  45

Gly His Lys Glu Glu Glu Asp Gly Glu Gly Ala Gly Ser Gly Glu Gln
    50                  55                  60

Gly Ser Gly Lys Leu Val Leu Ser Ser Leu Pro Lys Arg Leu Cys Leu
```

```
            65                  70                  75                  80
Val Cys Gly Asp Val Ala Ser Gly Tyr His Tyr Gly Val Ala Ser Cys
                85                  90                  95

Glu Ala Cys Lys Ala Phe Phe Lys Arg Thr Ile Gln Gly Ser Ile Glu
            100                 105                 110

Tyr Ser Cys Pro Ala Ser Asn Glu Cys Glu Ile Thr Lys Arg Arg Arg
            115                 120                 125

Lys Ala Cys Gln Ala Cys Arg Phe Thr Lys Cys Leu Arg Val Gly Met
130                 135                 140

Leu Lys Glu Gly Val Arg Leu Asp Arg Val Arg Gly Gly Arg Gln Lys
145                 150                 155                 160

Tyr Lys Arg Arg Pro Glu Val Asp Pro Leu Pro Phe Pro Gly Pro Phe
                165                 170                 175

Pro Ala Gly Pro Leu Ala Val Ala Gly Gly Pro Arg Lys Thr Ala Pro
            180                 185                 190

Val Asn Ala Leu Val Ser His Leu Leu Val Val Glu Pro Glu Lys Leu
            195                 200                 205

Tyr Ala Met Pro Asp Pro Ala Ser Pro Asp Gly His Leu Pro Ala Val
            210                 215                 220

Ala Thr Leu Cys Asp Leu Phe Asp Arg Glu Ile Val Val Thr Ile Ser
225                 230                 235                 240

Trp Ala Lys Ser Ile Pro Gly Phe Ser Ser Leu Ser Leu Ser Asp Gln
                245                 250                 255

Met Ser Val Leu Gln Ser Val Trp Met Glu Val Leu Val Leu Gly Val
            260                 265                 270

Ala Gln Arg Ser Leu Pro Leu Gln Asp Glu Leu Ala Phe Ala Glu Asp
            275                 280                 285

Leu Val Leu Asp Glu Glu Gly Ala Arg Ala Ala Gly Leu Gly Asp Leu
            290                 295                 300

Gly Ala Ala Leu Leu Gln Leu Val Arg Arg Leu Gln Ala Leu Arg Leu
305                 310                 315                 320

Glu Arg Glu Glu Tyr Val Leu Leu Lys Ala Leu Ala Leu Ala Asn Ser
                325                 330                 335

Asp Ser Val His Ile Glu Asp Ala Glu Ala Val Glu Gln Leu Arg Glu
            340                 345                 350

Ala Leu His Glu Ala Leu Leu Glu Tyr Glu Ala Gly Arg Ala Gly Pro
            355                 360                 365

Gly Gly Gly Ala Glu Arg Arg Arg Ala Gly Arg Leu Leu Leu Thr Leu
            370                 375                 380

Pro Leu Leu Arg Gln Thr Ala Gly Lys Val Leu Ala His Phe Tyr Gly
385                 390                 395                 400

Val Lys Leu Glu Gly Lys Val Pro Met His Lys Leu Phe Leu Glu Met
                405                 410                 415

Leu Glu Ala Met Met Asp
            420

<210> SEQ ID NO 13
<211> LENGTH: 2293
<212> TYPE: DNA
<213> ORGANISM: Homo sapiens

<400> SEQUENCE: 13
tagaggtctc ccgcgggcgg ggaggggggag gcgtagcaac tttaggcaac ttcccaaagg    60
tgtgcgcagg ttggggggcgg gacgcggcgc cccgggaggt ggcggcctct gcgacagcgg   120
```

```
gagtataaga gtggacctgc aggctggtcg cgaggaggtg gagcggcgcc cgccgtgtgc    180
ctgggaccgg catgctgggg caggagggca gccgcgtgtc aggtgaccag cgccatgtcc    240
agccaggtgg tgggcattga gcctctctac atcaaggcag agccggccag ccctgacagt    300
ccaaagggtt cctcggagac agagaccgag cctcctgtgg ccctggcccc tggtccagct    360
cccactcgct gcctcccagg ccacaaggaa gaggaggatg gggaggggc tgggcctggc     420 gagcagggcg gtgggaagct ggtgctcagc tccctgccca gcgcctctg cctggtctgt     480 ggggacgtgg cctccggcta ccactatggt gtggcatcct gtgaggcctg caaagccttc    540
ttcaagagga ccatccaggg gagcatcgag tacagctgtc cggcctccaa cgagtgtgag    600
atcaccaagc ggagacgcaa ggcctgccag gcctgccgct tcaccaagtg cctgcgggtg    660
ggcatgctca aggagggagt cgcgcctgac cgcgtccggg gtgggcggca gaagtacaag    720
cggcggccgg aggtggaccc actgcccttc ccgggcccct ccctgctgg gcccctggca     780 gtcgctggag gcccccggaa gacagcagcc ccagtgaatg cactggtgtc tcatctgctg    840
gtggttgagc ctgagaagct ctatgccatg cctgaccccg caggccctga tgggcacctc    900
ccagccgtgg ctaccctctg tgacctcttt gaccgagaga ttgtggtcac catcagctgg    960
gccaagagca tcccaggctt ctcatcgctg tcgctgtctg accagatgtc agtactgcag   1020
agcgtgtgga tggaggtgct ggtgctgggt gtggcccagc gctcactgcc actgcaggat   1080
gagctggcct tcgctgagga cttagtcctg gatgaagagg gggcacgggc agctggcctg   1140
ggggaactgg gggctgccct gctgcaacta gtgcggcggc tgcaggccct gcggctggag   1200
cgagaggagt atgttctact aaaggccttg gcccttgcca attcagactc tgtgcacatc   1260
gaagatgccg aggctgtgga gcagctgcga gaagctctgc acgaggccct gctggagtat   1320
gaagccggcc gggctggccc cggaggggt gctgagcggc ggcgggcggg caggctgctg    1380
ctcacgctac cgctcctccg ccagacagcg ggcaaagtgc tggcccattt ctatggggtg   1440
aagctggagg gcaaggtgcc catgcacaag ctgttcttgg agatgctcga ggccatgatg   1500
gactgaggca aggggtggga ctggtggggg ttctggcagg acctgcctag catggggtca   1560
gccccaaggg ctgggcgga gctggggtct gggcagtgcc acagcctgct ggcagggcca    1620
gggcaatgcc atcagcccct gggaacaggc cccacgccct ctcctccccc tcctaggggg   1680
tgtcagaagc tgggaacgtg tgtccaggct ctgggcacag tgctgcccct tgcaagccat   1740
aacgtgcccc cagagtgtag ggggccttgc ggaagccata gggggctgca cgggatgcgt   1800
gggaggcaga aacctatctc agggagggaa ggggatggag gccagagtct cccagtgggt   1860
gatgcttttg ctgctgctta atcctacccc ctcttcaaag cagagtggga cttggagagc   1920
aaaggcccat gccccttcg ctcctcctct catcatttgc attgggcatt agtgtccccc     1980
cttgaagcaa taactccaag cagactccag ccctggacc cctggggtgg ccagggcttc    2040
cccatcagct cccaacgagc ctcctcaggg ggtaggagag cactgcctct atgccctgca   2100
gagcaataac actatattta tttttgggtt tggccaggga ggcgcaggga catggggcaa   2160
gccagggccc agagcccttg gctgtacaga gactctattt taatgtatat ttgctgcaaa   2220
gagaaaccgc ttttggtttt aaacctttaa tgagaaaaaa atatataata ccgagctcaa   2280
aaaaaaaaaa aaa                                                     2293

<210> SEQ ID NO 14
<211> LENGTH: 2264
<212> TYPE: DNA
```

<213> ORGANISM: Mus musculus

<400> SEQUENCE: 14

| | | | | | |
|---|---|---|---|---|---|
| tggaggaagc | ggagtaggaa | gcagccgcga | tgtccttttg | tgtcctacaa | gcagccagcg | 60 |
| gcgccgccga | gtgaggggggg | acgcagcgcg | gcggggcggt | gcggccggag | gaggcggccc | 120 |
| ccgctcaccc | cggcgctccg | ggccgctcgg | ccccatgcc | tgcccgccag | ccctgccgga | 180 |
| gcccaaggtg | accagcacca | tgtccagcca | ggtggtgggc | atcgagcctc | tctacatcaa | 240 |
| ggcagagcca | gccagtcctg | acagtccaaa | gggttcctca | gagactgaga | ctgaaccccc | 300 |
| ggtgaccctg | gcctctggtc | cagctccagc | ccgctgcctt | ccagggcaca | aggaggagga | 360 |
| ggatggggag | ggggcagggt | ctggtgagca | gggcagtggg | aagctagtgc | tcagctctct | 420 |
| acccaaacgc | ctctgcctgg | tctgtgggga | tgtggcctct | ggctaccact | acggtgtggc | 480 |
| atcctgtgag | gcctgcaaag | ccttcttcaa | gaggaccatc | caggggagca | tcgagtacag | 540 |
| ctgtccggcc | tccaatgagt | gtgagatcac | caagcggaga | cgcaaggcct | gtcaggcctg | 600 |
| ccgcttcacc | aagtgcctgc | gggtgggcat | gctcaaggag | ggtgtgcgtc | tggaccgtgt | 660 |
| ccgcggcgga | cggcagaagt | acaaacggcg | gccagaggtg | gaccctttgc | ctttcccggg | 720 |
| cccctttccct | gctggacctc | tggcagtagc | tggaggaccc | aggaagacag | ccccagtgaa | 780 |
| cgctctggtg | tcgcatctgc | tggtggttga | acctgagaag | ctgtacgcca | tgcctgaccc | 840 |
| agcaagcccc | gatggacacc | tccccgctgt | ggccactctc | tgtgaccttt | ttgatcgaga | 900 |
| gatagtggtc | accatcagct | gggccaagag | catcccaggc | ttctcctcac | tgtcactgtc | 960 |
| tgaccagatg | tcagtactgc | agagtgtgtg | atggaagtg | ctggtgctgg | gtgtggccca | 1020 |
| gcgctcactg | ccactgcagg | atgagctggc | ctttgctgag | gacctggtcc | tagatgaaga | 1080 |
| ggggggcacgg | gcagctggcc | tgggggatct | gggggcagcc | ctgctgcagc | tggttcggcg | 1140 |
| actgcaagct | cttcggctgg | agcgggagga | gtacgtcctg | ctgaaagctc | tggcccttgc | 1200 |
| caattctgac | tctgtgcaca | ttgaagatgc | tgaggctgtg | gagcagctgc | gcgaagccct | 1260 |
| gcatgaggcc | ctgctggagt | atgaagctgg | ccgggctggc | cctggagggg | gtgctgagcg | 1320 |
| gaggcgtgca | gcaggctgc | tgcttacgct | gccactcctc | cgccagacag | caggcaaagt | 1380 |
| cctggcccat | ttctatgggg | tgaagctgga | gggcaaggtg | cccatgcaca | agctgttttt | 1440 |
| ggaaatgctt | gaggccatga | tggactgagg | caaggggtgg | gacagggtgg | ggtggctggc | 1500 |
| aggatctgcc | cagcataggg | tgttagcccc | aaagggggcaa | agctggagtc | tgggcagtgc | 1560 |
| catagcctgc | tggcagggcc | agggcaatgc | catccgcccc | tgggagaagg | cttcatgccc | 1620 |
| ttccctcccc | actttgtgtg | tgtgggggat | tgtcagaagc | caggaaagtg | aatgcccagg | 1680 |
| tgtgggcaca | gtgctgcccc | ttgcaagcca | taacgtgccc | cccaagagtg | ttggggggcct | 1740 |
| cgcggaagcc | atagggggct | gcaggggatg | tgcaggaggc | agacactgat | ctcagggagg | 1800 |
| gaagggatgg | aggccgccgg | ctcccactgg | gtgatgcttt | tgctgctgct | taatccgatc | 1860 |
| tcctctccgg | agcagagggg | ggcttggaaa | gcaaaggccc | cgtcccttcg | ctcctctcct | 1920 |
| catccgcatt | gggcattatt | gccccccctt | gaagcaataa | ctccaagcag | gctccagccc | 1980 |
| ctggaccccca | ggggtggcca | gggccccta | tcagctccca | cctcaagggg | tgggggacag | 2040 |
| cactgcctct | atgccctgca | gagcaataac | actatattta | tttttgggtt | tggccaggga | 2100 |
| ggcgcagggc | catggggcaa | gccagggccc | agagcccttg | gctgtacaga | gactctattt | 2160 |
| taatgtatat | ttgctgcaaa | gagaaaccgc | ttttggttt | gaacctttaa | tgagaaaaaa | 2220 |
| aatatactat | ggagctcaag | taaaaaaaaa | aaaaaaaaaa | aaaa | | 2264 |

<210> SEQ ID NO 15
<211> LENGTH: 458
<212> TYPE: PRT
<213> ORGANISM: Homo sapiens

<400> SEQUENCE: 15

```
Met Asp Ser Val Glu Leu Cys Leu Pro Glu Ser Phe Ser Leu His Tyr
1               5                   10                  15

Glu Glu Glu Leu Leu Cys Arg Met Ser Asn Lys Asp Arg His Ile Asp
            20                  25                  30

Ser Ser Cys Ser Ser Phe Ile Lys Thr Glu Pro Ser Ser Pro Ala Ser
            35                  40                  45

Leu Thr Asp Ser Val Asn His His Ser Pro Gly Gly Ser Ser Asp Ala
        50                  55                  60

Ser Gly Ser Tyr Ser Ser Thr Met Asn Gly His Gln Asn Gly Leu Asp
65                  70                  75                  80

Ser Pro Pro Leu Tyr Pro Ser Ala Pro Ile Leu Gly Gly Ser Gly Pro
                85                  90                  95

Val Arg Lys Leu Tyr Asp Asp Cys Ser Ser Thr Ile Val Glu Asp Pro
            100                 105                 110

Gln Thr Lys Cys Glu Tyr Met Leu Asn Ser Met Pro Lys Arg Leu Cys
            115                 120                 125

Leu Val Cys Gly Asp Ile Ala Ser Gly Tyr His Tyr Gly Val Ala Ser
        130                 135                 140

Cys Glu Ala Cys Lys Ala Phe Phe Lys Arg Thr Ile Gln Gly Asn Ile
145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
            180                 185                 190

Met Leu Lys Glu Gly Val Arg Leu Asp Arg Val Arg Gly Gly Arg Gln
            195                 200                 205

Lys Tyr Lys Arg Arg Ile Asp Ala Glu Asn Ser Pro Tyr Leu Asn Pro
        210                 215                 220

Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
                245                 250                 255

Val Pro Asp Ser Asp Ile Lys Ala Leu Thr Thr Leu Cys Asp Leu Ala
            260                 265                 270

Asp Arg Glu Leu Val Val Ile Ile Gly Trp Ala Lys His Ile Pro Gly
            275                 280                 285

Phe Ser Thr Leu Ser Leu Ala Asp Gln Met Ser Leu Leu Gln Ser Ala
        290                 295                 300

Trp Met Glu Ile Leu Ile Leu Gly Val Val Tyr Arg Ser Leu Ser Phe
305                 310                 315                 320

Glu Asp Glu Leu Val Tyr Ala Asp Asp Tyr Ile Met Asp Glu Asp Gln
                325                 330                 335

Ser Lys Leu Ala Gly Leu Leu Asp Leu Asn Asn Ala Ile Leu Gln Leu
            340                 345                 350

Val Lys Lys Tyr Lys Ser Met Lys Leu Glu Lys Glu Glu Phe Val Thr
            355                 360                 365

Leu Lys Ala Ile Ala Leu Ala Asn Ser Asp Ser Met His Ile Glu Asp
```

```
                    370                 375                 380
Val Glu Ala Val Gln Lys Leu Gln Asp Val Leu His Glu Ala Leu Gln
385                 390                 395                 400

Asp Tyr Glu Ala Gly Gln His Met Glu Asp Pro Arg Arg Ala Gly Lys
                405                 410                 415

Met Leu Met Thr Leu Pro Leu Leu Arg Gln Thr Ser Thr Lys Ala Val
            420                 425                 430

Gln His Phe Tyr Asn Ile Lys Leu Glu Gly Lys Val Pro Met His Lys
        435                 440                 445

Leu Phe Leu Glu Met Leu Glu Ala Lys Val
    450                 455

<210> SEQ ID NO 16
<211> LENGTH: 361
<212> TYPE: PRT
<213> ORGANISM: Mus musculus

<400> SEQUENCE: 16

Met Ser Asn Lys Asp Arg His Ile Asp Ser Ser Cys Ser Ser Phe Ile
1               5                   10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
    50                  55                  60

Ala Pro Ile Leu Gly Gly Ser Gly Pro Val Arg Lys Leu Tyr Asp Asp
65                  70                  75                  80

Cys Ser Ser Thr Ile Val Glu Asp Pro Gln Thr Lys Cys Glu Tyr Met
                85                  90                  95

Leu Asn Ser Met Pro Lys Arg Leu Cys Leu Val Cys Gly Asp Ile Ala
            100                 105                 110

Ser Gly Tyr His Tyr Gly Val Ala Ser Cys Glu Ala Cys Lys Ala Phe
        115                 120                 125

Phe Lys Arg Thr Ile Gln Gly Asn Ile Glu Tyr Ser Cys Pro Ala Thr
    130                 135                 140

Asn Glu Cys Glu Ile Thr Lys Arg Arg Arg Lys Ser Cys Gln Ala Cys
145                 150                 155                 160

Arg Phe Met Lys Cys Leu Lys Val Gly Met Leu Lys Glu Gly Val Arg
                165                 170                 175

Leu Asp Arg Val Arg Gly Gly Arg Gln Lys Tyr Lys Arg Arg Ile Asp
            180                 185                 190

Ala Glu Asn Ser Pro Tyr Leu Asn Pro Gln Leu Leu Gln Ser Ala Trp
        195                 200                 205

Met Glu Ile Leu Ile Leu Gly Val Val Tyr Arg Ser Leu Ser Phe Glu
    210                 215                 220

Asp Glu Leu Val Tyr Ala Asp Asp Tyr Ile Met Asp Glu Asp Gln Ser
225                 230                 235                 240

Lys Leu Ala Gly Leu Leu Asp Leu Asn Asn Ala Ile Leu Gln Leu Val
                245                 250                 255

Lys Lys Tyr Lys Ser Met Lys Leu Glu Lys Glu Glu Phe Val Thr Leu
            260                 265                 270

Lys Ala Ile Ala Leu Ala Asn Ser Asp Ser Met His Ile Glu Asp Val
        275                 280                 285
```

```
Glu Ala Val Gln Lys Leu Gln Asp Val Leu His Glu Ala Leu Gln Asp
    290                 295                 300

Tyr Glu Ala Gly Gln His Met Glu Asp Pro Arg Arg Ala Gly Lys Met
305                 310                 315                 320

Leu Met Thr Leu Pro Leu Leu Arg Gln Thr Ser Thr Lys Ala Val Gln
                325                 330                 335

His Phe Tyr Asn Ile Lys Leu Glu Gly Lys Val Pro Met His Lys Leu
                340                 345                 350

Phe Leu Glu Met Leu Glu Ala Lys Val
                355                 360

<210> SEQ ID NO 17
<211> LENGTH: 5230
<212> TYPE: DNA
<213> ORGANISM: Homo sapiens

<400> SEQUENCE: 17
aagctccaat cggggcttta agtccttgat taggagagtg tgagagcttt ggtcccaact    60
ggctgtgcct ataggcttgt cactaggaga acatttgtgt taattgcact gtgctctgtc   120
aaggaaactt tgatttatag ctggggtgca caaataatgg ttgccggtcg cacatggatt   180
cggtagaact ttgccttcct gaatcttttt ccctgcacta cgaggaagag cttctctgca   240
gaatgtcaaa caaagatcga cacattgatt ccagctgttc gtccttcatc aagacggaac   300
cttccagccc agcctccctg acggacagcg tcaaccacca cagccctggt ggctcttcag   360
acgccagtgg gagctacagt tcaaccatga atgccatca gaacggactt gactcgccac   420
ctctctaccc ttctgctcct atcctgggag gtagtgggcc tgtcaggaaa ctgtatgatg   480
actgctccag caccattgtt gaagatcccc agaccaagtg taatacatg ctcaactcga   540 tgcccaagag actgtgttta gtgtgtggtg acatcgcttc tgggtaccac tatgggtag   600 catcatgtga agcctgcaag gcattcttca gaggacaat tcaaggcaat atagaataca   660
gctgccctgc cacgaatgaa tgtgaaatca caaagcgcag acgtaaatcc tgccaggctt   720
gccgcttcat gaagtgttta aaagtgggca tgctgaaaga aggggtgcgt cttgacagag   780
tacgtggagg tcggcagaag tacaagcgca ggatagatgc ggagaacagc ccatacctga   840
accctcagct ggttcagcca gccaaaaagc catataacaa gattgtctca catttgttgg   900
tggctgaacc ggagaagatc tatgccatgc ctgaccctac tgtccccgac agtgacatca   960
aagccctcac tacactgtgt gacttggccg accgagagtt ggtggttatc attggatggg  1020
cgaagcatat tccaggcttc tccacgctgt ccctggcgga ccagatgagc cttctgcaga  1080
gtgcttggat ggaaattttg atccttggtg tcgtataccg gtctctttcg tttgaggatg  1140
aacttgtcta tgcagacgat tatataatgg acgaagacca gtccaaatta gcaggccttc  1200
ttgatctaaa taatgctatc ctgcagctgg taaagaaata caagagcatg aagctggaaa  1260 agaagaatt tgtcaccctc aaagctatag ctcttgctaa ttcagactcc atgcacatag  1320
aagatgttga agccgttcag aagcttcagg atgtcttaca tgaagcgctg caggattatg  1380
aagctggcca gcacatggaa gaccctcgtc gagctggcaa gatgctgatg acactgccac  1440
tcctgaggca gacctctacc aaggccgtgc agcatttcta caacatcaaa ctagaaggca  1500 agtcccaat gcacaaactt ttttggaaa tgttggaggc caaggtctga ctaaaagctc  1560
cctgggcctt cccatccttc atgttgaaaa agggaaaata aacccaagag tgatgtcgaa  1620
gaaacttaga gtttagttaa caacatcaaa aatcaacaga ctgcactgat aatttagcag  1680
```

```
caagactatg aagcagcttt cagattcctc cataggttcc tgatgagttt ctttctactt    1740
tctccatcat cttctttcct ctttcttccc acatttctct ttctctttat tttttctcct    1800
tttcttcttt cacctcccct attctttgc ttctttcatt cctagttccc attctccttt     1860
attttcttcc cgtctgcctg ccttcttcct tttcttacc tactctcatt cctctctttt     1920
ctcatccttc cccttttttc taaatttgaa atagctttag tttaaaaaaa aatcctccct    1980
tcccccttc ctttccctt ctttccttt tcccttcct tttcccttc ctttccttc         2040
ctcttgacct tctttccatc tttctttttc ttccttctgc tgctgaactt ttaaaagagg    2100
tctctaactg aagagagatg gaagccagcc ctgccaaagg atggagatcc ataatatgga    2160
tgccagtgaa cttattgtga accatactgt ccccaatgac taaggaatca agagagaga    2220
accaacgttc ctaaaagtac agtgcaacat atacaaattg actgagtgca gtattagatt    2280
tcatgggagc agcctctaat tagacaactt aagcaacgtt gcatcggctg cttcttatca    2340
ttgcttttcc atctagatca gttacagcca tttgattcct taattgtttt ttcaagtctt    2400
ccaggtattt gttagtttag ctactatgta acttttcag ggaatagttt aagctttatt     2460
cattcatgca atactaaaga gaaataagaa tactgcaatt ttgtgctggc tttgaacaat    2520
tacgaacaat aatgaaggac aaatgaatcc tgaaggaaga ttttttaaaaa tgttttgttt    2580
cttcttacaa atggagattt ttttgtacca gctttaccac ttttcagcca tttattaata    2640
tgggaattta acttactcaa gcaatagttg aagggaaggt gcatattatc acggatgcaa    2700
tttatgttgt gtgccagtct ggtcccaaac atcaatttct taacatgagc tccagtttac    2760
ctaaatgttc actgacacaa aggatgagat tacacctaca gtgactctga gtagtcacat    2820
atataagcac tgcacatgag atatagatcc gtagaattgt caggagtgca cctctctact    2880
tgggaggtac aattgccata tgatttctag ctgccatggt ggttaggaat gtgatactgc    2940
ctgtttgcaa agtcacagac cttgcctcag aaggagctgt gagccagtat tcatttaaga    3000
ggcaataagg caaatgccag aattaaaaaa aaaaatcatc aaagacagaa atgcctgac    3060
caaattctaa aacctaatcc atataagttt attcatttag gaatgttcgt ttaaattaat    3120
ctgcagtttt taccaagagc taagccaata tatgtgcttt tcaaccagta ttgtcacagc    3180
atgaaagtca agtcaggttc cagactgtta agaggtgtaa tctaatgaag aaatcaatta    3240
gatgccccga aatctacagt cgctgaataa ccaataaaca gtaacctcca tcaaatgcta    3300
taccaatgga ccagtgttag tagctgctcc ctgtattatg tgaacagtct tattctatgt    3360
acacagatgt aattaaaatt gtaatcctaa caaacaaaag aaatgtagtt cagcttttca    3420
atgtttcatg tttgctgtgc ttttctgaat tttatgttgc attcaaagac tgttgtcttg    3480
ttcttgtggt gtttggattc ttgtggtgtg tgcttttaga cacagggtag aattagagac    3540
aatattggat gtacaattcc tcaggagact acagtagtat attctattcc ttaccagtaa    3600
taaggttctt cctaataata attaagagat tgaaactcca aacaagtatt cattatgaac    3660
agatacacat caaaatcata ataatatttt caaaacaagg aataatttct ctaatggttt    3720
attatagaat accaatgtat agcttagaaa taaaactttg aatatttcaa gaatatagat    3780
aagtctaatt tttaaatgct gtatatatgg ctttcactca atcatctctc agatgttgtt    3840
attaactcgc tctgtgttgt tgcaaaactt tttggtgcag attcgtttcc aaaactattg    3900
ctactttgtg tgctttaaac aaaataccttt gggttgatga acatcaacc cagtgctagg    3960
aatactgtgt atctatcatt agctatatgg gactatattg tagattgtgg tttctcagta    4020
gagaagtgac tgtagtgtga ttctagataa atcatcatta gcaattcatt cagatggtca    4080
```

| | |
|---|---|
| ataacttgaa atttatagct gtgataggag ttcagaaatt ggcacatccc tttaaaaata | 4140 |
| acaacagaaa atacaactcc tgggaaaaaa ggtgctgatt ctataagatt atttatatat | 4200 |
| gtaagtgttt aaaaagatta ttttccagaa agtttgtgca gggtttaagt tgctactatt | 4260 |
| caactcacct atatataaat aaaatatata caatatatac attgttttca ctgtatcaca | 4320 |
| ttaaagtact tgggcttcag aagtaagagc caaccaactg aaaacctgag atggagatat | 4380 |
| gttcaaagaa tgagatacaa tttttttagtt ttcagtttaa gtaactctca gcattacaaa | 4440 |
| agagtaagta tctcacaaat aggaaataaa actaaaacgt ggatttaaaa agaactgcac | 4500 |
| gggcttagg gtaaatgctc atcttaaacc tcactagagg gaagtcttct caagtttcaa | 4560 |
| gcaagaccat ttacttaatg tgaagttttg gaaagttata aggtgtatg ttttagccat | 4620 |
| atgattttaa ttttaatttt gcttctttta ggttcgttct tatttaaagc aatatgattg | 4680 |
| tgtgactcct tgtagttaca cttgtgtttc aatcagatca gattgttgta tttattccac | 4740 |
| tattttgcat ttaaatgata acataaaaga tataaaaaat ttaaaactgc tattttttctt | 4800 |
| atagaagaga aaatgggtgt tggtgattgt atttttaatta tttaagcgtc tctgtttacc | 4860 |
| tgcctaggaa aacattttat ggcagtctta tgtgcaaaga tcgtaaaagg acaaaaaatt | 4920 |
| taaactgctt ataataatcc aggagttgca ttatagccag tagtaaaaat aataataata | 4980 |
| ataataaaac catgtctata gctgtagatg ggcttcacat ctgtaaagca atcaattgta | 5040 |
| tatttttgtg atgtgtacca tactgtgtgc tccagcaaat gtccatttgt gtaaatgtat | 5100 |
| ttattttata ttgtatatat tgttaaatgc aaaaaggaga tatgattctg taactccaat | 5160 |
| cagttcagat gtgtaactca aattattatg cctttcagga tgatggtaga gcaatattaa | 5220 |
| acaagcttcc | 5230 |

<210> SEQ ID NO 18
<211> LENGTH: 5374
<212> TYPE: DNA
<213> ORGANISM: Mus musculus

<400> SEQUENCE: 18

| | |
|---|---|
| agcccgaacc ccgtgcccga ttcctggtgc ggagtgcgag aggttcccgc ggcgcctggc | 60 |
| ggacagtctc gctggcctcc ggtgacttgt tttgtgttgg ttttcccctc ttgcagccgg | 120 |
| cgaccaagcg gacatcctcg ggacccccca aagccaccca ctcccgagag ctcggagagc | 180 |
| ggctctgcac gagggacctt agctacttgc tggttcatca atgaagcaac ccgaagtgat | 240 |
| gaagatgtaa ggaacgcatc ctacgctagc actgttgcag ttggaaaggc ttctctgcag | 300 |
| aatgtcaaac aaagatcgac acattgattc cagctgttcg tccttcatca agacggaacc | 360 |
| ctccagccca gcctccctga cggacagcgt caaccaccac agccctggtg ggtcttccga | 420 |
| cgccagtggg agttacagtt caaccatgaa tggccatcag aacggactgg actcgccacc | 480 |
| tctctacccc tctgctccga tcctggggag cagcgggcct gtccggaaac tgtatgatga | 540 |
| ctgctccagc accatcgtag aggatcccca gaccaagtgt gaatatatgc tcaactccat | 600 |
| gcccaagaga ctgtgcttag tgtgtggcga catcgcctct gggtaccact atggggttgc | 660 |
| atcatgtgaa gcctgcaagg cattcttcaa gaggacgatt caaggtaaca tagagtacag | 720 |
| ctgcccagcc acgaatgaat gtgagatcac aaagcgcaga cgcaaatcct gccaggcctg | 780 |
| ccgcttcatg aagtgtctca agtgggcat gctgaaagaa ggggtccgtc ttgacagagt | 840 |
| gcgtggaggt cggcagaagt acaagcgcag aatagatgct gagaacagcc catacctgaa | 900 |

| | |
|---|---|
| ccctcagctg gtgcagccag ccaaaaagcc atataacaag attgtctcgc atttgttggt | 960 |
| ggctgaacca gagaagatct atgccatgcc tgaccctact gtccccgaca gtgacatcaa | 1020 |
| agccctcacc acactctgtg acttggctga ccgagagttg gtggttatca ttggatgggc | 1080 |
| aaaacatatt ccaggcttct ccacactgtc cctggcagac cagatgagcc tcctccagag | 1140 |
| tgcatggatg gagattctga tcctcggcgt tgtgtaccga tcgctttcgt tgaggatga | 1200 |
| acttgtctat gcagacgatt atataatgga tgaagaccag tctaaattag caggccttct | 1260 |
| tgacctaaat aatgctatcc tgcagctggt gaagaagtac aagagcatga agctagagaa | 1320 |
| ggaagaattc gtcaccctca agcaatagc tcttgctaat tcagattcca tgcatataga | 1380 |
| agatgtggaa gctgtgcaga acttcagga tgtgttacat gaggccctgc aggattacga | 1440 |
| ggctggccag cacatggaag accctcgccg tgcaggcaag atgctgatga cgctgccgct | 1500 |
| gctgaggcag acctccacca aggcagtcca gcacttctac aacatcaaac tcgaaggcaa | 1560 |
| agtgcccatg cacaaacttt ttttggaaat gctggaggcc aaggtctgac taaaagcccc | 1620 |
| ccctgggccc tcccatcctg cacgttgaaa agggaagata aacccaagaa tgatgtcgaa | 1680 |
| gaatcttaga gtttagtgaa caacattaaa aatcaacaga ctgcactgat attttagcag | 1740 |
| ccacagtacg atgcagcctg cggattccgc tacatcttcc tgataggttt cctctacttt | 1800 |
| atcccacgat cctctggcca catccctgca ttcctccact cttccttgtt ctattattat | 1860 |
| gtttggcttc tttcactaat agttcatttt ccctcctccc ctcccttctc ttctccctcc | 1920 |
| ctcctctgtc tccccttcc ttccttctc ttccttttcca caatcttctc ctcttgcctt | 1980 |
| gctctcacct ctcttcgctt tctcacatct cctcccactc tgcgtacata gtcaatacct | 2040 |
| ctgattgtat ggaacatttc ttttacctct tgcatctctt ctccgtctct tccttcccca | 2100 |
| cttttttttg tttgtttgtt tgtttccttt ccttccttct gctgctgaac tcttaatagc | 2160 |
| agtctctaac tggagagaga aagagagaga gatggaagcc agccctgcca aaggacagag | 2220 |
| atccatacta tggatgccag tgaacttgtc atgaaccatg acatccccag tgagtaagga | 2280 |
| atcaaagaga gaaccgtacc taaagtacat tgcaacgcaa acggatcaac ttagtgcagt | 2340 |
| attagattct accgggcagc cttcgatcag acaacctaag tggcggcatt ggctgcttct | 2400 |
| ccttgctttc tcatctagat cagttacagc catttgattc cttaattctt ttgtcaagtc | 2460 |
| ttccaggtgt tggttagttt agctactatg taactttttc agggaatcct ttaagcttta | 2520 |
| ttcattcatg caatactaga gaggggtaag gataccgcaa cctcgtgctg gctttgaaca | 2580 |
| attgaacact aatgaaggac aaatgaaccc tgaaggaaga ttttaaaaa tgtttcgttt | 2640 |
| cttcttacaa atggagattt ttttgtacca gctttaccac ttttcagcca tttattaata | 2700 |
| tggggattta acttactcaa gcaatagttg aagggaaggt gcatattacc acggatgcaa | 2760 |
| tttatgttgt gtgccagtct ggtcccaaac atcagtttct tacatgagct ccagtttgcc | 2820 |
| taaatgttca ctgacaccaa ggattagatg atacctgccg tgacaccgag tggtcccatc | 2880 |
| cacgagcact gcacatggga tccctatctg tagaattagc accagtacac ctccctgccg | 2940 |
| ggagggacag tcgccatacg gtttctagct gccctcgtgg ttaggaacaa gatgctgcct | 3000 |
| gtatacaaac tctgtctcag aaggagctgt gagccaatac catttcagag gcaataaagg | 3060 |
| ctaagtgcca gaattcaaac caaccaacca tcaaagacag cagacgcctg accaaattct | 3120 |
| aaagtcctga tccataggag tcgattcact taggaatggt tgtttaaatt aacctgcagg | 3180 |
| tttgttttgt ttccttgttt gttttttttac caaaagctaa gccaatagat gtgcttttc | 3240 |
| aacaagtatg gtcacagcac gaaggtcagt caggtttcag actgtaacca ggtgtaatct | 3300 |

```
aatgaagaaa tcaaatgtcc cctcccgaaa cctacagtcg ccgaataacc agaaaccagt    3360
aacctccgta gaacgcttta ccaatggacc agtgttagta gctgctctct gtattctgtg    3420
gacagtctta ttctatgtac acagatgtaa ttaaagttgt actcctaaca aacaaaagaa    3480
tagttcagct tcaatgttcc atgtttgctg cgcttttctg aactttatgt tgcattcaga    3540
aactgtcgtc ttgttctcgt ggtgtttgga ttcttgtggt gtgtgctttt agacacaggg    3600
tagaattaga gacagtattg gatgtatact tcctcaggag actacagtag tatattctac    3660
tccttaccag taataactaa gagattgaaa ctccaaaaca gtattcatta cgatcagaca    3720
cacatcaaaa tcataataat attttcaaaa aagggataat ttctctaatg gtttattata    3780
gaataccaat gtatagctta gacataaaac tttgaatatt caagaatata gataagtcta    3840 attttttaaat gctgtatata aggcttccac ctgatcatct ctcagatgtt gttattaact    3900
cgctctgtgt tgttgcaaac cttttggtg cggacttgct tccaaaacta ttgctacttt    3960
gtgtgcgtta agcaaaatac cttggactga gggtgtctca gccctgtgct aggaatactg    4020
tgtatctatc attagctata tgggaatata tcgtagattg tggttctcag tagagaaagt    4080
gactgtagtg tgactctagg taaatcatca ttagcaattc attcggatgg tcaataactt    4140
gaaattgata gctgtgataa gttttaaaaa attggcaaat ccctgactaa acatcaacag    4200
aaaatacaac tcctgggggg gaaaggtgct catcctgtaa gattctttca tcatgtaagt    4260
gtttgaaaca ttactttgca gaaggtttat gcagggttta agttactacc gctcaataat    4320
gctatatata cacaaatgga atatagacaa tgtatgtacc caccgtttca ctgagtcgca    4380
gagaagaatc tgagcttcag aagccagagc ccacaagtga tcaggtgaga cagaggcaca    4440
tttaaggaag gaggtacaat gtgtagttct ccgtttaaaa gacttggcct tttaaaacaa    4500
caaatatctc acaactatgg tgaaaacaac aacagcttca agtgtggatc taaaggaaac    4560
gcacaggttt agggtaaata ccatttgtac cttgctcgag caaagtttat tgttttgttt    4620 tttttttgttt tgttttgttt tgttttcaag tttccagcaa gaccgtttag ttaatgccag    4680
ctgtcaggaa gataccaagg tgtatgtttt agccatgcaa tttgcagttt tattttcctt    4740
ttaggtttgt ccttatttaa ggcagtgcga ttgttttggc ttcttgtagt gactctcgtg    4800
ttttaatcaa gccagattgt tgtatttatt ccactatttt gcatttaaat gatgacataa    4860
aagatataaa aaatttaaaa ctgctatttt tcttatagaa gagaaaatgg atgttggtga    4920 ttgtattttta attatttaag catctctgtt tacctgcctg ggacaacatt ttatggcagt    4980
cttatgtgca aagatcgtga atggacaaaa caaaaaatta aactgcttac aatgatccag    5040
gagttgcatt atagccagta gtaaaaataa taatgataat taataataat taataataat    5100
aatgaaacca tgtctatagc tgtaggtggg catcacatct gtaaagcaat caattgtata    5160
tttttgtgat gtgtaccata ctgtgtgctc cagcaaatgt ccatttgtgt aaatgtattt    5220
attttatatt gtatatattg ttaaatgcaa aaaggagcta tgattctgtg actccaatca    5280
gttcagatat gtaactcaaa ttattatgcc tttcaggagg atggtagaac aatattaaac    5340
aagcttccac ttttaaaaaa aaaaaaaaaa aaaa                                5374
```

<210> SEQ ID NO 19
<211> LENGTH: 508
<212> TYPE: PRT
<213> ORGANISM: Homo sapiens

<400> SEQUENCE: 19

```
Met Ser Ser Asp Asp Arg His Leu Gly Ser Cys Gly Ser Phe Ile
1               5                  10                 15

Lys Thr Glu Pro Ser Ser Pro Ser Ser Gly Ile Asp Ala Leu Ser His
            20              25                  30

His Ser Pro Ser Gly Ser Ser Asp Ala Ser Gly Gly Phe Gly Leu Ala
        35              40                  45

Leu Gly Thr His Ala Asn Gly Leu Asp Ser Pro Pro Met Phe Ala Gly
    50              55                  60

Ala Gly Leu Gly Gly Thr Pro Cys Arg Lys Ser Tyr Glu Asp Cys Ala
65              70                  75                      80

Ser Gly Ile Met Glu Asp Ser Ala Ile Lys Cys Glu Tyr Met Leu Asn
                85                  90                  95

Ala Ile Pro Lys Arg Leu Cys Leu Val Cys Gly Asp Ile Ala Ser Gly
            100             105                 110

Tyr His Tyr Gly Val Ala Ser Cys Glu Ala Cys Lys Ala Phe Phe Lys
        115                 120                 125

Arg Thr Ile Gln Gly Asn Ile Glu Tyr Ser Cys Pro Ala Thr Asn Glu
        130                 135                 140

Cys Glu Ile Thr Lys Arg Arg Arg Lys Ser Cys Gln Ala Cys Arg Phe
145                 150                 155                 160

Met Lys Cys Leu Lys Val Gly Met Leu Lys Glu Gly Val Arg Leu Asp
                165                 170                 175

Arg Val Arg Gly Gly Arg Gln Lys Tyr Lys Arg Arg Leu Asp Ser Glu
            180                 185                 190

Ser Ser Pro Tyr Leu Ser Leu Gln Ile Ser Pro Pro Ala Lys Lys Pro
            195                 200                 205

Leu Thr Lys Ile Val Ser Tyr Leu Leu Val Ala Glu Pro Asp Lys Leu
    210                 215                 220

Tyr Ala Met Pro Pro Pro Gly Met Pro Glu Gly Asp Ile Lys Ala Leu
225                 230                 235                 240

Thr Thr Leu Cys Asp Leu Ala Asp Arg Glu Leu Val Val Ile Ile Gly
                245                 250                 255

Trp Ala Lys His Ile Pro Gly Phe Ser Ser Leu Ser Leu Gly Asp Gln
                260                 265                 270

Met Ser Leu Leu Gln Ser Ala Trp Met Glu Ile Leu Ile Leu Gly Ile
    275                 280                 285

Val Tyr Arg Ser Leu Pro Tyr Asp Asp Lys Leu Val Tyr Ala Glu Asp
    290                 295                 300

Tyr Ile Met Asp Glu Glu His Ser Arg Leu Ala Gly Leu Leu Glu Leu
305                 310                 315                 320

Tyr Arg Ala Ile Leu Gln Leu Val Arg Arg Tyr Lys Lys Leu Lys Val
                325                 330                 335

Glu Lys Glu Glu Phe Val Thr Leu Lys Ala Leu Ala Leu Ala Asn Ser
            340                 345                 350

Asp Ser Met Tyr Ile Glu Asp Leu Glu Ala Val Gln Lys Leu Gln Asp
        355                 360                 365

Leu Leu His Glu Ala Leu Gln Asp Tyr Glu Leu Ser Gln Arg His Glu
    370                 375                 380

Glu Pro Trp Arg Thr Gly Lys Leu Leu Leu Thr Leu Pro Leu Leu Arg
385                 390                 395                 400

Gln Thr Ala Ala Lys Ala Val Gln His Phe Tyr Ser Val Lys Leu Gln
                405                 410                 415

Gly Lys Val Pro Met His Lys Leu Phe Leu Glu Met Leu Glu Ala Lys
```

```
                420           425           430
Val Gly Gln Glu Gln Leu Arg Gly Ser Pro Lys Asp Glu Arg Met Ser
            435               440               445

Ser His Asp Gly Lys Cys Pro Phe Gln Ser Ala Ala Phe Thr Ser Arg
        450               455               460

Asp Gln Ser Asn Ser Pro Gly Ile Pro Asn Pro Arg Pro Ser Ser Pro
465               470               475               480

Thr Pro Leu Asn Glu Arg Gly Arg Gln Ile Ser Pro Ser Thr Arg Thr
                485               490               495

Pro Gly Gly Gln Gly Lys His Leu Trp Leu Thr Met
            500               505
```

<210> SEQ ID NO 20
<211> LENGTH: 3029
<212> TYPE: DNA
<213> ORGANISM: Homo sapiens

<400> SEQUENCE: 20

| | |
|---|---|
| ccgcagagag gtgtggtcag ggacatttcc cctggccggg agcccatgga gcactgtcct | 60 |
| cagagatgcg caggttaggc tcactgtcta ggccaggccc accttagtca ctgtggactg | 120 |
| gcaatggaag ctcttcctgg acacacctgc cctagccctc accctggggt ggaagagaaa | 180 |
| tgagcttggc ttgcaactca gaccattcca cggaggcatc ctccccttcc tgggctggtg | 240 |
| aataaaagtt tcctgaggtc aaggacttcc ttttccctgc aaaatggtg tccagaactt | 300 |
| tgaggccaga ggtgatccag tgatttggga gctgcaggtc acacaggctg ctcagagggc | 360 |
| tgctgaacag gatgtcctcg gacgacaggc acctgggctc cagctgcggc tccttcatca | 420 |
| agactgagcc gtccagcccg tcctcgggca tcgatgccct cagccaccac agccccagtg | 480 |
| gctcgtccga cgccagcggc ggctttggcc tggccctggg cacccacgcc aacggtctgg | 540 |
| actcgccacc catgttgca ggcgccgggc tgggaggcac cccatgccgc aagagctacg | 600 |
| aggactgtgc cagcggcatc atggaggact cggccatcaa gtgcgagtac atgctcaacg | 660 |
| ccatccccaa gcgcctgtgc ctcgtgtgcg ggacattgc ctctggctac cactacggcg | 720 |
| tggcctcctg cgaggcttgc aaggccttct tcaagaggac tatccaaggg aacattgagt | 780 |
| acagctgccc ggccaccaac gagtgcgaga tcaccaaacg gaggcgcaag tcctgccagg | 840 |
| cctgccgctt catgaaatgc ctcaaagtgg ggatgctgaa ggaaggtgtg cgccttgatc | 900 |
| gagtgcgtgg aggccgtcag aaatacaagc gacggctgga ctcagagagc agcccatacc | 960 |
| tgagcttaca aatttctcca cctgctaaaa agccattgac caagattgtc tcatacctac | 1020 |
| tggtggctga gccggacaag ctctatgcca tgcctccccc tggtatgcct gaggggaca | 1080 |
| tcaaggccct gaccactctc tgtgacctgg cagaccgaga gcttgtggtc atcattggct | 1140 |
| gggccaagca catcccaggc ttctcaagcc tctccctggg ggaccagatg agcctgctgc | 1200 |
| agagtgcctg gatggaaatc ctcatcctgg gcatcgtgta ccgctcgctg cctatgacg | 1260 |
| acaagctggt gtacgctgag gactacatca tggatgagga gcactcccgc tcgcggggc | 1320 |
| tgctggagct ctaccgggcc atcctgcagc tggtacgcag gtacaagaag ctcaaggtgg | 1380 |
| agaaggagga gtttgtgacg ctcaaggccc tggccctcgc caactccgat tccatgtaca | 1440 |
| tcgaggatct agaggctgtc cagaagctgc aggacctgct gcacgaggca ctgcaggact | 1500 |
| acgagctgag ccagcgccat gaggagccct ggagacgggg caagctgctg ctgacactgc | 1560 |
| cgctgctgcg gcagacggcc gccaaggccg tgcagcactt ctatagcgtc aaactgcagg | 1620 |

```
gcaaagtgcc catgcacaaa ctcttcctgg agatgctgga ggccaaggtt ggccaagagc    1680
agcttagagg atctcccaag gatgaaagaa tgtcaagcca tgatggaaaa tgccccttcc    1740
aatcagctgc cttcacaagc agggatcaga gcaactcccc ggggatcccc aatccacgcc    1800
cttctagtcc aaccccctc aatgagagag gcaggcagat ctcacccagc actaggacac    1860
caggaggcca gggaaagcat ctctggctca ccatgtaaca tctggcttgg agcaagtggg    1920
tgttctgcac accaggcagc tgcacctcac tggatctagt gttgctgcga gtgacctcac    1980
ttcagagccc ctctagcaga gtggggcgga agtcctgatg gttggtgtcc atgaggtgga    2040
agctgctttt atacttaaaa ctcagatcac aacaggaaat gtgtcagtaa caatggaact    2100
ccatccaatg ggaaagttcc tggtactgaa ggggtccatt ggacactcag aaaagaagtt    2160
caggggccaa cttcttagct ggaatcctgg ccagatgagg accctctccg ggaagggag    2220
aggactgact tagtggaagg tggtgaagtg aggagagttt aggggaacct tcccccagtg    2280
gaacagatct caagtttacc ctaaacctgc catttctgga aaatctgtaa agaggaaaca    2340
gcctgtctca gctgtactct catgatacag gtcatttgaa atgaaccaag aaataaaaca    2400
tgaaaatcca accatggaga aggtggtatg gctgggtttt gtttggtccc cttgtcctta    2460
tacgttctaa agtttccaga ctggctttgt cactttgtga actcgtcatg tgtgaaaacc    2520
aatctttgca tagggaac ttcctcgggc cacactttaa gaaccaagta agaggctctc    2580
aagactccag cagagtcggg aggccatggc agcgccttag aggagctgga acctgcaccc    2640
acctgtgtcg gtggggggg cctcctttcc ccatagactc tgccctccct ctgtgcagat    2700
ggaagtggca ggggaggggtg accagcttgt gacaagaaga ctgaagggtc cagagtccat    2760
gctcacggaa cagcaccaaa gaaaagcact atgtggaaag attgttttat tttctaataa    2820
tgataatatg gctggaatgg cttcttaaga tgtatatatt ttttaaaatg gcagttcccc    2880
attgcagcat cacctacttg tatgtctttc tgcctctgta tatgttctcc cagaaacccc    2940
catgtaaatc aaatgcccta ggatgcttcc atcctggtcc catgtatctg gaatctaata    3000
aataaggaaa ggaaaaaaaa aaaaaaaaa                                     3029
```

<210> SEQ ID NO 21
<211> LENGTH: 479
<212> TYPE: PRT
<213> ORGANISM: Homo sapiens

<400> SEQUENCE: 21

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125
```

Ser Ala Ser Ser Ser Ser Pro Ser Ser Gly Pro Ala Ser Ala
        130             135             140

Pro Ser Thr Cys Ser Phe Thr Tyr Pro Ile Arg Ala Gly Asn Asp Pro
145             150             155             160

Gly Val Ala Pro Gly Gly Thr Gly Gly Leu Leu Tyr Gly Arg Glu
            165             170             175

Ser Ala Pro Pro Pro Thr Ala Pro Phe Asn Leu Ala Asp Ile Asn Asp
        180             185             190

Val Ser Pro Ser Gly Gly Phe Val Ala Glu Leu Leu Arg Pro Glu Leu
        195             200             205

Asp Pro Val Tyr Ile Pro Pro Gln Gln Pro Gln Pro Gly Gly Gly
210             215             220

Leu Met Gly Lys Phe Val Leu Lys Ala Ser Leu Ser Ala Pro Gly Ser
225             230             235             240

Glu Tyr Gly Ser Pro Ser Val Ile Ser Val Ser Lys Gly Ser Pro Asp
            245             250             255

Gly Ser His Pro Val Val Ala Pro Tyr Asn Gly Gly Pro Pro Arg
            260             265             270

Thr Cys Pro Lys Ile Lys Gln Glu Ala Val Ser Ser Cys Thr His Leu
            275             280             285

Gly Ala Gly Pro Pro Leu Ser Asn Gly His Arg Pro Ala Ala His Asp
290             295             300

Phe Pro Leu Gly Arg Gln Leu Pro Ser Arg Thr Thr Pro Thr Leu Gly
305             310             315             320

Leu Glu Glu Val Leu Ser Ser Arg Asp Cys His Pro Ala Leu Pro Leu
            325             330             335

Pro Pro Gly Phe His Pro His Pro Gly Pro Asn Tyr Pro Ser Phe Leu
            340             345             350

Pro Asp Gln Met Gln Pro Gln Val Pro Pro Leu His Tyr Gln Glu Leu
        355             360             365

Met Pro Pro Gly Ser Cys Met Pro Glu Glu Pro Lys Pro Lys Arg Gly
        370             375             380

Arg Arg Ser Trp Pro Arg Lys Arg Thr Ala Thr His Thr Cys Asp Tyr
385             390             395             400

Ala Gly Cys Gly Lys Thr Tyr Thr Lys Ser Ser His Leu Lys Ala His
            405             410             415

Leu Arg Thr His Thr Gly Glu Lys Pro Tyr His Cys Asp Trp Asp Gly
        420             425             430

Cys Gly Trp Lys Phe Ala Arg Ser Asp Glu Leu Thr Arg His Tyr Arg
        435             440             445

Lys His Thr Gly His Arg Pro Phe Gln Cys Gln Lys Cys Asp Arg Ala
450             455             460

Phe Ser Arg Ser Asp His Leu Ala Leu His Met Lys Arg His Phe
465             470             475

<210> SEQ ID NO 22
<211> LENGTH: 483
<212> TYPE: PRT
<213> ORGANISM: Mus musculus

<400> SEQUENCE: 22

Met Arg Gln Pro Pro Gly Glu Ser Asp Met Ala Val Ser Asp Ala Leu
1               5               10              15

Leu Pro Ser Phe Ser Thr Phe Ala Ser Gly Pro Ala Gly Arg Glu Lys

-continued

```
                20                  25                  30
Thr Leu Arg Pro Ala Gly Ala Pro Thr Asn Arg Trp Arg Glu Glu Leu
            35                  40                  45
Ser His Met Lys Arg Leu Pro Pro Leu Pro Gly Arg Pro Tyr Asp Leu
        50                  55                  60
Ala Ala Thr Val Ala Thr Asp Leu Glu Ser Gly Ala Gly Ala Ala
65                  70                  75                  80
Cys Ser Ser Asn Asn Pro Ala Leu Leu Ala Arg Arg Glu Thr Glu Glu
                85                  90                  95
Phe Asn Asp Leu Leu Asp Leu Asp Phe Ile Leu Ser Asn Ser Leu Thr
            100                 105                 110
His Gln Glu Ser Val Ala Ala Thr Val Thr Thr Ser Ala Ser Ala Ser
        115                 120                 125
Ser Ser Ser Ser Pro Ala Ser Ser Gly Pro Ala Ser Ala Pro Ser Thr
    130                 135                 140
Cys Ser Phe Ser Tyr Pro Ile Arg Ala Gly Gly Asp Pro Gly Val Ala
145                 150                 155                 160
Ala Ser Asn Thr Gly Gly Gly Leu Leu Tyr Ser Arg Glu Ser Ala Pro
                165                 170                 175
Pro Pro Thr Ala Pro Phe Asn Leu Ala Asp Ile Asn Asp Val Ser Pro
            180                 185                 190
Ser Gly Gly Phe Val Ala Glu Leu Leu Arg Pro Glu Leu Asp Pro Val
        195                 200                 205
Tyr Ile Pro Pro Gln Gln Pro Gln Pro Pro Gly Gly Gly Leu Met Gly
    210                 215                 220
Lys Phe Val Leu Lys Ala Ser Leu Thr Thr Pro Gly Ser Glu Tyr Ser
225                 230                 235                 240
Ser Pro Ser Val Ile Ser Val Ser Lys Gly Ser Pro Asp Gly Ser His
                245                 250                 255
Pro Val Val Val Ala Pro Tyr Ser Gly Gly Pro Pro Arg Met Cys Pro
            260                 265                 270
Lys Ile Lys Gln Glu Ala Val Pro Ser Cys Thr Val Ser Arg Ser Leu
        275                 280                 285
Glu Ala His Leu Ser Ala Gly Pro Gln Leu Ser Asn Gly His Arg Pro
    290                 295                 300
Asn Thr His Asp Phe Pro Leu Gly Arg Gln Leu Pro Thr Arg Thr Thr
305                 310                 315                 320
Pro Thr Leu Ser Pro Glu Glu Leu Leu Asn Ser Arg Asp Cys His Pro
                325                 330                 335
Gly Leu Pro Leu Pro Pro Gly Phe His Pro His Pro Gly Pro Asn Tyr
            340                 345                 350
Pro Pro Phe Leu Pro Asp Gln Met Gln Ser Gln Val Pro Ser Leu His
        355                 360                 365
Tyr Gln Glu Leu Met Pro Pro Gly Ser Cys Leu Pro Glu Glu Pro Lys
    370                 375                 380
Pro Lys Arg Gly Arg Arg Ser Trp Pro Arg Lys Arg Thr Ala Thr His
385                 390                 395                 400
Thr Cys Asp Tyr Ala Gly Cys Gly Lys Thr Tyr Thr Lys Ser Ser His
                405                 410                 415
Leu Lys Ala His Leu Arg Thr His Thr Gly Glu Lys Pro Tyr His Cys
            420                 425                 430
Asp Trp Asp Gly Cys Gly Trp Lys Phe Ala Arg Ser Asp Glu Leu Thr
        435                 440                 445
```

```
Arg His Tyr Arg Lys His Thr Gly His Arg Pro Phe Gln Cys Gln Lys
        450                 455                 460

Cys Asp Arg Ala Phe Ser Arg Ser Asp His Leu Ala Leu His Met Lys
465                 470                 475                 480

Arg His Phe

<210> SEQ ID NO 23
<211> LENGTH: 2949
<212> TYPE: DNA
<213> ORGANISM: Homo sapiens

<400> SEQUENCE: 23
agtttcccga ccagagagaa cgaacgtgtc tgcgggcgcg cggggagcag aggcggtggc        60
gggcggcggc ggcaccggga ccgccgagt gaccctcccc cgcccctctg gccccccacc       120
ctcccacccg cccgtggccc gcgcccatgg ccgcgcgcgc tccacacaac tcaccggagt       180
ccgcgccttg cgccgccgac cagttcgcag ctccgcgcca cggcagccag tctcacctgg       240
cggcaccgcc cgcccaccgc cccggccaca gcccctgcgc ccacggcagc actcgaggcg       300
accgcgacag tggtgggga cgctgctgag tggaagagag cgcagcccgg ccaccggacc       360
tacttactcg ccttgctgat tgtctatttt tgcgtttaca acttttctaa gaacttttgt       420
atacaaagga acttttttaaa aaagacgctt ccaagttata tttaatccaa agaagaagga       480
tctcggccaa tttggggttt tgggttttgg cttcgtttct tctcttcgtt gactttgggg       540
ttcaggtgcc ccagctgctt cgggctgccg aggaccttct gggcccccac attaatgagg       600
cagccacctg gcgagtctga catggctgtc agcgacgcgc tgctcccatc tttctccacg       660
ttcgcgtctg gcccggcggg aagggagaag cacactgcgtc aagcaggtgc cccgaataac       720
cgctggcggg aggagctctc ccacatgaag cgacttcccc cagtgcttcc cggccgcccc       780
tatgacctgg cggcggcgac cgtggccaca gacctggaga gcggcggagc cggtgcggct       840
tgcggcggta gcaacctggc gcccctacct cggagagaga ccgaggagtt caacgatctc       900
ctggacctgg actttattct ctccaattcg ctgacccatc ctccggagtc agtggccgcc       960
accgtgtcct cgtcagcgtc agcctcctct tcgtcgtcgc cgtcgagcag cggccctgcc      1020
agcgcgccct ccacctgcag cttcacctat ccgatccggg ccgggaacga cccgggcgtg      1080
gcgccgggcg gcacgggcgg aggcctcctc tatggcaggg agtccgctcc ccctccgacg      1140
gctcccttca acctggcgga catcaacgac gtgagccct cgggcggctt cgtggccgag      1200
ctcctgcggc cagaattgga cccggtgtac attccgccgc agcagccgca gccgccaggt      1260
ggcgggctga tgggcaagtt cgtgctgaag gcgtcgctga gcgcccctgg cagcgagtac      1320
ggcagcccgt cggtcatcag cgtcagcaaa ggcagccctg acggcagcca ccggtggtg      1380 gtggcgccct acaacggcgg gccgccgcgc acgtgcccca gatcaagca ggaggcggtc      1440 tcttcgtgca cccacttggg cgctggaccc cctctcagca atggccaccg gccggctgca      1500
cacgacttcc ccctggggcg gcagctcccc agcaggacta ccccgaccct gggtcttgag      1560
gaagtgctga gcagcaggga ctgtcaccct gccctgccgc ttcctcccgg cttccatccc      1620
cacccggggc ccaattaccc atccttcctg cccgatcaga tgcagccgca agtcccgccg      1680
ctccattacc aagagctcat gccacccggt tcctgcatgc agaggagcc caagccaaag      1740 aggggaagac gatcgtggcc ccggaaaagg accgccaccc acacttgtga ttacgcgggc      1800
tgcggcaaaa cctacacaaa gagttcccat ctcaaggcac acctgcgaac ccacacaggt      1860
```

-continued

| | |
|---|---|
| gagaaacctt accactgtga ctgggacggc tgtggatgga aattcgcccg ctcagatgaa | 1920 |
| ctgaccaggc actaccgtaa acacacgggg caccgcccgt tccagtgcca aaaatgcgac | 1980 |
| cgagcatttt ccaggtcgga ccacctcgcc ttacacatga agaggcattt ttaaatccca | 2040 |
| gacagtggat atgacccaca ctgccagaag agaattcagt attttttact tttcacactg | 2100 |
| tcttcccgat gagggaagga gcccagccag aaagcactac aatcatggtc aagttcccaa | 2160 |
| ctgagtcatc ttgtgagtgg ataatcagga aaaatgagga atccaaaaga caaaaatcaa | 2220 |
| agaacagatg gggtctgtga ctggatcttc tatcattcca attctaaatc cgacttgaat | 2280 |
| attcctggac ttacaaaatg ccaagggggt gactggaagt tgtggatatc agggtataaa | 2340 |
| ttatatccgt gagttggggg agggaagacc agaattccct tgaattgtgt attgatgcaa | 2400 |
| tataagcata aaagatcacc ttgtattctc tttaccttct aaaagccatt attatgatgt | 2460 |
| tagaagaaga ggaagaaatt caggtacaga aaacatgttt aaatagccta aatgatggtg | 2520 |
| cttggtgagt cttggttcta aaggtaccaa acaaggaagc caagttttc aaactgctgc | 2580 |
| atactttgac aaggaaaatc tatatttgtc ttccgatcaa catttatgac ctaagtcagg | 2640 |
| taatatacct ggtttacttc tttagcattt ttatgcagac agtctgttat gcactgtggt | 2700 |
| ttcagatgtg caataatttg tacaatggtt tattcccaag tatgccttaa gcagaacaaa | 2760 |
| tgtgttttc tatatagttc cttgccttaa taaatatgta atataaattt aagcaaacgt | 2820 |
| ctattttgta tatttgtaaa ctacaaagta aaatgaacat tttgtggagt ttgtatttg | 2880 |
| catactcaag gtgagaatta agttttaaat aaacctataa tattttatct gaaaaaaaaa | 2940 |
| aaaaaaaaa | 2949 |

<210> SEQ ID NO 24
<211> LENGTH: 3057
<212> TYPE: DNA
<213> ORGANISM: Mus musculus

<400> SEQUENCE: 24

| | |
|---|---|
| agttccccgg ccaagagagc gagcgcggct ccgggcgcgc ggggagcaga ggcggtggcg | 60 |
| ggcggcggcg gcacccggag ccgccgagtg cccctccccg cccctccagc cccccaccca | 120 |
| gcaacccgcc cgtgacccgc gcccatggcc gcgcgcaccc ggcacagtcc ccaggactcc | 180 |
| gcaccccgcg ccaccgccca gctcgcagtt ccgcgccacc gcggccattc tcacctggcg | 240 |
| gcgccgcccg cccaccgccc ggaccacagc ccccgcgccg ccgacagcca cagtggccgc | 300 |
| gacaacggtg ggggacactg ctgagtccaa gagcgtgcag cctggccatc ggacctactt | 360 |
| atctgccttg ctgattgtct attttttataa gagtttacaa cttttctaag aattttttgta | 420 |
| tacaaaggaa cttttttaaa gacatcgccg gtttatattg aatccaaaga agaaggatct | 480 |
| cgggcaatct gggggttttg gtttgaggtt ttgtttctaa agttttttaat cttcgttgac | 540 |
| tttgggctc aggtacccct ctctcttctt cggactccgg aggaccttct ggcccccac | 600 |
| attaatgagg cagccacctg gcgagtctga catggctgtc agcgacgctc tgctcccgtc | 660 |
| cttctccacg ttcgcgtccg gcccggcggg aagggagaag acactgcgtc cagcaggtgc | 720 |
| cccgactaac cgttggcgtg aggaactctc tcacatgaag cgacttcccc cacttcccgg | 780 |
| ccgccccstac gacctggcgg cgacggtggc cacagacctg gagagtggcg gagctggtgc | 840 |
| agcttgcagc agtaacaacc cggccctcct agcccggagg gagaccgagg agttcaacga | 900 |
| cctcctggac ctagacttta tccttttccaa ctcgctaacc caccaggaat cggtggccgc | 960 |
| caccgtgacc acctcggcgt cagcttcatc ctcgtcttcc ccggcgagca gcggccctgc | 1020 |

-continued

```
cagcgcgccc tccacctgca gcttcagcta tccgatccgg gccggggstg acccgggcgt    1080
ggctgccagc aacacaggtg gagggctcct ctacagccga gaatctgcgc cacctcccac    1140
ggccccctcc aacctggcgg acatcaatga cgtgagcccc tcgggcggct cgtggctga     1200 gctcctgcgg ccggagttgg acccagtata cattccgcca cagcagcctc agccgccagg    1260
tggcgggctg atgggcaagt ttgtgctgaa ggcgtctctg accaccctg gcagcgagta     1320 cagcagccct tcggtcatca gtgttagcaa aggaagccca gacggcagcc accccgtggt    1380
agtggcgccc tacagcggtg gcccgccgcg catgtgcccc aagattaagc aagaggcggt    1440
cccgtcctgc acggtcagcc ggtccctaga ggcccatttg agcgctggac ccagctcag     1500 caacggccac cggcccaaca cacgacttt cccctgggg cggcagctcc ccaccaggac      1560
tacccctaca ctgagtcccg aggaactgct gaacagcagg gactgtcacc ctggcctgcc    1620
tcttccccca ggattccatc cccatccggg gcccaactac cctccttcc tgccagacca    1680 gatgcagtca caagtcccct ctctccatta tcaagagctc atgccaccgg ttcctgcct    1740 gccagaggag cccaagccaa agaggggaag aaggtcgtgg ccccggaaaa aacagccac    1800 ccacacttgt gactatgcag gctgtggcaa aacctatacc aagagttctc atctcaaggc    1860
acacctgcga actcacacag gcgagaaacc ttaccactgt gactgggacg gctgtgggtg    1920
gaaattcgcc cgctccgatg aactgaccag gcactaccgc aaacacacag gcaccggcc    1980 ctttcagtgc cagaagtgtg acagggcctt ttccaggtcg gaccaccttg ccttacacat    2040
gaagaggcac ttttaaatcc cacgtagtgg atgtgaccca cactgccagg agagagagtt    2100 cagtatttt ttttctaacc tttcacactg tcttcccacg aggggaggag cccagctggc    2160
aagcgctaca atcatggtca agttcccagc aagtcagctt gtgaatggat aatcaggaga    2220
aaggaagagt tcaagagaca aaacagaaat actaaaaaca aacaaacaaa aaacaaaca    2280 aaaaaaacaa gaaaaaaaaa tcacagaaca gatgggggtct gatactggat ggatcttcta    2340
tcattccaat accaaatcca acttgaacat gcccggactt acaaaatgcc aagggggtgac   2400 tggaagtttg tggatatcag ggtatacact aaatcagtga gcttgggggg agggaagacc    2460
aggattccct tgaattgtgt ttcgatgatg caatacacac gtaaagatca ccttgtatgc    2520
tctttgcctt cttaaaaaaa aaaaaagcca ttattgtgtc ggaggaagag gaagcgattc    2580
aggtacagaa catgttctaa cagcctaaat gatggtgctt ggtgagtcgt ggttctaaag    2640
gtaccaaacg ggggagccaa agttctccaa ctgctgcata cttttgacaa ggaaaatcta    2700
gttttgtctt ccgatctaca ttgatgacct aagccaggta aataagcctg gtttatttct    2760
gtaacatttt tatgcagaca gtctgttatg cactgtggtt tcagatgtgc aataatttgt    2820
acaatggttt attcccaagt atgcctttaa gcagaacaaa tgtgttttc tatatagttc      2880 cttgccttaa taaatatgta atataaattt aagcaaactt ctattttgta tatttgtaaa    2940
ctacaaagta aaaaaaatg aacatttgt ggagtttgta ttttgcatac tcaaggtgag     3000
aaataagttt taaataaacc tataatattt tatctgaacg acaaaaaaaa aaaaaa        3057
```

<210> SEQ ID NO 25
<211> LENGTH: 190
<212> TYPE: PRT
<213> ORGANISM: Homo sapiens

<400> SEQUENCE: 25

```
Met Gly Val Leu Phe Gly Lys Val Phe Ser Gln Thr Thr Ile Cys Arg
1               5                   10                  15
```

```
Phe Glu Ala Leu Gln Leu Ser Phe Lys Asn Met Cys Lys Leu Arg Pro
                20                  25                  30

Leu Leu Gln Lys Trp Val Glu Ala Asp Asn Asn Glu Asn Leu Gln
        35                  40                  45

Glu Ile Cys Lys Ala Glu Thr Leu Val Gln Ala Arg Lys Arg Lys Arg
 50                  55                  60

Thr Ser Ile Glu Asn Arg Val Arg Gly Asn Leu Glu Asn Leu Phe Leu
 65                  70                  75                  80

Gln Cys Pro Lys Pro Thr Leu Gln Gln Ile Ser His Ile Ala Gln Gln
                85                  90                  95

Leu Gly Leu Glu Lys Asp Val Val Arg Val Trp Phe Cys Asn Arg Arg
                100                 105                 110

Gln Lys Gly Lys Arg Ser Ser Ser Asp Tyr Ala Gln Arg Glu Asp Phe
                115                 120                 125

Glu Ala Ala Gly Ser Pro Phe Ser Gly Gly Pro Val Ser Phe Pro Leu
130                 135                 140

Ala Pro Gly Pro His Phe Gly Thr Pro Gly Tyr Gly Ser Pro His Phe
145                 150                 155                 160

Thr Ala Leu Tyr Ser Ser Val Pro Phe Pro Glu Gly Glu Ala Phe Pro
                165                 170                 175

Pro Val Ser Val Thr Thr Leu Gly Ser Pro Met His Ser Asn
                180                 185                 190

<210> SEQ ID NO 26
<211> LENGTH: 221
<212> TYPE: PRT
<213> ORGANISM: Mus musculus

<400> SEQUENCE: 26

Met Lys Ala Leu Gln Lys Glu Leu Glu Gln Phe Ala Lys Leu Leu Lys
 1               5                  10                  15

Gln Lys Arg Ile Thr Leu Gly Tyr Thr Gln Ala Asp Val Gly Leu Thr
                20                  25                  30

Leu Gly Val Leu Phe Gly Lys Val Phe Ser Gln Thr Thr Ile Cys Arg
        35                  40                  45

Phe Glu Ala Leu Gln Leu Ser Leu Lys Asn Met Cys Lys Leu Arg Pro
 50                  55                  60

Leu Leu Glu Lys Trp Val Glu Ala Asp Asn Asn Glu Asn Leu Gln
65                  70                  75                  80

Glu Ile Cys Lys Ser Glu Thr Leu Val Gln Ala Arg Lys Arg Lys Arg
                85                  90                  95

Thr Ser Ile Glu Asn Arg Val Arg Trp Ser Leu Glu Thr Met Phe Leu
                100                 105                 110

Lys Cys Pro Lys Pro Ser Leu Gln Gln Ile Thr His Ile Ala Asn Gln
                115                 120                 125

Leu Gly Leu Glu Lys Asp Val Val Arg Val Trp Phe Cys Asn Arg Arg
                130                 135                 140

Gln Lys Gly Lys Arg Ser Ser Ile Glu Tyr Ser Gln Arg Glu Glu Tyr
145                 150                 155                 160

Glu Ala Thr Gly Thr Pro Phe Pro Gly Gly Ala Val Ser Phe Pro Leu
                165                 170                 175

Pro Pro Gly Pro His Phe Gly Thr Pro Gly Tyr Gly Ser Pro His Phe
                180                 185                 190

Thr Thr Leu Tyr Ser Val Pro Phe Pro Glu Gly Glu Ala Phe Pro Ser
```

```
                  195                 200                 205
        Val Pro Val Thr Ala Leu Gly Ser Pro Met His Ser Asn
            210                 215                 220

<210> SEQ ID NO 27
<211> LENGTH: 1589
<212> TYPE: DNA
<213> ORGANISM: Homo sapiens

<400> SEQUENCE: 27
ggaaaaaagg aaagtgcact tggaagagat ccaagtgggc aacttgaaga acaagtgcca      60
aatagcactt ctgtcatgct ggatgtcagg gctctttgtc cactttgtat agccgctggc     120
ttatagaagg tgctcgataa atctcttgaa tttaaaaatc aattaggatg cctctatagt     180
gaaaaagata cagtaaagat gagggataat caatttaaaa aatgagtaag tacacacaaa     240
gcactttatc cattcttatg acacctgtta cttttttgct gtgtttgtgt gtatgcatgc     300
catgttatag tttgtgggac cctcaaagca agctggggag agtatatact gaatttagct     360
tctgagacat gatgctcttc ctttttaatt aacccagaac ttagcagctt atctatttct     420
ctaatctcaa aacatcctta aactgggggt gatacttgag tgagagaatt ttgcaggtat     480
taaatgaact atcttctttt tttttttttct ttgagacaga gtcttgctct gtcacccagg     540
ctggagtgca gtggcgtgat ctcagctcac tgcaacctcc gcctcccggg ttcaagtgat     600
tctcctgcct cagcctcctg agtagctggg attacagtcc caggacatca aagctctgca     660
gaaagaactc gagcaatttg ccaagctcct gaagcagaag aggatcaccc tgggatatac     720
acaggccgat gtgggctca ccctgggggt tctatttggg aaggtattca gccaaacgac     780
catctgccgc tttgaggctc tgcagcttag cttcaagaac atgtgtaagc tgcggccctt     840
gctgcagaag tgggtggagg aagctgacaa caatgaaaat cttcaggaga tatgcaaagc     900
agaaaccctc gtgcaggccc gaaagagaaa gcgaaccagt atcgagaacc gagtgagagg     960
caacctggag aatttgttcc tgcagtgccc gaaacccaca ctgcagcaga tcagccacat    1020
cgcccagcag cttgggctcg agaaggatgt ggttccgagtg tggttctgta accggcgcca    1080
gaagggcaag cgatcaagca gcgactatgc acaacgagag gattttgagg ctgctgggtc    1140
tcctttctca gggggaccag tgtcctttcc tctggcccca gggccccatt ttggtacccc    1200
aggctatggg agccctcact tcactgcact gtactcctcg gtccctttcc ctgaggggga    1260
agcctttccc cctgtctccg tcaccactct gggctctccc atgcattcaa actgaggtgc    1320
ctgcccttct aggaatgggg gacagggga ggggaggagc tagggaaaga aaacctggag    1380
tttgtgccag ggttttggg attaagttct tcattcacta aggaaggaat tgggaacaca    1440
aagggtgggg gcaggggagt ttggggcaac tggttgagg gaaggtgaag ttcaatgatg    1500
ctcttgattt taatcccaca tcatgtatca cttttttctt aaataaagaa gcctgggaca    1560
cagtagatag acacacttaa aaaaaaaaa                                       1589

<210> SEQ ID NO 28
<211> LENGTH: 991
<212> TYPE: DNA
<213> ORGANISM: Mus musculus

<400> SEQUENCE: 28
gcagccttaa aacttcttca gaatagggtg acattttgtc ctcagtgggg cggttttgag      60
taatctgtga gcagatagga acttgctggg tcccaggaca tgaaagccct gcagaaggag     120
```

```
ctagaacagt tgccaagct gctgaagcag aagaggatca ccttggggta cacccaggcc      180
gacgtggggc tcaccctggg cgttctcttt ggaaaggtgt tcagccagac caccatctgt      240
cgcttcgagg ccttgcagct cagccttaag aacatgtgta agctgcggcc cctgctggag      300
aagtgggtgg aggaagccga caacaatgag aaccttcagg agatatgcaa atcggagacc      360
ctggtgcagg cccggaagag aaagcgaact agcattgaga accgtgtgag gtggagtctg      420
gagaccatgt ttctgaagtg cccgaagccc tccctacagc agatcactca catcgccaat      480
cagcttgggc tagagaagga tgtggttcga gtatggttct gtaaccggcg ccagaagggc      540
aaaagatcaa gtattgagta ttcccaacga gaagagtatg aggctacagg gacacccttc      600
ccaggggggg ctgtatcctt tcctctgccc ccaggtcccc actttggcac cccaggctat      660
ggaagccccc acttcaccac actctactca gtccctttc ctgagggcga ggcctttccc      720
tctgttcccg tcactgctct gggctctccc atgcattcaa actgaggcac cagccctccc      780
tggggatgct gtgagccaag gcaagggagg tagacaagag aacctggagc tttggggtta      840
aattctttta ctgaggaggg attaaaagca caacaggggt gggggtgggg atggggaaag      900
aagctcagtg atgctgttga tcaggagcct ggcctgtctg tcactcatca ttttgttctt      960
aaataaagac tgggacacac agtagatagc t                                   991
```

<210> SEQ ID NO 29
<211> LENGTH: 798
<212> TYPE: PRT
<213> ORGANISM: Homo sapiens

<400> SEQUENCE: 29

```
Met Ala Trp Asp Met Cys Asn Gln Asp Ser Glu Ser Val Trp Ser Asp
1               5                   10                  15

Ile Glu Cys Ala Ala Leu Val Gly Glu Asp Gln Pro Leu Cys Pro Asp
                20                  25                  30

Leu Pro Glu Leu Asp Leu Ser Glu Leu Asp Val Asn Asp Leu Asp Thr
            35                  40                  45

Asp Ser Phe Leu Gly Gly Leu Lys Trp Cys Ser Asp Gln Ser Glu Ile
        50                  55                  60

Ile Ser Asn Gln Tyr Asn Asn Glu Pro Ser Asn Ile Phe Glu Lys Ile
65                  70                  75                  80

Asp Glu Glu Asn Glu Ala Asn Leu Leu Ala Val Leu Thr Glu Thr Leu
                85                  90                  95

Asp Ser Leu Pro Val Asp Glu Asp Gly Leu Pro Ser Phe Asp Ala Leu
            100                 105                 110

Thr Asp Gly Asp Val Thr Thr Asp Asn Glu Ala Ser Pro Ser Ser Met
        115                 120                 125

Pro Asp Gly Thr Pro Pro Gln Glu Ala Glu Pro Ser Leu Leu
    130                 135                 140

Lys Lys Leu Leu Leu Ala Pro Ala Asn Thr Gln Leu Ser Tyr Asn Glu
145                 150                 155                 160

Cys Ser Gly Leu Ser Thr Gln Asn His Ala Asn His Asn His Arg Ile
                165                 170                 175

Arg Thr Asn Pro Ala Ile Val Lys Thr Glu Asn Ser Trp Ser Asn Lys
            180                 185                 190

Ala Lys Ser Ile Cys Gln Gln Gln Lys Pro Gln Arg Arg Pro Cys Ser
        195                 200                 205

Glu Leu Leu Lys Tyr Leu Thr Thr Asn Asp Asp Pro Pro His Thr Lys
    210                 215                 220
```

```
Pro Thr Glu Asn Arg Asn Ser Ser Arg Asp Lys Cys Thr Ser Lys Lys
225                 230                 235                 240

Lys Ser His Thr Gln Ser Gln Ser Gln His Leu Gln Ala Lys Pro Thr
        245                 250                 255

Thr Leu Ser Leu Pro Leu Thr Pro Glu Ser Pro Asn Asp Pro Lys Gly
            260                 265                 270

Ser Pro Phe Glu Asn Lys Thr Ile Glu Arg Thr Leu Ser Val Glu Leu
        275                 280                 285

Ser Gly Thr Ala Gly Leu Thr Pro Pro Thr Thr Pro Pro His Lys Ala
        290                 295                 300

Asn Gln Asp Asn Pro Phe Arg Ala Ser Pro Lys Leu Lys Ser Ser Cys
305                 310                 315                 320

Lys Thr Val Val Pro Pro Ser Lys Lys Pro Arg Tyr Ser Glu Ser
            325                 330                 335

Ser Gly Thr Gln Gly Asn Asn Ser Thr Lys Lys Gly Pro Glu Gln Ser
        340                 345                 350

Glu Leu Tyr Ala Gln Leu Ser Lys Ser Ser Val Leu Thr Gly Gly His
        355                 360                 365

Glu Glu Arg Lys Thr Lys Arg Pro Ser Leu Arg Leu Phe Gly Asp His
370                 375                 380

Asp Tyr Cys Gln Ser Ile Asn Ser Lys Thr Glu Ile Leu Ile Asn Ile
385                 390                 395                 400

Ser Gln Glu Leu Gln Asp Ser Arg Gln Leu Glu Asn Lys Asp Val Ser
            405                 410                 415

Ser Asp Trp Gln Gly Gln Ile Cys Ser Ser Thr Asp Ser Asp Gln Cys
            420                 425                 430

Tyr Leu Arg Glu Thr Leu Glu Ala Ser Lys Gln Val Ser Pro Cys Ser
        435                 440                 445

Thr Arg Lys Gln Leu Gln Asp Gln Glu Ile Arg Ala Glu Leu Asn Lys
        450                 455                 460

His Phe Gly His Pro Ser Gln Ala Val Phe Asp Asp Glu Ala Asp Lys
465                 470                 475                 480

Thr Gly Glu Leu Arg Asp Ser Asp Phe Ser Asn Glu Gln Phe Ser Lys
            485                 490                 495

Leu Pro Met Phe Ile Asn Ser Gly Leu Ala Met Asp Gly Leu Phe Asp
            500                 505                 510

Asp Ser Glu Asp Glu Ser Asp Lys Leu Ser Tyr Pro Trp Asp Gly Thr
        515                 520                 525

Gln Ser Tyr Ser Leu Phe Asn Val Ser Pro Ser Cys Ser Ser Phe Asn
        530                 535                 540

Ser Pro Cys Arg Asp Ser Val Ser Pro Pro Lys Ser Leu Phe Ser Gln
545                 550                 555                 560

Arg Pro Gln Arg Met Arg Ser Arg Ser Arg Ser Phe Ser Arg His Arg
            565                 570                 575

Ser Cys Ser Arg Ser Pro Tyr Ser Ser Arg Ser Arg Ser Arg Pro Gly
            580                 585                 590

Ser Arg Ser Ser Ser Arg Ser Cys Tyr Tyr Tyr Glu Ser Ser His Tyr
        595                 600                 605

Arg His Arg Thr His Arg Asn Ser Pro Leu Tyr Val Arg Ser Arg Ser
        610                 615                 620

Arg Ser Pro Tyr Ser Arg Arg Pro Arg Tyr Asp Ser Tyr Glu Glu Tyr
625                 630                 635                 640
```

```
Gln His Glu Arg Leu Lys Arg Glu Glu Tyr Arg Arg Glu Tyr Glu Lys
            645                 650                 655

Arg Glu Ser Glu Arg Ala Lys Gln Arg Glu Arg Gln Arg Gln Lys Ala
        660                 665                 670

Ile Glu Glu Arg Arg Val Ile Tyr Val Gly Lys Ile Arg Pro Asp Thr
            675                 680                 685

Thr Arg Thr Glu Leu Arg Asp Arg Phe Glu Val Phe Gly Glu Ile Glu
690                 695                 700

Glu Cys Thr Val Asn Leu Arg Asp Asp Gly Asp Ser Tyr Gly Phe Ile
705                 710                 715                 720

Thr Tyr Arg Tyr Thr Cys Asp Ala Phe Ala Ala Leu Glu Asn Gly Tyr
                725                 730                 735

Thr Leu Arg Arg Ser Asn Glu Thr Asp Phe Glu Leu Tyr Phe Cys Gly
            740                 745                 750

Arg Lys Gln Phe Phe Lys Ser Asn Tyr Ala Asp Leu Asp Ser Asn Ser
        755                 760                 765

Asp Asp Phe Asp Pro Ala Ser Thr Lys Ser Lys Tyr Asp Ser Leu Asp
770                 775                 780

Phe Asp Ser Leu Leu Lys Glu Ala Gln Arg Ser Leu Arg Arg
785                 790                 795

<210> SEQ ID NO 30
<211> LENGTH: 797
<212> TYPE: PRT
<213> ORGANISM: Mus musculus

<400> SEQUENCE: 30

Met Ala Trp Asp Met Cys Ser Gln Asp Ser Val Trp Ser Asp Ile Glu
1               5                   10                  15

Cys Ala Ala Leu Val Gly Glu Asp Gln Pro Leu Cys Pro Asp Leu Pro
            20                  25                  30

Glu Leu Asp Leu Ser Glu Leu Asp Val Asn Asp Leu Asp Thr Asp Ser
        35                  40                  45

Phe Leu Gly Gly Leu Lys Trp Cys Ser Asp Gln Ser Glu Ile Ile Ser
    50                  55                  60

Asn Gln Tyr Asn Asn Glu Pro Ala Asn Ile Phe Glu Lys Ile Asp Glu
65                  70                  75                  80

Glu Asn Glu Ala Asn Leu Leu Ala Val Leu Thr Glu Thr Leu Asp Ser
                85                  90                  95

Leu Pro Val Asp Glu Asp Gly Leu Pro Ser Phe Asp Ala Leu Thr Asp
            100                 105                 110

Gly Ala Val Thr Thr Asp Asn Glu Ala Ser Pro Ser Ser Met Pro Asp
        115                 120                 125

Gly Thr Pro Pro Pro Gln Glu Ala Glu Glu Pro Ser Leu Leu Lys Lys
    130                 135                 140

Leu Leu Leu Ala Pro Ala Asn Thr Gln Leu Ser Tyr Asn Glu Cys Ser
145                 150                 155                 160

Gly Leu Ser Thr Gln Asn His Ala Ala Asn His Thr His Arg Ile Arg
                165                 170                 175

Thr Asn Pro Ala Ile Val Lys Thr Glu Asn Ser Trp Ser Asn Lys Ala
            180                 185                 190

Lys Ser Ile Cys Gln Gln Gln Lys Pro Gln Arg Arg Pro Cys Ser Glu
        195                 200                 205

Leu Leu Lys Tyr Leu Thr Thr Asn Asp Asp Pro Pro His Thr Lys Pro
    210                 215                 220
```

```
Thr Glu Asn Arg Asn Ser Ser Arg Asp Lys Cys Ala Ser Lys Lys Lys
225                 230                 235                 240

Ser His Thr Gln Pro Gln Ser Gln His Ala Gln Ala Lys Pro Thr Thr
            245                 250                 255

Leu Ser Leu Pro Leu Thr Pro Glu Ser Pro Asn Asp Pro Lys Gly Ser
                260                 265                 270

Pro Phe Glu Asn Lys Thr Ile Glu Arg Thr Leu Ser Val Glu Leu Ser
            275                 280                 285

Gly Thr Ala Gly Leu Thr Pro Pro Thr Thr Pro Pro His Lys Ala Asn
            290                 295                 300

Gln Asp Asn Pro Phe Lys Ala Ser Pro Lys Leu Lys Pro Ser Cys Lys
305                 310                 315                 320

Thr Val Val Pro Pro Pro Thr Lys Arg Ala Arg Tyr Ser Glu Cys Ser
                325                 330                 335

Gly Thr Gln Gly Ser His Ser Thr Lys Lys Gly Pro Glu Gln Ser Glu
            340                 345                 350

Leu Tyr Ala Gln Leu Ser Lys Ser Ser Gly Leu Ser Arg Gly His Glu
            355                 360                 365

Glu Arg Lys Thr Lys Arg Pro Ser Leu Arg Leu Phe Gly Asp His Asp
370                 375                 380

Tyr Cys Gln Ser Leu Asn Ser Lys Thr Asp Ile Leu Ile Asn Ile Ser
385                 390                 395                 400

Gln Glu Leu Gln Asp Ser Arg Gln Leu Asp Phe Lys Asp Ala Ser Cys
            405                 410                 415

Asp Trp Gln Gly His Ile Cys Ser Ser Thr Asp Ser Gly Gln Cys Tyr
            420                 425                 430

Leu Arg Glu Thr Leu Glu Ala Ser Lys Gln Val Ser Pro Cys Ser Thr
            435                 440                 445

Arg Lys Gln Leu Gln Asp Gln Glu Ile Arg Ala Glu Leu Asn Lys His
            450                 455                 460

Phe Gly His Pro Cys Gln Ala Val Phe Asp Asp Lys Ser Asp Lys Thr
465                 470                 475                 480

Ser Glu Leu Arg Asp Gly Asp Phe Ser Asn Glu Gln Phe Ser Lys Leu
                485                 490                 495

Pro Val Phe Ile Asn Ser Gly Leu Ala Met Asp Gly Leu Phe Asp Asp
            500                 505                 510

Ser Glu Asp Glu Ser Asp Lys Leu Ser Tyr Pro Trp Asp Gly Thr Gln
            515                 520                 525

Pro Tyr Ser Leu Phe Asp Val Ser Pro Ser Cys Ser Ser Phe Asn Ser
            530                 535                 540

Pro Cys Arg Asp Ser Val Ser Pro Pro Lys Ser Leu Phe Ser Gln Arg
545                 550                 555                 560

Pro Gln Arg Met Arg Ser Arg Ser Arg Ser Phe Ser Arg His Arg Ser
                565                 570                 575

Cys Ser Arg Ser Pro Tyr Ser Arg Ser Arg Ser Arg Ser Pro Gly Ser
            580                 585                 590

Arg Ser Ser Ser Arg Ser Cys Tyr Tyr Tyr Glu Ser Ser His Tyr Arg
            595                 600                 605

His Arg Thr His Arg Asn Ser Pro Leu Tyr Val Arg Ser Arg Ser Arg
            610                 615                 620

Ser Pro Tyr Ser Arg Arg Pro Arg Tyr Asp Ser Tyr Glu Ala Tyr Glu
625                 630                 635                 640
```

His Glu Arg Leu Lys Arg Asp Glu Tyr Arg Lys Glu His Glu Lys Arg
            645                 650                 655
Glu Ser Glu Arg Ala Lys Gln Arg Glu Arg Gln Lys Gln Lys Ala Ile
        660                 665                 670
Glu Glu Arg Arg Val Ile Tyr Val Gly Lys Ile Arg Pro Asp Thr Thr
    675                 680                 685
Arg Thr Glu Leu Arg Asp Arg Phe Glu Val Phe Gly Glu Ile Glu Glu
    690                 695                 700
Cys Thr Val Asn Leu Arg Asp Asp Gly Asp Ser Tyr Gly Phe Ile Thr
705                 710                 715                 720
Tyr Arg Tyr Thr Cys Asp Ala Phe Ala Ala Leu Glu Asn Gly Tyr Thr
                725                 730                 735
Leu Arg Arg Ser Asn Glu Thr Asp Phe Glu Leu Tyr Phe Cys Gly Arg
            740                 745                 750
Lys Gln Phe Phe Lys Ser Asn Tyr Ala Asp Leu Asp Thr Asn Ser Asp
        755                 760                 765
Asp Phe Asp Pro Ala Ser Thr Lys Ser Lys Tyr Asp Ser Leu Asp Phe
    770                 775                 780
Asp Ser Leu Leu Lys Glu Ala Gln Arg Ser Leu Arg Arg
785                 790                 795

<210> SEQ ID NO 31
<211> LENGTH: 6318
<212> TYPE: DNA
<213> ORGANISM: Homo sapiens

<400> SEQUENCE: 31

```
tagtaagaca ggtgccttca gttcactctc agtaagggc  tggttgcctg catgagtgtg    60
tgctctgtgt cactgtggat tggagttgaa aaagcttgac tggcgtcatt caggagctgg   120
atggcgtggg acatgtgcaa ccaggactct gagtctgtat ggagtgacat cgagtgtgct   180
gctctggttg gtgaagacca gcctctttgc ccagatcttc ctgaacttga tctttctgaa   240
ctagatgtga acgacttgga tacagacagc tttctgggtg gactcaagtg gtgcagtgac   300
caatcagaaa taatatccaa tcagtacaac aatgagcctt caaacatatt tgagaagata   360
gatgaagaga atgaggcaaa cttgctagca gtcctcacag agacactaga cagtctccct   420
gtggatgaag acggattgcc ctcatttgat gcgctgacag atggagacgt gaccactgac   480
aatgaggcta gtccttcctc catgcctgac ggcaccctc  caccccagga ggcagaagag   540
ccgtctctac ttaagaagct cttactggca ccagccaaca ctcagctaag ttataatgaa   600
tgcagtggtc tcagtaccca gaaccatgca aatcacaatc acaggatcag aacaaaccct   660
gcaattgtta agactgagaa ttcatggagc aataaagcga gagtatttg  tcaacagcaa   720
aagccacaaa gacgtccctg ctcggagctt ctcaaatatc tgaccacaaa cgatgaccct   780
cctcacacca acccacaga  gaacagaaac agcagcagag acaaatgcac ctccaaaaag   840
aagtcccaca cacagtcgca gtcacaacac ttacaagcca aaccaacaac tttatctctt   900
cctctgaccc cagagtcacc aaatgacccc aagggttccc catttgagaa caagactatt   960
gaacgcacct taagtgtgga actctctgga actgcaggcc taactccacc caccactcct  1020
cctcataaag ccaaccaaga taaccctttt agggcttctc caaagctgaa gtcctcttgc  1080
aagactgtgg tgccaccacc atcaaagaag cccaggtaca gtgagtcttc tggtacacaa  1140
ggcaataact ccaccaagaa agggccggag caatccgagt tgtatgcaca actcagcaag  1200
tcctcagtcc tcactggtgg acacgaggaa aggaagacca agcggcccag tctgcggctg  1260
```

| | |
|---|---|
| tttggtgacc atgactattg ccagtcaatt aattccaaaa cagaaatact cattaatata | 1320 |
| tcacaggagc tccaagactc tagacaacta gaaaataaag atgtctcctc tgattggcag | 1380 |
| gggcagattt gttcttccac agattcagac cagtgctacc tgagagagac tttggaggca | 1440 |
| agcaagcagg tctctccttg cagcacaaga aaacagctcc aagaccagga atccgagcc | 1500 |
| gagctgaaca agcacttcgg tcatcccagt caagctgttt tgacgacga agcagacaag | 1560 |
| accggtgaac tgagggacag tgatttcagt aatgaacaat tctccaaact acctatgttt | 1620 |
| ataaattcag gactagccat ggatggcctg tttgatgaca gcgaagatga aagtgataaa | 1680 |
| ctgagctacc cttgggatgg cacgcaatcc tattcattgt tcaatgtgtc tccttcttgt | 1740 |
| tcttctttta actctccatg tagagattct gtgtcaccac ccaaatcctt attttctcaa | 1800 |
| agacccaaa ggatgcgctc tcgttcaagg tccttttctc dacacaggtc gtgttcccga | 1860 |
| tcaccatatt ccaggtcaag atcaaggtct ccaggcagta gatcctcttc aagatcctgc | 1920 |
| tattactatg agtcaagcca ctacagacac cgcacgcacc gaaattctcc cttgtatgtg | 1980 |
| agatcacgtt caagatcgcc ctacagccgt cggcccaggt atgacagcta cgaggaatat | 2040 |
| cagcacgaga ggctgaagag gaagaatat cgcagagagt atgagaagcg agagtctgag | 2100 |
| agggccaagc aaagggagag gcagaggcag aaggcaattg aagagcgccg tgtgatttat | 2160 |
| gtcggtaaaa tcagacctga cacaacacgg acagaactga gggaccgttt tgaagttttt | 2220 |
| ggtgaaattg aggagtgcac agtaaatctg cgggatgatg gagacagcta tggtttcatt | 2280 |
| acctaccgtt atacctgtga tgcttttgct gctcttgaaa atggatacac tttgcgcagg | 2340 |
| tcaaacgaaa ctgactttga gctgtacttt tgtggacgca agcaattttt caagtctaac | 2400 |
| tatgcagacc tagattcaaa ctcagatgac tttgaccctg cttccaccaa gagcaagtat | 2460 |
| gactctctgg attttgatag tttactgaaa gaagctcaga gaagcttgcg caggtaacat | 2520 |
| gttccctagc tgaggatgac agagggatgg cgaatacctc atgggacagc gcgtccttcc | 2580 |
| ctaaagacta ttgcaagtca tacttaggaa tttctcctac tttacactct ctgtacaaaa | 2640 |
| acaaaacaaa acaacaacaa tacaacaaga acaacaacaa caataacaac aatggtttac | 2700 |
| atgaacacag ctgctgaaga ggcaagagac agaatgatat ccagtaagca catgtttatt | 2760 |
| catgggtgtc agctttgctt ttcctggagt ctcttggtga tggagtgtgc gtgtgtgcat | 2820 |
| gtatgtgtgt gtgtatgtat gtgtgtggtg tgtgtgcttg gtttagggga agtatgtgtg | 2880 |
| ggtacatgtg aggactgggg gcacctgacc agaatgcgca agggcaaacc atttcaaatg | 2940 |
| gcagcagttc catgaagaca cgcttaaaac ctagaacttc aaaatgttcg tattctattc | 3000 |
| aaaaggaaat atatatatat atatatatat atatatatat atatataaat taaaaaggaa | 3060 |
| agaaaactaa caaccaacca accaaccaac caaccacaaa ccaccctaaa atgacagccg | 3120 |
| ctgatgtctg ggcatcagcc tttgtactct gtttttttaa gaaagtgcag aatcaacttg | 3180 |
| aagcaagctt tctctcataa cgtaatgatt atatgacaat cctgaagaaa ccacaggttc | 3240 |
| catagaacta atatcctgtc tctctctctc tctctctctc tctcttttt ttttctttt | 3300 |
| cctttttgcca tggaatctgg gtgggagagg atactgcggg caccagaatg ctaaagtttc | 3360 |
| ctaacatttt gaagtttctg tagttcatcc ttaatcctga cacccatgta aatgtccaaa | 3420 |
| atgttgatct tccactgcaa atttcaaaag ccttgtcaat ggtcaagcgt gcagcttgtt | 3480 |
| cagcggttct tttctgaggag cggacaccgg gttacattac taatgagagt tgggtagaac | 3540 |
| tctctgagat gtgttcagat agtgtaattg ctacattctc tgatgtagtt aagtatttac | 3600 |

```
agatgttaaa tggagtattt ttattttatg tatatactat acaacaatgt tcttttttgt    3660
tacagctatg cactgtaaat gcagccttct tttcaaaact gctaaatttt tcttaatcaa    3720
gaatattcaa atgtaattat gaggtgaaac aattattgta cactaacata tttagaagct    3780
gaacttactg cttatatata tttgattgta aaaacaaaaa gacagtgtgt gtgtctgttg    3840
agtgcaacaa gagcaaaatg atgctttccg cacatccatc ccttaggtga gcttcaatct    3900
aagcatcttg tcaagaaata tcctagtccc ctaaaggtat taaccacttc tgcgatattt    3960
ttccacattt tcttgtcgct tgttttttctt tgaagtttta tacactggat ttgttagggg    4020
aatgaaattt tctcatctaa aattttttcta gaagatatca tgattttatg taaagtctct    4080
caatgggtaa ccattaagaa atgttttttat tttctctatc aacagtagtt ttgaaactag    4140
aagtcaaaaa tcttttttaaa atgctgtttt gttttaattt ttgtgatttt aatttgatac    4200
aaaatgctga ggtaataatt atagtatgat ttttacaata attaatgtgt gtctgaagac    4260
tatcttttgaa gccagtattt cttttcccttg gcagagtatg acgatggtat ttatctgtat    4320
tttttacagt tatgcatcct gtataaatac tgatatttca ttcctttgtt tactaaagag    4380
acatatttat cagttgcaga tagcctattt attataaatt atgagatgat gaaaataata    4440
aagccagtgg aaatttttcta cctaggatgc atgacaattg tcaggttgga gtgtaagtgc    4500
ttcatttggg aaattcagct tttgcagaag cagtgtttct acttgcacta gcatggcctc    4560
tgacgtgacc atggtgttgt tcttgatgac attgcttctg ctaaatttaa taaaaacttc    4620
agaaaaacct ccatttttgat catcaggatt tcatctgagt gtggagtccc tggaatggaa    4680
ttcagtaaca tttggagtgt gtattcaagt ttctaaattg agattcgatt actgtttggc    4740
tgacatgact tttctggaag acatgataca cctactactc aattgttctt ttccttttctc    4800
tcgcccaaca cgatcttgta agatggattt cacccccagg ccaatgcagc taattttgat    4860
agctgcattc atttatcacc agcatattgt gttctgagtg aatccactgt ttgtcctgtc    4920
ggatgcttgc ttgatttttt ggcttcttat ttctaagtag atagaaagca ataaaaatac    4980
tatgaaatga aagaacttgt tcacaggttc tgcgttacaa cagtaacaca tcttttaatcc    5040
gcctaattct tgttgttctg taggttaaat gcaggtattt taactgtgtg aacgccaaac    5100
taaagtttac agtctttctt tctgaatttt gagtatcttc tgttgtagaa taataataaa    5160
aagactatta agagcaataa attattttta agaaatcgag atttagtaaa tcctattatg    5220
tgttcaagga ccacatgtgt tctctatttt gcctttaaat ttttgtgaac caattttaaa    5280
tacattctcc ttttttgccct ggattgttga catgagtgga atacttggtt tctttttctta    5340
cttatcaaaa gacagcacta cagatatcat attgaggatt aatttatccc cctacccccc    5400
agcctgacaa atattgttac catgaagata gttttcctca atggacttca aattgcatct    5460
agaattagtg gagcttttgt atcttctgca gacactgtgg gtagcccatc aaaatgtaag    5520
ctgtgctcct ctcattttta ttttttatttt tttgggagag aatatttcaa atgaacacgt    5580
gcaccccatc atcactggag gcaaatttca gcatagatct gtaggatttt tagaagaccg    5640
tgggccattg ccttcatgcc gtggtaagta ccacatctac aattttggta accgaactgg    5700
tgctttagta atgtggattt ttttcttttt taaaagagat gtagcagaat aattcttcca    5760
gtgcaacaaa atcaattttt tgctaaacga ctccgagaac aacagttggg ctgtcaacat    5820
tcaaagcagc agagagggaa ctttgcacta ttggggtatg atgtttgggt cagttgataa    5880
aaggaaacct tttcatgcct ttagatgtga gcttccagta ggtaatgatt atgtgtcctt    5940
tcttgatggc tgtaatgaga acttcaatca ctgtagtcta agacctgatc tatagatgac    6000
```

```
ctagaatagc catgtactat aatgtgatga ttctaaattt gtacctatgt gacagacatt    6060
ttcaataatg tgaactgctg atttgatgga gctactttaa gatttgtagg tgaaagtgta    6120
atactgttgg ttgaactatg ctgaagaggg aaagtgagcg attagttgag cccttgccgg    6180
gccttttttc cacctgccaa ttctacatgt attgttgtgg ttttattcat tgtatgaaaa    6240
ttcctgtgat ttttttaaa tgtgcagtac acatcagcct cactgagcta ataaagggaa    6300
acgaatgttt caaatcta                                                  6318

<210> SEQ ID NO 32
<211> LENGTH: 6464
<212> TYPE: DNA
<213> ORGANISM: Mus musculus

<400> SEQUENCE: 32
gtcatgtgac tggggactgt agtaagacag gtgccttcag ttcactctca gtaaggggct      60
ggttgcctgc atgagtgtgt gctgtgtgtc agagtggatt ggagttgaaa aagcttgact     120
ggcgtcattc gggagctgga tggcttggga catgtgcagc caagactctg tatggagtga     180
catagagtgt gctgctctgg ttggtgagga ccagcctctt tgcccagatc ttcctgaact     240
tgacctttct gaacttgatg tgaatgactt ggatacagac agctttctgg gtggattgaa     300
gtggtgtagc gaccaatcgg aaatcatatc caaccagtac aacaatgagc ctgcgaacat     360
atttgagaag atagatgaag agaatgaggc aaacttgcta gcggttctca cagagacact     420
ggacagtctc cccgtggatg aagacggatt gccctcattt gatgcactga cagatggagc     480
cgtgaccact gacaacgagg ccagtccttc ctccatgcct gacggcaccc ctcccccctca    540 ggaggcagaa gagccgtctc tacttaagaa gctcttactg gcaccagcca acactcagct     600
cagctacaat gaatgcagcg gtcttagcac tcagaaccat gcagcaaacc acacccacag     660
gatcagaaca aaccctgcca ttgttaagac cgagaattca tggagcaata aagcgaagag     720
catttgtcaa cagcaaaagc cacaaagacg tccctgctca gagcttctca agtatctgac     780
cacaaacgat gaccctcctc acaccaaacc cacagaaaac aggaacagca gcagagacaa     840
atgtgcttcg aaaaagaagt cccatacaca accgcagtcg caacatgctc aagccaaacc     900
aacaacttta tctcttcctc tgaccccaga gtcaccaaat gaccccaagg gttccccatt     960
tgagaacaag actattgagc gaaccttaag tgtggaactc tctggaactg caggcctaac    1020
tcctcccaca actcctcctc ataaagccaa ccaagataac cctttcaagg cttcgccaaa    1080
gctgaagccc tcttgcaaga ccgtggtgcc accgccaacc aagagggccc ggtacagtga    1140
gtgttctggt acccaaggca gccactccac caagaaaggg cccgagcaat ctgagttgta    1200
cgcacaactc agcaagtcct cagggctcag ccgaggacac gaggaaagga agactaaacg    1260
gcccagtctc cggctgtttg gtgaccatga ctactgtcag tcactcaatt ccaaaacgga    1320
tatactcatt aacatatcac aggagctcca agactctaga caactagact tcaaagatgc    1380
ctcctgtgac tggcaggggc acatctgttc ttccacagat tcaggccagt gctacctgag    1440
agagactttg gaggccagca agcaggtctc tccttgcagc accagaaaac agctccaaga    1500
ccaggaaatc cgagcggagc tgaacaagca cttcggtcat ccctgtcaag ctgtgtttga    1560
cgacaaatca gacaagacca gtgaactaag ggatggcgac ttcagtaatg aacaattctc    1620
caaactacct gtgttaataa attcaggact agccatggat ggcctatttg atgacagtga    1680
agatgaaagt gataaactga gctacccttg ggatggcacg cagccctatt cattgttcga    1740
```

-continued

```
tgtgtcgcct tcttgctctt cctttaactc tccgtgtcga gactcagtgt caccaccgaa    1800
atccttattt tctcaaagac cccaaaggat gcgctctcgt tcaagatcct tttctcgaca    1860
caggtcgtgt tcccgatcac catattccag gtcaagatca aggtccccag gcagtagatc    1920
ctcttcaaga tcctgttact actatgaatc aagccactac agacaccgca cacaccgcaa    1980
ttctcccttg tatgtgagat cacgttcaag gtcaccctac agccgtaggc ccaggtacga    2040
cagctatgaa gcctatgagc acgaaaggct caagagggat gaataccgca aagagcacga    2100
gaagcgggag tctgaaaggg ccaaacagag agagaggcag aagcagaaag caattgaaga    2160
gcgccgtgtg atttacgttg gtaaaatcag acctgacaca acgcggacag aattgagaga    2220
ccgctttgaa gtttttggtg aaattgagga atgcaccgta atctgcggg atgatggaga    2280 cagctatggt ttcatcacct accgttacac ctgtgacgct ttcgctgctc ttgagaatgg    2340
atatacttta cgcaggtcga acgaaactga cttcgagctg tacttttgtg gacggaagca    2400 attttttcaag tctaactatg cagacctaga taccaactca gacgattttg accctgcttc    2460
caccaagagc aagtatgact ctctggattt tgatagttta ctgaaggaag ctcagagaag    2520
cttgcgcagg taacgtgttc ccaggctgag gaatgacaga gagatggtca atacctcatg    2580
ggacagcgtg tcctttccca agactcttgc aagtcatact taggaatttc tcctacttta    2640
cactctctgt acaaaaataa aacaaaacaa aacaacaata acaacaacaa caacaacaat    2700
aacaacaaca accataccag aacaagaaca acggtttaca tgaacacagc tgctgaagag    2760
gcaagagaca gaatgataat ccagtaagca cacgtttatt cacgggtgtc agctttgctt    2820
tccctggagg ctcttggtga cagtgtgtgt gcgtgtgtgt gtgtgggtgt gcgtgtgtgt    2880
atgtgtgtgt gtgtacttgt ttggaaagta catatgtaca catgtgagga cttgggggca    2940
cctgaacaga acgaacaagg gcgacccctt caaatggcag catttccatg aagcacact    3000 taaaacctac aacttcaaaa tgttcgtatt ctatacaaaa ggaaaataaa taaatataaa    3060
ttaaaaggaa agaaaactca caaaccaccc taaaatgaca ctgctgatgc ctgttgtcag    3120
cctccggtac cgtctttca gaaagtgcaa acccagaaa gtgcaaaacc aacctgcagc    3180
aagctctctc tctctcttaa tgtaatcatt acgtgacaat cccgaagaca ctacaggttc    3240
catagaactc atatccacct ctctctctct ctctctctct ctctctctct ctctctctct    3300
cctctctcct ctctcctctc tccctcccctt ctttgccatt gaatctgggt gggagaggat    3360
actgcaggca ccagatgcta aactttccta acattttgaa gtttctgtag tttgtccttt    3420
gtcctgacac ctatgtatat gttcaaaatg ttgatcttcc actgcagatt ttgaaaagcc    3480
ttgttattgg tcaagcgggg agtgtgttca gtggctcctt ctgaggagca gacgcggtgt    3540
tacatgagta ctgagagttg agtagaactc tctggatgtg ttcagatagt gtaattgcta    3600
cattctctga tgtagttaag tatttacaga tgttaaatgg agtatttta ttttatgtac    3660 atactctaca actatgttct tttttgttac agctatgcac tgtaaatgca gccttctttt    3720
caaaactgct aaatttttct taatcaagaa tattcaaatg taattatgag gtgaaacaat    3780
tattgtacac taacatattt agaagctaaa cttactgctt atatatattt gattgtaaaa    3840
aaaaaaaaaa acaaaaccaa caaaacaaaa gacagtgtgt gtgtgtgtgt ccgttgagtg    3900
caagtccaac aaaatggcgc ttcacgcaca tccatcccctt cttaggtgag cttcaatcta    3960
agcatcttgt caacaacaac aaaaatccta ggcccctcaa ggtattaacc acttctgcaa    4020
tatttttcca cattttcttg ttgcttgttt tcctttgaag ttttatacac tggatttgtt    4080 agggaatga aattttctca tctaaaattt ttctagacaa tatcatgatt ttatgtaaag    4140
```

```
tctctcaatg gggaaccatt aagaaatgtt tttattttct ctatcaacag tagatttgaa    4200
actagaggtc aaaaaaaatc tttttaaaat gctgttttgt tttaatttt gtgattttaa     4260 tttgatacaa aatgctgagg taataattac agtatgattt ttacaatagt caatgtgtgt    4320
ctgaagacta tctttgaagc cagtatctct ttcccttggc agagtatgat gatggtattt    4380
aatctgtatt ttttacagtt atacatcctg taaaatactg atatttcatt cctttgttta    4440
ctaaagagac atatttatca gttgcagata gcctatttat tataaattaa gagatgatga    4500
aaataataag gtcagtggag actttctacc cagggtgcat ggcagttgtc aggctggagt    4560
gtaccttctt cgtttgggaa actcagctct cgcagaagca gtgttccatc tttcactagc    4620
atggcctctg atacgaccat ggtgttgttc ttggtgacat tgcttctgct aaatttaata    4680
ttaataataa taaatgtcag aaaaaaaacc ctccatttg agcatcagga tttcatctga     4740
gtatggagtc gctgccatgg gagtcactaa actttggagt atgtatttca tttccaaatt    4800
gagatgcatt tactgtttgg ctgacatgaa ttttctggaa gatatgatag acctactact    4860
taaccgtttt tgtttgtttt tttttctttg ttgttgttgt tttgttttt gttttttttgt    4920 ttttctctct cacccaacac tatcttacaa aatgggtttc acccccaggc caatgcagct    4980
aattttgaca gctgcattca tttatcacca gcatattgtg ttctgagtga atccactgtc    5040
tgtcctgtcg aatgcttgct caagtgtttg gcttattatt tctaagtaga tagaaagcaa    5100
taaataacta tgaaataaaa aagaattgtg ttcacaggtt ctgcgttaca acagtaacac    5160
atctttaatc cgcctaattc ttgttctgta ggataaatgc aggtattta actcttgtg     5220 aacgccaaac taaagtttac agtctttctt tctgaatttt gagtatcttc tgttgtagaa    5280
taataataaa aagactatta agagcaataa attattttta agaaatcaat atttagtaaa    5340
tcctgttatg tgtttaagga ccagatgcgt tctctatttt gcctttaaat ttttgtgatc    5400
caactttaaa aacatacgtt gtcttgtttg ccctggatca tggacatgac taaaattttg    5460
tggtttcttt tcttacttat caaaagacaa cactacagat ttcatgttga ggattcattg    5520
agctctcacc ctctggcctg acaaatcttg ttaccatgaa gatagttttc ctccgtggac    5580
ttcaaattgc atctaaaatt agtgaagctt gtgtatctta tgcagacact gtgggtagcc    5640
catcaaaata taagctgtaa gctttgttcc tttcattttt tttttttac ttcttttggg     5700 agagaatatt ccaacaaac acatgcaccc caccaacagg ggaggcaaat ttcagcatag     5760
atctataaga ctttcagatg accatgggcc attgccttca tgctgtggta agtactacat    5820
ctacaatttt ggtacccgaa ctggtgcttt agaaatgcgg ggtttttatt aaaaaaaaa    5880 aaaagaaatg tagcagaata attctttag tgcagcaact cagttttgt aaaggactct      5940 gagaacactt gggctgtgaa cattcaaagc agcagagagg gaacctggca ctattggggt    6000
aaagtgtttg ggtcagttga aaaaaaggaa accttttcat gcctttagat gtgagctaac    6060
agtaggtaat gatcatgtgt ccctttttga tggctgtacg aagaacttca atcactgtag    6120
tctaagatct gatctataga tgacctagaa tagccatgta atataatgtg atgattctaa    6180
atttgtacct atgtgacaga catttcaat aatgtgaaaa ctgcagattt gatggagcta     6240
ctttaagatt tgtaggtgaa agtgtgctac tgttggttga actatgctga agagggaaag    6300
tgagtgatta gtttgagccc ttgctggctc ttttccacct gccaattcta catgtattgt    6360
tgtggtttta ttcattgtat gaaaattcct gtgattttt tttaaatgtg cagtacacat     6420
cagcctcact gagctaataa agggaaaaga atgtttcaaa tcta                     6464
```

```
<210> SEQ ID NO 33
<211> LENGTH: 984
<212> TYPE: PRT
<213> ORGANISM: Homo sapiens

<400> SEQUENCE: 33

Met Ala Gly Asn Asp Cys Gly Ala Leu Leu Asp Glu Glu Leu Ser Ser
1               5                   10                  15

Phe Phe Leu Asn Tyr Leu Ala Asp Thr Gln Gly Gly Ser Gly Glu
                20                  25                  30

Glu Gln Leu Tyr Ala Asp Phe Pro Glu Leu Asp Leu Ser Gln Leu Asp
            35                  40                  45

Ala Ser Asp Phe Asp Ser Ala Thr Cys Phe Gly Glu Leu Gln Trp Cys
50                  55                  60

Pro Glu Asn Ser Glu Thr Glu Pro Asn Gln Tyr Ser Pro Asp Asp Ser
65                  70                  75                  80

Glu Leu Phe Gln Ile Asp Ser Glu Asn Glu Ala Leu Leu Ala Glu Leu
                85                  90                  95

Thr Lys Thr Leu Asp Asp Ile Pro Glu Asp Asp Val Gly Leu Ala Ala
            100                 105                 110

Phe Pro Ala Leu Asp Gly Gly Asp Ala Leu Ser Cys Thr Ser Ala Ser
        115                 120                 125

Pro Ala Pro Ser Ser Ala Pro Pro Ser Pro Ala Pro Glu Lys Pro Ser
    130                 135                 140

Ala Pro Ala Pro Glu Val Asp Glu Leu Ser Leu Ala Asp Ser Thr Gln
145                 150                 155                 160

Asp Lys Lys Ala Pro Met Met Gln Ser Gln Ser Arg Ser Cys Thr Glu
                165                 170                 175

Leu His Lys His Leu Thr Ser Ala Gln Cys Cys Leu Gln Asp Arg Gly
            180                 185                 190

Leu Gln Pro Pro Cys Leu Gln Ser Pro Arg Leu Pro Ala Lys Glu Asp
        195                 200                 205

Lys Glu Pro Gly Glu Asp Cys Pro Ser Pro Gln Pro Ala Pro Ala Ser
    210                 215                 220

Pro Arg Asp Ser Leu Ala Leu Gly Arg Ala Asp Pro Gly Ala Pro Val
225                 230                 235                 240

Ser Gln Glu Asp Met Gln Ala Met Val Gln Leu Ile Arg Tyr Met His
                245                 250                 255

Thr Tyr Cys Leu Pro Gln Arg Lys Leu Pro Pro Gln Thr Pro Glu Pro
            260                 265                 270

Leu Pro Lys Ala Cys Ser Asn Pro Ser Gln Gln Val Arg Ser Arg Pro
        275                 280                 285

Trp Ser Arg His His Ser Lys Ala Ser Trp Ala Glu Phe Ser Ile Leu
    290                 295                 300

Arg Glu Leu Leu Ala Gln Asp Val Leu Cys Asp Val Ser Lys Pro Tyr
305                 310                 315                 320

Arg Leu Ala Thr Pro Val Tyr Ala Ser Leu Thr Pro Arg Ser Arg Pro
                325                 330                 335

Arg Pro Pro Lys Asp Ser Gln Ala Ser Pro Gly Arg Pro Ser Ser Val
            340                 345                 350

Glu Glu Val Arg Ile Ala Ala Ser Pro Lys Ser Thr Gly Pro Arg Pro
        355                 360                 365

Ser Leu Arg Pro Leu Arg Leu Glu Val Lys Arg Glu Val Arg Arg Pro
    370                 375                 380
```

```
Ala Arg Leu Gln Gln Gln Glu Glu Asp Glu Glu Glu Glu Glu
385                 390                 395                 400

Glu Glu Glu Glu Glu Lys Glu Glu Glu Glu Trp Gly Arg Lys Arg
            405                 410                 415

Pro Gly Arg Gly Leu Pro Trp Thr Lys Leu Gly Arg Lys Leu Glu Ser
        420                 425                 430

Ser Val Cys Pro Val Arg Arg Ser Arg Arg Leu Asn Pro Glu Leu Gly
        435                 440                 445

Pro Trp Leu Thr Phe Ala Asp Glu Pro Leu Val Pro Ser Glu Pro Gln
        450                 455                 460

Gly Ala Leu Pro Ser Leu Cys Leu Ala Pro Lys Ala Tyr Asp Val Glu
465                 470                 475                 480

Arg Glu Leu Gly Ser Pro Thr Asp Glu Asp Ser Gly Gln Asp Gln Gln
                485                 490                 495

Leu Leu Arg Gly Pro Gln Ile Pro Ala Leu Glu Ser Pro Cys Glu Ser
            500                 505                 510

Gly Cys Gly Asp Met Asp Glu Asp Pro Ser Cys Pro Gln Leu Pro Pro
        515                 520                 525

Arg Asp Ser Pro Arg Cys Leu Met Leu Ala Leu Ser Gln Ser Asp Pro
530                 535                 540

Thr Phe Gly Lys Lys Ser Phe Glu Gln Thr Leu Thr Val Glu Leu Cys
545                 550                 555                 560

Gly Thr Ala Gly Leu Thr Pro Pro Thr Thr Pro Pro Tyr Lys Pro Thr
                565                 570                 575

Glu Glu Asp Pro Phe Lys Pro Asp Ile Lys His Ser Leu Gly Lys Glu
            580                 585                 590

Ile Ala Leu Ser Leu Pro Ser Pro Glu Gly Leu Ser Leu Lys Ala Thr
            595                 600                 605

Pro Gly Ala Ala His Lys Leu Pro Lys Lys His Pro Glu Arg Ser Glu
        610                 615                 620

Leu Leu Ser His Leu Arg His Ala Thr Ala Gln Pro Ala Ser Gln Ala
625                 630                 635                 640

Gly Gln Lys Arg Pro Phe Ser Cys Ser Phe Gly Asp His Asp Tyr Cys
                645                 650                 655

Gln Val Leu Arg Pro Glu Gly Val Leu Gln Arg Lys Val Leu Arg Ser
            660                 665                 670

Trp Glu Pro Ser Gly Val His Leu Glu Asp Trp Pro Gln Gln Gly Ala
        675                 680                 685

Pro Trp Ala Glu Ala Gln Ala Pro Gly Arg Glu Glu Asp Arg Ser Cys
        690                 695                 700

Asp Ala Gly Ala Pro Pro Lys Asp Ser Thr Leu Leu Arg Asp His Glu
705                 710                 715                 720

Ile Arg Ala Ser Leu Thr Lys His Phe Gly Leu Leu Glu Thr Ala Leu
                725                 730                 735

Glu Glu Glu Asp Leu Ala Ser Cys Lys Ser Pro Glu Tyr Asp Thr Val
            740                 745                 750

Phe Glu Asp Ser Ser Ser Ser Gly Glu Ser Ser Phe Leu Pro Glu
        755                 760                 765

Glu Glu Glu Glu Glu Gly Glu Glu Glu Glu Asp Asp Glu Glu Glu
    770                 775                 780

Asp Ser Gly Val Ser Pro Thr Cys Ser Asp His Cys Pro Tyr Gln Ser
785                 790                 795                 800
```

```
Pro Pro Ser Lys Ala Asn Arg Gln Leu Cys Ser Arg Ser Arg Ser Ser
            805                 810                 815

Ser Gly Ser Ser Pro Cys His Ser Trp Ser Pro Ala Thr Arg Arg Asn
        820                 825                 830

Phe Arg Cys Glu Ser Arg Gly Pro Cys Ser Asp Arg Thr Pro Ser Ile
        835                 840                 845

Arg His Ala Arg Lys Arg Arg Glu Lys Ala Ile Gly Glu Gly Arg Val
    850                 855                 860

Val Tyr Ile Gln Asn Leu Ser Ser Asp Met Ser Ser Arg Glu Leu Lys
865                 870                 875                 880

Arg Arg Phe Glu Val Phe Gly Glu Ile Glu Glu Cys Glu Val Leu Thr
                885                 890                 895

Arg Asn Arg Arg Gly Glu Lys Tyr Gly Phe Ile Thr Tyr Arg Cys Ser
            900                 905                 910

Glu His Ala Ala Leu Ser Leu Thr Lys Gly Ala Ala Leu Arg Lys Arg
        915                 920                 925

Asn Glu Pro Ser Phe Gln Leu Ser Tyr Gly Gly Leu Arg His Phe Cys
        930                 935                 940

Trp Pro Arg Tyr Thr Asp Tyr Asp Ser Asn Ser Glu Glu Ala Leu Pro
945                 950                 955                 960

Ala Ser Gly Lys Ser Lys Tyr Glu Ala Met Asp Phe Asp Ser Leu Leu
                965                 970                 975

Lys Glu Ala Gln Gln Ser Leu His
            980

<210> SEQ ID NO 34
<211> LENGTH: 1014
<212> TYPE: PRT
<213> ORGANISM: Mus musculus

<400> SEQUENCE: 34

Met Ala Gly Asn Asp Cys Gly Ala Leu Leu Asp Glu Glu Leu Ser Ser
1               5                   10                  15

Phe Phe Leu Asn Tyr Leu Ser Asp Thr Gln Gly Gly Asp Ser Gly Glu
            20                  25                  30

Glu Gln Leu Cys Ala Asp Leu Pro Glu Leu Asp Leu Ser Gln Leu Asp
        35                  40                  45

Ala Ser Asp Phe Asp Ser Ala Thr Cys Phe Gly Glu Leu Gln Trp Cys
    50                  55                  60

Pro Glu Thr Ser Glu Thr Glu Pro Ser Gln Tyr Ser Pro Asp Asp Ser
65                  70                  75                  80

Glu Leu Phe Gln Ile Asp Ser Glu Asn Glu Ala Leu Leu Ala Ala Leu
                85                  90                  95

Thr Lys Thr Leu Asp Asp Ile Pro Glu Asp Asp Val Gly Leu Ala Ala
            100                 105                 110

Phe Pro Glu Leu Asp Glu Gly Asp Thr Pro Ser Cys Thr Pro Ala Ser
        115                 120                 125

Pro Ala Pro Leu Ser Ala Pro Pro Ser Pro Thr Leu Glu Arg Leu Leu
    130                 135                 140

Ser Pro Ala Ser Asp Val Asp Glu Leu Ser Leu Leu Gln Lys Leu Leu
145                 150                 155                 160

Leu Ala Thr Ser Ser Pro Thr Ala Ser Ser Asp Ala Leu Lys Asp Gly
                165                 170                 175

Ala Thr Trp Ser Gln Thr Ser Leu Ser Ser Arg Ser Gln Arg Pro Cys
            180                 185                 190
```

```
Val Lys Val Asp Gly Thr Gln Asp Lys Lys Thr Pro Thr Leu Arg Ala
        195                 200                 205

Gln Ser Arg Pro Cys Thr Glu Leu His Lys His Leu Thr Ser Val Leu
    210                 215                 220

Pro Cys Pro Arg Val Lys Ala Cys Ser Pro Thr Pro His Pro Ser Pro
225                 230                 235                 240

Arg Leu Leu Ser Lys Glu Glu Glu Glu Val Gly Glu Asp Cys Pro
                245                 250                 255

Ser Pro Trp Pro Thr Pro Ala Ser Pro Gln Asp Ser Leu Ala Gln Asp
                260                 265                 270

Thr Ala Ser Pro Asp Ser Ala Gln Pro Glu Glu Asp Val Arg Ala
                275                 280                 285

Met Val Gln Leu Ile Arg Tyr Met His Thr Tyr Cys Leu Pro Gln Arg
        290                 295                 300

Lys Leu Pro Gln Arg Ala Pro Glu Pro Ile Pro Gln Ala Cys Ser Ser
305                 310                 315                 320

Leu Ser Arg Gln Val Gln Pro Arg Ser Arg His Pro Pro Lys Ala Phe
                325                 330                 335

Trp Thr Glu Phe Ser Ile Leu Arg Glu Leu Leu Ala Gln Asp Ile Leu
            340                 345                 350

Cys Asp Val Ser Lys Pro Tyr Arg Leu Ala Ile Pro Val Tyr Ala Ser
                355                 360                 365

Leu Thr Pro Gln Ser Arg Pro Arg Pro Lys Asp Ser Gln Ala Ser
    370                 375                 380

Pro Ala His Ser Ala Met Ala Glu Glu Val Arg Ile Thr Ala Ser Pro
385                 390                 395                 400

Lys Ser Thr Gly Pro Arg Pro Ser Leu Arg Pro Leu Arg Leu Glu Val
                405                 410                 415

Lys Arg Asp Val Asn Lys Pro Thr Arg Gln Lys Arg Glu Glu Asp Glu
                420                 425                 430

Glu Glu Glu Glu Glu Glu Glu Glu Glu Glu Lys Glu Glu Glu
            435                 440                 445

Glu Glu Glu Trp Gly Arg Lys Arg Pro Gly Arg Gly Leu Pro Trp Thr
    450                 455                 460

Lys Leu Gly Arg Lys Met Asp Ser Ser Val Cys Pro Val Arg Arg Ser
465                 470                 475                 480

Arg Arg Leu Asn Pro Glu Leu Gly Pro Trp Leu Thr Phe Thr Asp Glu
                485                 490                 495

Pro Leu Gly Ala Leu Pro Ser Met Cys Leu Asp Thr Glu Thr His Asn
                500                 505                 510

Leu Glu Glu Asp Leu Gly Ser Leu Thr Asp Ser Ser Gln Gly Arg Gln
                515                 520                 525

Leu Pro Gln Gly Ser Gln Ile Pro Ala Leu Glu Ser Pro Cys Glu Ser
    530                 535                 540

Gly Cys Gly Asp Thr Asp Glu Asp Pro Ser Cys Pro Gln Pro Thr Ser
545                 550                 555                 560

Arg Asp Ser Ser Arg Cys Leu Met Leu Ala Leu Ser Gln Ser Asp Ser
                565                 570                 575

Leu Gly Lys Lys Ser Phe Glu Glu Ser Leu Thr Val Glu Leu Cys Gly
                580                 585                 590

Thr Ala Gly Leu Thr Pro Pro Thr Pro Pro Tyr Lys Pro Met Glu
    595                 600                 605
```

```
Glu Asp Pro Phe Lys Pro Asp Thr Lys Leu Ser Pro Gly Gln Asp Thr
610                 615                 620

Ala Pro Ser Leu Pro Ser Pro Glu Ala Leu Pro Leu Thr Ala Thr Pro
625                 630                 635                 640

Gly Ala Ser His Lys Leu Pro Lys Arg His Pro Glu Arg Ser Glu Leu
            645                 650                 655

Leu Ser His Leu Gln His Ala Thr Thr Gln Pro Val Ser Gln Ala Gly
            660                 665                 670

Gln Lys Arg Pro Phe Ser Cys Ser Phe Gly Asp His Asp Tyr Cys Gln
            675                 680                 685

Val Leu Arg Pro Glu Ala Ala Leu Gln Arg Lys Val Leu Arg Ser Trp
690                 695                 700

Glu Pro Ile Gly Val His Leu Glu Asp Leu Ala Gln Gln Gly Ala Pro
705                 710                 715                 720

Leu Pro Thr Glu Thr Lys Ala Pro Arg Arg Glu Ala Asn Gln Asn Cys
            725                 730                 735

Asp Pro Thr His Lys Asp Ser Met Gln Leu Arg Asp His Glu Ile Arg
            740                 745                 750

Ala Ser Leu Thr Lys His Phe Gly Leu Leu Glu Thr Ala Leu Glu Gly
            755                 760                 765

Glu Asp Leu Ala Ser Cys Lys Ser Pro Glu Tyr Asp Thr Val Phe Glu
770                 775                 780

Asp Ser Ser Ser Ser Gly Glu Ser Ser Phe Leu Leu Glu Glu Glu
785                 790                 795                 800

Glu Glu Glu Glu Gly Gly Glu Glu Asp Asp Glu Gly Glu Asp Ser
            805                 810                 815

Gly Val Ser Pro Pro Cys Ser Asp His Cys Pro Tyr Gln Ser Pro Pro
            820                 825                 830

Ser Lys Ala Ser Arg Gln Leu Cys Ser Arg Ser Arg Ser Ser Ser Gly
            835                 840                 845

Ser Ser Ser Cys Ser Ser Trp Ser Pro Ala Thr Arg Lys Asn Phe Arg
            850                 855                 860

Arg Glu Ser Arg Gly Pro Cys Ser Asp Gly Thr Pro Ser Val Arg His
865                 870                 875                 880

Ala Arg Lys Arg Arg Glu Lys Ala Ile Gly Glu Gly Arg Val Val Tyr
            885                 890                 895

Ile Arg Asn Leu Ser Ser Asp Met Ser Ser Arg Glu Leu Lys Lys Arg
            900                 905                 910

Phe Glu Val Phe Gly Glu Ile Val Glu Cys Gln Val Leu Thr Arg Ser
            915                 920                 925

Lys Arg Gly Gln Lys His Gly Phe Ile Thr Phe Arg Cys Ser Glu His
            930                 935                 940

Ala Ala Leu Ser Val Arg Asn Gly Ala Thr Leu Arg Lys Arg Asn Glu
945                 950                 955                 960

Pro Ser Phe His Leu Ser Tyr Gly Gly Leu Arg His Phe Arg Trp Pro
            965                 970                 975

Arg Tyr Thr Asp Tyr Asp Pro Thr Ser Glu Glu Ser Leu Pro Ser Ser
            980                 985                 990

Gly Lys Ser Lys Tyr Glu Ala Met  Asp Phe Asp Ser Leu  Leu Lys Glu
            995                 1000                1005

Ala Gln  Gln Ser Leu His
    1010
```

<210> SEQ ID NO 35
<211> LENGTH: 10525
<212> TYPE: DNA
<213> ORGANISM: Homo sapiens

<400> SEQUENCE: 35

| | | | | | |
|---|---|---|---|---|---|
| ctcctccctc | ctcccttgct | cgctcgctgg | ctccctcccc | ccgggccggc | tcggcgttga | 60 |
| ctccgccgca | cgctgcagcc | gcggctggaa | gatggcgggg | aacgactgcg | gcgcgctgct | 120 |
| ggacgaagag | ctctcctcct | tcttcctcaa | ctatctcgct | gacacgcagg | gtggagggtc | 180 |
| cggggaggag | caactctatg | ctgactttcc | agaacttgac | ctctcccagc | tggatgccag | 240 |
| cgactttgac | tcggccacct | gctttgggga | gctgcagtgg | tgcccagaga | actcagagac | 300 |
| tgaacccaac | cagtacagcc | ccgatgactc | cgagctcttc | cagattgaca | gtgagaatga | 360 |
| ggccctcctg | gcagagctca | ccaagaccct | ggatgacatc | cctgaagatg | acgtgggtct | 420 |
| ggctgccttc | ccagccctgg | atggtggaga | cgctctatca | tgcacctcag | cttcgcctgc | 480 |
| cccctcatct | gcaccccca | gcctgcccc | ggagaagccc | tcggcccag | ccctgaggt | 540 |
| ggacgagctc | tcactggcgg | acagcaccca | agacaagaag | gctcccatga | tgcagtctca | 600 |
| gagccgaagt | tgtacagaac | tacataagca | cctcacctcg | gcacagtgct | gcctgcagga | 660 |
| tcggggtctg | cagccaccat | gcctccagag | tccccggctc | cctgccaagg | aggacaagga | 720 |
| gccgggtgag | gactgcccga | gccccagcc | agctccagcc | tctccccggg | actccctagc | 780 |
| tctgggcagg | gcagaccccg | gtgccccggt | tcccaggaa | gacatgcagg | cgatggtgca | 840 |
| actcatacgc | tacatgcaca | cctactgcct | ccccagagg | aagctgcccc | cacagacccc | 900 |
| tgagccactc | cccaaggcct | gcagcaaccc | ctcccagcag | gtcagatccc | ggccctggtc | 960 |
| ccggcaccac | tccaaagcct | cctgggctga | gttctccatt | ctgagggaac | ttctggctca | 1020 |
| agacgtgctc | tgtgatgtca | gcaaacccta | ccgtctggcc | acgcctgttt | atgcctccct | 1080 |
| cacacctcgg | tcaaggccca | ggccccccaa | agacagtcag | gcctcccctg | gtcgcccgtc | 1140 |
| ctcggtggag | gaggtaagga | tcgcagcttc | acccaagagc | accgggccca | gaccaagcct | 1200 |
| gcgcccactg | cggctggagg | tgaaaaggga | ggtccgccgg | cctgccagac | tgcagcagca | 1260 |
| ggaggaggaa | gacgaggaag | aagaggagga | ggaagaggaa | gaagaaaaag | aggaggagga | 1320 |
| ggagtggggc | aggaaaaggc | caggccgagg | cctgccatgg | acgaagctgg | ggaggaagct | 1380 |
| ggagagctct | gtgtgccccg | tgcggcgttc | tcggagactg | aaccctgagc | tgggcccctg | 1440 |
| gctgacattt | gcagatgagc | cgctggtccc | ctcggagccc | caaggtgctc | tgccctcact | 1500 |
| gtgcctggct | cccaaggcct | acgacgtaga | gcggagctg | ggcagcccca | cggacgagga | 1560 |
| cagtggccaa | gaccagcagc | tcctacgggg | accccagatc | cctgccctgg | agagccctg | 1620 |
| tgagagtggg | tgtggggaca | tggatgagga | ccccagctgc | ccgcagctcc | ctcccagaga | 1680 |
| ctctcccagg | tgcctcatgc | tggccttgtc | acaaagcgac | ccaacttttg | gcaagaagag | 1740 |
| ctttgagcag | accttgacag | tggagctctg | tggcacagca | ggactcaccc | cacccaccac | 1800 |
| accaccgtac | aagcccacag | aggaggatcc | cttcaaacca | gacatcaagc | atagtctagg | 1860 |
| caaagaaata | gctctcagcc | tcccctcccc | tgagggcctc | tcactcaagg | ccaccccagg | 1920 |
| ggctgcccac | aagctgccaa | agaagcaccc | agagcgaagt | gagctcctgt | cccacctgcg | 1980 |
| acatgccaca | gcccagccag | cctcccaggc | tggccagaag | cgtcccttct | cctgttcctt | 2040 |
| tggagaccat | gactactgcc | aggtgctccg | accagaaggc | gtcctgcaaa | ggaaggtgct | 2100 |
| gaggtcctgg | gagccgtctg | gggttcacct | tgaggactgg | ccccagcagg | gtgccccttg | 2160 |

```
ggctgaggca caggcccctg gcagggagga agacagaagc tgtgatgctg gcgccccacc    2220
caaggacagc acgctgctga gagaccatga gatccgtgcc agcctcacca aacactttgg    2280
gctgctggag accgccctgg aggaggaaga cctggcctcc tgcaagagcc ctgagtatga    2340
cactgtcttt gaagacagca gcagcagcag cggcgagagc agcttcctcc cagaggagga    2400
agaggaagaa ggggaggagg aggaggagga cgatgaagaa gaggactcag gggtcagccc    2460
cacttgctct gaccactgcc cctaccagag cccaccaagc aaggccaacc ggcagctctg    2520
ttcccgcagc cgctcaagct ctggctcttc accctgccac tcctggtcac cagccactcg    2580
aaggaacttc agatgtgaga gcagagggcc gtgttcagac agaacgccaa gcatccggca    2640
cgccaggaag cggcgggaaa aggccattgg ggaaggccgc gtggtgtaca ttcaaaatct    2700
ctccagcgac atgagctccc gagagctgaa gaggcgcttt gaagtgtttg gtgagattga    2760
ggagtgcgag gtgctgacaa gaaataggag aggcgagaag tacggcttca tcacctaccg    2820
gtgttctgag cacgcggccc tctctttgac aaagggcgct gccctgagga agcgcaacga    2880
gccctccttc cagctgagct acggagggct ccggcacttc tgctggccca gatacactga    2940
ctacgattcc aattcagaag aggcccttcc tgcgtcaggg aaaagcaagt atgaagccat    3000
ggattttgac agcttactga agaggcccca gcagagcctg cattgataac agccttaacc    3060
ctcgaggaat acctcaatac ctcagacaag gcccttccaa tatgtttacg ttttcaaaga    3120
aatcaagtat atgaggagag cgagcgagcg tgagagaaca cccgtgagag agacttgaaa    3180
ctgctgtcct ttaaaaaaaa aaaaaatcaa tgtttacatt gaacaaagct gcttctgtct    3240
gtgagtttcc atggtgttga cgttccactg ccacattagt gtcctcgctt ccaacgggtt    3300
gtcccgggtg cacctcgaag tgccgggtcc gtcacccatc gccccttcct tcccgactga    3360
cttcctctcg tagacttgca gctgtgttca ccataacatt tcttgtctgt agtgtgtgat    3420
gatgaaattg ttacttgtga atagaatcag gactataaac ttcatttttta attgaaaaaa    3480 aaagtatatc cttaaaataa tgtatttatg gctcagatgt actgtgcctg ggattattgt    3540
attgcttcct tgatttttta actatgcact gtcatgaggt gtttgccact gagctgccct    3600 gctcccttg ccagattgcc ctggaggtgc tgggtggccg ctaggctggt ctgcaggaaa    3660
gcgcggcctg ccgtttccgg gccgtatctg ccaagccctg ccttgtctct tactgagcaa    3720
gtttggctca aattatagga gcccccatct tgtgcccagc tcatgctcca agtgtgtgtc    3780
tatccatttg tactcagact cttgagtacc ttgtaaggaa ggcggggcaa gctgcatcat    3840
tcctgttttc caggggaggc tggcagctcc tcaagaggcg aaatgactgt gggaggtccg    3900
gttaccagtg aggaggcaga gcggtgaccc agaccaggcc ttctggttct tggtcccgtg    3960
cttccgtagt agctggggta agacaccgt ttcaggggact ggtagaggtg agttcggcta    4020
aattgggcac cgggctagaa gcctaagggc tcattttagg ggttacatta ggtgttgatt    4080
caccagcatc aggtgaattc aagccctggc atgtgtcttg gatgcaccat cagctttgat    4140
cctgagtggt cctgcggttt gtctgtgcct gtggacacac tgtcagaact tcagtgacac    4200
ccctggcagc ggtacagaca ggtggtctgg gagcagtcat cttttttggg ccagccacca    4260
gcccatccta ctccctcagg tagtccttcg tctttacctt gtccttgtct gtaaagttgt    4320
tttggtggct ggggcagggg agccaggagg agggagtgaa ggttgggaat agataggaca    4380
atctcctagc tctcctccaa ttgagaaaac actccaattg ggctttgctt taaactttgt    4440
gttcttaagt gatgtcaaag ccatttccag cttaatgttc tgtgggtacc ttgggggcca    4500
ttcatgcagg gagcatggcc aggcagggta tgagtacatt gtttctgatt tctttcatac    4560
```

```
atcagggttc ctcgggaaat ttttgtattt ttttttttaag tcctgctgct ttaaaaattt    4620
gaaagtggct cattaaacta aacaggctaa tgtaatttgt tgcttatgcc aagcctagac    4680
tgttgagaat tgacgttttt aaagattatc aaatacctca gtaggtaaaa tgagcccatg    4740
atcttccact gagtggtgag catactccca gcccatggac aaggccggaa gagacaggct    4800
ttagtagggg tagggaattt gaactgttgt gtgtcacagc agttgacctc tctggactcc    4860
aatttccttt cctgtgaaat gaactgatta gacatgtttc aacattgtta gcttctgctg    4920
aggcagtgtc tagcccaaga tggcaaatac atagctcatg tgccactact cccacctcct    4980
tgaccaatac agacataact aatcaatcac accactcagg ttccctgagc ctggatgtgc    5040
tataagaatc ctgaaatcag tgctctggta agtcattact aattgattag agttcaatct    5100
atttgacatc ttgggctaat ctttggaagg tttccaacaa tcacacaaaa ccatatgctg    5160
gctgggtttc atgctggcct atccctgtct gtgatgttcc gttccatgag agaaaactcc    5220
cctaatgcta ttccatggcg taacactccc aatactattt tgacgcccac gtccccttgc    5280
agagggtgca gggggcggta gacgaatgac agacaggaac atatttgggg aaggcagggc    5340
ttaggaagat ggaccaaaaa gggacttccc acagcacaga cctgatcatt cggatttcct    5400
ctttagctat tcactgccta gcacatagta ggcacacaat aaatgattat ggaatgggat    5460
aaaatttaga tctttctgct gcctccacta agttaagtcc tgatttacat caaggagaga    5520
actgagatag gaaagaacac tagattccaa gtctggagag ttgggggagt ccagattcta    5580
ccaagaattt ccttttgtaac tttggtaagt ccctttttact ccctggcacc ccggtgtgct    5640
gaaaggagtt ggtccatata tgatctctta gcccctccta tttgcttctt ccttgattgc    5700
tcttggtcaa agggtcagcc ttgggctggt gatactttag agtaaagaaa tggagagttt    5760
tagcaaagga ccagtctgtc cctccctgct ttggggtcag ctaaagctgt cctttcatgt    5820
cagattaacc taggacactt gtagttagct tagacgttgg cccttgagca gagacctgag    5880
cgtggcattg ggacatgaca tacctaaagt cagggctagg ggacgctgcc tgccaagggc    5940
atcgagtagt ctctacttgc tatcccgtac ataaaatgct acaagttcta aaatttaccg    6000
accctgcaga caacctctat cccgaaggac tcattcggtg ctgtgtatta tttagggcaa    6060
ctccaaggtc tattcagaaa aacgagtgaa ccttggtctc tttcccacca aattgaggag    6120
taacccagag ggagcagctg ccattggcaa ccatctcgtt gtagctctgt cctagtgttt    6180
gctcttgatg atgtttacat gtgatcgcca taaagcttgc tgtagactgt gtcgatagcc    6240
gcccgcacag ggcaggtcgt actgtccgtt tctgtgccgt gctggtgttt ccaaaaatg    6300 tctgatccaa ccactaagtg gaattcttcc atctccttcc tcagtctgta caaggctgaa    6360
tcagaatccc cattctcggg ggctctggtt accgaaggaa aatgcatcaa agagttaaag    6420
aatatgagtg gatggagtgc agctaaggcc cccacccccct gctccgtcac aacttgcccc    6480
ctcaaccaaa aagctgcttt gagtcaaaaa gcacccataa gatacctgca tctgccttga    6540
aatcttgcag catggagtgt catatgtact caggagagag gcagggcttt gcgggcagga    6600
gaaggaaggg aggaatgctc tgagctgcaa agacccagta ctcaagttct gacgtgggag    6660
gagatgcagt gagacgtctc ttgttgccta agcctgttc ctgttggttt tcttagagtg    6720
atttctccta gacatgtgca gtaggcccac tggggctgct gtgcagtggt gagtaaaagg    6780
gcagggaagg catggacagc ctggtccttc tgcatggaca gctcagtcca tgcccatcc    6840 caggtataga gttcagttaa tcccatttga gcctgcagct taagagatgg ctcatcctaa    6900
```

-continued

```
ctgtgaagca aaatcagccc cagaggatgt attgatctga ctcactgatg tcaaaattgc    6960 agtattttt  tagcatttga gatttagcag ctgccttcag tttggggtta cccacatccc    7020
agcatcagat atgattaagg aaagaaattg gatgtacaac agcaaagaaa gtgaatgtca    7080
tggtttccct ggccaaagaa gagggaccct gtcatcctta ccaatgggga agaagaaaac    7140
tagtgcatgt gcaatatgtc aaagttagtc ccctagtccc tgaggggttt ttacacacag    7200
atgggctcca ggtctgctcg tcaagtttgg aggtaccggg taaatggagg ggagctgcag    7260
agttggaaac ccacatgcat ggatgtgtcc ttggcccaga accaccatgg gatgggggag    7320
gccctgagcc ggctacaaga cacccaggaa gtaggcaaag gctgactttg cattaaacaa    7380
taaaagcact ttgagaaaac cccaacactt cagcctgggt ccgtgtttct acactggaaa    7440
atacgagtct cctttggctg tgtgaagtga tcttctagag actgggacag ggagtttggg    7500
aatggggctg ctgtcaggta ggagagagca gagatgcctt tggagatgtc agcagcagga    7560
gagccagtgc tggggccaac cctttgctgg cctttgttg  gaagcccttg aaacagggag    7620
ccatgggttt agatcttggt acctaccttt acagaaagat gaaaacagcc cagctgagtg    7680
aaatgagttt gtagagtaag tcacttaact gtaagccatc tcagaatcag aaaccctaat    7740
gtttcttact tgctatgtga ccttgggccc ctgtttcctc atctaccaaa tgagaatgtt    7800
gaatatgagc attaaagtcc ctttcacctc tgagggctc  agatcccaa  ccaggagcat    7860 tgggaatcca tcactcctcc ttgaaactga ttccattctc tgacttgacc cagctcctgt    7920
tcagggtgag ggttctctgc aagaaccaac cagcagtagg ttcaatccca ctgtgtcctg    7980
gctgagttgc cttatccaag aagaccagct ccccgggaca gatctaagcc atagtttcta    8040
gtggggacag taaggaatta aaccccccaac ttggctaggt aacgatgtca aatctcacat    8100
taaccttgtc tttgtcccca ctggatagct gttaatccga atgttgtgac catttggctg    8160
tttctctctt gttctcagac aatactagca atacactttt ttttttttt  tttaaagaaa    8220 aacagcttag gagcttttca cacatttctt tcaaatgatt gtaaaacata tggggcaaca    8280
ggaggcattg atcgcgctgc atatgtttag ggcagctttt gtttttttgtt tctttaatgg    8340 tatagcagca gtgactgagc cttcgtgatt cctggggaca gcttttcaga tactctgttt    8400
catcagtatg ctttgcacat ccggaaggag tacaaaaatc caactgccca aatttggggc    8460
ttggaaaata ggttttatag gtggtcggtc cctgggctgt gcaacaactc ctcaaagagg    8520
ggtttatata actagaaccc ccctgggctg tattttggt  caaggagtc  tccaaggcgg    8580 cttacaaaag cttccttttt cacttgacca cccttgctca ttggttactt gtgaagggaa    8640
ttggtcagtt tccacctcag cactttgcct tatcaacatg cggtcgccat ctagtggcca    8700
aaggttgtct ccaccagcta cccagatgga aggcaaataa atcctttcgg ccaccctgct    8760
gtccatcgtg aactttggga atgaaatata atggcctgaa cgaactgcct ttgtgttcag    8820
agatcagtgc aacactaggg tcagaagact ccagaagcag ccacttagta gactctcacg    8880
cagaactgag aaatgcacta gctgtcctgt gggcagaaga gacaggagtg gaccaggaga    8940
ggtccaggtg cccgggaagg gtttactgta actgcaatac tggcagccca gctgctgacc    9000
ttgttaagta aaccttttgct gggtggtccg aattctgccc tcaaggcaag ataagaagtt    9060
gggtgtaagg atttttgtggg gggcctggcc atgatctttg atatgatccc cgaatagcca    9120
aatagttttt tttgttcaat tttttgtttc tgtattttgt attttaaaa tcttgtcaaa    9180 tgttttttgt ttaggaataa aaagtcataa actattccca actttgtttc ttgagggatg    9240
ttctgattcc aatggaaaca ggtgggaaat ctcaagggga gcgtggacaa ggtggtatgt    9300
```

```
gcagcagggg aatagactgc ttggatttcc aaatggtttc tggggaagat gaccatccag    9360
aagtccagct tagtgcagtc tgctctggaa ttcacaccca cccctcgcc tccttgtgcc     9420 atgttgttag cattggcttg gagcatctgc ttcttccaga ggcagctgct aatgttgaaa    9480
ccaacacgag ccctctcccc aaccccaggt tctaaagaa ggtgtctgta gccagcctta    9540
atcaactggg caaggtggtc cctatggtcc tttccagcat ttccaaatct tggactcaaa    9600
ttattttctc ttggtgtgac cacacagcct agagaattct gagcaatagg agccagggct    9660
ttccctgact ctgcgacagg gtcaaaccaa ggaatggcta aacctgtgag gttttgtcat    9720 ccccggggggt actactgtag gggcattat ttattaggaa gcttaacaag gtaactacgg     9780
cctgagtgcg tgagtgtaag gctgtgtttg tggtgggggt gtgtgtgtgt gtatctgtgc    9840
acacatacac acgtctgtgc ctgtgtgtgt gtgtttgtgt gtgtgtgtgt gtgtggaatt    9900
acattgatgc atttattgag aaaggtgcaa gaatttcacc tacacagagg gacacatctg    9960
ctttgttatt tataatagaa agctaaattt taatttttta aaggacactg ctaatgattg   10020
agaatcaagt ttttagtttt gctatttttt ttaattggta gaggattttt atatatttt   10080 tccattttgt tggggttgtgt ccttatttat ataaatactt tatccgtaag aggcaaggag   10140
gaaaccttct ttgcttttac atattgtggt tgtcatcgtc cctattttat ttctggtgtg    10200
atttctctgt cttaccttct aaatgagaaa atgttttctt gtatttgtac attgtcagat   10260
tctatagttt cctagataat ttaaccaaat tgctctatgt attattattc tgtgagtata    10320
aagttctatt ttaatgtctg taaatacttc agaactggct tcttttctca aactcccact    10380
gtggggttat tgtttacatc acagaaactg tagaatctct atgctcatgt actgtaaata    10440
gtgaagtgat ctgcttataa ataaacttaa caaatacact atggagatta aaacaaaat    10500 accacccaca aaaaaaaaaa aaaaa                                          10525
```

<210> SEQ ID NO 36
<211> LENGTH: 3656
<212> TYPE: DNA
<213> ORGANISM: Mus musculus

<400> SEQUENCE: 36

```
ctcgctccct cccccgggcg ggctcggcgc tgactccgcc gcacgctgca gccgcggctg      60
gaagatggcg gggaacgact gcggcgcgct gctggatgaa gagctctcgt ccttcttcct     120
caactatctc tctgacacgc agggtgggga ctctggagag gaacagctgt gtgctgactt     180
gccagagctt gacctctccc agctggacgc cagtgacttt gactcagcca cgtgctttgg    240
ggagctgcag tggtgcccgg agacctcaga gacagagccc agccagtaca gccccgatga    300
ctccgagctc ttccagattg acagtgagaa tgaagctctc ttggctgcgc ttacgaagac    360
cctggatgac atccccgaag acgatgtggg gctggctgcc ttcccagaac tggatgaagg    420
cgacacacca tcctgcaccc cagcctcacc tgccccctta tctgcaccccc ccagcccccac    480 cctggagagg cttctgtccc cagcgtctga cgtggacgag ctttcactgc tacagaagct    540
cctcctggcc acatcctccc caacagcaag ctctgacgct ctgaaggacg gggccacctg    600
gtcccagacc agcctcagtt ccagaagtca gcggccttgt gtcaaggtgg atggcaccca    660
ggataagaag acccccacac tgcgggctca gagccggcct tgtacggaac tgcataagca    720
cctcacttcg gtgctgccct gtcccagagt gaaagcctgc tccccaactc cgcacccgag    780
ccctcggctc ctctccaaag aggaggagga ggaggtgggg gaggattgcc caagcccttg    840
```

```
gccgactcca gcctcgcccc aagactccct agcacaggac acggccagcc ccgacagtgc      900
ccagcctccc gaggaggatg tgagggccat ggtacagctc attcgctaca tgcataccta      960
ctgcctgcct cagaggaagc tgccccaacg ggccccagag ccaatccccc aggcctgcag     1020
cagcctctcc aggcaggttc aaccccgatc ccggcatccc cccaaagcct tctggactga     1080
gttctctatc ctaagggaac ttctggccca agatatcctc tgtgatgtta gcaagcccta     1140
ccgcctggcc atacctgtct atgcttccct cacacctcag tccaggccca ggcccccaa      1200
ggacagtcag gcctcccctg cccactctgc catggcagaa gaggtgagaa tcactgcttc     1260
ccccaagagc accgggccta gacccagcct gcgtcctctg aggctggagg tgaaacggga     1320
tgttaacaag cctacaaggc aaaagcggga ggaagatgag gaggaggagg aggaagaaga     1380
agaagaggaa gaagaaaaag aagaggaaga agaggagtgg ggcaggaaga gaccaggtcg     1440
tggcctgcca tggaccaaac tagggaggaa gatggacagc tccgtgtgcc ccgtgcggcg     1500
ctccaggaga ctgaatccag agctgggtcc ctggctgaca ttcactgatg agcccttagg     1560
tgctctgccc tcgatgtgcc tggatacaga gaccacaaac ctggaggaag acctgggcag     1620
cctcacagac agtagtcaag gccggcagct cccccaggga tcccagatcc ccgccctgga     1680
aagcccctgt gagagtgggt gcggagacac agatgaagat ccaagctgcc cacagcccac     1740
ttccagagac tcctccaggt gcctcatgct ggccttgtca caaagcgact ctcttggcaa     1800
gaaagctttt gaggagtccc tgacggtgga gctttgcggc acggcaggac tcacgccacc     1860
caccacacct ccatacaagc caatggagga ggaccccttc aagccagaca ccaagctcag     1920
cccaggccaa gacacagctc ccagccttcc ctcccccgag gctcttccgc tcacagccac     1980
cccaggagct tcccacaagc tgcccaagag gcacccagag cgaagcgagc tcctgtccca     2040
tttgcagcat gccacaaccc aaccagtctc acaggctggc cagaagcgcc ccttctcctg     2100
ctccttttgga gaccacgact actgccaggt gctcaggcca gaggctgccc tgcagaggaa     2160
ggtgctgcgg tcctgggagc caatcggggt ccaccttgaa gacttggccc agcagggtgc     2220
ccctctgcca acggaaacaa aggcccctag agggaggca aaccagaact gtgaccctac      2280
ccacaaggac agcatgcagc taagagacca tgagatccgt gccagtctca caaagcactt     2340
tgggctgctg gagactgctc tggaaggtga agacctggcg tcctgtaaaa gcccggagta     2400
tgacaccgta tttgaggaca gcagcagcag cagtggcgag agtagcttcc tgcttgagga     2460
ggaggaggaa gaggaggagg gaggggaaga ggacgatgaa ggagaggact caggggtcag     2520
ccctccctgc tctgatcact gcccctacca gagcccaccc agtaaggcca gtcgcagct      2580
ctgctcccga agccgctcca gttccggctc ctcgtcctgc agctcctggt caccagccac     2640
ccggaagaac ttcagacgtg agagcagagg gccctgttca gatggaaccc caagcgtccg     2700
gcatgccagg aagcggcggg aaaaggccat cggtgaaggc cgtgtggtat acattcgaaa     2760
tctctccagt gacatgagct ctcgggaact aaagaagcgc tttgaggtgt tcggtgagat     2820
tgtagagtgc caggtgctga cgagaagtaa aagaggccaa agcacggtt ttatcacctt      2880
ccggtgttca gagcacgctg ccctgtccgt gaggaacggc gccaccctga gaaagcgcaa     2940
tgagccctcc ttccacctga gctatggagg gctccggcac ttccgttggc ccagatacac     3000
tgactatgat cccacatctg aggagtccct tccctcatct gggaaaagca gtacgaagc      3060
catggatttt gacagcttac tgaaagaggc ccagcagagc ctgcattgat atcagcctta     3120
accttcgagg aatacctcaa tacctcagac aaggcccttc caatatgttt acgtttcaa      3180
agaaaagagt atatgagaag gagagcgagc gagcgagcga gcgagcgagt gagcgtgaga     3240
```

-continued

```
gatcacacag gagagagaaa gacttgaatc tgctgtcgtt tcctttaaaa aaaaaaaaac    3300
gaaaaacaaa aacaaatcaa tgtttacatt gaacaaagct gcttccgtcc gtctgtccgt    3360
ccgtccgtcc gtccgtgagt ttccatgctg ttgatgttcc actgccacgt tagcgtcgtc    3420
ctcgcttcca gcggatcgtc ctgggtgcgc ctccaagtgc tgtcagtcgt cctctgcccc    3480
tcccacccga ctgacttcct tctgttagac ttgagctgtg ttcacataac atcttctgtc    3540
tgtagagtgt gatgatgaca ttgttacttg tgaatagaat caggagttag aaactcattt    3600
ttaattgaag aaaaaaaaag tatatcctta aaagaaaaa aaaaaaaaca aatgta         3656
```

<210> SEQ ID NO 37
<211> LENGTH: 317
<212> TYPE: PRT
<213> ORGANISM: Homo sapiens

<400> SEQUENCE: 37

```
Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300
```

```
Gly Thr Ala Ile Asn Gly Thr Leu Pro Leu Ser His Met
305                 310                 315
```

<210> SEQ ID NO 38
<211> LENGTH: 319
<212> TYPE: PRT
<213> ORGANISM: Mus musculus

<400> SEQUENCE: 38

```
Met Tyr Asn Met Met Glu Thr Glu Leu Lys Pro Pro Gly Pro Gln Gln
1               5                   10                  15

Ala Ser Gly Gly Gly Gly Gly Gly Asn Ala Thr Ala Ala Ala Ala Thr
            20                  25                  30

Gly Gly Asn Gln Lys Asn Ser Pro Asp Arg Val Lys Arg Pro Met Asn
        35                  40                  45

Ala Phe Met Val Trp Ser Arg Gly Gln Arg Arg Lys Met Ala Gln Glu
    50                  55                  60

Asn Pro Lys Met His Asn Ser Glu Ile Ser Lys Arg Leu Gly Ala Glu
65                  70                  75                  80

Trp Lys Leu Leu Ser Glu Thr Glu Lys Arg Pro Phe Ile Asp Glu Ala
                85                  90                  95

Lys Arg Leu Arg Ala Leu His Met Lys Glu His Pro Asp Tyr Lys Tyr
            100                 105                 110

Arg Pro Arg Arg Lys Thr Lys Thr Leu Met Lys Lys Asp Lys Tyr Thr
        115                 120                 125

Leu Pro Gly Gly Leu Leu Ala Pro Gly Gly Asn Ser Met Ala Ser Gly
130                 135                 140

Val Gly Val Gly Ala Gly Leu Gly Ala Gly Val Asn Gln Arg Met Asp
145                 150                 155                 160

Ser Tyr Ala His Met Asn Gly Trp Ser Asn Gly Ser Tyr Ser Met Met
                165                 170                 175

Gln Glu Gln Leu Gly Tyr Pro Gln His Pro Gly Leu Asn Ala His Gly
            180                 185                 190

Ala Ala Gln Met Gln Pro Met His Arg Tyr Asp Val Ser Ala Leu Gln
        195                 200                 205

Tyr Asn Ser Met Thr Ser Ser Gln Thr Tyr Met Asn Gly Ser Pro Thr
210                 215                 220

Tyr Ser Met Ser Tyr Ser Gln Gln Gly Thr Pro Gly Met Ala Leu Gly
225                 230                 235                 240

Ser Met Gly Ser Val Val Lys Ser Glu Ala Ser Ser Ser Pro Pro Val
                245                 250                 255

Val Thr Ser Ser Ser His Ser Arg Ala Pro Cys Gln Ala Gly Asp Leu
            260                 265                 270

Arg Asp Met Ile Ser Met Tyr Leu Pro Gly Ala Glu Val Pro Glu Pro
        275                 280                 285

Ala Ala Pro Ser Arg Leu His Met Ala Gln His Tyr Gln Ser Gly Pro
    290                 295                 300

Val Pro Gly Thr Ala Ile Asn Gly Thr Leu Pro Leu Ser His Met
305                 310                 315
```

<210> SEQ ID NO 39
<211> LENGTH: 2520
<212> TYPE: DNA
<213> ORGANISM: Homo sapiens

<400> SEQUENCE: 39

```
ggatggttgt ctattaactt gttcaaaaaa gtatcaggag ttgtcaaggc agagaagaga      60
gtgtttgcaa aagggggaaa gtagtttgct gcctctttaa gactaggact gagagaaaga     120
agaggagaga gaaagaaagg gagagaagtt tgagccccag gcttaagcct ttccaaaaaa     180
taataataac aatcatcggc ggcggcagga tcggccagag gaggagggaa gcgcttttt     240
tgatcctgat tccagtttgc ctctctcttt ttttccccca aattattctt cgcctgattt     300
tcctcgcgga gccctgcgct cccgacaccc ccgcccgcct cccctcctcc tctcccccccg    360
cccgcgggcc ccccaaagtc ccggccgggc cgaggtcgg cggccgccgg cgggccgggc      420
ccgcgcacag cgcccgcatg tacaacatga tggagacgga gctgaagccg ccgggcccgc     480
agcaaacttc gggggggcgg ggcggcaact ccaccgcggc ggcggccggc ggcaaccaga     540
aaaacagccc ggaccgcgtc aagcggccca tgaatgcctt catggtgtgg tcccgcgggc    600
agcggcgcaa gatggcccag gagaaccccca agatgcacaa ctcggagatc agcaagcgcc    660
tgggcgccga gtggaaactt ttgtcggaga cggagaagcg gccgttcatc gacgaggcta    720
agcggctgcg agcgctgcac atgaaggagc acccggatta taaataccgg ccccggcgga    780
aaaccaagac gctcatgaag aaggataagt acacgctgcc cggcgggctg ctggcccccg    840
gcggcaatag catggcgagc ggggtcgggg tgggcgccgg cctgggcgcg ggcgtgaacc    900
agcgcatgga cagttacgcg cacatgaacg gctggagcaa cggcagctac agcatgatgc    960
aggaccagct gggctacccg cagcacccgg gcctcaatgc gcacggcgca gcgcagatgc   1020
agcccatgca ccgctacgac gtgagcgccc tgcagtacaa ctccatgacc agctcgcaga   1080
cctacatgaa cggctcgccc acctacagca tgtcctactc gcagcagggc acccctggca   1140
tggctcttgg ctccatgggt tcggtggtca agtccgaggc cagctccagc ccccctgtgg   1200
ttacctcttc ctcccactcc agggcgccct gccaggccgg ggacctccgg gacatgatca   1260
gcatgtatct ccccggcgcc gaggtgccgg aacccgccgc ccccagcaga cttcacatgt   1320
cccagcacta ccagagcggc ccggtgcccg gcacggccat taacggcaca ctgcccctct   1380
cacacatgtg agggccggac agcgaactgg aggggggaga aatttttcaaa gaaaaacgag   1440
ggaaatggga ggggtgcaaa agaggagagt aagaaacagc atggagaaaa cccggtacgc   1500
tcaaaaagaa aaaggaaaaa aaaaaatccc atcacccaca gcaaatgaca gctgcaaaag   1560
agaacaccaa tcccatccac actcacgcaa aaaccgcgat gccgacaaga aaacttttat   1620
gagagagatc ctggacttct ttttggggga ctatttttgt acagagaaaa cctggggagg   1680
gtggggaggg cggggggaatg gaccttgtat agatctggag gaaagaaagc tacgaaaaac   1740
tttttaaaag ttctagtggt acggtaggag ctttgcagga agtttgcaaa agtctttacc   1800
aataatattt agagctagtc tccaagcgac gaaaaaaatg ttttaatatt tgcaagcaac   1860
ttttgtacag tatttatcga gataaacatg gcaatcaaaa tgtccattgt ttataagctg   1920
agaatttgcc aatattttc aaggagaggc ttcttgctga attttgattc tgcagctgaa   1980
atttaggaca gttgcaaacg tgaaagaag aaaattattc aaatttggac attttaattg   2040
tttaaaaatt gtacaaaagg aaaaaattag aataagtact ggcgaaccat ctctgtggtc   2100
ttgtttaaaa agggcaaaag ttttagactg tactaaattt tataacttac tgttaaaagc   2160
aaaaatggcc atgcaggttg acaccgttgg taatttataa tagcttttgt tcgatcccaa   2220
cttttccattt tgttcagata aaaaaaacca tgaaattact gtgttgaaa tatttttctta   2280
tggtttgtaa tatttctgta aatttattgt gatattttaa ggttttcccc cctttatttt   2340
```

```
ccgtagttgt attttaaaag attcggctct gtattatttg aatcagtctg ccgagaatcc    2400
atgtatatat ttgaactaat atcatcctta taacaggtac attttcaact taagttttta    2460
ctccattatg cacagtttga gataaataaa tttttgaaat atggacactg aaaaaaaaaa    2520

<210> SEQ ID NO 40
<211> LENGTH: 2457
<212> TYPE: DNA
<213> ORGANISM: Mus musculus

<400> SEQUENCE: 40
ctattaactt gttcaaaaaa gtatcaggag ttgtcaaggc agagaagaga gtgtttgcaa      60
aaagggaaaa gtactttgct gcctcttaa gactagggct gggagaaaga agaggagaga     120
gaaagaaagg agagaagttt ggagcccgag gcttaagcct ttccaaaaac taatcacaac     180
aatcgcggcg gcccgaggag gagagcgcct gttttttcat cccaattgca cttcgcccgt     240
ctcgagctcc gcttccccc aactattctc cgccagatct ccgcgcaggg ccgtgcacgc     300
cgaggccccc gcccgcggcc cctgcatccc ggccccgag cgcggccccc acagtcccgg     360
ccgggccgag ggttggcggc cgccggcggg ccgcgcccgc ccagcgcccg catgtataac     420
atgatggaga cggagctgaa gccgccgggc ccgcagcaag cttcgggggg cggcggcgga     480
ggaggcaacg ccacggcggc ggcgaccggc ggcaaccaga gaacagcccc ggaccgcgtc     540
aagaggccca tgaacgcctt catggtatgg tcccggggc agcggcgtaa gatgcccag     600 gagaaccca agatgcacaa ctcggagatc agcaagcgcc tgggcgcgga gtggaaactt     660
ttgtccgaga ccgagaagcg gccgttcatc gacgaggcca agcggctgcg cgctctgcac     720
atgaaggagc acccggatta taaataccgg ccgcggcgga aaaccaagac gctcatgaag     780
aaggataagt acacgcttcc cggaggcttg ctggcccccg gcgggaacag catggcgagc     840
ggggttgggg tgggcgccgg cctgggtgcg ggcgtgaacc agcgcatgga cagctacgcg     900
cacatgaacg gctggagcaa cggcagctac agcatgatgc aggagcagct gggctacccg     960
cagcacccgg gcctcaacgc tcacggcgcg gcacagatgc aaccgatgca ccgctacgac    1020
gtcagcgccc tgcagtacaa ctccatgacc agctcgcaga cctacatgaa cggctcgccc    1080
acctacagca tgtcctactc gcagcagggc acccccggta tggcgctggg ctccatgggc    1140
tctgtggtca gtccgaggc cagctccagc ccccccgtgg ttacctcttc ctcccactcc    1200
agggcgccct gccaggccgg ggacctccgg gacatgatca gcatgtacct cccggcgcc    1260 gaggtgccgg agcccgctgc gcccagtaga ctgcacatgg cccagcacta ccagagcggc    1320
ccggtgcccg gcacggccat taacggcaca ctgccctgt cgcacatgtg agggctggac    1380
tgcgaactgg agaagggggag agattttcaa agagatacaa gggaattggg aggggtgcaa    1440
aaagaggaga gtaggaaaaa tctgataatg ctcaaaagga aaaaaatct ccgcagcgaa    1500 acgacagctg cggaaaaaaa ccaccaatcc catccaaatt aacgcaaaaa ccgtgatgcc    1560
gactagaaaa ctttttatgag agatcttggg acttcttttt gggggactat ttttgtacag    1620
agaaaccctg agggcggcgg ggagggcggg ggaatcggac catgtataga tctggaggaa    1680
aaaaactacg caaaacttt ttttaaagtt ctagtggtac gttaggcgct cgcagggag    1740 ttcgcaaaag tctttaccag taatatttag agctagactc cgggcgatga aaaaaaagtt    1800
ttaatatttg caagcaactt ttgtacagta tttatcgaga taaacatggc aatcaaatgt    1860 ccattgtttta taagctgaga atttgccaat attttttcgag gaagggttc ttgctgggtt    1920 ttgattctgc agcttaaatt taggaccgtt acaaacaagg aaggagttta ttcggatttg    1980
```

```
aacattttag ttttaaaatt gtacaaaagg aaaacatgag agcaagtact ggcaagaccg   2040 tttcgtggt cttgtttaag gcaaacgttc tagattgtac taaattttta acttactgtt   2100
aaaggcaaaa aaaaaatgtc catgcaggtt gatatcgttg gtaatttata atagcttttg   2160
ttcaatccta ccctttcatt ttgttcacat aaaaaatatg gaattactgt gtttgaaata   2220
ttttcttatg gtttgtaata tttctgtaaa ttgtgatatt ttaaggtttt tccccccttt   2280 tatttccgt agttgtattt taaaagattc ggctctgtta ttggaatcag gctgccgaga    2340
atccatgtat atatttgaac taataccatc cttataacag ctacattttc aacttaagtt   2400
tttactccat tatgcacagt ttgagataaa taaattttg aaatatggac actgaaa       2457
```

<210> SEQ ID NO 41
<211> LENGTH: 366
<212> TYPE: PRT
<213> ORGANISM: Homo sapiens

<400> SEQUENCE: 41

```
Met Ala Gly Pro Ala Trp Ile Ser Lys Val Ser Arg Leu Leu Gly Ala
1               5                   10                  15

Phe His Asn Pro Lys Gln Val Thr Arg Gly Phe Thr Gly Gly Val Gln
                20                  25                  30

Thr Val Thr Leu Ile Pro Gly Asp Gly Ile Gly Pro Glu Ile Ser Ala
            35                  40                  45

Ala Val Met Lys Ile Phe Asp Ala Ala Lys Ala Pro Ile Gln Trp Glu
        50                  55                  60

Glu Arg Asn Val Thr Ala Ile Gln Gly Pro Gly Gly Lys Trp Met Ile
65                  70                  75                  80

Pro Ser Glu Ala Lys Glu Ser Met Asp Lys Asn Lys Met Gly Leu Lys
                85                  90                  95

Gly Pro Leu Lys Thr Pro Ile Ala Ala Gly His Pro Ser Met Asn Leu
            100                 105                 110

Leu Leu Arg Lys Thr Phe Asp Leu Tyr Ala Asn Val Arg Pro Cys Val
        115                 120                 125

Ser Ile Glu Gly Tyr Lys Thr Pro Tyr Thr Asp Val Asn Ile Val Thr
    130                 135                 140

Ile Arg Glu Asn Thr Glu Gly Glu Tyr Ser Gly Ile Glu His Val Ile
145                 150                 155                 160

Val Asp Gly Val Val Gln Ser Ile Lys Leu Ile Thr Glu Gly Ala Ser
                165                 170                 175

Lys Arg Ile Ala Glu Phe Ala Phe Glu Tyr Ala Arg Asn Asn His Arg
            180                 185                 190

Ser Asn Val Thr Ala Val His Lys Ala Asn Ile Met Arg Met Ser Asp
        195                 200                 205

Gly Leu Phe Leu Gln Lys Cys Arg Glu Val Ala Glu Ser Cys Lys Asp
    210                 215                 220

Ile Lys Phe Asn Glu Met Tyr Leu Asp Thr Val Cys Leu Asn Met Val
225                 230                 235                 240

Gln Asp Pro Ser Gln Phe Asp Val Leu Val Met Pro Asn Leu Tyr Gly
                245                 250                 255

Asp Ile Leu Ser Asp Leu Cys Ala Gly Leu Ile Gly Gly Leu Gly Val
            260                 265                 270

Thr Pro Ser Gly Asn Ile Gly Ala Asn Gly Val Ala Ile Phe Glu Ser
        275                 280                 285
```

```
Val His Gly Thr Ala Pro Asp Ile Ala Gly Lys Asp Met Ala Asn Pro
    290                 295                 300

Thr Ala Leu Leu Leu Ser Ala Val Met Met Leu Arg His Met Gly Leu
305                 310                 315                 320

Phe Asp His Ala Ala Arg Ile Glu Ala Ala Cys Phe Ala Thr Ile Lys
                325                 330                 335

Asp Gly Lys Ser Leu Thr Lys Asp Leu Gly Gly Asn Ala Lys Cys Ser
                340                 345                 350

Asp Phe Thr Glu Glu Ile Cys Arg Arg Val Lys Asp Leu Asp
                355                 360                 365

<210> SEQ ID NO 42
<211> LENGTH: 366
<212> TYPE: PRT
<213> ORGANISM: Mus musculus

<400> SEQUENCE: 42

Met Ala Gly Ser Ala Trp Val Ser Lys Val Ser Arg Leu Leu Gly Ala
1               5                   10                  15

Phe His Asn Thr Lys Gln Val Thr Arg Gly Phe Ala Gly Gly Val Gln
                20                  25                  30

Thr Val Thr Leu Ile Pro Gly Asp Gly Ile Gly Pro Glu Ile Ser Ala
            35                  40                  45

Ser Val Met Lys Ile Phe Asp Ala Ala Lys Ala Pro Ile Gln Trp Glu
        50                  55                  60

Glu Arg Asn Val Thr Ala Ile Gln Gly Pro Gly Gly Lys Trp Met Ile
65                  70                  75                  80

Pro Pro Glu Ala Lys Glu Ser Met Asp Lys Asn Lys Met Gly Leu Lys
                85                  90                  95

Gly Pro Leu Lys Thr Pro Ile Ala Ala Gly His Pro Ser Met Asn Leu
            100                 105                 110

Leu Leu Arg Lys Thr Phe Asp Leu Tyr Ala Asn Val Arg Pro Cys Val
        115                 120                 125

Ser Ile Glu Gly Tyr Lys Thr Pro Tyr Thr Asp Val Asn Ile Val Thr
    130                 135                 140

Ile Arg Glu Asn Thr Glu Gly Glu Tyr Ser Gly Ile Glu His Val Ile
145                 150                 155                 160

Val Asp Gly Val Val Gln Ser Ile Lys Leu Ile Thr Glu Glu Ala Ser
                165                 170                 175

Lys Arg Ile Ala Glu Phe Ala Phe Glu Tyr Ala Arg Asn Asn His Arg
            180                 185                 190

Ser Asn Val Thr Ala Val His Lys Ala Asn Ile Met Arg Met Ser Asp
        195                 200                 205

Gly Leu Phe Leu Gln Lys Cys Arg Glu Val Ala Glu Asn Cys Lys Asp
    210                 215                 220

Ile Lys Phe Asn Glu Met Tyr Leu Asp Thr Val Cys Leu Asn Met Val
225                 230                 235                 240

Gln Asp Pro Ser Gln Phe Asp Val Leu Val Met Pro Asn Leu Tyr Gly
                245                 250                 255

Asp Ile Leu Ser Asp Leu Cys Ala Gly Leu Ile Gly Gly Leu Gly Val
            260                 265                 270

Thr Pro Ser Gly Asn Ile Gly Ala Asn Gly Val Ala Ile Phe Glu Ser
        275                 280                 285

Val His Gly Thr Ala Pro Asp Ile Ala Gly Lys Asp Met Ala Asn Pro
    290                 295                 300
```

```
Thr Ala Leu Leu Leu Ser Ala Val Met Met Leu Arg His Met Gly Leu
305                 310                 315                 320

Phe Asp His Ala Ala Lys Ile Glu Ala Ala Cys Phe Ala Thr Ile Lys
            325                 330                 335

Asp Gly Lys Ser Leu Thr Lys Asp Leu Gly Gly Asn Ala Lys Cys Ser
        340                 345                 350

Asp Phe Thr Glu Glu Ile Cys Arg Arg Val Lys Asp Leu Asp
        355                 360                 365

<210> SEQ ID NO 43
<211> LENGTH: 2701
<212> TYPE: DNA
<213> ORGANISM: Homo sapiens

<400> SEQUENCE: 43
```

| | | | | | |
|---|---|---|---|---|---|
| gttgctgcgg | agccaggagg | ggaagcgatg | gctgggcccg | cgtggatctc | taaggtctct | 60 |
| cggctgctgg | gggcattcca | caacccaaaa | caggtgacca | gaggttttac | tggtggtgtt | 120 |
| cagacagtaa | ctttaattcc | aggagatggt | attgcccag | aaatttcagc | tgcagttatg | 180 |
| aagattttg | atgctgccaa | agcacctatt | cagtgggagg | agcggaacgt | cactgccatt | 240 |
| caaggacctg | aggaaagtg | gatgatccct | tcagaggcta | aagagtccat | ggataagaac | 300 |
| aagatgggct | tgaaaggccc | tttgaagacc | ccaatagcag | ccggtcaccc | atctatgaat | 360 |
| ttactgctgc | gcaaaacatt | tgacctttac | gcgaatgtcc | gaccatgtgt | ctctatcgaa | 420 |
| ggctataaaa | ccccttacac | cgatgtaaat | attgtgacca | ttcgagagaa | cacagaagga | 480 |
| gaatacagtg | gaattgagca | tgtgattgtt | gatggagtcg | tgcagagtat | caagctcatc | 540 |
| accgaggggg | cgagcaagcg | cattgctgag | tttgcctttg | agtatgcccg | gaacaaccac | 600 |
| cggagcaacg | tcacggcggt | gcacaaagcc | aacatcatgc | ggatgtcaga | tgggcttttt | 660 |
| ctacaaaaat | gcaggggaagt | tgcagaaagc | tgtaaagata | ttaaatttaa | tgagatgtac | 720 |
| cttgatacag | tatgtttgaa | tatggtacaa | gatccttccc | aatttgatgt | tcttgttatg | 780 |
| ccaaatttgt | atggagacat | ccttagtgac | ttgtgtgcag | gattgatcgg | aggtctcggt | 840 |
| gtgacaccaa | gtggcaacat | tggagccaat | ggggttgcaa | tttttgagtc | ggttcatggg | 900 |
| acggctccag | acattgcagg | caaggacatg | gcgaatccca | cagccctcct | gctcagtgcc | 960 |
| gtgatgatgc | tgcgccacat | gggactttt | gaccatgctg | caagaattga | ggctgcgtgt | 1020 |
| tttgctacaa | ttaaggacgg | aaagagcttg | acaaagatt | gggaggcaa | tgcaaaatgc | 1080 |
| tcagacttca | cagaggaaat | ctgtcgccga | gtaaagatt | tagattaaca | cttctacaac | 1140 |
| tggcatttac | atcagtcact | ctaaatggac | accacatgaa | cctctgttta | gaatacctac | 1200 |
| gtatgtatgc | attggtttgc | ttgtttcttg | acagtacatt | tttagatctg | gccttttctt | 1260 |
| aacaaaatct | gtgcaaaaga | tgcaggtgga | tgtccctagg | tctgttttca | agaacttt | 1320 |
| tccaagtgct | tgttttattt | attaagtgtc | tacctggtaa | atgtttttt | tgtaaactct | 1380 |
| gagtggactg | tatcatttgc | tattctaaac | cattttacac | ttaagttaaa | atagtttctc | 1440 |
| ttcagctgta | aataacagga | tacagaatta | acaagagaaa | atgtctaact | ttttaagaaa | 1500 |
| aaccttattt | tcttcggttt | ttgaaaaaca | taatggaaat | aaaacaggat | attgacataa | 1560 |
| tagcacaaaa | tgacactctt | ctaaaactaa | atgggcacaa | gagaattttc | ctgggaaagt | 1620 |
| tcacatcaaa | aagagtgaat | gtggtatatt | tctaaatgat | atggaaaata | gagacagatt | 1680 |
| tgtccttta | agaaattact | gagtgtgaat | aaaaacttca | gatccaagaa | atatataatg | 1740 |

-continued

| | | | |
|---|---|---|---|
| agagatataa tttttgttaa taagacaaag gtaatatatt ggatacaaag acacaaatgt | 1800 | | |
| attgtgtgtt caattatttt gttgtcttga gatttaatat tctttccaag agcttttaat | 1860 | | |
| gaagcagaga gctagtactt cattttcact ggatacattt tcagcatcat gagttgtcac | 1920 | | |
| agcctctgag ccctgatct gaagccagaa gggctgagtg tattgtaaac ttattcttgc | 1980 | | |
| atgttgctgt ctgggaatgg accacactac agcaggtagt tctgggggcg atactgccga | 2040 | | |
| aaggcccgaa cacatgtatt ttggctgcaa ttgaggaact tgggatgcta ttaattttgt | 2100 | | |
| atttcagcaa ctgccccttc tcctatccca aagcaccaat tactgccctc tgcctcagca | 2160 | | |
| gtaccagtat aagatgacat ccaaagact ggaggcaact cagcctgagt taattcacaa | 2220 | | |
| aattatgcca tgctggggct tgagcttgag cttgggctta ggcttgggct cagcttttga | 2280 | | |
| ccctcaggca tctcctttcc cttcctgtct tcctctccct tctcctctgc tgcagcatga | 2340 | | |
| ttttcttaat cttcagacac tcactatttt catgaacagt taccctctgt ccccacaacc | 2400 | | |
| aaagacaact catggcctcc tttgcccctt gtgtaacatt gcaaacctgt ggctttgcaa | 2460 | | |
| aatgtaccca ggtcacaagg ggattttttt tttttagca atgatatccc tgtctgggtc | 2520 | | |
| acttttaag cttgtaaccg cccccccaga cttataatct taaatgtatt ttcctttgtt | 2580 | | |
| taagctgctg cttcctctgt ttcattggat tgtgccagtt atcagtggct cttgggttca | 2640 | | |
| aagtaataaa gaattccaaa actgaaaaaa aaaaaaaaaa aaaaaaaaaa aaaaaaaaa | 2700 | | |
| a | 2701 | | |

<210> SEQ ID NO 44
<211> LENGTH: 2418
<212> TYPE: DNA
<213> ORGANISM: Mus musculus

<400> SEQUENCE: 44

| | |
|---|---|
| gacgcgatgg ccgggtccgc gtgggtgtcc aaggtctctc ggctgctggg tgcattccac | 60 |
| aacacaaaac aggtgacaag aggttttgct ggtggtgttc agacagtaac tttaattcct | 120 |
| ggagatggaa ttggcccaga aatttcagcc tcagtcatga agattttga tgctgccaaa | 180 |
| gcacctattc agtgggagga gcgcaatgtc acagcaattc aaggaccagg aggaaagtgg | 240 |
| atgatccctc cagaagccaa ggagtccatg gataagaaca agatgggctt gaaaggccca | 300 |
| ctaaagaccc caatagccgc tggccatcca tctatgaatc tgttgcttcg taagacattt | 360 |
| gacctttatg ccaatgtccg gccatgtgtc tcaattgaag gttataaaac cccttacacg | 420 |
| gatgtaaata tcgtcaccat ccgagagaac acggaaggag aatacagtgg aattgagcat | 480 |
| gtgatcgttg atggggttgt gcagagcatc aagctcatca ccgaagaagc aagcaagcgc | 540 |
| attgcagagt ttgccttcga gtacgctcgg aacaaccacc ggagcaacgt cacagctgtg | 600 |
| cacaaagcta acatcatgag gatgtcagat gggctctttc tgcaaaaatg cagggaagtt | 660 |
| gcggagaact gtaaagacat taaatttaac gagatgtacc ttgatactgt atgtttaaat | 720 |
| atggtacaag acccatccca gtttgatgtt cttgtcatgc caaatttata cggagacatc | 780 |
| cttagtgatc tgtgtgcagg actgattgga ggtcttgggg tgactccaag tggcaatatt | 840 |
| ggagccaacg tgttgccat cttgaatcg gttcatggaa cagccccgga cattgcaggc | 900 |
| aaggacatgg ccaaccccac ggccctcctg cttagtgctg tgatgatgct cgccacatg | 960 |
| ggacttttg accatgcagc aaaaatcgag gctgcatgtt ttgctacaat taaggatgga | 1020 |
| aagagcttaa caaagatct gggaggcaac gcgaagtgct ctgacttcac agaagaaatc | 1080 |
| tgtcgtagag tcaaagactt agattagcac tcctgctggt ggatttgctg cagtcagtca | 1140 |

-continued

```
atcactccaa aaggataccc tgtaatcctc cttgagggcg cccaccattg gtttgcttgc    1200
ttcttgacag agtacgtttt ttgaatctgg cctttcttcta acaaaaccct tgcaatggat    1260
gcacatgatg gccccaggcc ttcattcaaa gggttttccc aagtgctggt tgtatttatt    1320
gtccgtctgg taaaccttat tttgtaaact gtaagtgaac tgtatcattt atcattgtta    1380
acccatttta cacttcaggc aaaatcattt tcctcaactg taaatattct gatacagaat    1440
taataagaga agatatttaa cttttaaca aagccctgg attttggtt tatgaaaaac       1500 aaactgggaa taaaacaggg ttttaacaat cgcacaagat aacattattc taatactaat    1560
gggtacaaaa gaaatttact gggaaagttc acagcaaaaa aatggtatat ttcttaaaaa    1620
tatggaaata aagtatttgt cctatacatg aattactatt aataaaaatg taagctccaa    1680
gaaatccata atgaatgatg taattttgtt actacatcgg taatccttgt caaggccccg    1740
gatgctctct gtgtatttga ttcttttgtt accttgagat tcactatttt ggggaagag    1800 ctttcagata agggagatca ctcctcacta gacagatcgt cagcattgcg agctgtcagc    1860
catgagagcc agccactgca gatcccctcc cacgtggcca cactccagcc agtgctgcag    1920
gtgaccctgg aaaggcctgg ctgcccctttg actttcccta aagcaaccag tcactgcctt    1980
ctgccccagt agcacccatt acagacttaa ttgccgaggt ggagctgact cagcccacgc    2040
tcatacaaat caggccaagc gggggcctgt gttaccagct gctgaccatc aggttctgcc    2100
cctcattctt cccacagcct ctgctccaca gcatgaacct agcctttggc ccacaccaaa    2160
gccaagctgt cttcccttag cccttgcact agtttgcaaa ctcgtggctt tgcataatgt    2220
accctggtcc caaggggatt tcttaacaac agatgtccct gtctgggtca ttttttaaa    2280 gcttttattt ggacttacaa tcttctgtgt attttacttt aaaactgctg ctttccctgt    2340
ctcactggat tgttctggtt agcagtggct ttgggttcac agtaataaag aacttaagaa    2400
ctgaaaaaaa aaaaaaaa                                                 2418
```

<210> SEQ ID NO 45
<211> LENGTH: 385
<212> TYPE: PRT
<213> ORGANISM: Homo sapiens

<400> SEQUENCE: 45

```
Met Ala Ala Leu Ser Gly Val Arg Trp Leu Thr Arg Ala Leu Val Ser
1               5                   10                  15

Ala Gly Asn Pro Gly Ala Trp Arg Gly Leu Ser Thr Ser Ala Ala Ala
            20                  25                  30

His Ala Ala Ser Arg Ser Gln Ala Glu Asp Val Arg Val Glu Gly Ser
        35                  40                  45

Phe Pro Val Thr Met Leu Pro Gly Asp Gly Val Gly Pro Glu Leu Met
    50                  55                  60

His Ala Val Lys Glu Val Phe Lys Ala Ala Val Pro Val Glu Phe
65                  70                  75                  80

Gln Glu His His Leu Ser Glu Val Gln Asn Met Ala Ser Glu Glu Lys
                85                  90                  95

Leu Glu Gln Val Leu Ser Ser Met Lys Glu Asn Lys Val Ala Ile Ile
            100                 105                 110

Gly Lys Ile His Thr Pro Met Glu Tyr Lys Gly Glu Leu Ala Ser Tyr
        115                 120                 125

Asp Met Arg Leu Arg Arg Lys Leu Asp Leu Phe Ala Asn Val Val His
    130                 135                 140
```

-continued

```
Val Lys Ser Leu Pro Gly Tyr Met Thr Arg His Asn Asn Leu Asp Leu
145                 150                 155                 160

Val Ile Ile Arg Glu Gln Thr Glu Gly Glu Tyr Ser Ser Leu Glu His
            165                 170                 175

Glu Ser Ala Arg Gly Val Ile Glu Cys Leu Lys Ile Val Thr Arg Ala
        180                 185                 190

Lys Ser Gln Arg Ile Ala Lys Phe Ala Phe Asp Tyr Ala Thr Lys Lys
            195                 200                 205

Gly Arg Gly Lys Val Thr Ala Val His Lys Ala Asn Ile Met Lys Leu
210                 215                 220

Gly Asp Gly Leu Phe Leu Gln Cys Cys Glu Glu Val Ala Glu Leu Tyr
225                 230                 235                 240

Pro Lys Ile Lys Phe Glu Thr Met Ile Ile Asp Asn Cys Cys Met Gln
                245                 250                 255

Leu Val Gln Asn Pro Tyr Gln Phe Asp Val Leu Val Met Pro Asn Leu
            260                 265                 270

Tyr Gly Asn Ile Ile Asp Asn Leu Ala Ala Gly Leu Val Gly Gly Ala
                275                 280                 285

Gly Val Val Pro Gly Glu Ser Tyr Ser Ala Glu Tyr Ala Val Phe Glu
290                 295                 300

Thr Gly Ala Arg His Pro Phe Ala Gln Ala Val Gly Arg Asn Ile Ala
305                 310                 315                 320

Asn Pro Thr Ala Met Leu Leu Ser Ala Ser Asn Met Leu Arg His Leu
                325                 330                 335

Asn Leu Glu Tyr His Ser Ser Met Ile Ala Asp Ala Val Lys Lys Val
            340                 345                 350

Ile Lys Val Gly Lys Val Arg Thr Arg Asp Met Gly Gly Tyr Ser Thr
            355                 360                 365

Thr Thr Asp Phe Ile Lys Ser Val Ile Gly His Leu Gln Thr Lys Gly
        370                 375                 380

Ser
385

<210> SEQ ID NO 46
<211> LENGTH: 384
<212> TYPE: PRT
<213> ORGANISM: Mus musculus

<400> SEQUENCE: 46

Met Ala Ala Leu Ser Asn Val Arg Trp Leu Thr Arg Ala Val Leu Ala
1               5                   10                  15

Ala Arg Asn Ser Gly Ala Trp Arg Gly Leu Gly Thr Ser Thr Ala His
            20                  25                  30

Ala Ala Ser Gln Ser Gln Ala Gln Asp Val Arg Val Glu Gly Ala Phe
        35                  40                  45

Pro Val Thr Met Leu Pro Gly Asp Gly Val Gly Pro Glu Leu Met His
    50                  55                  60

Ala Val Lys Glu Val Phe Lys Ala Ala Val Pro Val Glu Phe Lys
65                  70                  75                  80

Glu His His Leu Ser Glu Val Gln Asn Met Ala Ser Glu Glu Lys Leu
                85                  90                  95

Glu Gln Val Leu Ser Ser Met Lys Glu Asn Lys Val Ala Ile Ile Gly
            100                 105                 110

Lys Ile Tyr Thr Pro Met Glu Tyr Lys Gly Glu Leu Ala Ser Tyr Asp
```

```
                115                 120                 125
Met Gln Leu Arg Arg Lys Leu Asp Leu Phe Ala Asn Val Val His Val
        130                 135                 140

Lys Ser Leu Pro Gly Tyr Lys Thr Arg His Asn Asn Leu Asp Leu Val
145                 150                 155                 160

Ile Ile Arg Glu Gln Thr Glu Gly Glu Tyr Ser Ser Leu Glu His Glu
                165                 170                 175

Ser Ala Lys Gly Val Ile Glu Cys Leu Lys Ile Val Thr Arg Thr Lys
                180                 185                 190

Ser Gln Arg Ile Ala Lys Phe Ala Phe Asp Tyr Ala Thr Lys Lys Gly
                195                 200                 205

Arg Ser Lys Val Thr Ala Val His Lys Ala Asn Ile Met Lys Leu Gly
        210                 215                 220

Asp Gly Leu Phe Leu Gln Cys Cys Glu Glu Val Ala Glu Leu Tyr Pro
225                 230                 235                 240

Lys Ile Lys Phe Glu Thr Met Ile Ile Asp Asn Cys Cys Met Gln Leu
                245                 250                 255

Val Gln Asn Pro Tyr Gln Phe Asp Val Leu Val Met Pro Asn Leu Tyr
                260                 265                 270

Gly Asn Ile Ile Asp Asn Leu Ala Ala Gly Leu Val Gly Gly Ala Gly
                275                 280                 285

Val Val Pro Gly Glu Ser Tyr Ser Ala Glu Tyr Ala Val Phe Glu Thr
        290                 295                 300

Gly Ala Arg His Pro Phe Ala Gln Ala Val Gly Arg Asn Ile Ala Asn
305                 310                 315                 320

Pro Thr Ala Met Leu Leu Ser Ala Thr Asn Met Leu Arg His Leu Asn
                325                 330                 335

Leu Glu Tyr His Ser Ser Met Ile Ala Asp Ala Val Lys Lys Val Ile
                340                 345                 350

Lys Ala Gly Lys Val Arg Thr Arg Asp Met Gly Gly Tyr Ser Thr Thr
        355                 360                 365

Thr Asp Phe Ile Lys Ser Val Ile Gly His Leu His Pro His Gly Gly
370                 375                 380

<210> SEQ ID NO 47
<211> LENGTH: 1561
<212> TYPE: DNA
<213> ORGANISM: Homo sapiens

<400> SEQUENCE: 47
gtcacttccc acgcgacttc ctgcgggaaa catggcggca ttgagcggag tccgctggct      60
gacccgagcg ctggtctccg ccgggaaccc tggggcatgg agaggtctga gtacctcggc     120
cgcggcgcac gctgcatcgc ggagccaggc cgaggacgtg agggtggagg gctcctttcc     180
cgtgaccatg cttccgggag acggtgtggg gcctgagctg atgcacgccg tcaaggaggt     240
gttcaaggct gccgctgtcc cagtggagtt ccaggagcac cacctgagtg aggtgcagaa     300
tatggcatct gaggagaagc tggagcaggt gctgagttcc atgaaggaga caaagtggc     360 catcattgga aagattcata ccccgatgga gtataagggg gagctagcct cctatgatat     420
gcggctgagg cgtaagttgg acttatttgc caacgtagtc catgtgaagt cacttcctgg     480
gtatatgact cggcacaaca atctagacct ggtgatcatt cgagagcaga cagaagggga     540
gtacagctct ctggaacatg agagtgcaag gggtgtgatt gagtgtttga agattgtcac     600
acgagccaag tctcagcgga ttgcaaagtt cgcctttgac tatgccacca agaaggggcg     660
```

-continued

```
gggcaaggtc actgctgtcc acaaggccaa catcatgaaa cttggggatg ggttgttcct      720
gcagtgctgt gaggaagttg ctgaactgta ccccaaaatc aaatttgaga caatgatcat      780
agacaactgc tgcatgcagc tggtgcagaa tccttaccag tttgatgtgc ttgtgatgcc      840
caatctctat gggaacatta ttgacaatct ggctgctggc ctggttgggg agctggtgt       900
ggtccctggt gagagctata gtgcagaata cgcagtcttt gagacgggtg cccggcaccc      960
atttgcccag gcagtgggca ggaatatagc caatcccacg gccatgctgc tgtcggcttc     1020
caacatgctg cggcatctta atcttgagta tcactccagc atgatcgcag atgcggtgaa     1080
gaaggtgatc aaagttggca aggtgcggac tcgagacatg ggcggctaca gcaccacaac     1140
cgacttcatc aagtctgtca tcggtcacct gcagactaaa gggagctaga gcccttttatt    1200
tcttccaacc ttgcaaggac cacactcccc atacccttca gtgcagtgta ccagggaaga    1260
gaccttgtgc ctctaagcag tggaccatgg tcaccttgct gggtagagcc taggttgtcc    1320
ttgggccggc ttccttaggg gacagactgt tgggtggtga tggggattgt taggatggag    1380
cccaggccac atggatgatg atgattctcc cccacaggtt cgaacctctg acatgggtgg    1440
ctatgctact tgccatgact tcactgaggc tgtcattgct gccttgcccc acccataggc    1500
cctgtccata cccatgtaag gtgttcaata aagaacatga accaaaaaaa aaaaaaaaaa    1560
a                                                                    1561
```

<210> SEQ ID NO 48
<211> LENGTH: 1520
<212> TYPE: DNA
<213> ORGANISM: Mus musculus

<400> SEQUENCE: 48

```
ggcgtcactt cccccgcgac ttcctcggcc gaacatggca gcgctgagca atgtccgctg       60
gctgacccga gcggtgctcg ccgctcggaa ctccggggca tggagaggtc tcggaacatc      120
tacggctcac gccgcttccc agagccaggc acaagatgtg agggtggagg gtgcctttcc      180
tgtgaccatg ctgcctggag acggcgtggg gccagagctc atgcatgctg tcaaggaagt      240
gttcaaggct gctgctgtcc ctgtggaatt taaggagcat catctgagcg aggtgcagaa      300
tatggcttct gaggagaagc tggagcaggt gctgagttcc atgaaggaga caaagttgc       360
catcattgga aagatctata ccccaatgga gtataagggt gaactagcct cctatgatat      420
gcagctgagg cgtaagttgg atttgtttgc caacgtagtc cacgtgaagt cacttcctgg      480
atacaagact cggcacaaca atctagacct ggttatcatt cgagagcaga cagaagggga      540
gtatagctct ctggaacatg agagcgccaa gggtgtcatt gagtgcctga agatcgtcac      600
tcgcaccaag tctcagagga ttgcaaagtt tgcgttcgac tatgccacca agaaagggcg      660
gagcaaggtc acagccgtcc ataaagccaa catcatgaaa ctagggatg gcttgttctt      720
gcagtgctgt gaggaagttg ctgaactgta ccctaaaatc aagtttgaaa ccatgatcat      780
agacaactgc tgcatgcagc tggtgcagaa cccttaccag tttgatgtgc tcgtgatgcc      840
caatctctat ggcaacataa ttgacaatct ggctgctggc cttgttgggg agctggcgt       900
ggttcctggg gagagctaca gtgcagagta tgcagttttt gagacgggtg ctcggcaccc      960
atttgcccag gcagtgggca ggaatatagc caaccccaca gccatgctgc tgtcggccac     1020
caacatgctg cggcatctca atcttgagta tcactccagc atgattgcag atgcagtgaa     1080
gaaagtgatc aaagctggca aggtacggac tcgagacatg ggaggctaca gcaccacaac     1140
```

```
tgacttcatc aagtctgtca tcggccacct gcaccccat gggggctaga gcccttactc    1200
cctccaattt caaaaggacc atgcttcgta tacatccctt cagtacaatg gaccagaaga    1260
gaacatctag acagtagact ataatagctt ttctgaggct aggctgtcct gggggctggt    1320 gttaaggta tctcaaaggg tgggttgttg cgacaaggcc cagaccctaa gatgataact    1380
ttttcccaca ggttcgaacc tcagatatgg gtggttatgc cacatgtcat gacttcactg    1440
aagctgtcat tactgccctg tcataaatcc tatacatgcc catgaaaaaa atagtcaata    1500
aacaaaatac acacatacta                                                1520
```

<210> SEQ ID NO 49
<211> LENGTH: 393
<212> TYPE: PRT
<213> ORGANISM: Homo sapiens

<400> SEQUENCE: 49

```
Met Ala Leu Lys Val Ala Thr Val Ala Gly Ser Ala Ala Lys Ala Val
1               5                   10                  15

Leu Gly Pro Ala Leu Leu Cys Arg Pro Trp Glu Val Leu Gly Ala His
                20                  25                  30

Glu Val Pro Ser Arg Asn Ile Phe Ser Glu Gln Thr Ile Pro Pro Ser
            35                  40                  45

Ala Lys Tyr Gly Gly Arg His Thr Val Thr Met Ile Pro Gly Asp Gly
        50                  55                  60

Ile Gly Pro Glu Leu Met Leu His Val Lys Ser Val Phe Arg His Ala
65                  70                  75                  80

Cys Val Pro Val Asp Phe Glu Glu Val His Val Ser Ser Asn Ala Asp
                85                  90                  95

Glu Glu Asp Ile Arg Asn Ala Ile Met Ala Ile Arg Arg Asn Arg Val
            100                 105                 110

Ala Leu Lys Gly Asn Ile Glu Thr Asn His Asn Leu Pro Pro Ser His
        115                 120                 125

Lys Ser Arg Asn Asn Ile Leu Arg Thr Ser Leu Asp Leu Tyr Ala Asn
130                 135                 140

Val Ile His Cys Lys Ser Leu Pro Gly Val Val Thr Arg His Lys Asp
145                 150                 155                 160

Ile Asp Ile Leu Ile Val Arg Glu Asn Thr Glu Gly Glu Tyr Ser Ser
                165                 170                 175

Leu Glu His Glu Ser Val Ala Gly Val Val Glu Ser Leu Lys Ile Ile
            180                 185                 190

Thr Lys Ala Lys Ser Leu Arg Ile Ala Glu Tyr Ala Phe Lys Leu Ala
        195                 200                 205

Gln Glu Ser Gly Arg Lys Lys Val Thr Ala Val His Lys Ala Asn Ile
    210                 215                 220

Met Lys Leu Gly Asp Gly Leu Phe Leu Gln Cys Cys Arg Glu Val Ala
225                 230                 235                 240

Ala Arg Tyr Pro Gln Ile Thr Phe Glu Asn Met Ile Val Asp Asn Thr
                245                 250                 255

Thr Met Gln Leu Val Ser Arg Pro Gln Gln Phe Asp Val Met Val Met
            260                 265                 270

Pro Asn Leu Tyr Gly Asn Ile Val Asn Asn Val Cys Ala Gly Leu Val
        275                 280                 285

Gly Gly Pro Gly Leu Val Ala Gly Ala Asn Tyr Gly His Val Tyr Ala
    290                 295                 300
```

-continued

Val Phe Glu Thr Ala Thr Arg Asn Thr Gly Lys Ser Ile Ala Asn Lys
305                 310                 315                 320

Asn Ile Ala Asn Pro Thr Ala Thr Leu Leu Ala Ser Cys Met Met Leu
            325                 330                 335

Asp His Leu Lys Leu His Ser Tyr Ala Thr Ser Ile Arg Lys Ala Val
            340                 345                 350

Leu Ala Ser Met Asp Asn Glu Asn Met His Thr Pro Asp Ile Gly Gly
        355                 360                 365

Gln Gly Thr Thr Ser Glu Ala Ile Gln Asp Val Ile Arg His Ile Arg
    370                 375                 380

Val Ile Asn Gly Arg Ala Val Glu Ala
385                 390

<210> SEQ ID NO 50
<211> LENGTH: 393
<212> TYPE: PRT
<213> ORGANISM: Mus musculus

<400> SEQUENCE: 50

Met Ala Leu Lys Val Ala Ile Ala Ala Gly Gly Ala Ala Lys Ala Met
1               5                   10                  15

Leu Lys Pro Thr Leu Leu Cys Arg Pro Trp Glu Val Leu Ala Ala His
            20                  25                  30

Val Ala Pro Arg Ser Ile Ser Ser Gln Gln Thr Ile Pro Pro Ser
        35                  40                  45

Ala Lys Tyr Gly Gly Arg His Thr Val Thr Met Ile Pro Gly Asp Gly
    50                  55                  60

Ile Gly Pro Glu Leu Met Leu His Val Lys Ser Val Phe Arg His Ala
65                  70                  75                  80

Cys Val Pro Val Asp Phe Glu Glu Val His Val Ser Ser Asn Ala Asp
                85                  90                  95

Glu Glu Asp Ile Arg Asn Ala Ile Met Ala Ile Arg Arg Asn Arg Val
            100                 105                 110

Ala Leu Lys Gly Asn Ile Glu Thr Asn His Asn Leu Pro Pro Ser His
        115                 120                 125

Lys Ser Arg Asn Asn Ile Leu Arg Thr Ser Leu Asp Leu Tyr Ala Asn
    130                 135                 140

Val Ile His Cys Lys Ser Leu Pro Gly Val Val Thr Arg His Lys Asp
145                 150                 155                 160

Ile Asp Ile Leu Ile Val Arg Glu Asn Thr Glu Gly Glu Tyr Ser Ser
                165                 170                 175

Leu Glu His Glu Ser Val Ala Gly Val Val Glu Ser Leu Lys Ile Ile
            180                 185                 190

Thr Lys Ala Lys Ser Leu Arg Ile Ala Glu Tyr Ala Phe Lys Leu Ala
        195                 200                 205

Gln Glu Ser Gly Arg Lys Lys Val Thr Ala Val His Lys Ala Asn Ile
    210                 215                 220

Met Lys Leu Gly Asp Gly Leu Phe Leu Gln Cys Cys Arg Glu Val Ala
225                 230                 235                 240

Ala His Tyr Pro Gln Ile Thr Phe Asp Ser Met Ile Val Asp Asn Thr
                245                 250                 255

Thr Met Gln Leu Val Ser Arg Pro Gln Gln Phe Asp Val Met Val Met
            260                 265                 270

Pro Asn Leu Tyr Gly Asn Ile Val Asn Asn Val Cys Ala Gly Leu Val
        275                 280                 285

```
Gly Gly Pro Gly Leu Val Ala Gly Ala Asn Tyr Gly His Val Tyr Ala
    290                 295                 300

Val Phe Glu Thr Ala Thr Arg Asn Thr Gly Lys Ser Ile Ala Asn Lys
305                 310                 315                 320

Asn Ile Ala Asn Pro Thr Ala Thr Leu Leu Ala Ser Cys Met Met Leu
                325                 330                 335

Asp His Leu Lys Leu His Ser Tyr Ala Thr Ser Ile Arg Lys Ala Val
                340                 345                 350

Leu Ala Ser Met Asp Asn Glu Asn Met His Thr Pro Asp Ile Gly Gly
            355                 360                 365

Gln Gly Thr Thr Ser Gln Ala Ile Gln Asp Ile Ile Arg His Ile Arg
    370                 375                 380

Ile Ile Asn Gly Arg Ala Val Glu Ala
385                 390
```

<210> SEQ ID NO 51
<211> LENGTH: 1502
<212> TYPE: DNA
<213> ORGANISM: Homo sapiens

<400> SEQUENCE: 51

```
ggggcccagc tggtcgcggt ccccccctca acatggcggc agcggtgctc taggcgccgg      60
aagggggcgt gaatcggtgc gaccgcgcgc gtgcgcagta ccgggtccgc gcctgtcccc     120
gaaacttcgc accccgtcga actctcgcga gagcggtatc tgcgtgtcgg acgtgcgga     180
ggctctcact ttccgtcatg cgctgaagg tagcgaccgt cgccggcagc gccgcgaagg     240
cggtgctcgg gccagccctt ctctgccgtc cctgggaggt tctaggcgcc acgaggtcc     300
cctcgaggaa catcttttca gaacaaacaa ttcctccgtc cgctaagtat ggcgggcggc     360
acacggtgac catgatccca ggggatggca tcgggccaga gctcatgctg catgtcaagt     420
ccgtcttcag gcacgcatgt gtaccagtgg actttgaaga ggtgcacgtg agttccaatg     480
ctgatgaaga ggacattcgc aatgccatca tggccatccg ccggaaccgc gtggccctga     540
agggcaacat cgaaaccaac cataacctgc accgtcgca caaatctcga acaacatcc     600
ttcgcaccag cctggacctc tatgccaacg tcatccactg taagagcctt ccaggcgtgg     660
tgacccggca aaggacata gacatcctca ttgtccggga aacacagag ggcgagtaca     720
gcagcctgga gcatgagagt gtggcgggag tggtggagag cctgaagatc atcaccaagg     780
ccaagtccct gcgcattgcc gagtatgcct tcaagctggc gcaggagagc gggcgcaaga     840
aagtgacggc cgtgcacaag gccaacatca tgaaactggg cgatgggctt ttcctccagt     900
gctgcaggga ggtggcagcc cgctaccctc agatcacctt cgagaacatg attgtggata     960
acaccaccat gcagctggtg tcccggcccc agcagtttga tgtcatggtg atgcccaatc    1020
tctatggcaa catcgtcaac aatgtctgcg cgggactggt cggggggccca ggccttgtgg    1080
ctggggccaa ctatggccat gtgtacgcgg tgtttgaaac agctacgagg aacaccggca    1140
agagtatcgc caataagaac atcgccaacc ccacggccac cctgctggcc agctgcatga    1200
tgctggacca cctcaagctg cactcctatg ccacctccat ccgtaaggct gtcctggcat    1260
ccatggacaa tgagaatatg cacactccgg acatcggggg ccagggcaca acatctgaag    1320
ccatccagga cgtcatccgc cacatccgcg tcatcaacgg ccgggccgtg gaggcctagg    1380
ctggccctag gaccttcttg gtttgctcct tggattcccc ttcccactcc agcacccag    1440
ccagcctggt acgcagatcc cagaataaag caccttctcc ctagaaaaaa aaaaaaaaa    1500
``` aa                                                                              1502

<210> SEQ ID NO 52
<211> LENGTH: 1335
<212> TYPE: DNA
<213> ORGANISM: Mus musculus

<400> SEQUENCE: 52

```
ggtgcttaat gttttgacct gtagaggtcc tcacttttcg tcatggcgct gaaggtggcg     60
atagctgctg gcggtgctgc aaaggcaatg ctcaagccaa ctctcctctg ccgtccttgg    120
gaggttctgg ctgcccatgt ggcccccega aggagcattt cctcacaaca aacaattcct    180
ccatctgcta agtatggtgg gcggcataca gtgactatga tcccagggga tggcatcggc    240
ccagagctca tgttgcatgt taagtctgta ttcaggcatg catgtgtgcc ggtggacttt    300
gaagaggtgc atgtaagctc caacgctgat gaggaggaca tccgcaatgc catcatggcc    360
atccgccgga accgtgtggc cctgaagggc aacattgaaa caaatcataa cctgccacca    420
tcccacaaat ctcgaaacaa catccttcgc accagcctag acctctatgc caacgtcatc    480
cactgtaaga gcctgccagg agtggtgacc cggcacaagg acatagacat cctcattgta    540
cgggaaaaca cagaaggcga gtacagcagc ctggagcatg agagcgtagc aggagtggtg    600
gagagcttga agattatcac caaagccaag tccctgcgca ttgctgaata tgctttcaag    660
ctggcccagg agagtgggcg taagaaagtg acggctgtgc acaaggccaa catcatgaaa    720
ctgggtgatg gactcttcct ccagtgctgc agggaagtag cagcccacta ccctcagatc    780
acctttgaca gcatgattgt agacaacaca acaatgcagc tggtatcccg gcctcagcag    840
tttgatgtca tggtgatgcc taatctctat ggtaacattg tcaacaacgt ctgtgcaggg    900
ctagttggag gcccaggcct tgtggctggg gccaactatg gccatgtgta tgcagtattc    960
gagacagcta caaggaacac aggcaaaagt attgccaata agaacattgc taacccgact   1020
gccacactgc tagcaagctg catgatgcta gaccacctca agctccactc ctatgccact   1080
tccatccgca aagctgtctt agcatccatg gacaatgaaa atatgcatac cccagatatt   1140
ggaggccagg gcaccacatc ccaagccatc caggacatca ttcgtcatat ccgcatcatt   1200
aatggacggg ctgtggaggc ttagctatcc ctacagtttt gctcagcttg tctgtaggac   1260
tctcttctca ctttagcact ccagctagct tgggggacag gacccagaat aaagccactt   1320
ctgttccaga aaaaa                                                    1335
```